United States Patent
Wu

(10) Patent No.: US 10,744,139 B2
(45) Date of Patent: Aug. 18, 2020

(54) INHIBITORS OF FIBROBLAST GROWTH FACTOR RECEPTOR AND USE THEREOF

(71) Applicant: Nanjing TransThera Biosciences Co. Ltd., Nanjing, Jiangsu (CN)

(72) Inventor: Frank Wu, Nanjing (CN)

(73) Assignee: Nanjing TransThera Biosciences Co. Ltd., Nanjing (CN)

( * ) Notice: Subject to any disclaimer, the term of this patent is extended or adjusted under 35 U.S.C. 154(b) by 0 days.

(21) Appl. No.: 16/328,817

(22) PCT Filed: Aug. 10, 2017

(86) PCT No.: PCT/CN2017/096848
§ 371 (c)(1),
(2) Date: Feb. 27, 2019

(87) PCT Pub. No.: WO2018/040885
PCT Pub. Date: Mar. 8, 2018

(65) Prior Publication Data
US 2019/0209564 A1 Jul. 11, 2019
US 2020/0108070 A2 Apr. 9, 2020

(30) Foreign Application Priority Data

Sep. 1, 2016 (CN) .......................... 2016 1 0802100
May 18, 2017 (CN) .......................... 2017 1 0351160

(51) Int. Cl.
| | |
|---|---|
| *C07D 403/12* | (2006.01) |
| *A61K 31/517* | (2006.01) |
| *C07D 401/12* | (2006.01) |
| *C07D 403/14* | (2006.01) |
| *C07D 413/12* | (2006.01) |
| *A61P 35/00* | (2006.01) |
| *C07D 487/08* | (2006.01) |
| *A61P 35/02* | (2006.01) |
| *C07D 413/14* | (2006.01) |
| *A61K 31/5377* | (2006.01) |
| *A61K 31/553* | (2006.01) |
| *A61K 45/06* | (2006.01) |

(52) U.S. Cl.
CPC ........ *A61K 31/517* (2013.01); *A61K 31/5377* (2013.01); *A61K 31/553* (2013.01); *A61K 45/06* (2013.01); *A61P 35/00* (2018.01); *A61P 35/02* (2018.01); *C07D 401/12* (2013.01); *C07D 403/12* (2013.01); *C07D 403/14* (2013.01); *C07D 413/12* (2013.01); *C07D 413/14* (2013.01); *C07D 487/08* (2013.01)

(58) Field of Classification Search
CPC .................................................... C07D 471/04
See application file for complete search history.

(56) References Cited

U.S. PATENT DOCUMENTS 9,340,514 B2    5/2016  Bifulco, Jr. et al.
9,434,700 B2 *  9/2016  Bifulco, Jr. .......... C07D 471/04

FOREIGN PATENT DOCUMENTS

| CN | 104540809 A | 4/2015 |
|---|---|---|
| CN | 105658642 A | 6/2016 |
| EP | 1878727 A1 | 1/2008 |
| RU | 2011122539 A | 12/2012 |
| WO | 2006/118256 A1 | 11/2006 |
| WO | 2014/174307 A1 | 10/2014 |
| WO | 2015/061572 A1 | 4/2015 |
| WO | WO-2015/108992 A1 | 7/2015 |
| WO | 2017/070256 A2 | 4/2017 |

OTHER PUBLICATIONS

International Search Report and Written Opinion for Application No. PCT/CN2017/096848, dated Nov. 10, 2017, 9 pages.
Russian Office Action for Application No. 2019107910/04(015259), dated Nov. 28, 2019, 10 pages.

\* cited by examiner

*Primary Examiner* — Paul V Ward
(74) *Attorney, Agent, or Firm* — McCarter & English, LLP; Steven G. Davis; Wei Song

(57) ABSTRACT

Provided are an irreversible inhibitor of a fibroblast growth factor receptor (FGFR) as indicated by formula I, a pharmaceutically acceptable salt, a stereoisomer, a pharmaceutical preparation, a pharmaceutical composition and an application thereof. $R_1$, $R_2$, $R_3$, $R_4$, ring A, Ar, ring B and warhead are as defined in the specification. The compound has high-efficiency and high-selectivity inhibition of a fibroblast growth factor receptor and can be applied to treatment of abnormal FGF/FGFR-mediated diseases, in particular the treatment of cancers.

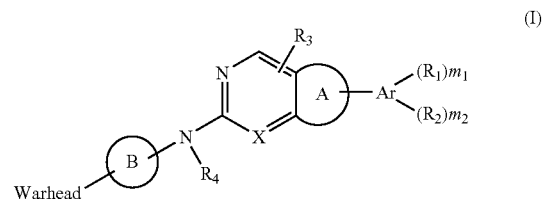

19 Claims, No Drawings

INHIBITORS OF FIBROBLAST GROWTH FACTOR RECEPTOR AND USE THEREOF

CROSS-REFERENCE TO RELATED APPLICATIONS

This application is a U.S. national stage filing, under 35 U.S.C. § 371(c), of International Application No. PCT/CN2017/096848, filed on Aug. 10, 2017, which claims the priority of the Chinese patent application No. 201610802100.5, entitled "A NOVEL INHIBITOR OF FIBROBLAST GROWTH FACTOR RECEPTOR AND USE THEREOF", filed before the CNIPA on Sep. 1, 2016; and the Chinese patent application No. 201710351160.4, entitled "INHIBITORS OF FIBROBLAST GROWTH FACTOR RECEPTOR AND USE THEREOF", filed before the CNIPA on May 18, 2017. The entire contents of each of the aforementioned applications are incorporated herein by reference.

TECHNICAL FIELD

The present invention belongs to the field of medical technology and relates to an irreversible inhibitor of fibroblast growth factor receptor (FGFR), or a pharmaceutically acceptable salt, a stereoisomer and an application thereof.

BACKGROUND

Tyrosine kinase receptors play an important role in tumor angiogenesis, proliferation, migration and infiltration of tumor cells. More than 100 tyrosine kinase inhibitor drugs have been marketed or entered into clinical trial phase successively. These small molecule tyrosine kinase inhibitors (TKIs) play a role in a manner of reversible inhibition, which brings some disadvantages: 1) the selectivity is not good enough, 2) the efficacy is not strong and lasting enough, 3) it is easy to cause drug resistance. Therefore, scientists are encouraged to focus their research on the development of irreversible TKIs.

Irreversible TKIs are typically based on the backbone structure of a reversible TKI, with an electrophilic functional group attached at appropriate position. The electrophilic functional group can form a covalent bond by an electrophilic reaction with a cysteine residue (electron-rich nucleophilic structure) near the ATP-binding domain of tyrosine kinase, thereby irreversibly inhibiting kinase activity. Compared with reversible TKIs, irreversible TKIs have many unique advantages: 1) irreversible TKIs function in a permanent inactivation manner, and this way of inhibiting enzyme activity makes its effect stronger and longer, thereby maintaining the efficacy even if the drug molecule is completely removed from the circulatory system; 2) the development of drug resistance is reduced or avoided due to the absence of ATP competition for binding TKIs to kinase, which reduces the likelihood of mutation of kinase; and 3) the selectivity of the irreversible TKIs is very high due to the electrophilic functional group on the molecular structure of TKIs selectively reacts with a thiol group on a cysteine residue. Based on the above characteristics, the development of irreversible TKIs is gradually becoming a hot spot for research and development.

Fibroblast growth factor receptor (FGFR) is an important member of the tyrosine kinase receptor family. FGFR contains four members, namely FGFR-1, FGFR-2, FGFR-3 and FGFR-4. They are mostly single-chain glycoprotein molecule with molecule mass ranging from 110 kd to 150 kd, comprising an extracellular region, a transmembrane region and an intracellular region. Under normal physiological conditions, FGFR binds to its ligand, fibroblast growth factor (FGF), and results in dimerization and phosphorylation itself, thereby activating downstream signalling pathway, such as the JAK/STAT pathway, the phospholipase C pathway, the phosphatidylinositol-3-kinase PI3K pathway, and the MAPK signalling pathway, which play important roles in tumor growth and angiogenesis. The abnormal high expression of FGFR is closely related to the development of various tumors such as lung cancer, liver cancer, glioma, rhabdomyosarcoma and melanoma.

There are currently no irreversible FGFR inhibitor drugs available, especially the irreversible inhibitors with high selectivity for pan-FGFR.

SUMMARY OF THE INVENTION

An object of the present invention is to provide a novel irreversible pan-FGFR inhibitor having high selectivity. Such compound has potent inhibitory activity against pan-FGFR, and provides the possibilities for the treatment of diseases mediated abnormally by pan-FGFR. The present invention also provides a use of the above FGFR inhibitor.

The technical solutions adopted by the present invention are as follows.

Solution 1: An irreversible inhibitor of fibroblast growth factor receptor (FGFR) represented by general formula (I), or a pharmaceutically acceptable salt or a stereoisomer thereof:

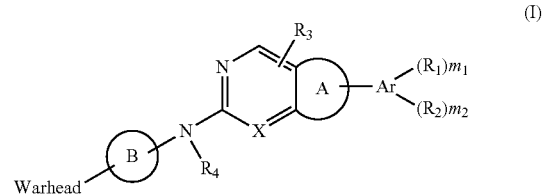

wherein,
$R_1$ and $R_2$ are each independently selected from the group consisting of hydrogen, hydroxyl, amino, cyano, nitro, halogen atom, carboxyl, $C_{1-6}$ alkyl, $C_{1-6}$ alkoxy, $C_{1-6}$ alkylamino, $(C_{1-6}$ alkyl$)_2$ amino, halo $C_{1-6}$ alkyl, halo $C_{1-6}$ alkoxy, $C_{2-8}$ alkenyl, $C_{2-8}$ alkynyl, $C_{1-6}$ alkylsulfonyl, $C_{1-6}$ alkylcarbonylamino, $C_{1-6}$ alkyl-substituted 3-8 membered cycloalkyl, $C_{1-6}$ alkyl-substituted 3-8 membered heterocyclyl, alternatively, $R_1$ and $R_2$ together with two atoms on an aromatic ring or heteroaromatic ring to which they are connected respectively may form a 3-8 membered cycloalkyl, a 3-8 membered heterocyclyl, a 6-14 membered aryl or a 5-10 membered heteroaryl, and an S atom in any ring may be optionally oxidized to S(O) or S(O)$_2$, and a carbon atom in any ring may be optionally oxidized to C(O);
$R_3$ and $R_4$ are each independently selected from the group consisting of hydrogen, hydroxyl, amino, cyano, nitro, halogen atom, carboxyl, $C_{1-6}$ alkyl, $C_{1-6}$ alkoxy, $C_{1-6}$ alkylamino, $(C_{1-6}$ alkyl$)_2$ amino, halo $C_{1-6}$ alkyl, halo $C_{1-6}$ alkoxy, $C_{2-8}$ alkenyl, $C_{2-8}$ alkynyl, $C_{1-6}$ alkylsulfonyl, $C_{1-6}$ alkylcarbonylamino, $C_{1-6}$ alkylaminocarbonyl, 3-8 membered cycloalkyl, 3-8 membered heterocyclyl, 6-14 membered aryl or 5-10 membered heteroaryl, $C_{1-6}$ alkyl-substituted 3-8 membered cycloalkyl, $C_{1-6}$ alkyl-substituted 3-8 membered heterocyclyl, $C_{1-6}$ alkyl-substituted 6-14 membered aryl or $C_{1-6}$ alkyl-substituted 5-10 membered heteroaryl;

Ar is 6-14 membered aromatic ring group or 5-10 membered heteroaryl optionally containing 0-3 O, S and/or N atom;
Ring A is selected from the group consisting of 3-8 membered cycloalkyl, 3-8 membered heterocyclyl, 6-14 membered aryl, and 5-10 membered heteroaryl having 0-3 O, S and/or N atom, optionally substituted with 1-3 $R_5$ groups, wherein an S atom in any ring may be optionally oxidized to S(O) or S(O)$_2$, and a carbon atom in any ring may be optionally oxidized to C(O);
Ring B is 3-10 membered saturated or unsaturated heterocyclyl containing at least one N hetero atom or 5-6 membered N-containing heteroaryl, optionally substituted with 1-3 $R_6$ groups, and the N atom on ring B is directly bonded to Warhead, wherein any S atom in ring B can be optionally oxidized to S(O) or S(O)$_2$, and any carbon atom in ring B can be optionally oxidized to C(O);
X is $CR_7$ or N;
$R_5$, $R_6$, and $R_7$ are each independently selected from the group consisting of
(i) hydrogen,
(ii) hydroxyl, amino, carboxyl, cyano, nitro, or halogen atom,
(iii) $C_{1-6}$ alkyl, $C_{1-6}$ alkoxy, $C_{1-6}$ alkylamino, ($C_{1-6}$ alkyl)$_2$ amino, halo $C_{1-6}$ alkyl, halo $C_{1-6}$ alkoxy, $C_{2-8}$ alkenyl, $C_{2-8}$ alkynyl, $C_{1-6}$ alkylsulfonyl, or $C_{1-6}$ alkylthio optionally substituted with hydroxyl, amino, carboxyl, cyano, nitro, halogen, $C_{1-6}$ alkyl, $C_{1-6}$ alkoxy, $C_{1-6}$ alkoxy $C_{1-6}$ alkoxy, $C_{1-6}$ alkylamino, ($C_{1-6}$ alkyl)$_2$ amino, $C_{1-6}$ alkylcarbonylamino, $C_{1-6}$ alkylsulfonylamino, or 3-8 membered heterocyclyl, wherein the 3-8 membered heterocyclyl may be optionally substituted with hydroxyl, amino, carboxyl, cyano, nitro, halogen, $C_{1-6}$ alkyl, $C_{1-6}$ alkoxy, $C_{1-6}$ alkylamino, or ($C_{1-6}$ alkyl)$_2$ amino,
(iv) 3-8 membered cycloalkyl or 3-8 membered heterocyclyl optionally substituted with hydroxyl, amino, carboxyl, cyano, nitro, halogen, $C_{1-6}$ alkyl, $C_{1-6}$ alkoxy, $C_{1-6}$ alkylamino, or ($C_{1-6}$ alkyl)$_2$ amino, and
(v) aminocarbonyl, cyanocarbonyl, $C_{1-6}$ alkylcarbonyl, $C_{1-6}$ alkylaminocarbonyl, ($C_{1-6}$ alkyl)$_2$ aminocarbonyl, $C_{1-6}$ alkoxycarbonyl, 3-8 membered cycloalkylcarbonyl, or 3-8 membered heterocyclyl carbonyl;
$m_1$ and $m_2$ represent 1, 2 or 3, and the sum of $m_1$ and $m_2$ is less than or equal to 5; and
Warhead refers to a moiety that is capable of forming a covalent bond with a nucleophile.

Solution 2: The compound according to solution 1 or the pharmaceutically acceptable salt or the stereoisomer thereof, wherein,
$R_1$ is independently selected from the group consisting of hydrogen, halogen, and hydroxyl;
$R_2$ is independently selected from the group consisting of hydrogen, halogen, hydroxyl, $C_{1-4}$ alkyl, $C_{1-4}$ alkoxy, cyano, halo $C_{1-4}$ alkyl, and halo $C_{1-4}$ alkoxy;
Ar is 6-14 membered aromatic ring group or 5-6 membered heteroaryl optionally containing 0-3 O, S and/or N atom;
$m_1$ and $m_2$ represent 1, 2 or 3, and the sum of $m_1$ and $m_2$ is less than or equal to 5.

Solution 3: The compound according to solution 2 or the pharmaceutically acceptable salt or the stereoisomer thereof, wherein,
$R_1$ is independently selected from the group consisting of hydrogen, halogen, and hydroxyl;
$R_2$ is independently selected from the group consisting of hydrogen, halogen, hydroxyl, $C_{1-4}$ alkyl, $C_{1-4}$ alkoxy, cyano, halo $C_{1-4}$ alkyl, and halo $C_{1-4}$ alkoxy;
$R_3$ and $R_4$ are each independently selected from the group consisting of hydrogen, hydroxyl, amino, cyano, nitro, halogen atom, carboxyl, $C_{1-4}$ alkyl, $C_{1-4}$ alkoxy, $C_{1-4}$ alkylamino, ($C_{1-4}$ alkyl)$_2$ amino, halo $C_{1-4}$ alkyl, halo $C_{1-4}$ alkoxy, $C_{2-4}$ alkenyl, $C_{2-4}$ alkynyl, $C_{1-4}$ alkylsulfonyl, and $C_{1-4}$ alkylcarbonylamino;
Ar is phenyl;
Ring A is phenyl optionally substituted with 1-3 $R_5$; Ring B is 4-10 membered saturated or unsaturated heterocyclyl containing at least one N heteroatom optionally substituted with 1-3 $R_6$, and an N atom on ring B is directly bonded to Warhead;
X is $CR_7$ or N;
$R_5$ and $R_7$ are each independently selected from the group consisting of hydrogen, hydroxyl, amino, carboxyl, cyano, nitro, halogen atom, $C_{1-4}$ alkyl, and $C_{1-4}$ alkoxy;
$R_6$ is selected from the group consisting of
(i) hydrogen,
(ii) hydroxyl, amino, carboxyl, cyano, nitro, or halogen atom,
(iii) $C_{1-4}$ alkyl, $C_{1-4}$ alkoxy, $C_{1-4}$ alkylamino, ($C_{1-4}$ alkyl)$_2$ amino, halo $C_{1-4}$ alkyl, halo $C_{1-4}$ alkoxy, $C_{2-4}$ alkenyl, $C_{2-4}$ alkynyl, $C_{1-4}$ alkylsulfonyl, or $C_{1-4}$ alkylthio optionally substituted with hydroxyl, amino, carboxyl, cyano, nitro, halogen, $C_{1-4}$ alkyl, $C_{1-4}$ alkoxy, $C_{1-4}$ alkoxy $C_{1-4}$ alkoxy, $C_{1-4}$ alkylamino, ($C_{1-4}$ alkyl)$_2$ amino, $C_{1-4}$ alkylcarbonylamino, $C_{1-4}$ alkylsulfonylamino, or 3-8 membered heterocyclyl, wherein the 3-8 membered heterocyclyl may be optionally substituted with hydroxyl, amino, carboxyl, cyano, nitro, halogen, $C_{1-4}$ alkyl, $C_{1-4}$ alkoxy, $C_{1-4}$ alkylamino, or ($C_{1-4}$ alkyl)$_2$ amino,
(iv) 3-8 membered cycloalkyl, or 3-8 membered heterocyclyl optionally substituted with hydroxyl, amino, carboxyl, cyano, nitro, halogen, $C_{1-4}$ alkyl, a $C_{1-4}$ alkoxy, $C_{1-4}$ alkylamino, or ($C_{1-4}$ alkyl)$_2$ amino, and
(v) aminocarbonyl, cyanocarbonyl, $C_{1-4}$ alkylcarbonyl, $C_{1-4}$ alkylamino carbonyl, ($C_{1-4}$ alkyl)$_2$ aminocarbonyl, $C_{1-4}$ alkoxycarbonyl, 3-8 membered cycloalkylcarbonyl, or 3-8 membered heterocyclyl carbonyl;
$m_1$ and $m_2$ represent 1, 2 or 3, and the sum of $m_1$ and $m_2$ is less than or equal to 5;
Warhead refers to a moiety that is capable of forming a covalent bond with a nucleophile.

Solution 4: The compound of formula (I) according to any one of solutions 1 to 3 or the pharmaceutically acceptable salt or the stereoisomer thereof, having a structure as shown in general formula (II):

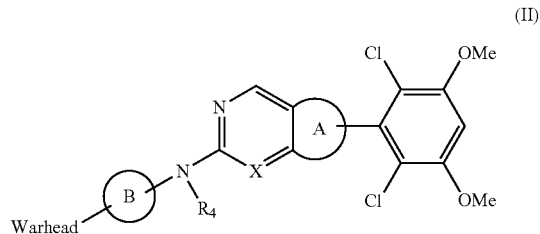

(II)

$R_4$ is H or $C_{1-4}$ alkyl;
Ring A is phenyl;
Ring B is selected from the group consisting of 4-6 membered saturated or unsaturated monoheterocyclyl or 6-10 membered saturated or unsaturated fused heterocyclyl containing at least one N heteroatom, optionally substituted with 1-3 $R_6$, and a N atom on ring B is directly connected to a Warhead bond;

X is N;

$R_6$ is selected from the group consisting of
(i) hydrogen,
(ii) hydroxyl, amino, carboxyl, cyano, nitro, or halogen atom, (iii) $C_{1-4}$ alkyl, $C_{1-4}$ alkoxy, $C_{1-4}$ alkylamino, $(C_{1-4}$ alkyl$)_2$ amino, halo $C_{1-4}$ alkyl, halo $C_{1-4}$ alkoxy, $C_{2-4}$ alkenyl, $C_{2-4}$ alkynyl, $C_{1-4}$ alkylsulfonyl, or $C_{1-4}$ alkylthio optionally substituted with hydroxyl, amino, carboxyl, cyano, nitro, halogen, $C_{1-4}$ alkyl, $C_{1-4}$ alkoxy, $C_{1-4}$ alkoxy $C_{1-4}$ alkoxy, $C_{1-4}$ alkylamino, $(C_{1-4}$ alkyl$)_2$ amino, $C_{1-4}$ alkylcarbonylamino, $C_{1-4}$ alkylsulfonylamino, or 3-8 membered heterocyclyl, wherein the 3-8 membered heterocyclyl may be optionally substituted with hydroxyl, amino, carboxyl, cyano, nitro, halogen, $C_{1-4}$ alkyl, $C_{1-4}$ alkoxy, $C_{1-4}$ alkylamino, or $(C_{1-4}$ alkyl$)_2$ amino, and
(iv) aminocarbonyl, cyanocarbonyl, $C_{1-4}$ alkylcarbonyl, $C_{1-4}$ alkylamino carbonyl, $(C_{1-4}$ alkyl$)_2$ aminocarbonyl, $C_{1-4}$ alkoxycarbonyl, 3-8 membered cycloalkylcarbonyl, or 3-8 membered heterocyclyl carbonyl;

Warhead is selected from the group consisting of

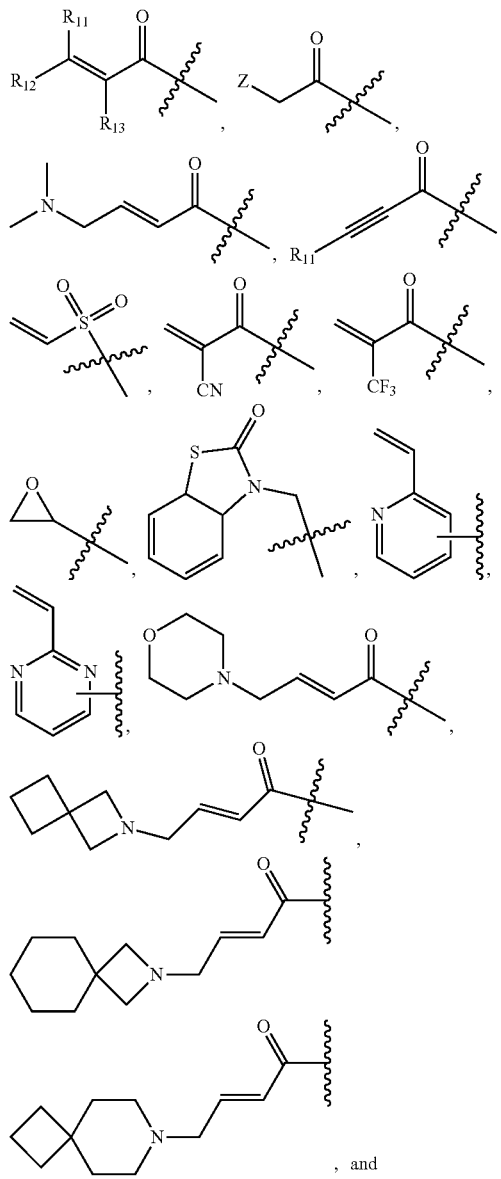

, and

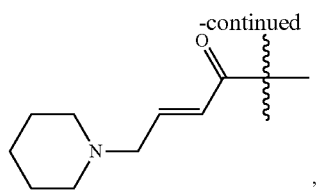

,

Z refers to a leaving group or an activated hydroxyl moiety, $R_{11}$, $R_{12}$, and $R_{13}$ are each independently selected from the group consisting of hydrogen, halogen, cyano, $C_{1-4}$ alkyl, halo $C_{1-4}$ alkyl, 3-8 membered cycloalkyl, 3-8 membered heterocyclyl, 5-8 membered aryl and 5-10 membered heteroaryl, the $C_{1-4}$ alkyl, halo $C_{1-4}$ alkyl, 3-8 membered cycloalkyl, 3-8 membered heterocyclyl, 5-8 membered aryl or 5-10 membered heteroaryl is optionally substituted with a substituent, wherein the substituent is selected from the group consisting of hydroxyl, amino, carboxyl, cyano, nitro, halogen, $C_{1-4}$ alkyl, $C_{1-4}$ alkoxy, $C_{1-4}$ alkoxy $C_{1-4}$ alkoxy, $C_{1-4}$ alkylamino, $(C_{1-4}$ alkyl$)_2$ amino, $C_{1-4}$ alkylcarbonylamino, $C_{1-4}$ alkylsulfonylamino, and 3-8 membered heterocyclyl; and $R_{11}$, $R_{12}$ and $R_{13}$ are preferably hydrogen.

Solution 5: The compound according to any one of solutions 1 to 4 or the pharmaceutically acceptable salt or the stereoisomer thereof, having a structure as shown in general formula (II):

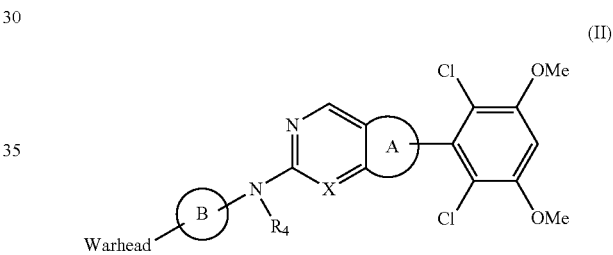

(II)

Warhead is directly connected to an N atom on ring B as follows:

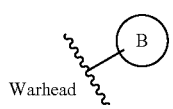

wherein ring B is selected from the group consisting of:

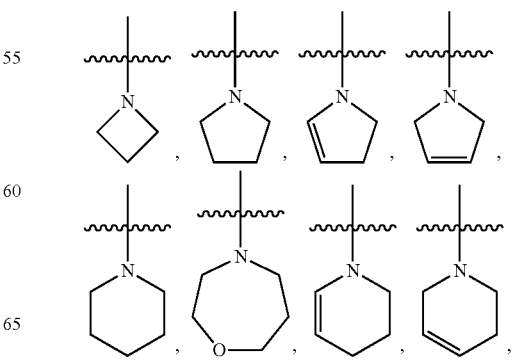

,

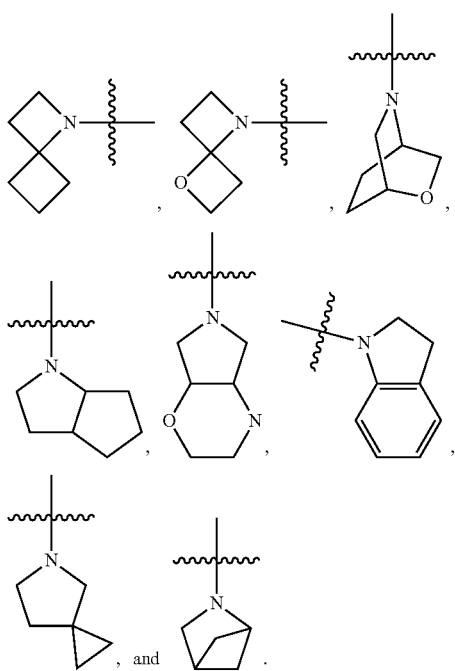

Solution 6: The compound according to any one of solutions 1 to 5 or the pharmaceutically acceptable salt or the stereoisomer thereof, wherein Warhead is selected from the group consisting of:

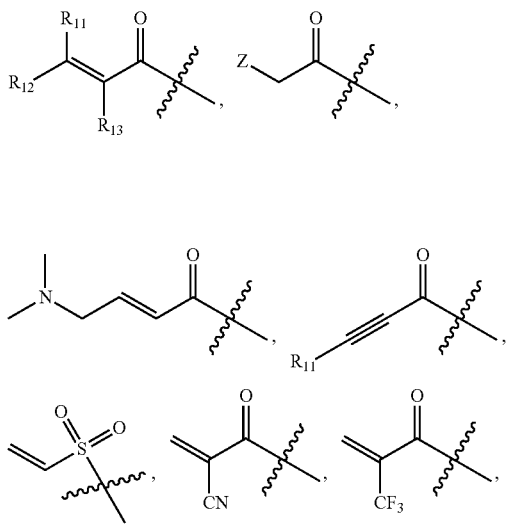

Z refers to a leaving group or an activated hydroxyl moiety, and $R_{11}$, $R_{12}$, and $R_{13}$ are each independently H or $C_{1-4}$ alkyl.

Solution 7: The compound of the present invention, the pharmaceutically acceptable salt or the stereoisomer thereof is:

| No. | Structure |
|---|---|
| 1 | 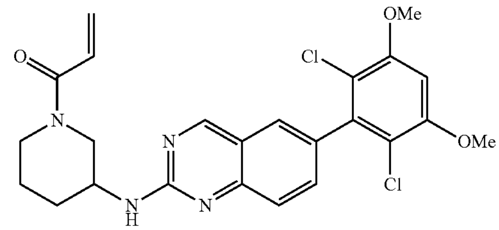 [SMILES: C=CC(=O)N1CCCC(Nc2ncc3cc(-c4c(Cl)c(OC)cc(OC)c4Cl)ccc3n2)C1] |
| 2 | 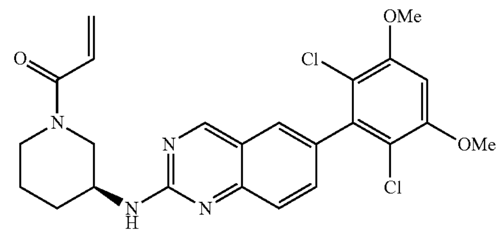 [SMILES: C=CC(=O)N1CCC[C@H](Nc2ncc3cc(-c4c(Cl)c(OC)cc(OC)c4Cl)ccc3n2)C1] |
| 3 | 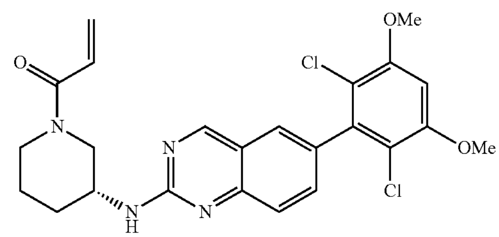 [SMILES: C=CC(=O)N1CCC[C@@H](Nc2ncc3cc(-c4c(Cl)c(OC)cc(OC)c4Cl)ccc3n2)C1] |
| 4 | 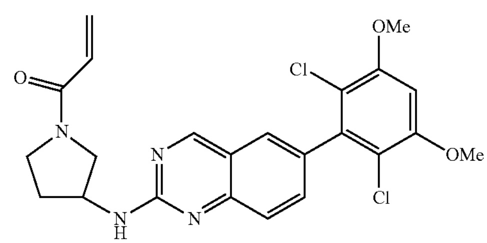 |
| 5 | 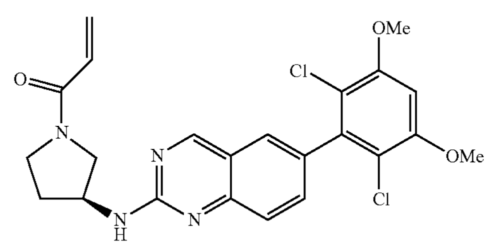 [SMILES: C=CC(=O)N1CC[C@H](Nc2ncc3cc(-c4c(Cl)c(OC)cc(OC)c4Cl)ccc3n2)C1] |
| 6 | 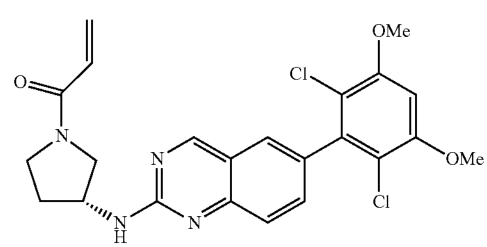 [SMILES: C=CC(=O)N1CC[C@@H](Nc2ncc3cc(-c4c(Cl)c(OC)cc(OC)c4Cl)ccc3n2)C1] |

| No. | Structure |
|---|---|
| 7 | 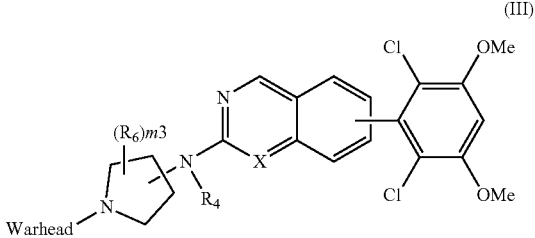 (structure 7) |
| 8 | (structure 8) |
| 9 | (structure 9) |
| 10 | (structure 10) |
| 11 | (structure 11) |

Solution 8: The compound according to solution 4 or the pharmaceutically acceptable salt or the stereoisomer thereof, wherein Ring B is selected from 5-6 membered saturated monoheterocyclyl containing at least one N heteroatom optionally substituted with 1-3 $R_6$, and an N atom on ring B is directly bonded to Warhead.

Solution 9: The compound according to solution 8 or the pharmaceutically acceptable salt or the stereoisomer thereof, having a structure as shown in general formula (III):

(III)

$R_4$ is H or $C_{1-4}$ alkyl;

X is N;

$R_6$ is selected from the group consisting of (i) hydrogen, (ii) hydroxyl, amino, carboxyl, cyano, nitro, or halogen atom, (iii) $C_{1-4}$ alkyl, $C_{1-4}$ alkoxy, $C_{1-4}$ alkylamino, $(C_{1-4}$ alkyl$)_2$ amino, halo $C_{1-4}$ alkyl, halo $C_{1-4}$ alkoxy, $C_{2-4}$ alkenyl, $C_{2-4}$ alkynyl, $C_{1-4}$ alkylsulfonyl, or $C_{1-4}$ alkylthio optionally substituted with hydroxyl, amino, carboxyl, cyano, nitro, halogen, $C_{1-4}$ alkyl, $C_{1-4}$ alkoxy, $C_{1-4}$ alkoxy $C_{1-4}$ alkoxy, $C_{1-4}$ alkylamino, $(C_{1-4}$ alkyl$)_2$ amino, $C_{1-4}$ alkylcarbonylamino, $C_{1-4}$ alkylsulfonylamino, or 3-8 membered heterocyclyl, wherein the 3-8 membered heterocyclyl may be optionally substituted with hydroxyl, amino, carboxyl, cyano, nitro, halogen, $C_{1-4}$ alkyl, $C_{1-4}$ alkoxy, $C_{1-4}$ alkylamino, or $(C_{1-4}$ alkyl$)_2$ amino, and (iv) aminocarbonyl, cyanocarbonyl, $C_{1-4}$ alkylcarbonyl, $C_{1-4}$ alkylamino carbonyl, $(C_{1-4}$ alkyl$)_2$ aminocarbonyl, $C_{1-4}$ alkoxycarbonyl, 3-8 membered cycloalkylcarbonyl, or 3-8 membered heterocyclyl carbonyl;

m is an integer from 1 to 3;

Warhead is selected from the group consisting of

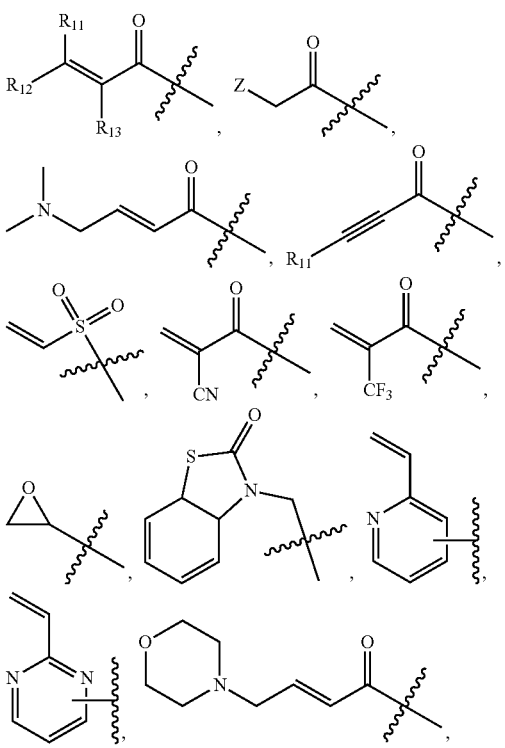

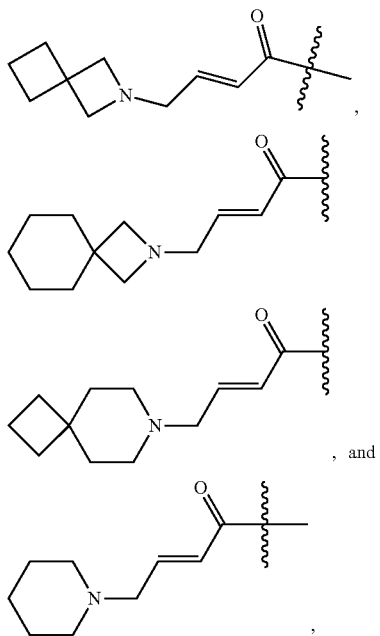

,

, and

,

Z refers to a leaving group or an activated hydroxyl moiety;

$R_{11}$, $R_{12}$, and $R_{13}$ are each independently selected from the group consisting of hydrogen, halogen, cyano, $C_{1-4}$ alkyl, halo $C_{1-4}$ alkyl, 3-8 membered cycloalkyl, 3-8 membered heterocyclyl, 5-8 membered aryl and 5-10 membered heteroaryl, the $C_{1-4}$ alkyl, halo $C_{1-4}$ alkyl, 3-8 membered cycloalkyl, 3-8 membered heterocyclyl, 5-8 membered aryl or 5-10 membered heteroaryl is optionally substituted with a substituent, wherein the substituent is selected from the group consisting of hydroxyl, amino, carboxyl, cyano, nitro, halogen, $C_{1-4}$ alkyl, $C_{1-4}$ alkoxy, $C_{1-4}$ alkoxy $C_{1-4}$ alkoxy, $C_{1-4}$ alkylamino, $(C_{1-4}$ alkyl$)_2$ amino, $C_{1-4}$ alkylcarbonylamino, $C_{1-4}$ alkylsulfonylamino, and 3-8 membered heterocyclyl; and $R_{11}$, $R_{12}$ and $R_{13}$ are preferably hydrogen.

Solution 10: The compound according to solution 9 or the pharmaceutically acceptable salt or the stereoisomer thereof, wherein $R_6$ is selected from the group consisting of (i) hydrogen, (ii) hydroxyl, amino, carboxyl, cyano, nitro, or halogen atom, (iii) $C_{1-4}$ alkyl, or $C_{1-4}$ alkoxy optionally substituted with hydroxyl, amino, carboxyl, cyano, nitro, halogen, $C_{1-4}$ alkyl, $C_{1-4}$ alkoxy, $C_{1-4}$ alkoxy $C_{1-4}$ alkoxy, $C_{1-4}$ alkylamino, $(C_{1-4}$ alkyl$)_2$ amino, $C_{1-4}$ alkylcarbonylamino, $C_{1-4}$ alkylsulfonylamino, or 3-8 membered heterocyclyl, wherein the 3-8 membered heterocyclyl may be optionally substituted with hydroxyl, amino, carboxyl, cyano, nitro, halogen, $C_{1-4}$ alkyl, $C_{1-4}$ alkoxy, $C_{1-4}$ alkylamino, $(C_{1-4}$ alkyl$)_2$ amino, wherein the 3-8 membered heterocyclyl is preferably 4-6 membered saturated heterocyclyl, more preferably azetidinyl, pyrrolidinyl, piperidinyl or morpholinyl; and (iv) aminocarbonyl, cyanocarbonyl, $C_{1-4}$ alkylcarbonyl, $C_{1-4}$ alkylamino carbonyl, $(C_{1-4}$ alkyl$)_2$ aminocarbonyl, $C_{1-4}$ alkoxycarbonyl, 3-8 membered cycloalkylcarbonyl, or 3-8 membered heterocyclyl carbonyl;

Warhead is selected from the group consisting of

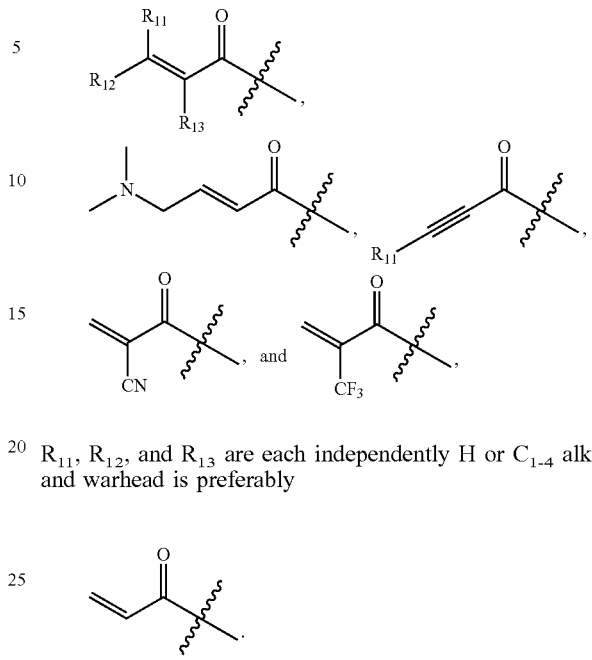

$R_{11}$, $R_{12}$, and $R_{13}$ are each independently H or $C_{1-4}$ alkyl, and warhead is preferably

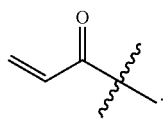 [SMILES: *C(=O)C=C]

.

Solution 11: The compound according to solution 10 or the pharmaceutically acceptable salt or the stereoisomer thereof, which may have a structure selected from the group consisting of:

| No. | Structure |
|---|---|
| 20 | 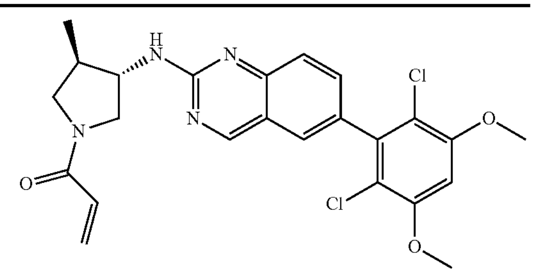 |
| 21 | 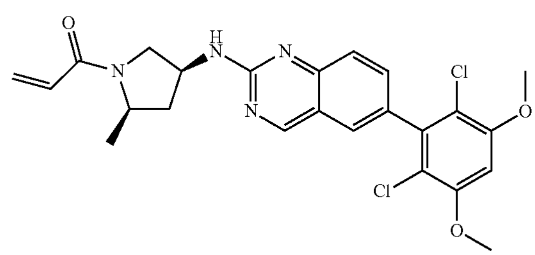 [SMILES: C=CC(=O)N1C[C@@H](Nc2ncc3cc(-c4c(Cl)c(OC)cc(OC)c4Cl)ccc3n2)C[C@H]1C] |
| 22 | 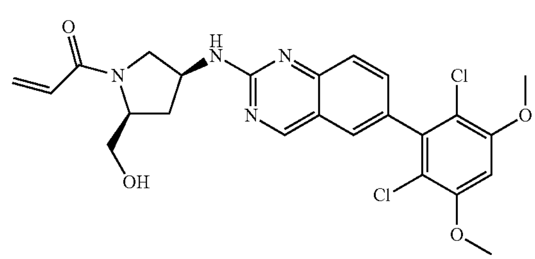 [SMILES: C=CC(=O)N1C[C@@H](Nc2ncc3cc(-c4c(Cl)c(OC)cc(OC)c4Cl)ccc3n2)C[C@H]1CCl] |

| No. | Structure |
|---|---|
| 23 | 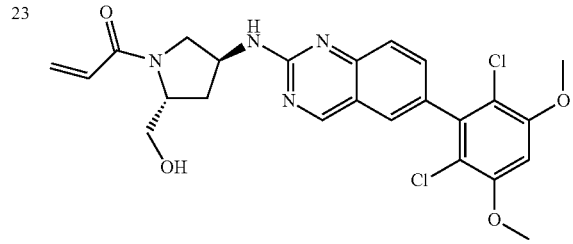 |
| 24 | 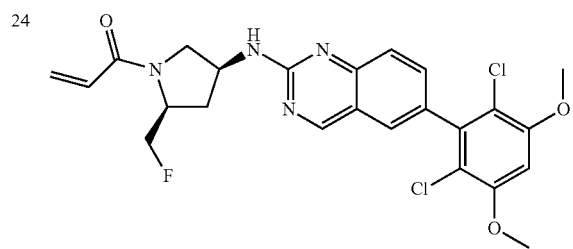 |
| 25 | 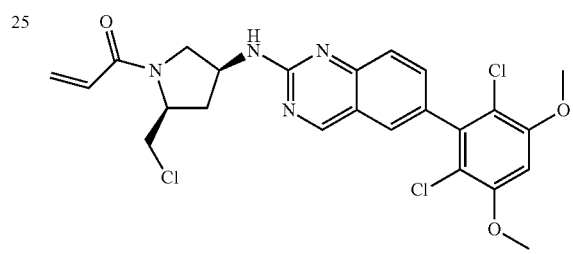 |
| 26 | 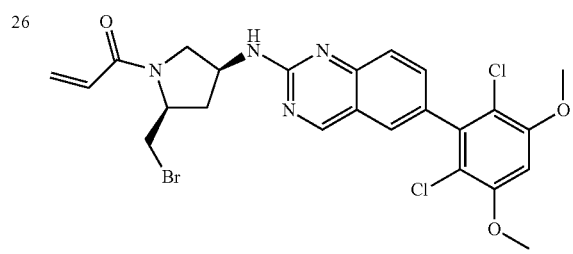 |
| 27 | 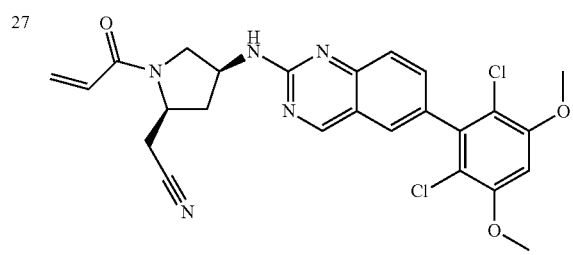 |
| 28 | 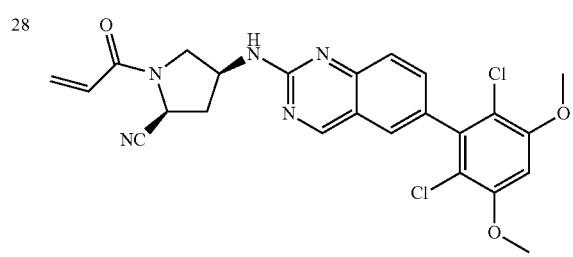 |
| 29 | 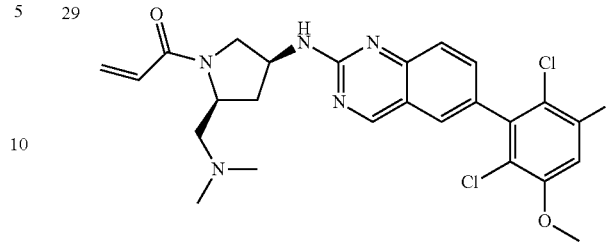 |
| 30 | 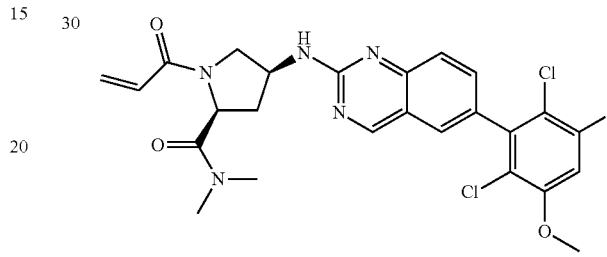 |
| 31 | 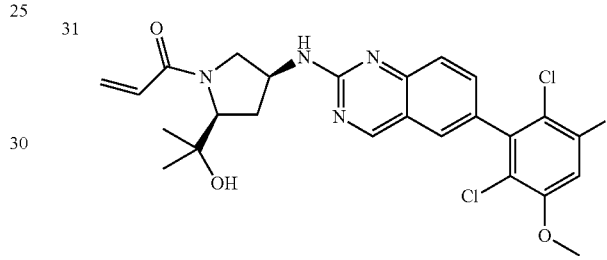 |
| 32 | 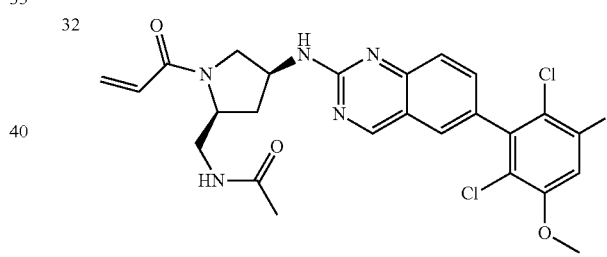 |
| 33 | 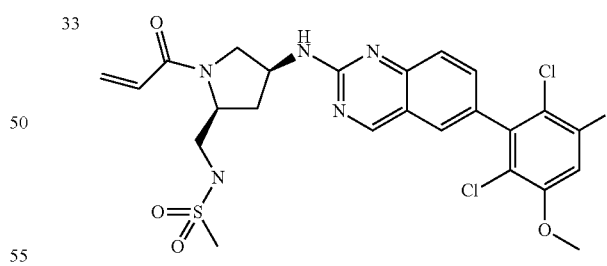 |
| 34 | 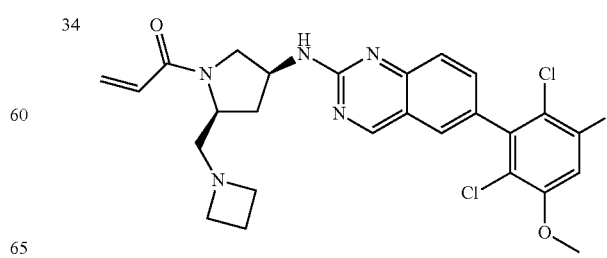 |

-continued

| No. | Structure |
|-----|-----------|
| 35  | 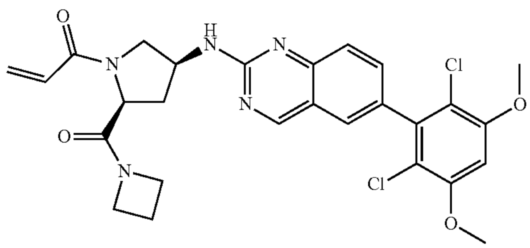 [SMILES: C=CC(=O)N1C[C@@H](Nc2ncc3cc(-c4c(Cl)c(OC)cc(OC)c4Cl)ccc3n2)C[C@H]1C(=O)N1CCC1]          |
| 36  | 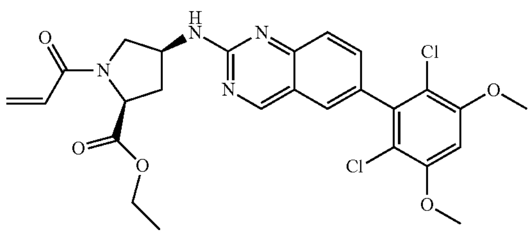 [SMILES: C=CC(=O)N1C[C@@H](Nc2ncc3cc(-c4c(Cl)c(OC)cc(OC)c4Cl)ccc3n2)C[C@H]1C(=O)OCC]          |
| 37  | 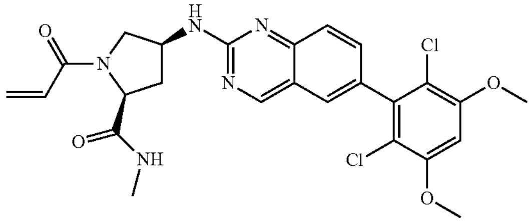 [SMILES: C=CC(=O)N1C[C@@H](Nc2ncc3cc(-c4c(Cl)c(OC)cc(OC)c4Cl)ccc3n2)C[C@H]1C(=O)NC]          |
| 38  | 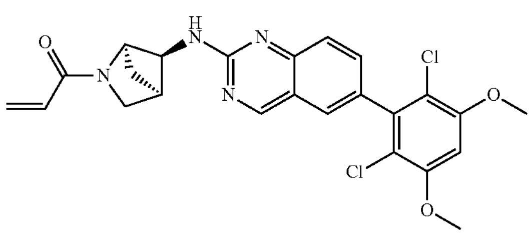 [SMILES: C=CC(=O)N1C[C@H]2C[C@@H]1[C@H]2Nc1ncc2cc(-c3c(Cl)c(OC)cc(OC)c3Cl)ccc2n1]          |
| 39  | 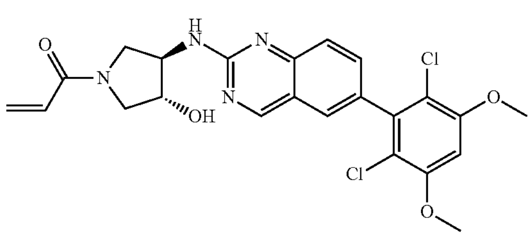 [SMILES: C=CC(=O)N1C[C@@H](O)[C@H](Nc2ncc3cc(-c4c(Cl)c(OC)cc(OC)c4Cl)ccc3n2)C1]          |
| 40  | 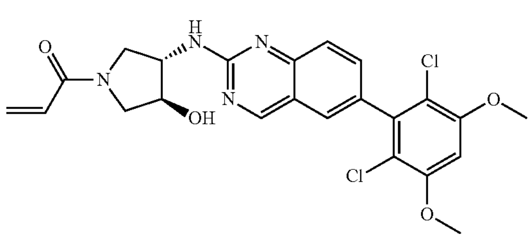 [SMILES: C=CC(=O)N1C[C@H](Nc2ncc3cc(-c4c(Cl)c(OC)cc(OC)c4Cl)ccc3n2)[C@@H](O)C1]          |

-continued

| No. | Structure |
|-----|-----------|
| 41  | 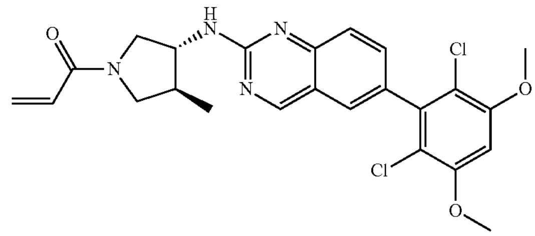 [SMILES: C=CC(=O)N1C[C@H](Nc2ncc3cc(-c4c(Cl)c(OC)cc(OC)c4Cl)ccc3n2)[C@@H](C)C1]          |
| 42  | 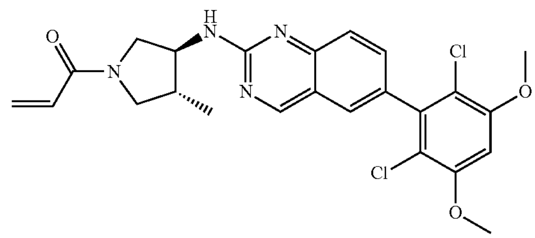 [SMILES: C=CC(=O)N1C[C@@H](C)[C@H](Nc2ncc3cc(-c4c(Cl)c(OC)cc(OC)c4Cl)ccc3n2)C1]          |
| 43  | 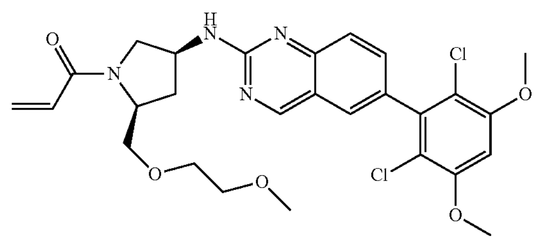 [SMILES: C=CC(=O)N1C[C@@H](Nc2ncc3cc(-c4c(Cl)c(OC)cc(OC)c4Cl)ccc3n2)C[C@H]1COCCOC]          |
| 44  | 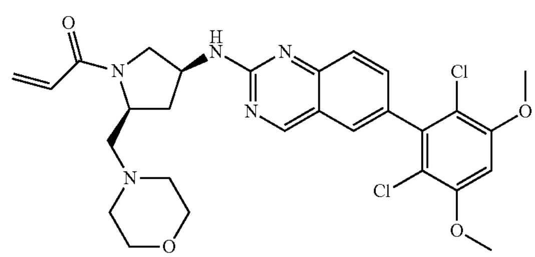 [SMILES: C=CC(=O)N1C[C@@H](Nc2ncc3cc(-c4c(Cl)c(OC)cc(OC)c4Cl)ccc3n2)C[C@H]1CN1CCOCC1]          |
| 45  | 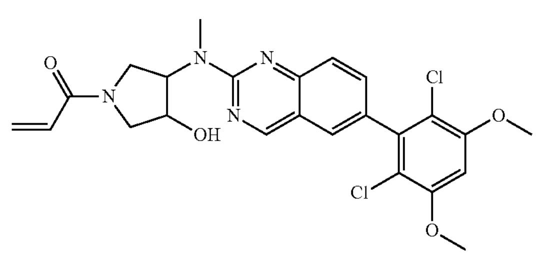 [SMILES: C=CC(=O)N1CC(O)C(N(C)c2ncc3cc(-c4c(Cl)c(OC)cc(OC)c4Cl)ccc3n2)C1]          |
| 46  | 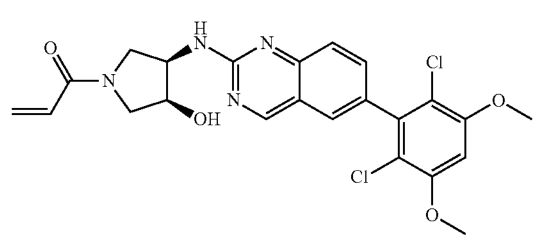 [SMILES: C=CC(=O)N1C[C@H](O)[C@H](Nc2ncc3cc(-c4c(Cl)c(OC)cc(OC)c4Cl)ccc3n2)C1]          |

| No. | Structure |
|---|---|
| 47 | 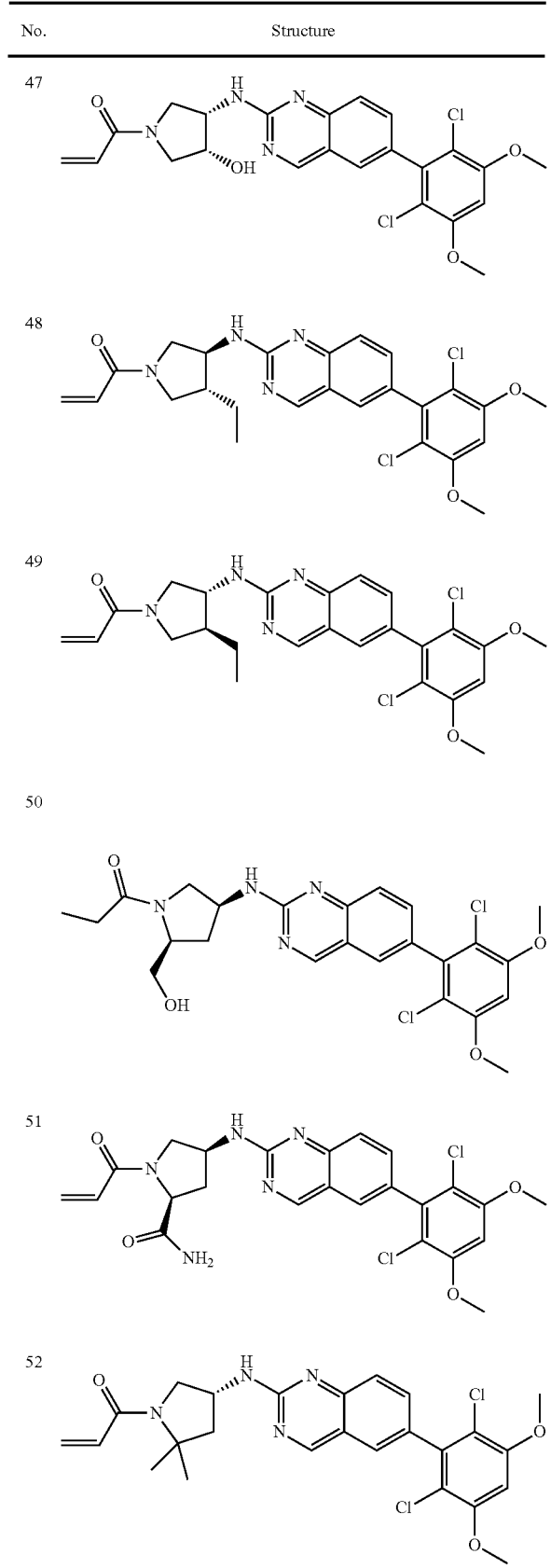 |
| 48 | |
| 49 | |
| 50 | |
| 51 | |
| 52 | |
| No. | Structure |
|---|---|
| 53 | 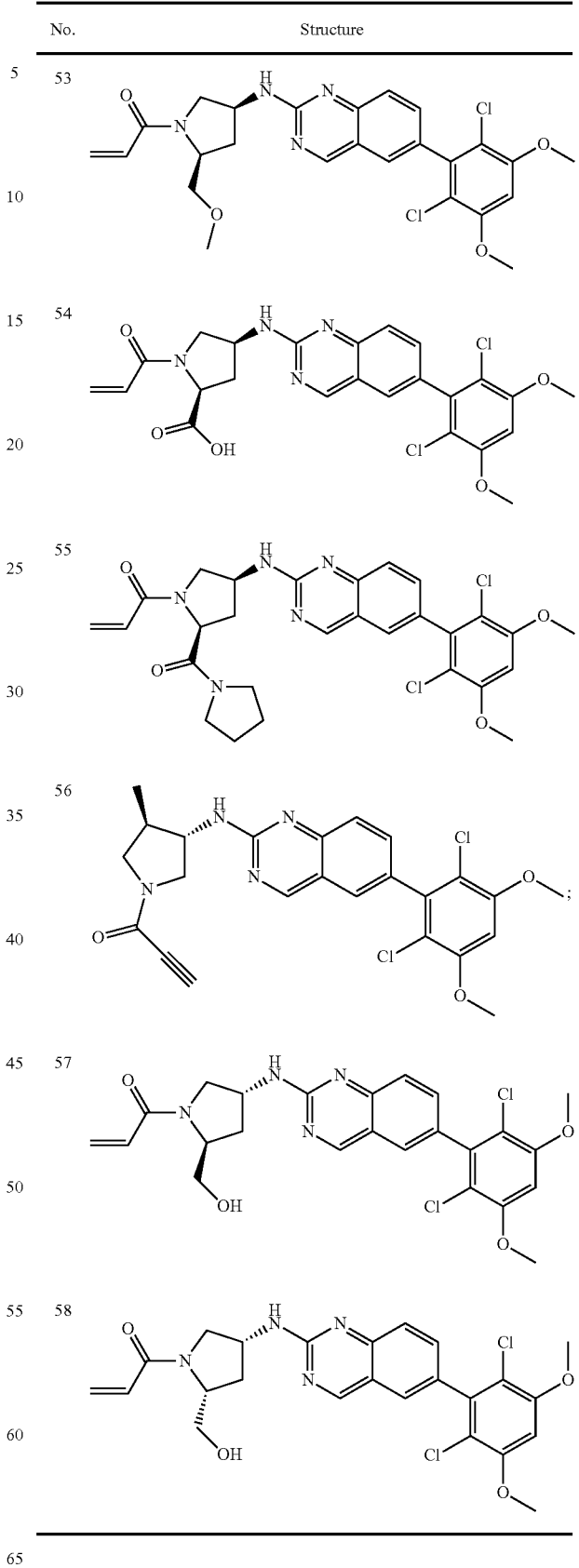 |
| 54 | |
| 55 | |
| 56 | |
| 57 | |
| 58 | |
The compound of the present invention, the pharmaceutically acceptable salt or the stereoisomer thereof is:

| No. | Structure |
|---|---|
| 59 | 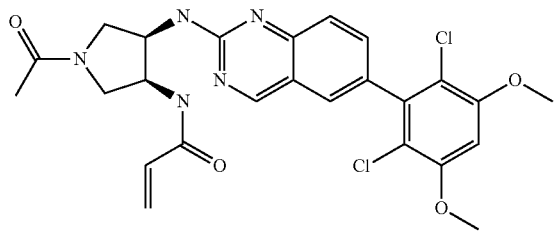 [SMILES: C=CC(=O)N[C@H]1CN(C(C)=O)C[C@H]1Nc1ncc2cc(-c3c(Cl)c(OC)cc(OC)c3Cl)ccc2n1] |
| 60 | 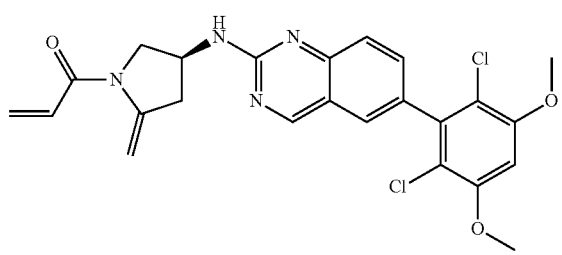 [SMILES: C=CC(=O)N1C[C@@H](Nc2ncc3cc(-c4c(Cl)c(OC)cc(OC)c4Cl)ccc3n2)CC1=C] |
| 61 | 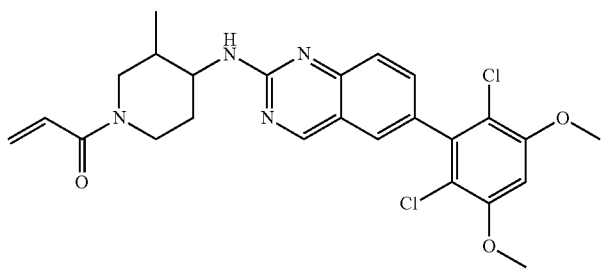 [SMILES: C=CC(=O)N1CCC(Nc2ncc3cc(-c4c(Cl)c(OC)cc(OC)c4Cl)ccc3n2)C(C)C1] |
| 62 | 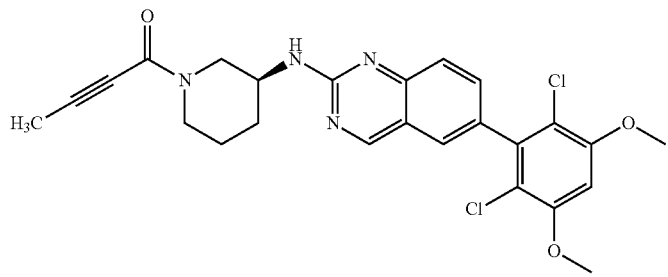 [SMILES: CC#CC(=O)N1CCC[C@H](Nc2ncc3cc(-c4c(Cl)c(OC)cc(OC)c4Cl)ccc3n2)C1] |
| 63 | 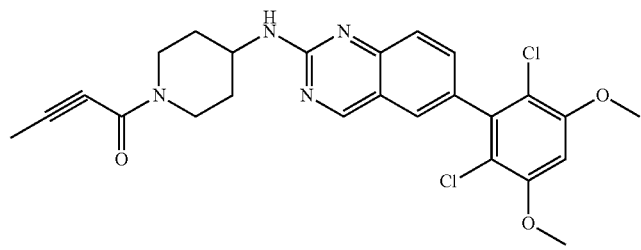 [SMILES: CC#CC(=O)N1CCC(Nc2ncc3cc(-c4c(Cl)c(OC)cc(OC)c4Cl)ccc3n2)CC1] |

-continued

| No. | Structure |
|---|---|
| 64 | 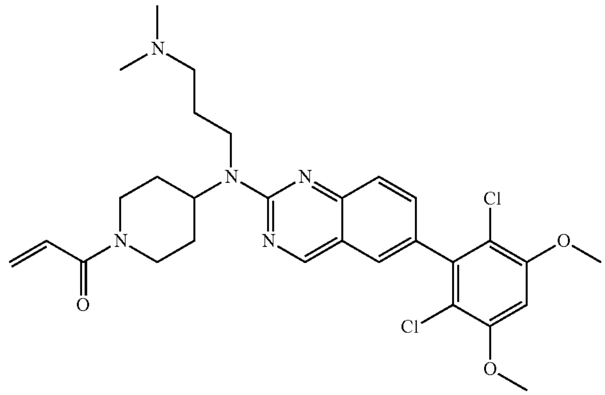 [SMILES: C=CC(=O)N1CCC(N(CCCN(C)C)c2ncc3cc(-c4c(Cl)c(OC)cc(OC)c4Cl)ccc3n2)CC1] |
| 65 | 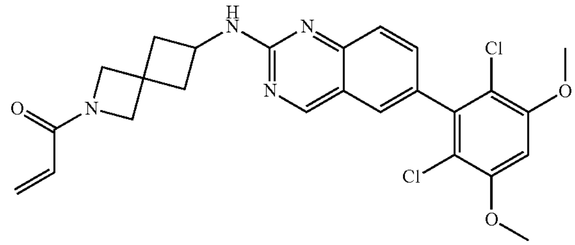 [SMILES: C=CC(=O)N1CC2(CC(Nc3ncc4cc(-c5c(Cl)c(OC)cc(OC)c5Cl)ccc4n3)C2)C1] |
| 66 | 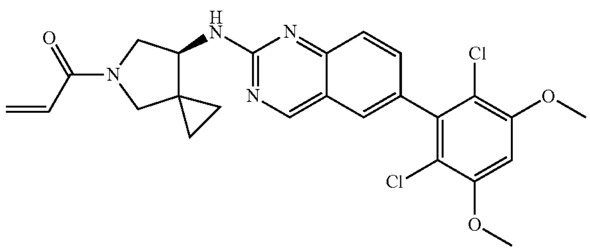 [SMILES: C=CC(=O)N1C[C@@H](Nc2ncc3cc(-c4c(Cl)c(OC)cc(OC)c4Cl)ccc3n2)C2(CC2)C1] |
| 67 | 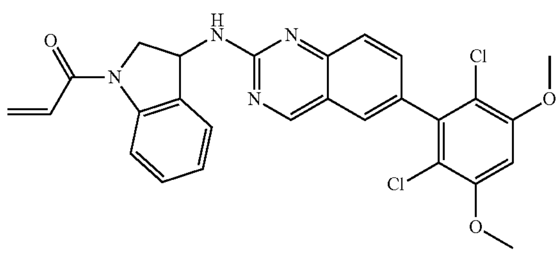 [SMILES: C=CC(=O)N1CC(Nc2ncc3cc(-c4c(Cl)c(OC)cc(OC)c4Cl)ccc3n2)c2ccccc21] |

The present invention further claims a pharmaceutical formulation of any one of the compounds or the pharmaceutically acceptable salts or the stereoisomers thereof according to the present invention. The pharmaceutical formulation further comprises one or more pharmaceutical acceptable carriers.

The pharmaceutical carriers of the present invention may be one or more solid or liquid fillers or gel materials suitable for human use. Preferably, the pharmaceutical carriers have sufficient purity and sufficiently low toxicity, which are compatible with the active ingredient of the present invention, and do not significantly reduce the efficacy of the active ingredient. For example, the pharmaceutical carriers can be fillers, binders, disintegrants, lubricants, aqueous solvents or non-aqueous solvents, and the like.

The pharmaceutical formulation of the present invention can be formulated into any pharmaceutically acceptable dosage form, and administrated to a patient or a subject in need thereof by any suitable administration mode, such as oral, parenteral, rectal or intrapulmonary administration. For oral administration, it can be formulated into tablets, capsules, pills, granules, and the like. For parenteral administration, it can be formulated into an injection solution, a sterile powder for injection, and the like.

The pharmaceutical formulation of the present invention further comprises one or more second therapeutically active agents. The second therapeutically active agents are antimetabolites, growth factor inhibitors, mitotic inhibitors, antitumor hormones, alkylating agents, metals, topoisomerase inhibitors, hormone drugs, immunomodulators, tumor suppressor genes, cancer vaccines, or antibodies and small molecule drugs related to immune checkpoints or tumor immunotherapy.

The present invention also claims use of any one of the compounds or the pharmaceutically acceptable salts or the stereoisomers thereof according to the present invention, or the pharmaceutical formulation according to the present invention, in the manufacture of a medicament for treating a disease mediated by FGF/FGFR abnormality. The disease mediated by FGF/FGFR abnormality according to the present invention is a cancer, and the cancer includes lung cancer, squamous epithelial cell carcinoma, bladder cancer, gastric cancer, ovarian cancer, peritoneal cancer, breast cancer, breast ductal carcinoma, head and neck cancer, endometrial cancer, uterine corpus carcinoma, rectal cancer, liver cancer, kidney cancer, renal pelvic cancer, esophageal cancer, esophageal adenocarcinoma, glioma, prostate cancer, thyroid cancer, female reproductive system cancer, carcinoma in situ, lymphoma, neurofibromatosis, bone cancer, skin cancer, brain cancer, colon cancer, testicular cancer, gastrointestinal stromal tumor, oral cancer, pharyngeal cancer, multiple myeloma, leukemia, non-Hodgkin's lymphoma, chorioadenoma of large intestine, melanoma, cytoma and sarcoma, and myelodysplastic syndrome.

The present invention also provides a method for treating a disease mediated by FGF/FGFR abnormality. The method comprises administering to a subject in need thereof any one of the compounds of the present invention or the pharmaceutically acceptable salts or stereoisomers thereof, or the pharmaceutical formulation according to the present invention. The disease mediated by FGF/FGFR abnormality according to the present invention is a cancer, and the cancer includes lung cancer, squamous epithelial cell carcinoma, bladder cancer, gastric cancer, ovarian cancer, peritoneal cancer, breast cancer, breast ductal carcinoma, head and neck cancer, endometrial cancer, uterine corpus carcinoma, rectal cancer, liver cancer, kidney cancer, renal pelvic cancer, esophageal cancer, esophageal adenocarcinoma, glioma, prostate cancer, thyroid cancer, female reproductive system cancer, carcinoma in situ, lymphoma, neurofibromatosis, bone cancer, skin cancer, brain cancer, colon cancer, testicular cancer, gastrointestinal stromal tumor, oral cancer, pharyngeal cancer, multiple myeloma, leukemia, non-Hodgkin's lymphoma, chorioadenoma of large intestine, melanoma, cytoma and sarcoma, and myelodysplastic syndrome.

The present invention further relates to any one of the compounds of the present invention, the pharmaceutically acceptable salts or the stereoisomer thereof, or the pharmaceutical formulation according to the present invention for use as a medicament.

DETAILED DESCRIPTION OF THE INVENTION

"Halogen" used in the present invention means fluorine, chlorine, bromine, iodine or the like, preferably fluorine and chlorine.

"Oxo" used in the present invention means that any C in the substituent may be replaced by "—C(O)—"; if a heteroatom is contained, the heteroatom can form an oxide, for example,

can be replaced by

and S can be oxidized to S(O) or S(O)$_2$.

"Halo" used in the present invention means that any hydrogen atom in the substituent may be substituted with one or more same or different halogen atoms. "Halogen" is as defined above.

"C$_{1-6}$ alkyl" used in the present invention means a linear or branched alkyl group derived by removing one hydrogen atom from a hydrocarbon moiety having 1 to 6 carbon atoms, such as methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl and 1-methyl-2-methylpropyl, etc. "C$_{1-4}$ alkyl" used in the present invention means the above examples containing 1 to 4 carbon atoms.

"C$_{2-8}$ alkenyl" used in the present invention means a linear or branched or cyclic alkene group derived by removing one hydrogen atom from an olefin moiety having 2 to 8 carbon atoms and containing carbon-carbon double bonds, such as vinyl, 1-propenyl, 2-propenyl, 1-butenyl, 2-butenyl, 1,3-butadienyl, 1-pentenyl, 2-pentenyl, 3-pentenyl, 1,3-pentadienyl, 1,4-pentadienyl, 1-hexenyl, 1,4-hexadienyl, cyclobutenyl, cyclopentenyl, cyclohexenyl, 1,4-cyclohexadienyl, cycloheptenyl, 1,4-cycloheptadienyl, cyclooctenyl, 1,5-cyclooctadienyl, etc., and a possibly formed polycyclic system, for example, spiro-cycloolefin, ortho-fused cycloolefin, bridged cycloolefin, etc.

"C$_{2-8}$ alkynyl" used in the present invention means a linear or branched alkyne group derived by removing one hydrogen atom from an alkyne moiety having 2 to 8 carbon atoms and containing carbon-carbon triple bonds, such as, ethynyl, propynyl, 2-butynyl, 2-pentynyl, 3-pentynyl, 4-methyl-2-pentynyl, 2-hexynyl, 3-hexynyl, etc.

"C$_{1-6}$ alkylamino", "(C$_{1-6}$ alkyl)$_2$ amino", "C$_{1-6}$ alkylcarbonylamino", "C$_{1-6}$ alkylsulfonylamino", "C$_{1-6}$ alkylaminocarbonyl", "(C$_{1-6}$ alkyl)$_2$ amino carbonyl", "C$_{1-6}$ alkoxy carbonyl", "C$_{1-6}$ alkylsulfonyl", "C$_{1-6}$ alkylthio", "C$_{1-6}$ alkylcarbonyl", "3-8 membered cycloalkyl carbonyl", "3-8 membered heterocyclyl carbonyl" used in the present invention means C$_{1-6}$ alkyl-NH—, (C$_{1-6}$ alkyl)(C$_{1-6}$ alkyl)N—, C$_{1-6}$ alkyl-C(O)—NH—, C$_{1-6}$ alkyl-S(O)$_2$—NH$_2$—, C$_{1-6}$ alkyl-NH—C(O)—, (C$_{1-6}$ alkyl)(C$_{1-6}$ alkyl)N—C(O)—, C$_{1-6}$ alkyl-O—C(O)—, C$_{1-6}$ alkyl-S(O)$_2$—, C$_{1-6}$ alkyl-S—, C$_{1-6}$ alkyl-C(O)—, 3-8 membered cycloalkyl-C(O)—, 3-8 membered heterocyclyl-C(O)—, respectively; the "C$_{1-6}$ alkyl" is as defined above, preferably "C$_{1-4}$ alkyl".

"C$_{1-6}$ alkoxy" used in the present invention means a group in which the "C$_{1-6}$ alkyl" as defined above is linked to a parent molecule through an oxygen atom, that is, a "C$_{1-6}$ alkyl-O—" group, such as, methoxy, ethoxy, n-propoxy, isopropoxy, n-butoxy, tert-butoxy, n-pentyloxy, neopentyloxy, n-hexyloxy, etc. "C$_{1-4}$ alkoxy" used in the present invention means the above examples containing 1 to 4 carbon atoms, that is, a "C$_{1-4}$ alkyl-O—" group.

"Fused ring" used in the present invention means a polycyclic structure formed by two or more cyclic structures connected in the form of ortho-fused ring, spiro-ring or bridged ring. The ortho-fused ring refers to a fused ring structure formed by two or more cyclic structures sharing two adjacent ring atoms with each other (i.e., sharing one bond). The bridged ring refers to a fused ring structure formed by two or more cyclic structures sharing two non-adjacent ring atoms with each other. The spiro-ring refers to a fused ring structure formed by two or more cyclic structures sharing one ring atom with each other.

"Cycloalkyl" used in the present invention refers to a monocyclic cycloalkyl, bicyclic cycloalkyl or polycyclic cycloalkyl system (also known as a fused ring system). The monocyclic cycloalkyl system is a cycloalkyl group containing 3 to 8 carbon atoms. The examples of 3-8 membered cycloalkyl include but not limited to cyclopropyl, cyclobutyl, cyclopentyl, cyclohexyl, cycloheptyl, cyclooctyl, etc. The fused cycloalkyl includes ortho-fused cycloalkyl, bridged cycloalkyl, spiro-cycloalkyl.

The ortho-fused cycloalkyl may be 6-12 membered ortho-fused cycloalkyl, 7-10 membered ortho-fused cycloalkyl, and the typical examples include but not limited to bicyclic [3.1.1]heptane, bicyclic[2.2.1]heptane, bicyclic[2.2.2]octane, bicyclic[3.2.2]nonane, bicyclic[3.3.1]nonane and bicyclic[4.2.1]nonane.

The spiro-cycloalkyl may be 6-12 membered spiro-ring group and 7-11 membered spiro-ring group, and the examples include but not limited to:

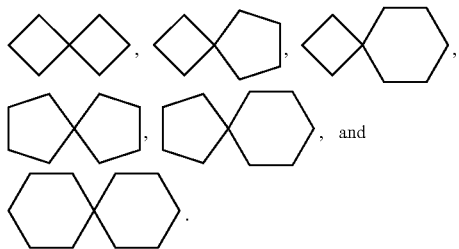

The bridged cycloalkyl may be 6-12 membered bridged ring group and 7-11 membered bridged ring group, and the examples include but not limited to:

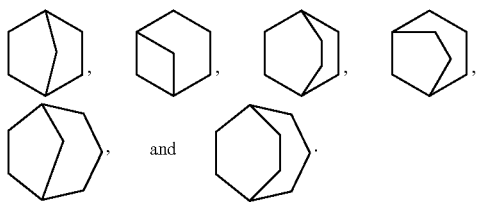

"Heterocyclyl" used in the present invention means a non-aromatic cyclic group in which at least one carbon atom in the ring is substituted with a heteroatom selected from O, S and N, preferably substituted with 1-3 heteroatoms, and wherein a carbon atom, a nitrogen atom and a sulfur atom can be oxidized.

"Heterocyclyl" means monocyclic heterocyclyl, bicyclic heterocyclyl or polycyclic heterocyclyl system (also known as a fused ring system), including saturated, and partially saturated heterocyclyl, but excluding aromatic rings. The monoheterocyclyl may be 3-8 membered heterocyclyl, 3-8 membered saturated heterocyclyl, 3-6 membered heterocyclyl, 4-7 membered heterocyclyl, 5-7 membered heterocyclyl, 5-6 membered heterocyclyl, 5-6 membered oxygen-containing heterocyclyl, 5-6 membered nitrogen-containing heterocyclyl, 5-6 membered saturated heterocyclyl or the like. Examples of "3-8 membered saturated heterocyclyl" include but not limited to aziridinyl, oxiranyl, thiiranyl, azetidinyl, oxetanyl, thietanyl, tetrahydrofuranyl, tetrahydropyrrolyl, tetrahydrothiophenyl, imidazolidinyl, pyrazolidinyl, 1,2-oxazolidinyl, 1,3-oxazolidinyl, 1,2-thiazolidinyl, 1,3-thiazolidinyl, tetrahydro-2H-pyranyl, tetrahydro-2H-thiopyranyl, piperidinyl, piperazinyl, morpholinyl, 1,4-dioxanyl, 1,4-oxathianyl. Examples of 3-8 membered partially saturated heterocyclyl include but not limited to 4,5-dihydroisooxazolyl, 4,5-dihydrooxazolyl, 2,5-dihydrooxazolyl, 2,3-dihydrooxazolyl, 3,4-dihydro-2H-pyrrolyl, 2,3-dihydro-1H-pyrrolyl, 2,5-dihydro-1H-imidazolyl, 4,5-dihydro-1H-imidazolyl, 4,5-dihydro-1H-pyrazolyl, 4,5-dihydrogen-3H-pyrazolyl, 4,5-dihydrothiazolyl, 2,5-dihydrothiazolyl, 2H-pyranyl, 4H-pyranyl, 2H-thiopyranyl, 4H-thiopyranyl, 2,3,4,5-tetrahydropyridyl, 1,2-isooxazinyl, 1,4-isooxazinyl, or 6H-1,3-oxazinyl and the like. The fused heterocyclic ring includes ortho-fused heterocyclyl, spiro-heterocyclyl, bridged heterocyclyl, and may be saturated, partially saturated or unsaturated, but are not aromatic. The fused heterocyclyl is 5-6 membered monocyclic heterocyclic ring fused to benzene ring, 5-6 membered monocyclic cycloalkyl, 5-6 membered monocyclic cycloalkenyl, 5-6 membered monocyclic heterocyclyl, or 5-6 membered monocyclic heteroaryl. The ortho-fused heterocyclyl can be 6-12 membered ortho-fused heterocyclyl, 7-10 membered ortho-fused heterocyclyl, 6-10 membered ortho-fused heterocyclyl and 6-12 membered saturated ortho-fused heterocyclyl, and the representative examples include but not limited to 3-azabicyclo[3.1.0.]hexyl, 3,6-diazabicyclo[3.2.0]heptyl, 3,8-diazabicyclo[4.2.0]octyl, 3,7-diazabicyclo[4.2.0]octyl, octahydropyrrolo[3,4-c]pyrrolyl, octahydropyrrolo[3,4-b]pyrrolyl, octahydropyrrolo[3,4-b][1,4]oxazinyl, octahydro-1H-pyrrolo[3,4-c]pyridinyl, 2,3-dihydrobenzofuran-2-yl, 2,3-dihydrobenzofuranyl-3-yl, indolin-1-yl, indolin-2-yl, indolin-3-yl, 2,3-dihydrobenzothiophen-2-yl, octahydro-1H-indolyl, octahydrobenzofuranyl.

The spiro-heterocyclyl may be 6-12 membered spiro-heterocyclyl, 7-11 membered spiro-heterocyclyl, and 6-12 membered saturated spiro-cyclyl, and the examples include but not limited to:

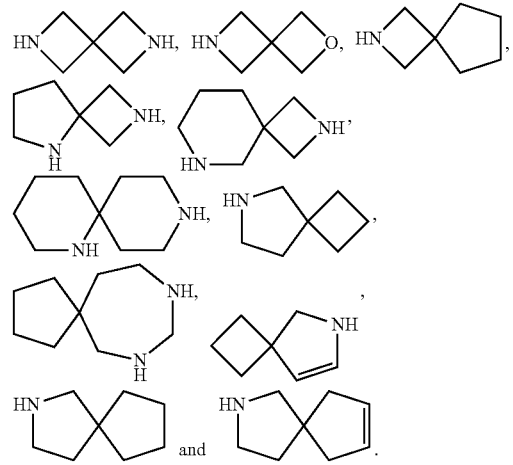

The bridged heterocyclyl may be 6-12 membered bridged heterocyclyl, 7-11 membered bridged heterocyclyl, and 6-12 membered saturated bridged heterocyclyl, and the examples include but not limited to:

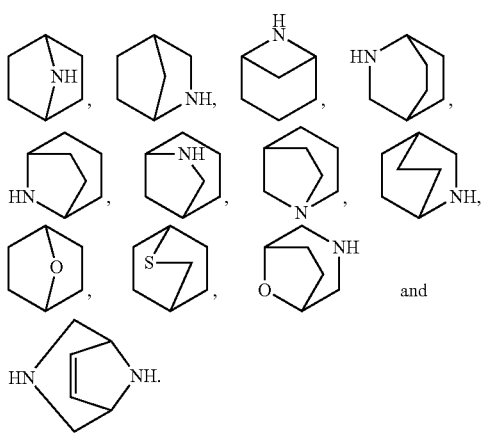

"6-14 membered aryl" used in the present invention means a cyclic aromatic group having 6 to 14 carbon atoms, and includes "6-8 membered monocyclic aryl" such as phenyl, "8-14 membered fused ring aryl", such as pentalenyl, naphthyl, phenanthryl, and the like.

"Heteroaryl" used in the present invention can be an 5-10 membered heteroaryl group, and refers to an aromatic cyclic group in which at least one carbon atom in the ring is substituted with a heteroatom selected from O, S and N, preferably 1 to 3 heteroatoms, including the condition that a carbon atom or a sulfur atom is oxidized, for example, the carbon atom is substituted with C(O), and the sulfur atom is substituted with S(O) or S(O)$_2$. Heteroaryl includes monocyclic heteroaryl and fused heteroaryl. The monocyclic heteroaryl may be 5-7 membered heteroaryl or 5-6 membered heteroaryl, and the examples of monocyclic heteroaryl include but not limited to furanyl, imidazolyl, isoxazolyl, thiazolyl, isothiazolyl, oxadiazolyl, oxazolyl, pyridyl, pyridazinyl, pyrimidinyl, pyrazinyl, pyrazolyl, pyrrolyl, tetrazolyl, thiadiazolyl, thienyl, triazolyl and triazinyl. In certain embodiments, the fused heteroaryl is 5- or 6-membered monocyclic heteroaryl ring fused to phenyl ring, 5- or 6-membered monocyclic cycloalkyl, 5- or 6-membered monocyclic cycloalkenyl, 5- or 6-membered monocyclic heterocyclyl, or a 5- or 6-membered monocyclic heteroaryl, wherein the fused cycloalkyl, fused cycloalkenyl and fused heterocyclyl are optionally substituted with one or two groups as independent oxo or thio group. The fused heteroaryl may be 8-12 membered ortho-fused heteroaryl or 9-10 membered ortho-fused heteroaryl, and examples of fused heteroaryl include but not limited to benzimidazolyl, benzofuranyl, benzothienyl, benzooxadiazolyl, benzothiadiazolyl, benzothiazolyl, cinnolinyl, 5,6-dihydroquinolin-2-yl, 5,6-dihydroisoquinolin-1-yl, furopyridinyl, indazolyl, indolyl, isoquinolyl, naphthyridinyl, purinyl, quinolyl, 5,6,7,8-tetrahydroquinol-2-yl, 5,6,7,8-tetrahydroquinolyl, 5,6,7,8-tetrahydroquinol-4-yl, 5,6,7,8-tetrahydroisoquinol-1-yl, thienopyridinyl, 4,5,6,7-tetrahydro[c][1,2,5]oxadiazolyl and 6,7-dihydro[c][1,2,5]oxadiazole-4(5H) keto.

The "pharmaceutically acceptable salts" used herein means pharmaceutically acceptable acid and basic addition salts and solvates. Such pharmaceutically acceptable salts include salts of acids such as hydrochloric acid, phosphoric acid, hydrobromic acid, sulfuric acid, sulfurous acid, formic acid, toluenesulfonic acid, methanesulfonic acid, nitric acid, benzoic acid, citric acid, tartaric acid, maleic acid, hydroiodic acid, alkanoic acid (such as acetic acid, HOOC—($CH_2$)$_n$—COOH (where n is 0 to 4)), and the like; and include salts of the bases such as sodium, potassium, calcium, ammonium and the like. A variety of non-toxic pharmaceutically acceptable addition salts are known to those skilled in the art.

The "stereoisomer" of the compound of formula (I) of the present invention means an enantiomer in the case that the compound of formula (I), (II) or (III) has an asymmetric carbon atom; a cis-trans isomer in the case that the compound has a carbon-carbon double bond or a cyclic structure; tautomers in the case that a ketone or oxime is present in the compound. The enantiomers, diastereomers, racemic isomers, cis-trans isomers, tautomers, geometric isomers, epimers of the compound of formula (I), (II) or (III) and mixtures thereof are all included within the scope of the invention.

"Warhead" used in the present invention refers to a moiety that is capable of forming a covalent bond with a nucleophile. The "nucleophile" refers to a substance that supplies electron pairs to an electrophile to form a chemical bond in the reaction. In some embodiments, the nucleophile can be an oxygen nucleophile, for example, water or hydroxyl; a nitrogen nucleophile, for example, an amine; or a sulfur nucleophile, for example, thiol, such as thiol in the side chain of a cystine residue.

"Warhead" used in the present invention refers to a moiety in the inhibitor that is reversibly or irreversibly involved in the reaction of a donor (e.g., a protein) with a substrate. For example, warhead can form a covalent bond with a protein, or can form a stable transition state, or is a reversible or irreversible alkylating agent. For example, warhead can be a functional group on an inhibitor, which participates in a bond-forming reaction, wherein a new covalent bond is formed between a portion of warhead and a donor (e.g., an amino acid residue of a protein). Warhead is an electrophile and the "donor" is a nucleophile such as a side chain of a cysteine residue. Suitable warhead moiety includes but not limited to the following structures:

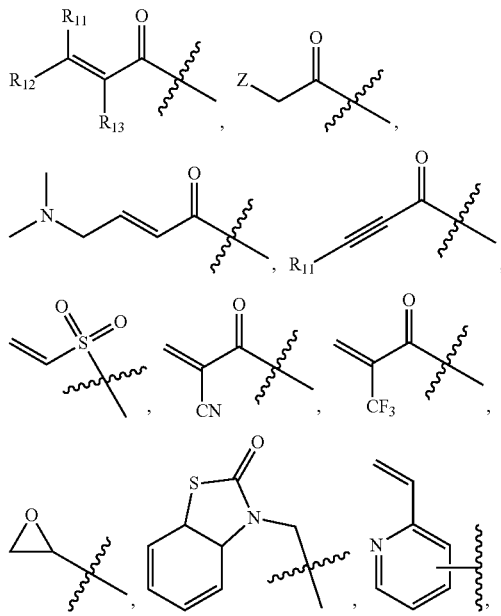

-continued

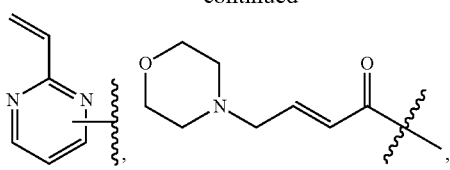

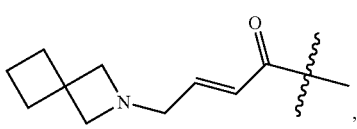

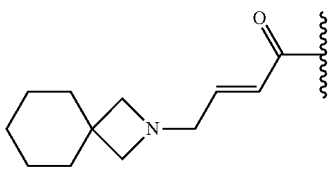

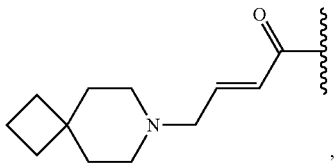

, and

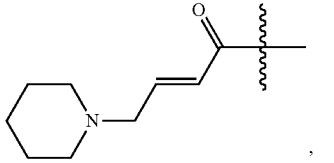

wherein,

Z refers to a leaving group (such as a halogen) or an activated hydroxyl moiety (such as a triflate);

$R_{11}$, $R_{12}$, and $R_{13}$ are independently selected from the group consisting of hydrogen, halogen, cyano, $C_{1-4}$ alkyl, halo $C_{1-4}$ alkyl, 3-8 membered cycloalkyl, 3-8 membered heterocyclyl, 5-8 membered aryl and 5-10 membered heteroaryl, the $C_{1-4}$ alkyl, halo $C_{1-4}$ alkyl, 3-8 membered cycloalkyl, 3-8 membered heterocyclyl, 5-8 membered aryl or 5-10 membered heteroaryl is optionally substituted with a substituent, wherein the substituent is selected from the group consisting of hydroxyl, amino, carboxyl, cyano, nitro, halogen, $C_{1-4}$ alkyl, $C_{1-4}$ alkoxy, $C_{1-4}$ alkoxy $C_{1-4}$ alkoxy, $C_{1-4}$ alkylamino, $(C_{1-4}$ alkyl$)_2$ amino, $C_{1-4}$ alkylcarbonylamino, $C_{1-4}$ alkylsulfonylamino, 3-8 membered heterocyclyl; and $R_{11}$, $R_{12}$ and $R_{13}$ are preferably hydrogen.

The abbreviation "NMP" used herein means N-methylpyrrolidone; "DIPEA" means N,N-diisopropylethylamine; "TLC" means thin layer chromatography; "PE:EA" means petroleum ether:ethyl acetate; "TFA" means trifluoroacetic acid; "THF" means tetrahydrofuran; "EA" means ethyl acetate; "DCM:MeOH" means dichloromethane:methanol; "DCM" means dichloromethane; "MTBE" means methyl tert-butyl ether; and "TFAA" means trifluoroacetic anhydride.

EMBODIMENTS

Example 1: Synthesis of Compound 1

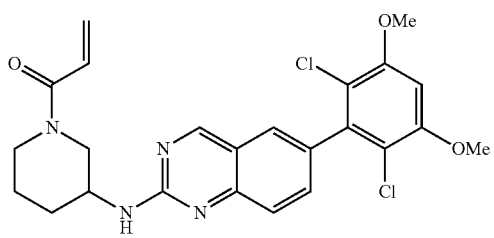

Compound 1

The synthetic route is as follows:

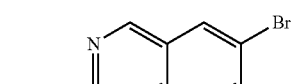

SM1

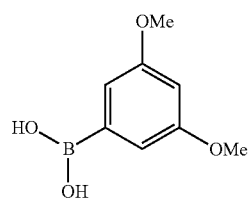

SM2

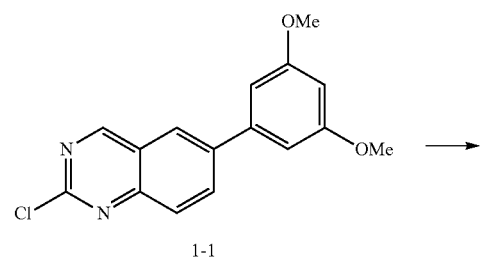

1-1

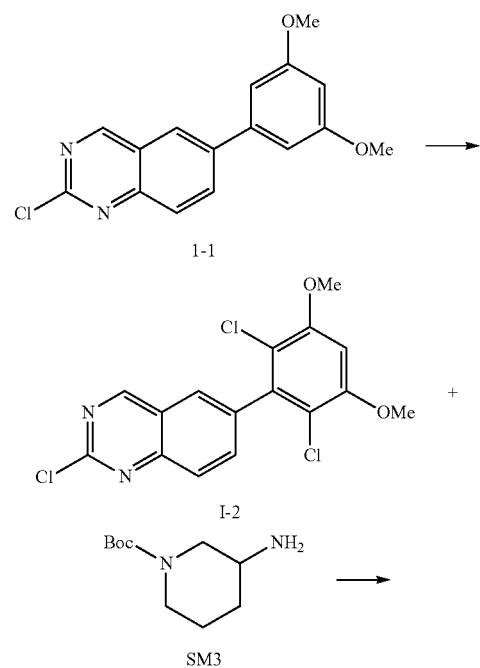

I-2

SM3

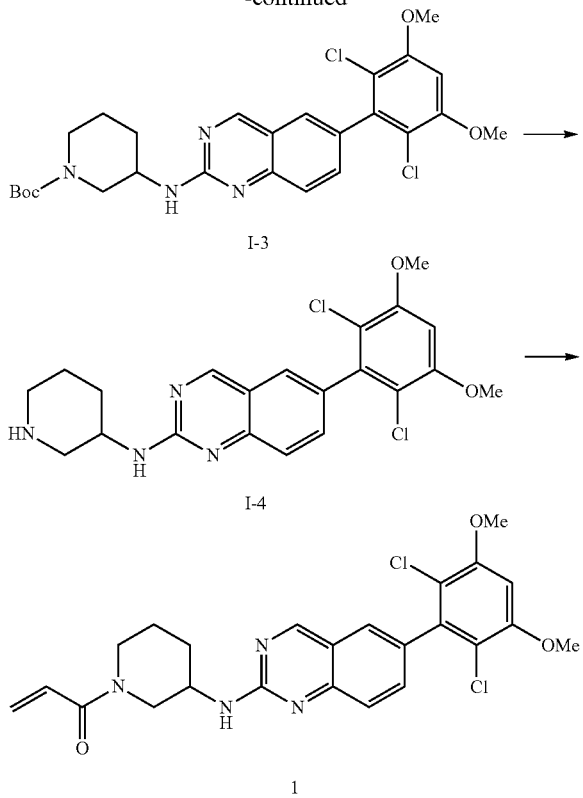

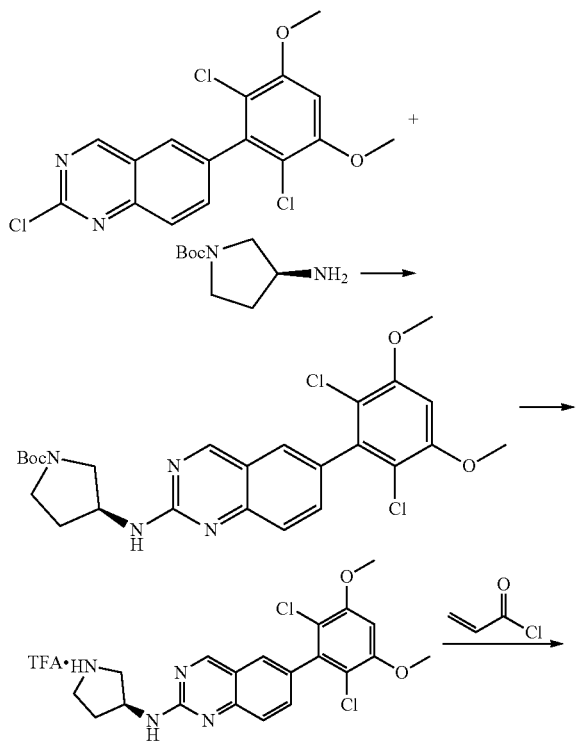

gel, petroleum ether/ethyl acetate=3/1) to obtain intermediate I-3 (100 mg, yield of 54%) as a pale yellow solid.

Synthesis of Intermediate I-4

I-3 (100 mg, 0.19 mmol) was dissolved in dichloromethane (5 ml), added with trifluoroacetic acid (1 ml), and the mixture obtained was reacted at ambient temperature for 4 h.

The reaction solution was concentrated to dryness, added with toluene, and then concentrated under reduced pressure to remove residual trifluoroacetic acid. The resulting crude product I-4 (81 mg, yield of 100%) as a yellow oil was used directly for the next reaction.

Synthesis of Compound 1

I-4 (81 mg, 0.18 mmol) was dissolved in tetrahydrofuran (10 ml), added with triethylamine (0.1 ml, 0.54 mmol) and acryloyl chloride (25 mg, 0.21 mmol), and the mixture obtained was reacted at ambient temperature for 4 h. A small amount of methanol was added to quench the remaining acryloyl chloride, and the resulting mixture was concentrated under reduced pressure. The obtained crude product was subjected to column chromatography (200-300 mesh silica gel, petroleum ether/ethyl acetate=1/1) to obtain compound 1 (11 mg, yield of 15%) as a pale yellow solid.

$^1$H NMR (400 MHz, DMSO-$d_6$) δ (ppm) 9.18 (s, 1H), 7.51-7.69 (m, 4H), 7.01 (s, 1H), 6.79-6.86 (m, 1H), 6.04-6.09 (m, 1H) 5.66-5.87 (m, 1H), 3.86-4.40 (m, 9H), 3.07-3.17 (m, 1H), 2.90-2.95 (m, 1H), 1.99-2.01 (m, 1H), 1.36-1.84 (m, 3H); LC-MS [M+H]=488.

Example 2: Synthesis of (S)-1-(3-((6-(2,6-dichloro-3,5-dimethoxyphenyl)quinazolin-2-yl)amino)pyrrolidin-1-yl)propyl-2-en-1-one (Compound 5)

Synthesis of Intermediate I-1

SM1 (5.00 g, 20.5 mmol) and SM2 (3.73 g, 20.5 mmol) were dissolved in tetrahydrofuran (30 ml), added with a solution of cesium carbonate (20.00 g, 61.5 mmol) in water (30 ml), and added with a catalytic amount of Pd(PPh$_3$)Cl$_2$. The resulting mixture was heated to reflux for 4 h under nitrogen atmosphere.

The reaction solution was concentrated to dryness and extracted with ethyl acetate. The organic phase was washed once with saturated sodium chloride, dried over anhydrous sodium sulfate, and concentrated under reduced pressure. The resulting crude product was subjected to column chromatography (200-300 mesh silica gel, petroleum ether/ethyl acetate=10/1) to obtain intermediate I-1 (3.80 g, yield of 62%) as a pale yellow solid.

Synthesis of Intermediate I-2

I-1 (3.80 g, 12.6 mmol) was dissolved in tetrahydrofuran (100 ml), cooled to a temperature of −20 to 30° C. under nitrogen atmosphere, and dropwise added with sulfonyl chloride (5.11 g, 37.9 mmol). The resulting mixture was reacted for 2 h at the same temperature.

The reaction solution was slowly warmed to ambient temperature, added with acetonitrile (100 ml), and stirred for 10 min. The produced solid was collected by filtration, and dried to obtain intermediate I-2 (2.80 g, yield of 60%) as a pale yellow solid.

Synthesis of Intermediate I-3

SM3 (81 mg, 0.40 mmol) and I-2 (100 mg, 0.35 mmol) were added into N-methylpyrrolidone (3 ml), and N,N-diisopropylethylamine (80 mg, 0.80 mmol) was added. The resulting mixture was heated to 100° C. and reacted for 4 h.

The reaction solution was poured into ice water, and the precipitated solid was collected by filtration. The solid was subjected to column chromatography (200-300 mesh silica

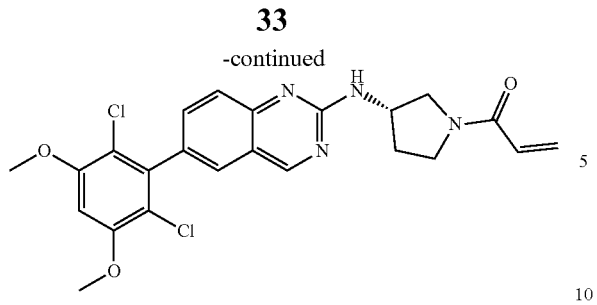

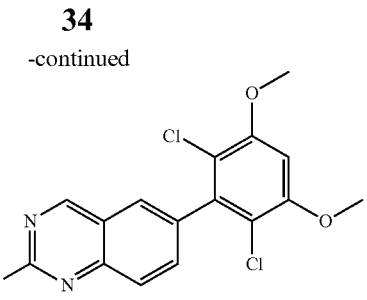

Step 1: Synthesis of Tert-Butyl (S)-3-((6-(2,6-dichloro-3,5-dimethoxyphenyl)quinazolin-2-yl)amino)pyrrolidin-1-carboxylate

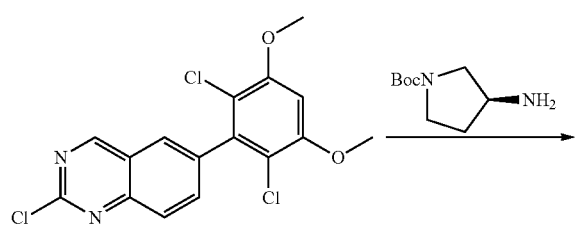

The material 2-chloro-6-(2,6-dichloro-3,5-dimethoxyphenyl)quinazoline (100.0 mg, 0.27 mol, 1.0 eq) was dissolved in NMP (3 mL), added with tert-butyl (S)-3-aminopyrrolidine-1-carboxylate (55.4 mg, 0.30 mmol, 1.1 eq) and DIPEA (104.9 mg, 0.81 mol, 3.0 eq), heated to 100° C. and reacted for 4 h. The completion of the reaction was detected by TLC, and the reaction solution was cooled to room temperature, poured into ice water, and filtered by suction to collect filter cake. The crude product was subjected to silica gel column chromatography (PE:EA=10:1 to 2:1) to obtain tert-butyl (S)-3-((6-(2,6-dichloro-3,5-dimethoxyphenyl)quinazolin-2-yl)amino)pyrrolidin-1-carboxylate (78.7 mg, yield of 47%) as a yellow liquid.

Step 2: Synthesis of (S)-6-(2,6-dichloro-3,5-dimethoxyphenyl)-N-(pyrrolidin-3-yl)quinazolin-2-amine Trifluoroacetate

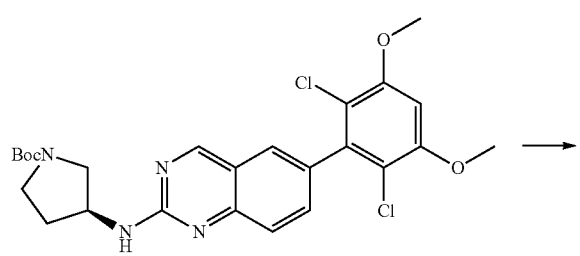

tert-butyl (S)-3-((6-(2,6-dichloro-3,5-dimethoxyphenyl)quinazolin-2-yl)amino)pyrrolidin-1-carboxylate (78.7 mg, 0.15 mmol, 1.0 eq) was dissolved in dichloromethane (8 mL), added with TFA (1 mL), and reacted at room temperature for 8 h. The completion of the reaction was detected by TLC. (S)-6-(2,6-dichloro-3,5-dimethoxyphenyl)-N-(pyrrolidin-3-yl)quinazolin-2-amine trifluoroacetate (77.9 mg, yield: 100%) as a yellow liquid was obtained by concentration.

Step 3: Synthesis of (S)-1-(3-((6-(2,6-dichloro-3,5-dimethoxyphenyl)quinazolin-2-yl)amino)pyrrolidin-1-yl)propyl-2-en-1-one

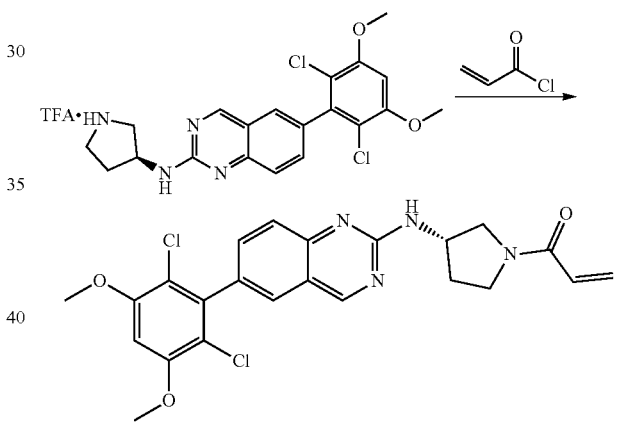

(S)-6-(2,6-dichloro-3,5-dimethoxyphenyl)-N-(pyrrolidin-3-yl)quinazolin-2-amine trifluoroacetate (77.9 mg, 0.15 mmol, 1.0 eq) was dissolved in THF (10 mL), added with triethylamine (45.5 mg, 0.45 mmol, 2.0 eq), stirred to react for 30 min, added with acryloyl chloride (27.0 mg, 0.30 mmol, 2.0 eq) and reacted for 8 h. The completion of the reaction was detected by TLC. A saturated solution of sodium bicarbonate (20 mL) was added, followed by extraction with EA (3×20 mL). The organic phases were combined, dried with anhydrous magnesium sulfate, filtered and concentrated. The crude was purified by silica gel column chromatography (200-300 mesh silica gel, DCM:MeOH=100:1 to 20:1) to obtain (S)-1-(3-((6-(2,6-dichloro-3,5-dimethoxyphenyl)quinazolin-2-yl)amino)pyrrolidin-1-yl)prop-2-en-1-one (28.4 mg, yield: 40%).

$^1$HNMR (400 MHz, DMSO-d$^6$) δ (ppm): 9.19 (s, 1H), 7.84-7.89 (m, 1H), 7.69 (s, 1H), 7.50-7.59 (m, 2H), 7.01 (s, 1H), 6.52-6.63 (m, 1H), 6.10-6.17 (m, 1H), 5.61-5.70 (m, 1H), 4.40-4.60 (m, 1H), 3.93 (s, 6H), 3.49-3.78 (m, 4H), 2.20-2.35 (m, 3H).

Molecular formula: $C_{23}H_{22}Cl_2N_4O_3$ Molecular weight: 473.35 LC-MS (m/z)=473.25 [M+H$^+$].

Example 3: Synthesis of (R)-1-(3-((6-(2,6-dichloro-3,5-dimethoxyphenyl)quinazolin-2-yl)amino)pyrrolidin-1-yl)prop-2-en-1-one (Compound 6)

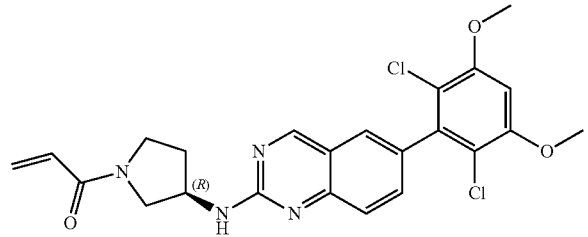

Step 1: Synthesis of tert-butyl (R)-3-((6-(2,6-dichloro-3,5-dimethoxyphenyl)quinazolin-2-yl)amino)pyrrolidin-1-carboxylate

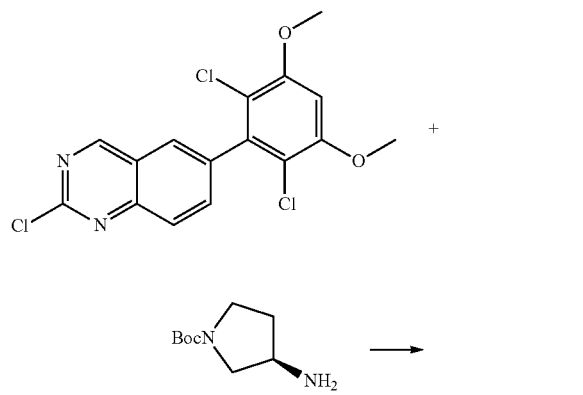

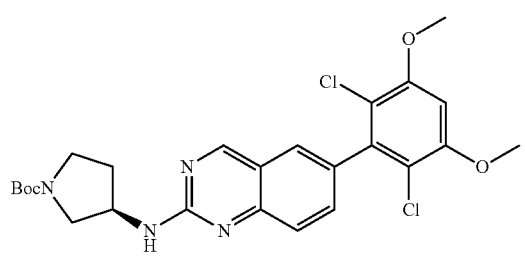

The material 2-chloro-6-(2,6-dichloro-3,5-dimethoxyphenyl)quinazoline (100.0 mg, 0.27 mol, 1.0 eq) was dissolved in NMP (3 mL), added with tert-butyl (R)-3-aminopyrrolidin-1-carboxylate (57.4 mg, 0.31 mmol, 1.5 eq) and DIPEA (80.2 mg, 0.62 mol, 2.3 eq), heated to 100° C. and reacted for 4 h. The completion of the reaction was detected by TLC. The reaction solution was cooled to room temperature and poured into ice water, and filtered by suction to collect filter cake. The crude product was subjected to silica gel column chromatography (PE:EA=10:1 to 2:1) to obtain tert-butyl (R)-3-((6-(2,6-dichloro-3,5-dimethoxyphenyl)quinazolin-2-yl)amino)pyrrolidin-1-carboxylate (88 mg, yield: 67%).

Step 2: Synthesis of (R)-6-(2,6-dichloro-3,5-dimethoxyphenyl)-N-(pyrrolidin-3-yl)quinazolin-2-amine Trifluoroacetate

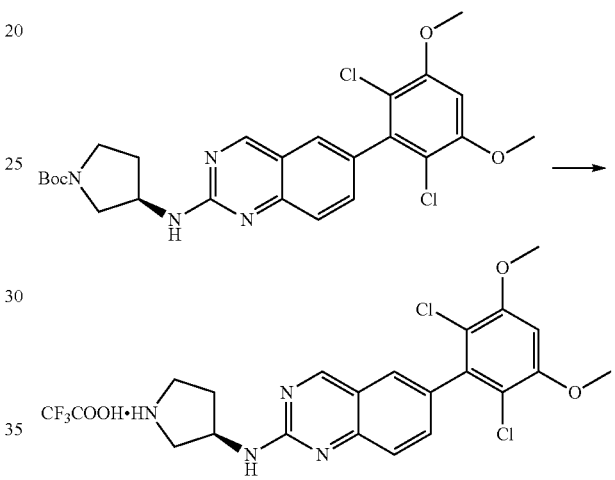

Intermediate tert-butyl (R)-3-((6-(2,6-dichloro-3,5-dimethoxyphenyl)quinazolin-2-yl)amino)pyrrolidin-1-carboxylate (88.0 mg, 0.17 mmol, 1.0 eq) was dissolved in DCM (15 mL), added with TFA (2.5 mL), and reacted at room temperature for 8 h. The completion of the reaction was detected by TLC, and the solution was concentrated directly to dryness to give (R)-6-(2,6-dichloro-3,5-dimethoxyphenyl)-N-(pyrrolidin-3-yl)quinazolin-2-amine trifluoroacetate (90.4 mg, yield: 100%).

Step 3: Synthesis of (R)-1-(3-((6-(2,6-dichloro-3,5-dimethoxyphenyl)quinazolin-2-yl)amino)pyrrolidin-1-yl)prop-2-en-1-one

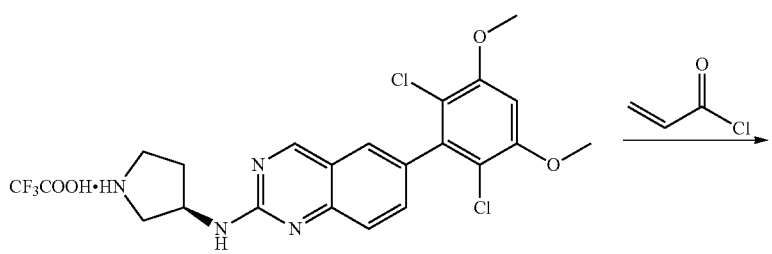

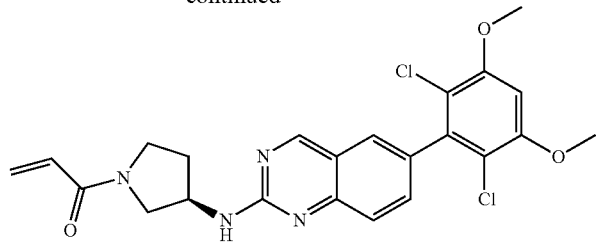

Intermediate (R)-6-(2,6-dichloro-3,5-dimethoxyphenyl)-N-(pyrrolidin-3-yl)quinazolin-2-amine trifluoroacetate (90.4 mg, 0.17 mmol, 1.0 eq) was dissolved in THF (8 mL), added with triethylamine (68.6 mg, 0.68 mmol, 4.0 eq), stirred to react for 30 min, and added with acryloyl chloride (18.4 mg, 0.20 mmol, 1.2 eq) to react for 8 h. The completion of the reaction was detected by TLC. A saturated sodium bicarbonate solution (20 mL) was added, followed by extraction with EA (3×15 mL). The organic phases were combined, dried over anhydrous magnesium sulfate, filtered, and concentrated. The crude product was subjected to silica gel column chromatography (DCM:MeOH=100:1 to 40:1) to obtain (R)-1-(3-((6-(2,6-dichloro-3,5-dimethoxyphenyl)quinazolin-2-yl)amino)pyrrolidin-1-yl)prop-2-en-1-one (56.0 mg, yield: 70%).

$^1$HNMR (400 MHz, DMSO-$d_6$) δ (ppm): 9.19 (m, 1H), 7.82 (m, 2H), 7.51-7.69 (m, 2H), 7.02 (s, 1H), 6.53-6.63 (m, 1H), 6.11-6.17 (m, 1H), 5.62-5.69 (m, 1H), 4.53-5.61 (d, 1H), 3.97 (s, 6H), 3.52-3.78 (m, 3H), 2.07-2.29 (m, 3H).

Molecular formula: $C_{23}H_{22}Cl_2N_4O_3$ Molecular weight: 473.35.

Example 4: Synthesis of 1-(4-(((6-(2,6-dichloro-3,5-dimethoxyphenyl)quinazolin-2-yl)amino)piperidin-1-yl)prop-2-en-1-one (Compound 10)

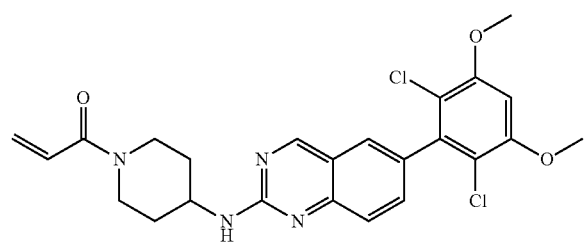 [SMILES: C=CC(=O)N1CCC(Nc2ncc3cc(-c4c(Cl)c(OC)cc(OC)c4Cl)ccc3n2)CC1]

Step 1: Synthesis of Tert-Butyl 4-((6-(2,6-dichloro-3,5-dimethoxyphenyl)quinazolin-2-yl)amino)piperidin-1-carboxylate

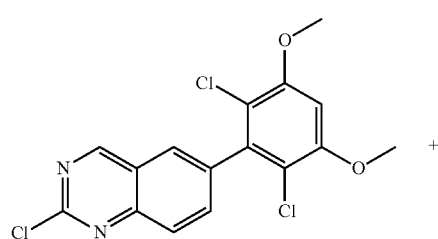
+
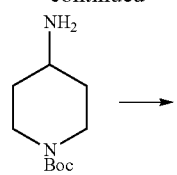
→

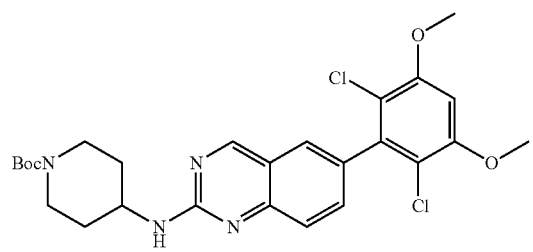

The material 2-chloro-6-(2,6-dichloro-3,5-dimethoxyphenyl)quinazoline (100.0 mg, 0.27 mol, 1.0 eq) was dissolved in NMP (3 mL), added with tert-butyl 4-aminopiperidin-1-carboxylate (61.7 mg, 0.31 mmol, 1.2 eq) and DIPEA (80.0 mg, 0.62 mol, 2.3 eq), heated to 100° C. and reacted for 4 h. The completion of the reaction was detected by TLC. The reaction solution was cooled to room temperature and poured into ice water, filtered by suction to collect the filter cake. The crude product was subjected to silica gel column chromatography (PE:EA=10:1 to 2:1) to obtain tert-butyl 4-((6-(2,6-dichloro-3,5-dimethoxyphenyl)quinazolin-2-yl)amino)piperidin-1-carboxylate (62.6 mg, yield: 43%).

Step 2: Synthesis of 6-(2,6-dichloro-3,5-dimethoxyphenyl)-N-(piperidin-4-yl)quinazolin-2-amine Trifluoroacetate

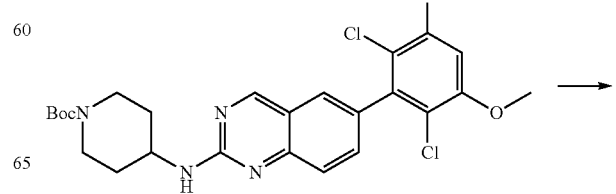

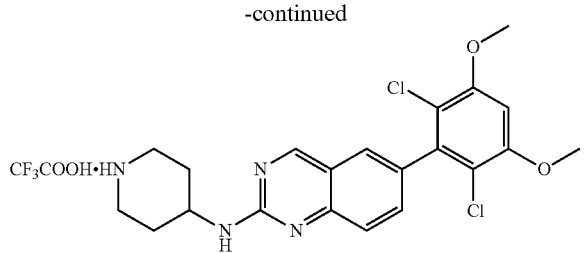

Intermediate tert-butyl 4-((6-(2,6-dichloro-3,5-dimethoxyphenyl)quinazolin-2-yl)amino)piperidin-1-carboxylate (62.6 mg, 0.12 mmol, 1.0 eq) was dissolved in ethanol (5 mL), added with TFA (2.5 mL), reacted at room temperature for 8 h. The completion of the reaction was detected by TLC, and the solution was concentrated directly to dryness to give 6-(2,6-dichloro-3,5-dimethoxyphenyl)-N-(piperidin-4-yl)quinazolin-2-amine trifluoroacetate (64.2 mg, yield: 100%).

Step 3: Synthesis of 1-(4-((6-(2,6-dichloro-3,5-dimethoxyphenyl)quinazolin-2-yl)amino)piperidin-1-yl)prop-2-en-1-one

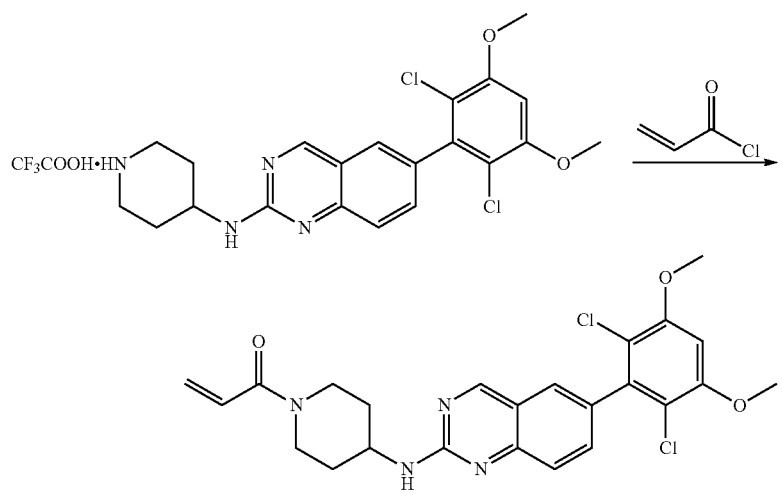

Intermediate 6-(2,6-dichloro-3,5-dimethoxyphenyl)-N-(piperidin-4-yl)quinazolin-2-amine trifluoroacetate (64.2 mg, 0.12 mmol, 1.0 eq) was dissolved in THF (8 mL), added with triethylamine (48.5 mg, 0.48 mmol, 4.0 eq), stirred to react for 30 min, added with acryloyl chloride (12.7 mg, 0.14 mmol, 1.2 eq) to react for 8 h. The completion of the reaction was detected by TLC. A saturated sodium bicarbonate solution (20 mL) was added, followed by extraction with EA (3×15 mL). The organic phases were combined, dried over anhydrous magnesium sulfate, filtered, and concentrated. The crude product was subjected to silica gel column chromatography (DCM:MeOH=100:1 to 40:1) to obtain 1-(4-((6-(2,6-dichloro-3,5-dimethoxyphenyl)quinazolin-2-yl)amino)piperidin-1-yl) prop-2-en-1-one (40.0 mg, yield: 70%).

$^{1}$HNMR (400 MHz, DMSO) δ (ppm): 9.15 (m, 1H), 7.47-7.66 (m, 3H), 7.01 (s, 1H), 6.82-6.89 (m, 1H), 6.09-6.14 (m, 1H), 5.66-5.70 (m, 1H), 4.05-4.36 (m, 8H), 2.90-2.96 (m, 1H), 1.99 (m, 2H), 1.44-1.47 (m, 2H).

Molecular formula: $C_{24}H_{24}Cl_2N_4O_3$ Molecular weight: 487.38 LC-MS (m/z)=487.28 [M+H$^+$].

Example 5: Synthesis of 1-(trans-5-((6-(2,6-dichloro-3,5-dimethoxyphenyl)quinazolin-2-yl)amino)-2-azabicyclo[2.1.1]hexane-2-yl)prop-2-en-1-one (Compound 11)

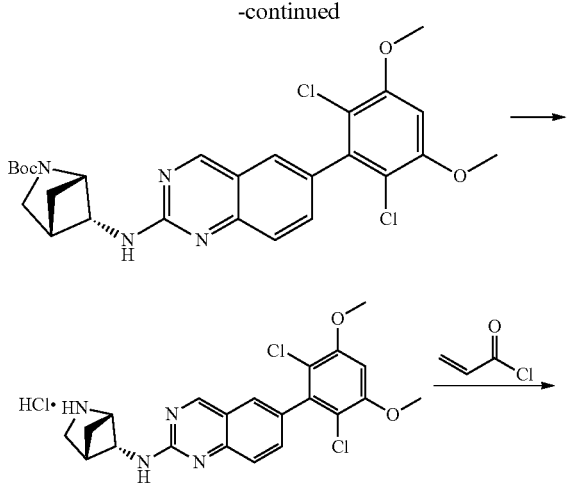

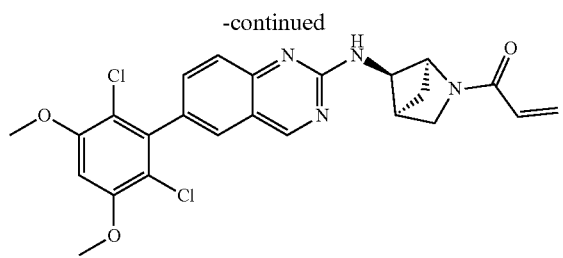

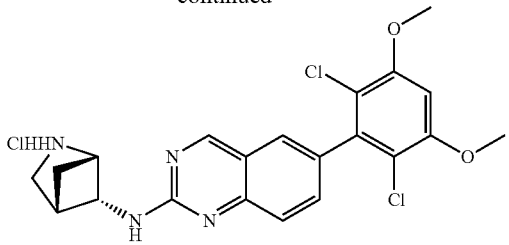

Step 1: Synthesis of Tert-Butyl trans-5-((6-(2,6-dichloro-3,5-dimethoxyphenyl)quinazolin-2-yl)amino)-2-azabicyclo[2.1.1]hexane-2-carboxylate Tert-butyl trans-5-((6-(2,6-dichloro-3,5-dimethoxyphenyl)quinazolin-2-yl)amino)2-azabicyclo[2.1.1]hexane-2-carboxylate (510 mg, 0.96 mmol, 1.0 eq) was dissolved in ethanol (10 mL), added with HCl-ethanol (10 mL), and reacted at room temperature for 8 h. The completion of the reaction was detected by TLC. The reaction solution was concentrated to give trans-N-(6-(2,6-dichloro-3,5-dimethoxyphenyl)quinazolin-2-yl)-2-azabicyclo[2.1.1]hexane-5-amine hydrochloride (480 mg, yield: 100%) as a yellow solid.

Step 3: Synthesis of 1-(trans-5-((6-(2,6-dichloro-3,5-dimethoxyphenyl)quinazolin-2-yl)amino)-2-azabicyclo[2.1.1]hexane-2-yl)prop-2-en-1-one (Compound 11)

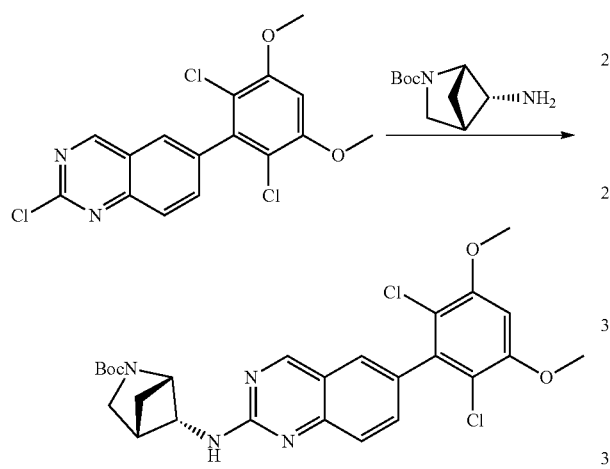

The material 2-chloro-6-(2,6-dichloro-3,5-dimethoxyphenyl)quinazoline (500.0 mg, 1.35 mol, 1.0 eq) was dissolved in NMP (5 mL), added with tert-butyl trans-5-amino-2-azabicyclo[2.1.1]hexane-2-carboxylate (402.3 mg, 2.03 mmol, 1.5 eq) and DIPEA (524.6 mg, 4.06 mol, 3.0 eq), heated to 100° C. and reacted for 4 h. The completion of the reaction was detected by TLC. The reaction solution was cooled to room temperature and poured into ice water, filtered by suction to collect the filter cake. The crude product was subjected to silica gel column chromatography (200-300 mesh silica gel, PE:EA=10:1 to 2:1) to obtain tert-butyl trans-5-((6-(2,6-dichloro-3,5-dimethoxyphenyl)quinazolin-2-yl)amino)-2-azabicyclo[2.1.1]hexane-2-carboxylate (520 mg, yield of 72%) as a pale yellow solid.

Step 2: Synthesis of trans-N-(6-(2,6-dichloro-3,5-dimethoxyphenyl)quinazolin-2-yl)-2-azabicyclo[2.1.1]hexane-5-amine Hydrochloride

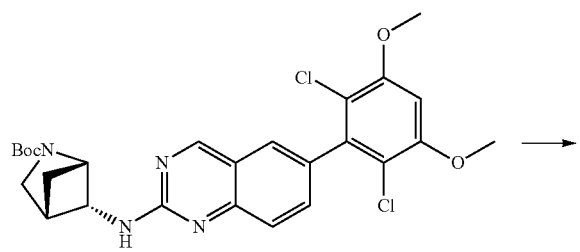

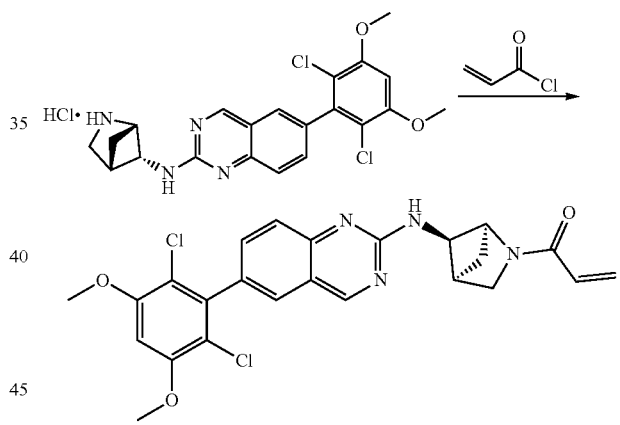

Trans-N-(6-(2,6-dichloro-3,5-dimethoxyphenyl)quinazolin-2-yl)-2-azabicyclo[2.1.1]hexane-5-amine hydrochloride (480 mg, 1.03 mmol, 1.0 eq) was dissolved in THF (22 mL), added with triethylamine (415.3 mg, 4.10 mmol, 4.0 eq), stirred to react for 30 min, and added with acryloyl chloride (138.6 mg, 1.54 mmol, 1.5 eq) to react for 8 h. The completion of the reaction was detected by TLC. A saturated sodium bicarbonate solution (50 mL) was added, followed by extraction with EA (3×30 mL). The organic phases were combined, dried with anhydrous magnesium sulfate, filtered and concentrated. The crude product was subjected to silica gel column chromatography (200-300 mesh silica gel, DCM:MeOH=100:1 to 40:1) to obtain 1-(trans-5-((6-(2,6-dichloro-3,5-dimethoxyphenyl)quinazolin-2-yl)amino)-2-azabicyclo[2.1.1]hexane-2-yl)prop-2-en-1-one (350 mg, yield: 70%) as a white solid.

$^{1}$HNMR (400 MHz, DMSO-d6) δ (ppm): 9.15-9.17 (d, 1H), 7.51-7.69 (m, 4H), 7.00 (s, 1H), 6.43-6.55 (m, 1H), 6.07-6.12 (m, 1H), 5.92-5.97 (m, 1H), 5.65-5.68 (m, 1H), 4.77-4.79 (m, 1H), 4.12 (m, 1H), 3.92 (s, 6H), 3.83-3.85 (m, 1H), 3.26-3.59 (m, 2H), 2.96-3.01 (m, 1H), 1.85-1.87 (m, 1H), 1.21-1.23 (m, 1H).

Molecular formula: $C_{24}H_{22}Cl_2N_4O_3$ Molecular weight: 485.37 LC-MS (m/z)=485.00 [M+H$^+$].

Example 6: Synthesis of 1-((3S,4R)-3-((6-(2,6-dichloro-3,5-dimethoxyphenyl)quinazolin-2-yl)amino)-4-methylpyrrolidin-1-yl)propyl-2-en-1-one (Compound 20)

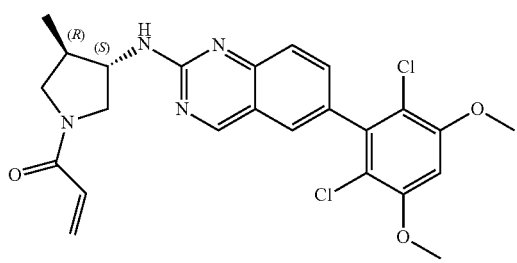

Step 1: Synthesis of Tert-Butyl (3S,4R)-3-((6-(2,6-dichloro-3,5-dimethoxyphenyl)quinazolin-2-yl)amino)-4-methylpyrrolidin-1-carboxylate

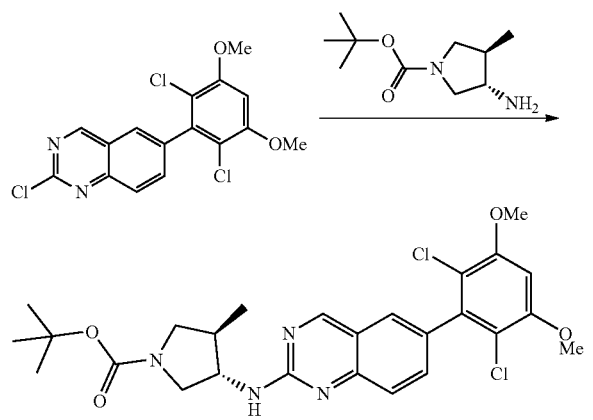

The material 2-chloro-6-(2,6-dichloro-3,5-dimethoxyphenyl)quinazoline (400.0 mg, 1.1 mmol, 1.0 eq) and tert-butyl (3S,4R)-3-amino-4-methylpyrrolidin-1-carboxylate (440.6 mg, 2.2 mmol, 2.0 eq) were dissolved in N-methylpyrrolidone (3.0 mL), added with N,N-diisopropylethylamine (568.7 mg, 4.4 mmol, 4.0 eq), and gradually heated to 110° C. to react overnight. The completion of the reaction was detected by TLC. The reaction solution was cooled to room temperature, added with 15 mL of ice water, and filtered. The filter cake was washed with a small amount of ice water, dissolved in dichloromethane (5 mL), dried over anhydrous magnesium sulfate, filtered and concentrated. The crude product was subjected to silica gel column chromatography (200-300 mesh silica gel, PE:EA=10:1 to 3:1) to give tert-butyl (3S,4R)-3-((6-(2,6-dichloro-3,5-dimethoxyphenyl)quinazolin-2-yl)amino)-4-methylpyrrolidin-1-carboxylate (346.0 mg, yield: 59.0%) as a yellow solid.

Step 2: Synthesis of 6-(2,6-dichloro-3,5-dimethoxyphenyl)-N-((3S,4R)-4-methylpyrrolidin-3-yl)quinazolin-2-amine Hydrochloride

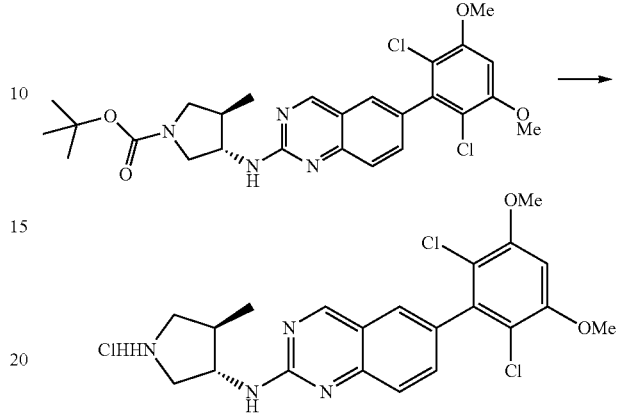

Tert-butyl (3S,4R)-3-((6-(2,6-dichloro-3,5-dimethoxyphenyl)quinazolin-2-yl)amino)-4-methylpyrrolidin-1-carboxylate (346.0 mg, 0.65 mmol, 1.0 eq) was dissolved in ethanol (5.0 mL), cooled to 0° C. in an ice bath, added with hydrogen chloride ethanol solution (5.0 mL), and gradually warmed to room temperature to react overnight. The completion of the reaction was detected by TLC. The reaction solution was directly concentrated to give 6-(2,6-dichloro-3,5-dimethoxyphenyl)-N-((3S,4R)-4-methylpyrrolidin-3-yl)quinazolin-2-amine hydrochloride (313.0 mg crude product, yield: 100%) as a yellow solid.

Step 3: Synthesis of 1-((3S,4R)-3-((6-(2,6-dichloro-3,5-dimethoxyphenyl)quinazolin-2-yl)amino)-4-methylpyrrolidin-1-yl)propyl-2-en-1-one (Compound 20)

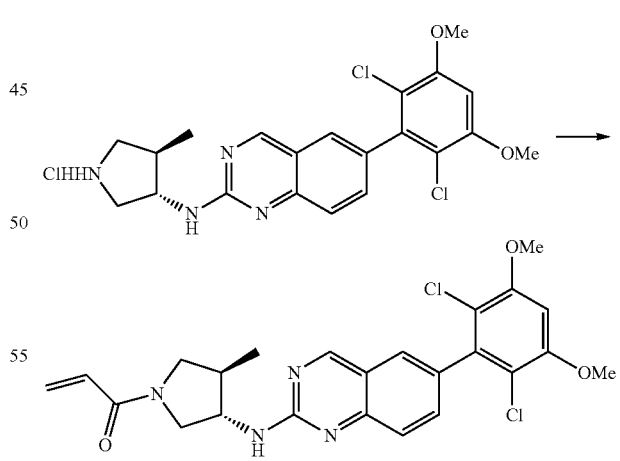

6-(2,6-dichloro-3,5-dimethoxyphenyl)-N-((3 S,4R)-4-methylpyrrolidin-3-yl)quinazolin-2-amine hydrochloride (313.0 mg, 0.67 mmol, 1.0 eq) was dissolved in THF (10.0 mL), added with triethylamine (203.0 mg, 2.0 mmol, 3.0 eq), stirred at room temperature for 30 min, cooled to 0° C., slowly added with acryloyl chloride (122.4 mg, 1.35 mmol, 2.0 eq), warmed to room temperature gradually to react for 1 h. The completion of the reaction was detected by TLC. A saturated sodium bicarbonate solution (20 mL) was added to the reaction solution, followed by adding ethyl acetate (8.0 mL) for solution separation. The aqueous phase was extracted with ethyl acetate (8.0 mL×2). The organic phases were combined, washed with saturated brine, dried over anhydrous magnesium sulfate, filtered, and concentrated. The crude product was subjected to silica gel column chromatography (DCM:MeOH=125:1 to 80:1) to obtain 1-((3S,4R)-3-((6-(2,6-dichloro-3,5-dimethoxyphenyl)quinazolin-2-yl)amino)-4-methylpyrrolidin-1-yl)propyl-2-en-1-one (160.5 mg, yield: 49.2%) as a yellow solid.

¹HNMR (400 MHz, DMSO) δ (ppm): 9.18 (s, 1H), 7.82 (s, 1H), 7.79 (s, 1H), 7.49-7.54 (m, 2H), 7.02 (s, 1H), 6.60-6.71 (m, 1H), 6.16 (d, 1H), 5.67 (m, 1H), 4.12-4.20 (m, 2H), 4.03 (s, 6H), 3.97 (m, 1H), 3.24 (m, 1H), 3.05 (m, 1H), 2.48 (m, 1H), 1.23 (s, 3H).

Molecular formula: $C_{24}H_{24}Cl_2N_4O_3$ Molecular weight: 487.39 LC-MS (m/z)=489.07 [M+H⁺].

Example 7: Synthesis of 1-((2R,4S)-4-((6-(2,6-dichloro-3,5-dimethoxyphenyl)quinazolin-2-yl)amino)-2-methylpyrrolidin-1-yl)propyl-2-en-1-one (Compound 21)

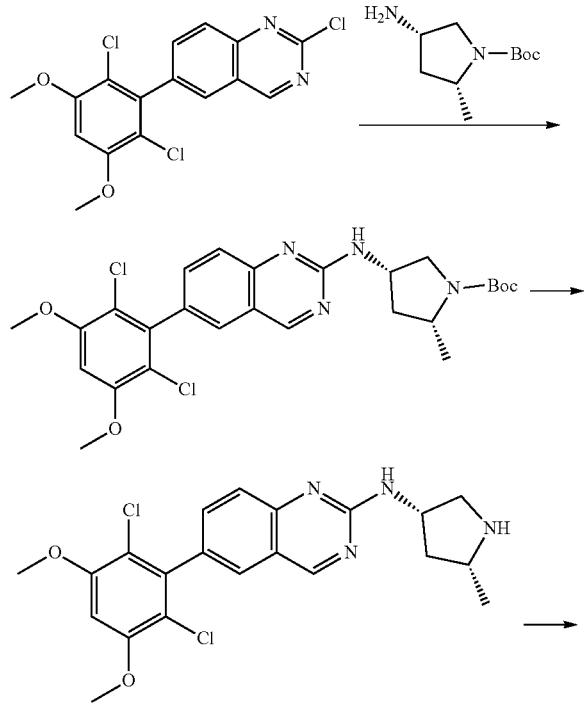

Step 1: Synthesis of Tert-Butyl (2R,4S)-4-((6-(2,6-dichloro-3,5-dimethoxyphenyl)quinazolin-2-yl)amino)-2-methylpyrrolidin-1-carboxylate

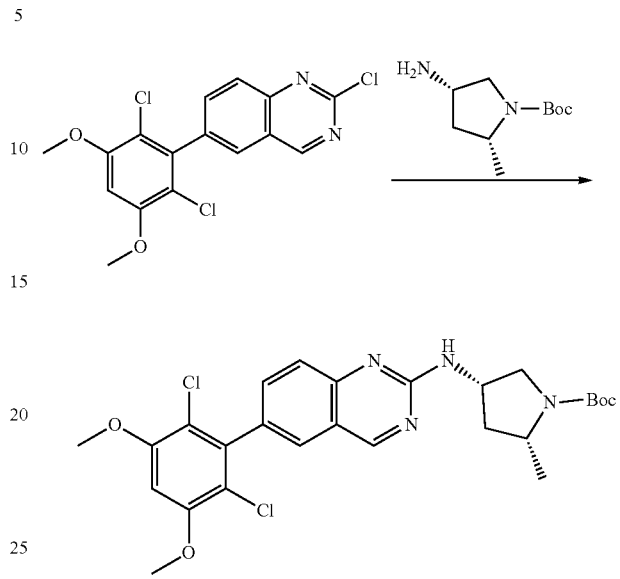

2-chloro-6-(2,6-dichloro-3,5-dimethoxyphenyl)quinazolin (200 mg, 0.514 mmol, 1.0 eq), tert-butyl (2R,4S)-4-amino-2-methylpyrrolidin-1-carboxylate (162.63 mg, 0.812 mmol, 1.5 eq) and N,N-diisopropylethylamine (139.85 mg, 1.082 mmol, 2.0 eq) were dissolved in N-methylpyrrolidone (2 mL), heated to 120° C. to react overnight. It was found that there was still a small amount of material remaining through TLC detection. The reaction solution was poured into cold water (20 mL) to precipitate brown solid, and filtered by suction. The filtrate was extracted with EA (10 mL×3), and the brown solid was dissolved in DCM. The organic phases were combined and washed with water (20 mL×3), followed by solution separation.

The resulting organic phase was dried with anhydrous sodium sulfate, filtered, and filter cake was rinsed with DCM. The mother liquid was concentrated under reduced pressure, and the crude product was subjected to silica gel column chromatography (PE:EA=5:1 to 3:1) to obtain a solid of tert-butyl (2R,4S)-4-((6-(2,6-dichloro-3,5-dimethoxyphenyl)quinazolin-2-yl)amino)-2-yl-methylpyrrolidin-1-carboxylate (100 mg, yield: 35%).

Step 2: Synthesis of 6-(2,6-dichloro-3,5-dimethoxyphenyl)-N-((3S,5R)-5-methylpyrrolidin-3-yl)quinazolin-2-amine

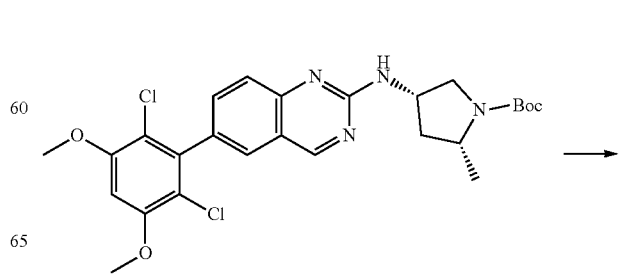

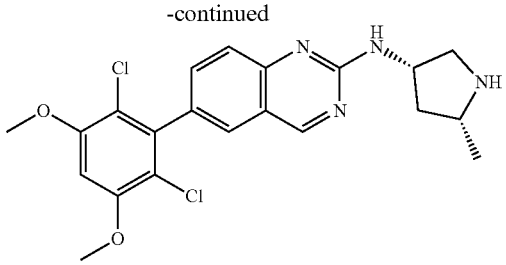

Tert-butyl (2R,4S)-4-((6-(2,6-dichloro-3,5-dimethoxyphenyl)quinazolin-2-yl)amino)-2-methylpyrrolidin-1-carboxylate (100 mg, 0.187 mmol, 1.0 eq) was dissolved into HCl-ethanol (15 mL), heated to 45° C. and reacted for 3 h. The completion of the reaction was detected by TLC. The reaction solution was concentrated. The crude product was dissolved in THF and concentrated, repeating for three times. The crude product was used in the next step without purification.

Step 3: Synthesis of 1-((2R,4S)-4-((6-(2,6-dichloro-3,5-dimethoxyphenyl)quinazolin-2-yl)amino)-2-methylpyrrolidin-1-yl)prop-2-en-1-one (Compound 21)

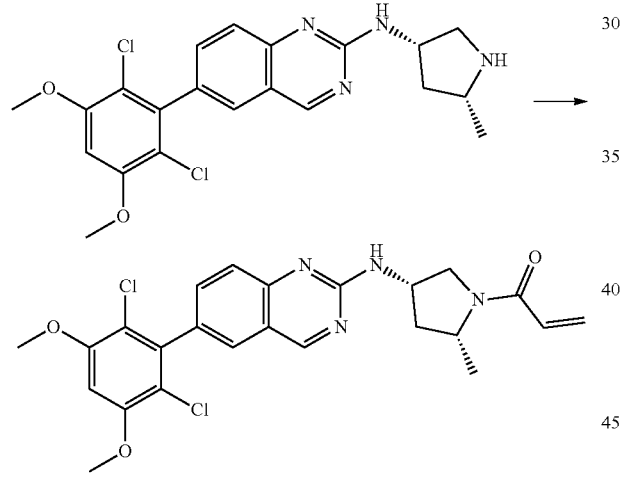

6-(2,6-dichloro-3,5-dimethoxyphenyl)-N-((3S,5R)-5-methylpyrrolidin-3-yl)quinazolin-2-amine (88 mg, 0.203 mmol, 1.0 eq) was dissolved in THF (15 mL), added with triethylamine (102.71 mg, 1.015 mmol, 5.0 eq), cooled to 0° C., and slowly added with acryloyl chloride (18.37 mg, 0.203 mmol, 1.0 eq) to react overnight. The completion of the reaction was detected by TLC. A saturated sodium bicarbonate solution (10 mL) was added for solution separation. The aqueous phase was extracted with EA (10 mL×3), and separated. The organic phase was dried with anhydrous sodium sulfate, and filtered. The filter cake was rinsed with EA, and the mother liquor was concentrated under reduced pressure. The crude product was separated by PTLC (DCM:MeOH=15:1) to obtain a solid of 1-((2R,4S)-4-((6-(2,6-dichloro-3,5-dimethoxyphenyl)quinazolin-2-yl)amino)-2-methylpyrrolidin-1-yl)prop-2-en-1-one (21 mg, yield: 21%).

$^1$HNMR (400 MHz, DMSO) δ (ppm): 9.18 (s, 1H), 7.82 (s, 1H), 7.68 (s, 1H), 7.49-7.57 (m, 2H), 7.00 (s, 1H), 6.54-6.58 (m, 1H), 6.16-6.18 (m, 1H), 5.63-5.67 (m, 1H), 4.45-4.47 (m, 3H), 4.11-4.13 (m, 6H), 3.40-3.44 (m, 1H).

Molecular formula: $C_{24}H_{24}Cl_2N_4O_3$ Molecular weight: 487.38 LC-MS (m/z)=487.1 [M+H$^+$].

Example 8: Synthesis of 1-((2S,4S)-4-((6-(2,6-dichloro-3,5-dimethoxyphenyl)quinazolin-2-yl)amino)-2-(hydroxymethyl)pyrrolidin-1-yl)prop-2-en-1-one (Compound 22)

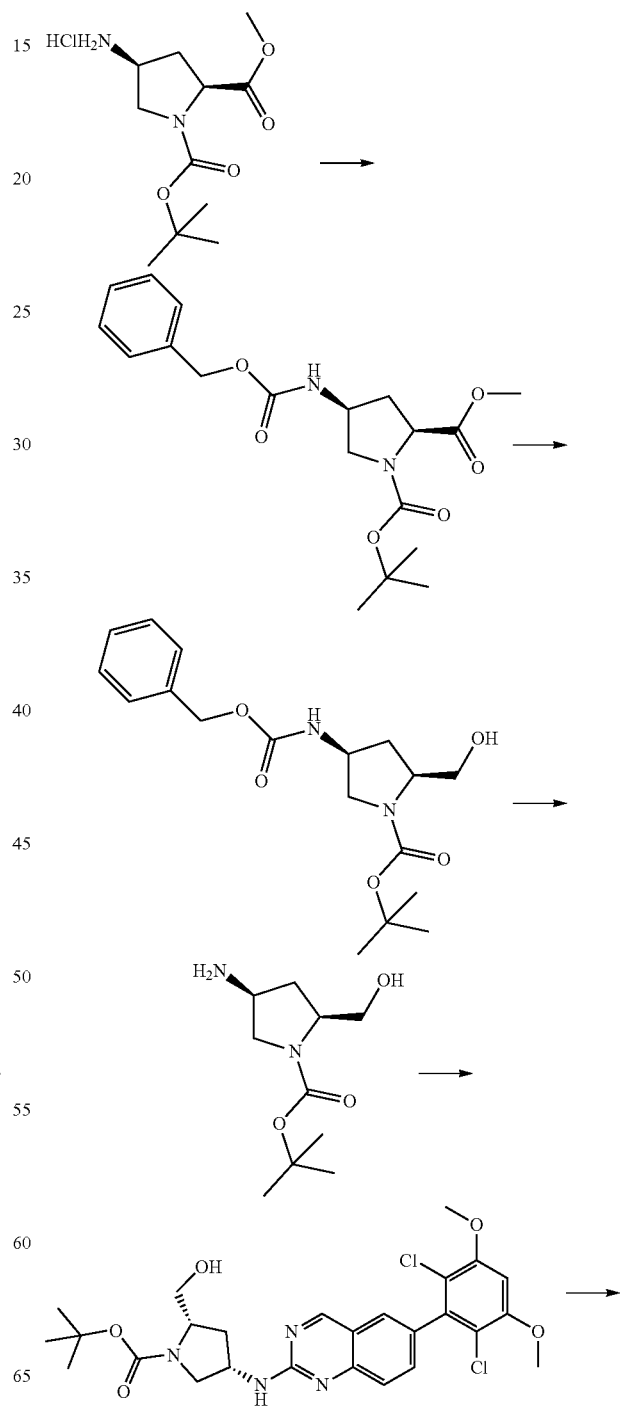

-continued

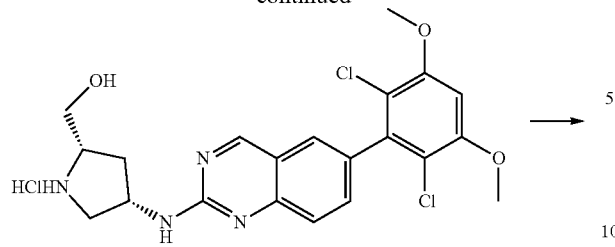

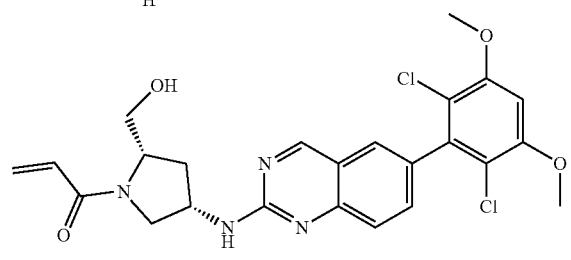

Step 1: Synthesis of 1-tert-butyl 2-methyl (2S,4S)-4-(((benzyloxy)carbonyl)amino)pyrrolidin-1,2-dicarboxylate

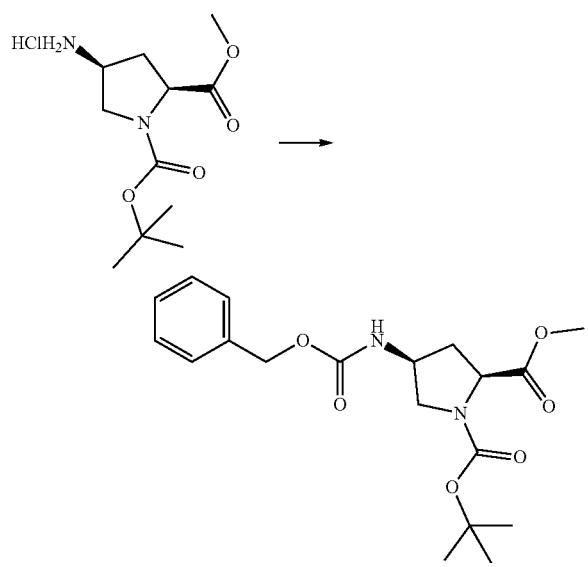

The material 1-(tert-butyl)2-methyl(2S,4S)-4-aminopyrrolidin-1,2-dicarboxylate hydrochloride (10.5 g, 36.8 mmol, 1.0 eq) was dissolved in DCM (100 mL), added with triethylamine (11.7 g, 115.8 mmol, 3.0 eq), stirred for 0.5 h at room temperature and cooled to 0° C. in an ice bath, then slowly added with benzyl chloroformate (7.9 g, 46.3 mmol, 1.2 eq) dissolved in DCM by a constant pressure dropping funnel, warmed to room temperature gradually and reacted overnight. The completion of the reaction was detected by TLC. A saturated sodium bicarbonate solution (100 mL) was added for solution separation. The aqueous phase was extracted with DCM (50 mL×2), and the organic phases were combined, washed with saturated brine, dried over anhydrous sodium sulfate, filtered, and concentrated. The crude product was subjected to silica gel column chromatography (200-300 mesh silica gel, PE:EA=10:1 to 3:1) to obtain 1-tert-butyl 2-methyl(2S,4S)-4-(((benzyloxy)carbonyl)amino)pyrrolidin-1,2-dicarboxylate (3.6 g, yield: 24.7%) as a colorless oil.

Step 2: Synthesis of Tert-Butyl (2S,4S)-4-((((benzyloxy)carbonyl)amino)-2-(hydroxymethyl)pyrrolidin-1-carboxylate

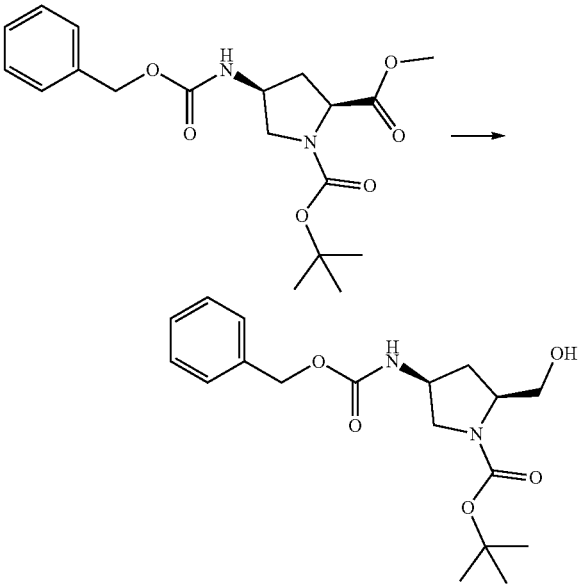

Lithium aluminium hydride (0.7 g, 19.0 mmol, 2.0 eq) was dissolved in anhydrous THF (20 mL) at 0° C., stirred for 0.5 h, slowly added with 1-tert-butyl 2-methyl(2S,4S)-4-(((benzyloxy)carbonyl)amino)pyrrolidin-1,2-dicarboxylate (3.6 g, 9.5 mmol, 1.0 eq) dissolved in THF solution, warmed to room temperature gradually and reacted for 2 h. The completion of the reaction was detected by TLC. The reaction solution was cooled to 0° C., slowly added with water (0.7 mL) and 10% sodium hydroxide solution (0.7 mL), supplemented with water (2.1 mL), and stirred for 0.5 h. The reaction solution was filtered and the filtrate was concentrated. The crude product was subjected to silica gel column chromatography (200-300 mesh silica gel, PE:EA=10:1 to 2:1) to obtain tert-butyl (2S,4S)-4-((((benzyloxy)carbonyl)amino)-2-(hydroxymethyl)pyrrolidin-1-carboxylate (1.05 g, yield: 30.0%) as a colorless oil.

Step 3: Synthesis of Tert-Butyl (2S,4S)-4-amino-2-(hydroxymethyl)pyrrolidin-1-carboxylate

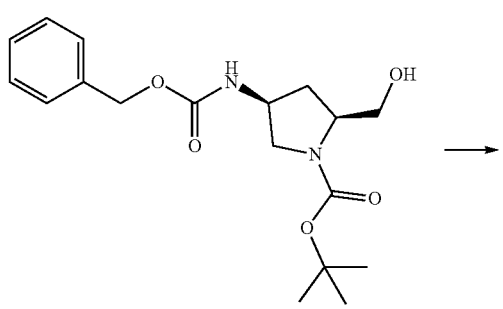

-continued

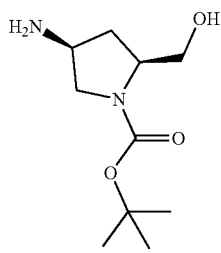

tert-butyl (2S,4S)-4-((((benzyloxy)carbonyl)amino)-2-(hydroxymethyl)pyrrolidin-1-carboxylate (250 mg, 0.71 mmol, 1.0 eq) was dissolved in menthol (5.0 mL), added with palladium on carbon (75.2 mg, 7.2 mmol, 0.01 eq), added with hydrogen for 4 times, stirred at room temperature and reacted overnight. The completion of the reaction was detected by TLC. The reaction solution was filtered by suction with celite, and the filtrate was concentrated to obtain tert-butyl (2S,4S)-4-amino-2-(hydroxymethyl)pyrrolidin-1-carboxylate (123.0 mg, yield 80.2%) as a colorless transparent oil.

Step 4: Synthesis of Tert-Butyl (2S,4S)-4-((6-(2,6-dichloro-3,5-dimethoxyphenyl)quinazolin-2-yl)amino)-2-(hydroxymethyl)pyrrolidin-1-carboxylate

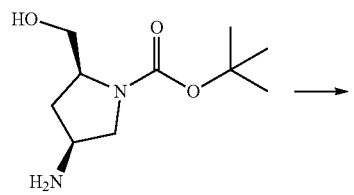

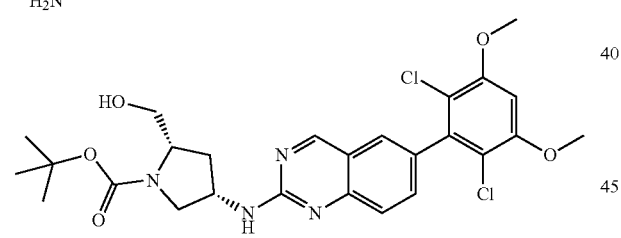

The materials tert-butyl (2S,4S)-4-amino-2-(hydroxymethyl)pyrrolidin-1-carboxylate (123.0 mg, 0.57 mmol, 1.0 eq) and 2-chloro-6-(2,6-dichloro-3,5-dimethoxyphenyl)quinazoline (231.5 mg, 0.63 mmol, 1.1 eq) were dissolved in N-methylpyrrolidone (4.0 mL), added with N,N-diisopropylethylamine (147.3 mg, 1.14 mmol, 2.0 eq), gradually heated to 110° C., stirred and reacted for 5 h. The completion of the reaction was detected by TLC. The reaction solution was cooled to room temperature, added with 20 mL of ice water, stirred for 10 min, and filtered. The filter cake was washed with a small amount of ice water, then dissolved in dichloromethane (10 mL), dried over anhydrous sodium sulfate, filtered and concentrated. The crude product was subjected to silica gel column chromatography (200-300 mesh silica gel, DCM:MeOH=100:1 to 50:1) to give tert-butyl (2S,4S)-4-((6-(2,6-dichloro-3,5-dimethoxyphenyl)quinazolin-2-yl)amino)-2-(hydroxymethyl)pyrrolidin-1-carboxylate (113.0 mg, yield: 36.1%) as a maple solid.

Step 5: Synthesis of ((2S,4S)-4-((6-(2,6-dichloro-3,5-dimethoxyphenyl)quinazolin)-2-amino)pyrrolidin)-2-methanol Hydrochloride

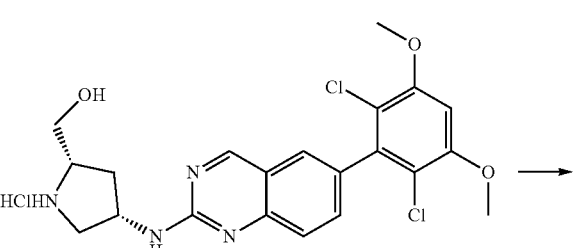

The material tert-butyl (2S,4S)-4-((6-(2,6-dichloro-3,5-dimethoxyphenyl)quinazolin-2-yl)amino)-2-(hydroxymethyl)pyrrolidin-1-carboxylate (113.0 mg, 0.21 mmol, 1.0 eq) was dissolved in ethanol (5.0 mL), cooled to 0° C. in an ice bath, added with hydrogen chloride ethanol solution (5.0 mL), warmed gradually to room temperature and reacted overnight. The completion of the reaction was detected by TLC. The reaction solution was directly concentrated to give ((2S,4S)-4-((6-(2,6-dichloro-3,5-dimethoxyphenyl)quinazolin)-2-amino)pyrrolidin)-2-methanol hydrochloride (180.0 mg crude product, yield: 100%) as a yellow solid.

Step 6: Synthesis of 1-((2S,4S)-4-((6-(2,6-dichloro-3,5-dimethoxyphenyl)quinazolin-2-yl)amino)-2-(hydroxymethyl)pyrrolidin)-1-propyl-2-en-1-one (Compound 22)

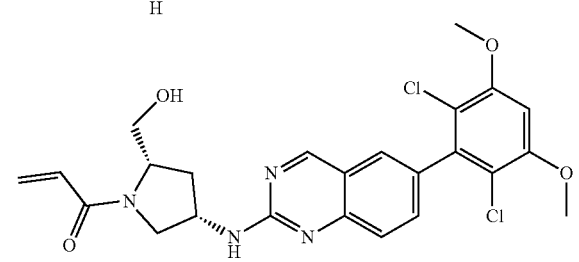

The material ((2S,4S)-4-((6-(2,6-dichloro-3,5-dimethoxyphenyl)quinazolin)-2-amino)pyrrolidin)-2-methanol hydrochloride (160.0 mg, 0.35 mmol, 1.0 eq) was dissolved in THF (10.0 mL), added with triethylamine (106.0 mg, 1.1 mmol, 3.0 eq), stirred at room temperature to react for 0.5 h, cooled to 0° C., slowly added with acryloyl chloride (38.0 mg, 0.42 mmol, 1.2 eq), warmed to room temperature gradually and reacted for 1 h. The completion of the reaction was detected by TLC. A saturated sodium bicarbonate solution (15 mL) was added to the reaction solution, followed by adding ethyl acetate (8 mL) for solution separation. The aqueous phase was extracted with EA (8.0 mL×2), and the organic phases were combined, washed with saturated brine, dried over anhydrous sodium sulfate, filtered, and concentrated. The crude product was subjected to silica gel column chromatography (200-300 mesh silica gel, DCM:MeOH=100:1 to 50:1) to obtain 1-((2S,4S)-4-((6-(2,6-dichloro-3,5-dimethoxyphenyl)quinazolin-2-yl)amino)-2-(hydroxymethyl)pyrrolidin-1-yl)prop-2-en-1-one (75.0 mg, yield: 42.5%) as a pale yellow solid.

$^1$HNMR (400 MHz, DMSO) δ (ppm): 9.18 (s, 1H), 7.89 (s, 1H), 7.8 (s, 1H), 7.55 (d, 1H), 7.52 (d, 1H), 7.00 (s, 1H), 6.60-6.71 (m, 1H), 6.16 (d, 1H), 5.67 (d, 1H), 5.09 (s, 1H), 4.55 (m, 1H), 4.12-4.20 (m, 2H), 4.03 (s, 6H), 3.97 (m, 1H), 3.74 (m, 1H), 3.52 (m, 1H), 1.98 (m, 2H).

Molecular formula: $C_{24}H_{24}Cl_2N_4O_4$ Molecular weight: 503.39 LC-MS (m/z)=505.40 [M+H$^+$].

Example 9: Synthesis of 1-((2S,4S)-4-((6-(2,6-dichloro-3,5-dimethoxyphenyl)quinazolin-2-yl)amino)-2-(fluoromethyl)pyrrolidin-1-yl)prop-2-en-1-one (Compound 24)

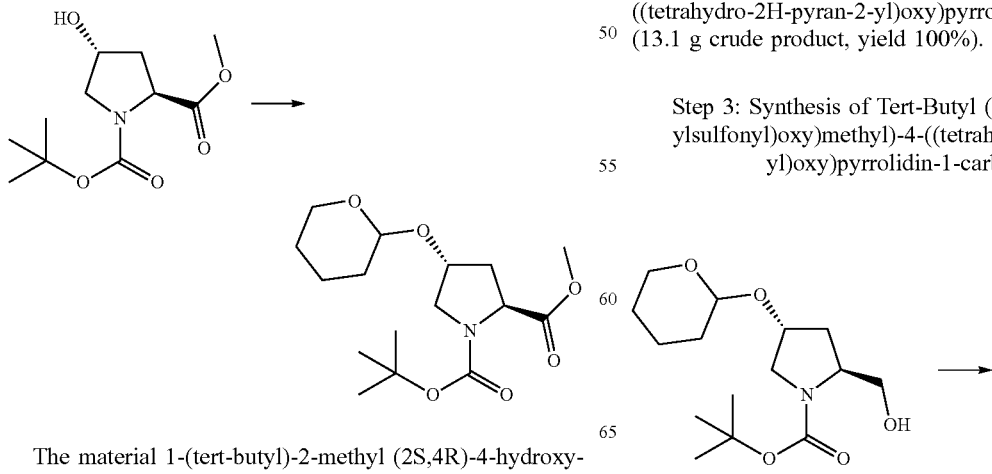

Step 1: Synthesis of 1-(tert-butyl)-2-methyl (2S,4R)-4-((tetrahydro-2H-pyran-2-yl)oxy)pyrrolidin-1,2-dicarboxylate

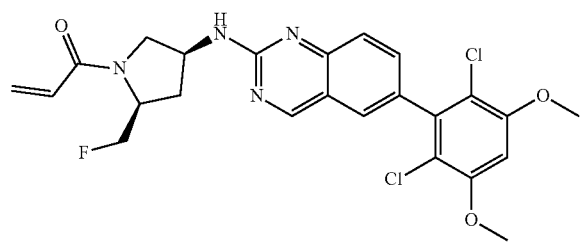 [SMILES: C=CC(=O)N1C[C@@H](Nc2ncc3cc(-c4c(Cl)c(OC)cc(OC)c4Cl)ccc3n2)C[C@H]1CF]

The material 1-(tert-butyl)-2-methyl (2S,4R)-4-hydroxypyrrolidin-1,2-dicarboxylate (10.0 g, 40.8 eq) was dissolved in tert-butyl methyl ether (100 mL), added with p-toluenesulfonic acid (234.2 mg, 1.36 mmol), cooled to 0° C. in an ice bath, slowly added with 3,4-dihydro-2H-pyran (10.3 g, 122.4 mmol), slowly warmed to room temperature and reacted for 3 h. The completion of the reaction was detected by TLC. 1-(tert-butyl)2-methyl (2S,4R)-4-((tetrahydro-2H-pyran-2-yl)oxy)pyrrolidin-1,2-dicarboxylate (14 g) was obtained by concentration under reduced pressure.

Step 2: Synthesis of Tert-Butyl (2S,4R)-2-(hydroxymethyl)-4-((tetrahydro-2H-pyran-2-yl)oxy) pyrrolidin-1-carboxylate

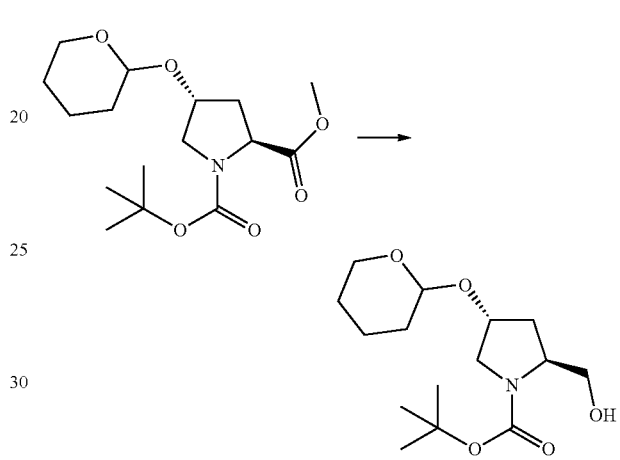

Lithium aluminum hydride (3.1 g, 81.6 mmoL) was added to tetrahydrofuran (100.0 mL), cooled to −20° C. with ethanol, water and dry ice, dropwise added with 1-(tert-butyl)-2-methyl (2S,4R)-4-((tetrahydro-2H-pyran-2-yl)oxy)pyrrolidin-1,2-dicarboxylate (13.43 g, 40.8 mmoL) in tetrahydrofuran solution (100 mL), and stirred at −20° C. under nitrogen atmosphere and reacted for 3 h. The completion of the reaction was detected by TLC. Water (3.1 mL), 10% NaOH (3.1 mL), and water (9.3 mL) were added to the reaction solution under an ice bath, stirred for 10 min, filtered by suction with celite. The filtrate was concentrated directly to dryness to give tert-butyl (2S,4R)-2-(hydroxymethyl)-4-((tetrahydro-2H-pyran-2-yl)oxy)pyrrolidin-1-carboxylate (13.1 g crude product, yield 100%).

Step 3: Synthesis of Tert-Butyl (2S,4R)-2-(((methylsulfonyl)oxy)methyl)-4-((tetrahydro-2H-pyran-2-yl)oxy)pyrrolidin-1-carboxylate

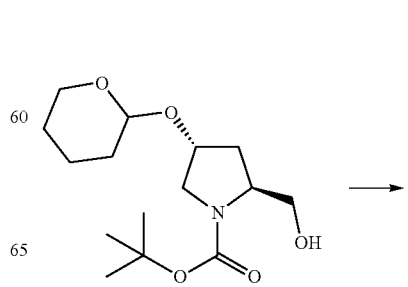

-continued

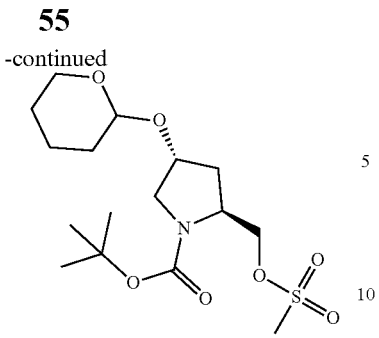

The material tert-butyl (2S,4R)-2-(hydroxymethyl)-4-((tetrahydro-2H-pyran-2-yl)oxy)pyrrolidin-1-carboxylate (2.0 g, 6.65 mmoL) was dissolved in dichloromethane (10.0 mL), cooled to 0° C. in an ice bath, added with triethylamine (1.35 g, 13.3 mmoL), slowly added with methanesulfonyl chloride (1.15 g, 9.975 mmoL) at 0° C., slowly warmed to room temperature and reacted for 1 h. The completion of the reaction was detected by TLC. Dichloromethane (10 mL) was added and then saturated ammonium chloride (10 mL) was added for separation. The organic phases were combined, washed with water (3×5 mL), then washed with saturated brine, dried over anhydrous sodium sulfate, and subjected to column chromatography (PE:EA=15:1, 10:1, DCM:MeOH=100:1) to give tert-butyl (2S,4R)-2-(((methylsulfonyl)oxy)methyl)-4-((tetrahydro-2H-pyran-2-yl)oxy)pyrrolidin-1-carboxylate (2.0 g, yield 79.3%).

Step 4: Synthesis of Tert-Butyl (2S,4R)-2-(fluromethyl)-4-((tetrahydro-2H-pyran-2-yl)oxy)pyrrolidin-1-carboxylate

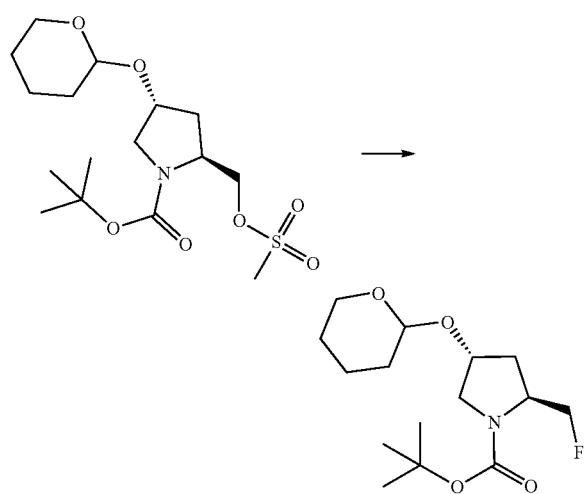

The material tert-butyl (2S,4R)-2-(((methylsulfonyl)oxy)methyl)-4-((tetrahydro-2H-pyran-2-yl)oxy)pyrrolidin-1-carboxylate (7.5 g, 19.8 mmoL) was dissolved in tetrahydrofuran (45.0 mL), added with tetramethylammonium fluoride (1.5 g, 4.75 mmoL), heated to 80° C. and detected under reflux. The completion of the reaction was detected by TLC. The reaction solution was dried under reduced pressure, added with ethyl acetate (10 mL), washed with water (5×10 mL). The organic phases were combined, dried over anhydrous sodium sulfate, and subjected to column chromatography (DCM:MeOH=200:1, 150:1, 100:1) to give tert-butyl (2S,4R)-2-(((methylsulfonyl)oxy)methyl)-4-((tetrahydro-2H-pyran-2-yl)oxy)pyrrolidin-1-carboxylate (3.2 g, yield 53.3%).

Step 5: Synthesis of Tert-Butyl (2S,4R)-2-(fluoromethyl)-4-hydroxypyrrolidin-1-carboxylate

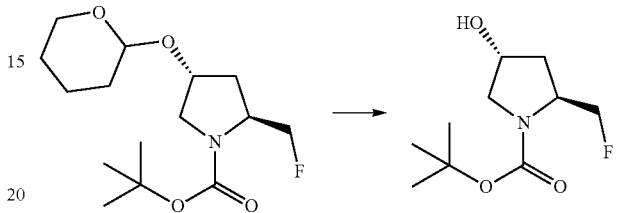

The material tert-butyl (2S,4R)-2-(fluoromethyl)-4-((tetrahydro-2H-pyran-2-yl)oxy)pyrrolidin-1-carboxylate (3.2 g, 10.55 mmoL) was dissolved in a mixed solvent of acetic acid (33.0 mL), tetrahydrofuran (33.0 mL), and water (33.0 mL), and heated to reflux. The completion of the reaction was detected by TLC. The pH was adjusted with saturated sodium bicarbonate (8-9), and tetrahydrofuran was removed by evaporation. The aqueous phase was extracted with ethyl acetate (3×50 mL). The organic phases were combined, washed with water (1×10 mL) followed by saturated brine, dried over anhydrous sodium sulfate, and subjected to column chromatography (DCM:MeOH=200:1, 150:1, 100:1, 50:1) to give tert-butyl (2S,4R)-2-(fluoromethyl)-4-hydroxypyrrolidin-1-carboxylate (2.0 g, yield 87%).

Step 6: Synthesis of Tert-Butyl (2S,4S)-4-azido-2-(fluoromethyl)pyrrolidine-1-carboxylate

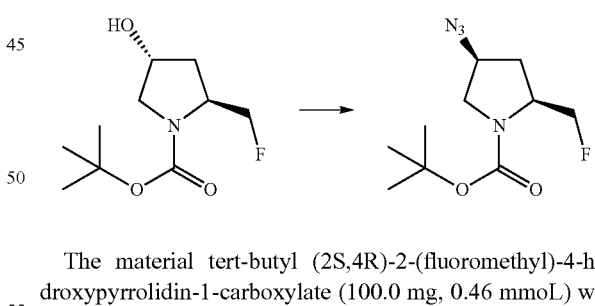

The material tert-butyl (2S,4R)-2-(fluoromethyl)-4-hydroxypyrrolidin-1-carboxylate (100.0 mg, 0.46 mmoL) was dissolved in tetrahydrofuran (1.5 mL), cooled to 0° C. in an ice bath, added with triphenylphosphine (144.8 mg, 0.552 mmoL), then added with diisopropyl azodicarboxylate (111.6 mg, 0.552 mmoL) at 0° C., stirred at 0° C. for 20 minutes, slowly added with DDPA (151.9 mg, 0.552 mmoL) at 0° C., and slowly warmed to room temperature overnight. The completion of the reaction was detected by TLC, and tetrahydrofuran was removed by evaporation, followed by column chromatography (PE:EA=5:1, 2:1) to give tert-butyl (2S,4S)-4-azido-2-(fluoromethyl)pyrrolidine-1-carboxylate (170.0 mg, yield 100%).

Step 7: Synthesis of Tert-Butyl (2S,4S)-4-amino-2-(fluoromethyl)pyrrolidin-1-carboxylate

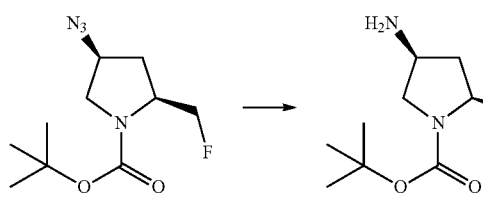

The material tert-butyl (2S,4S)-4-azido-2-(fluoromethyl) pyrrolidin-1-carboxylate (112.3 mg, 0.46 mmol) was dissolved in menthol (2 mL), added with palladium on carbon (5.62 mg, 5% wt), and added with hydrogen for three times followed by hydrogenation overnight. The completion of the reaction was detected by TLC. The mixture was filtered by suction with celite, and the filtrate was evaporated to give tert-butyl (2S,4S)-4-amino-2-(fluoromethyl)pyrrolidin-1-carboxylate (105.0 mg).

Step 8: Synthesis of Tert-Butyl (2S,4S)-4-((6-(2,6-dichloro-3,5-dimethoxyphenyl)quinazolin-2-yl)amino)-2-(fluoro methyl)pyrrolidin-1-carboxylate

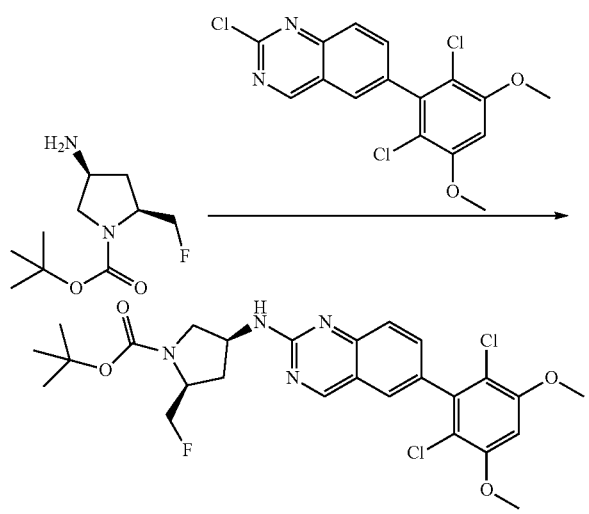

The material tert-butyl (2S,4S)-4-amino-2-(fluoromethyl) pyrrolidin-1-carboxylate (100.3 mg, 0.46 mmol) was dissolved in N-methylpyrrolidone (2.0 mL), added with N,N-diisopropylethylamine (178.21 mg, 1.38 mmol) and 2-chloro-6-(2,6-dichloro-3,5-dimethoxyphenyl)quinazoline (203.1 mg, 0.552 mmoL), gradually heated to 110° C. and heated to reflux overnight. The completion of the reaction was detected by TLC. The reaction solution was cooled to room temperature, added with 10 mL of water, and filtered. The filter cake was washed with small amount of ice water, dissolved in dichloromethane (10 mL), dried over anhydrous sodium sulfate, purified with preparative silica gel plate (DCM:MeOH=20:1) to obtain tert-butyl (2S,4S)-4-((6-(2,6-dichloro-3,5-dimethoxyphenyl)quinazolin-2-yl)amino)-2-(fluoro methyl)pyrrolidin-1-carboxylate (50.0 mg, yield: 19.8%).

Step 9: Synthesis of 6-(2,6-dichloro-3,5-dimethoxyphenyl)-N-((3S,5S)-5-(fluoromethyl)pyrrolidin-3-yl)quinazolin-2-amine

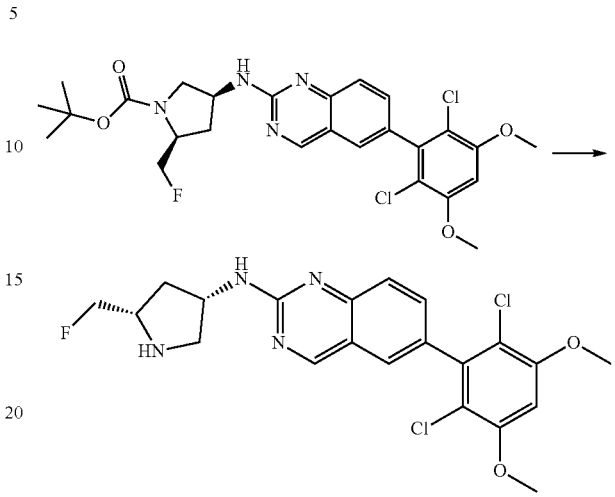

The material tert-butyl (2S,4S)-4-((6-(2,6-dichloro-3,5-dimethoxyphenyl)quinazolin-2-yl)amino)-2-(fluoro methyl) pyrrolidin-1-carboxylate (45.0 mg, 0.082 mmol) was dissolved in DCM (2.0 mL), cooled to 0° C. in an ice bath, added with hydrogen chloride ethanol solution (1.0 mL), warmed gradually to room temperature and reacted for 2 h. The completion of the reaction was detected by TLC. The reaction solution was concentrated directly to dryness to obtain 6-(2,6-dichloro-3,5-dimethoxyphenyl)-N-((3S,5S)-5-(fluoromethyl)pyrrolidin-3-yl)quinazolin-2-amine (40.0 mg).

Step 10: Synthesis of 1-((2S,4S)-4-((6-(2,6-dichloro-3,5-dimethoxyphenyl)quinazolin-2-yl)amino)-2-(flu oromethyl)pyrrolidin-1-yl)prop-2-en-1-one

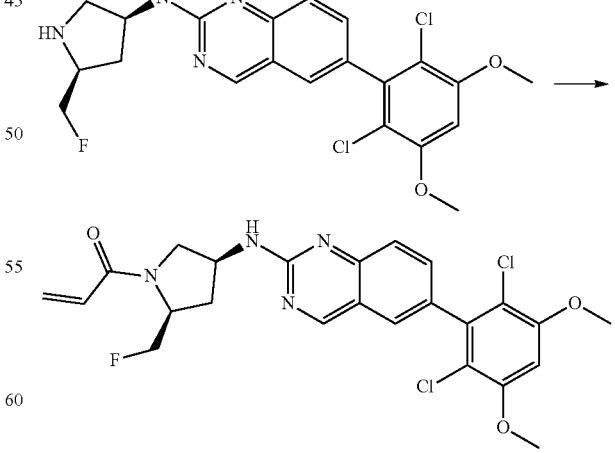

The material 6-(2,6-dichloro-3,5-dimethoxyphenyl)-N-((3S,5S)-5-(fluoromethyl)pyrrolidin-3-yl)quinazolin-2-amine (37.0 mg, 0.082 mmol) was dissolved in THF (1.0 mL), cooled to 0° C. in an ice bath, added with triethylamine (24.0 mg, 0.246 mmol), then added with acryloyl chloride (11.13 mg, 0.123 mmoL) at 0° C., warmed gradually to room temperature and reacted for 2 h. The completion of the reaction was detected by TLC. After adding water (5 mL), the aqueous phase was extracted with ethyl acetate (8.0 mL×3). The organic phases were combined, washed with saturated brine, dried with anhydrous sodium sulfate, and subjected to column chromatography (DCM:MeOH=250:1, 200:1, 150:1, 100:1) to obtain 1-((2S,4S)-4-((6-(2,6-dichloro-3,5-dimethoxyphenyl)quinazolin-2-yl)amino)-2-(fluoromethyl)pyrrolidin-1-yl)prop-2-en-1-one (11.5 mg, yield: 27.7%).

$^1$HNMR (400 MHz, DMSO-d$_6$) δ (ppm): 11.93 (s, 1H), 9.19 (s, 1H), 7.85-7.83 (d, 1H), 7.69 (s, 1H), 7.58-7.50 (m, 2H), 7.01 (s, 1H), 6.59 (s, 2H), 6.19-6.15 (d, 1H), 5.71-5.69 (d, 1H), 5.31 (s, 1H), 4.65-4.54 (d, 4H), 4.44 (s, 1H), 4.27-4.19 (d, 3H), 3.97 (s, 6H), 3.81-3.75 (d, 2H), 2.19-2.16 (t, 2H), 2.10-1.98 (m, 3H).

Molecular formula: C$_{24}$H$_{22}$Cl$_2$N$_4$O$_3$ Molecular weight: 485.37 LC-MS (Pos, m/z)=485.43 [M+H$^+$].

Example 10: Synthesis of 2-((2S,4S)-1-acryloyl-4-((6-(2,6-dichloro-3,5-dimethoxyphenyl)quinazolin-2-yl)amino)pyrrolidin-2-yl)acetonitrile (Compound 27)

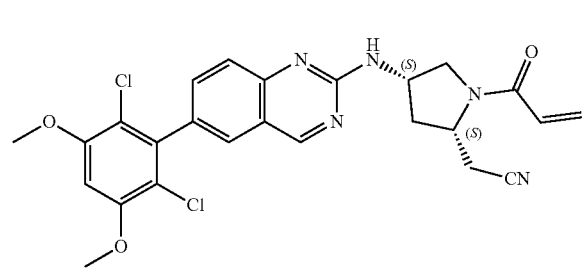

Step 1: Synthesis of Tert-Butyl (2S,4S)-2-(bromomethyl)-4-((6-(2,6-dichloro-3,5-dimethoxyphenyl)quinazolin-2-yl)amino)pyrrolidin-1-carboxylate

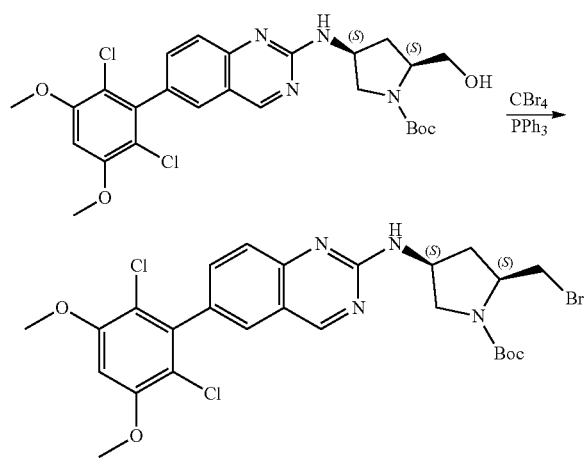

The material tert-butyl (2S,4S)-4-((6-(2,6-dichloro-3,5-dimethoxyphenyl)quinazolin-2-yl)amino)-2-(hydroxymethyl)pyrrolidin-1-carboxylate (1571 mg, 2.859 mmol, 1.0 eq) was dissolved in DCM (20 mL), stirred, then added with carbon tetrabromide (1185 mg, 3.574 mmol, 1.25 eq), and cooled to 0° C. Triphenylphosphine (2250 mg, 8.577 mmol, 3 eq) was added in portions, the reaction system was slowly warmed to room temperature under nitrogen atmosphere and reacted overnight. The completion of the reaction was detected by TLC. The reaction solution was directly added with silica gel, and the solvent was removed by evaporation, followed by separation with column chromatography (eluent, PE:EA=3:1) to obtain tert-butyl (2S,4S)-2-(bromomethyl)-4-((6-(2,6-dichloro-3,5-dimethoxyphenyl)quinazolin-2-yl)amino)pyrrolidin-1-carboxylate (800 mg, yield of 45.7%).

Step 2: Synthesis of tert-butyl (2S,4S)-2-(cyanomethyl)-4-((6-(2,6-dichloro-3,5-dimethoxyphenyl)quinazolin-2-yl)amino)pyrrolidin-1-carboxylate

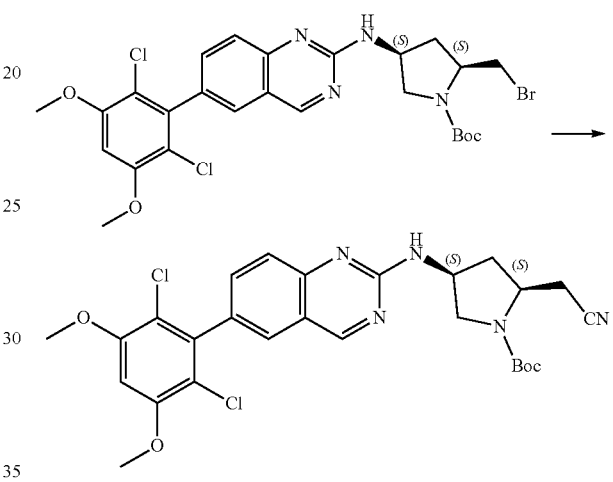

The intermediate tert-butyl (2S,4S)-2-(bromomethyl)-4-((6-(2,6-dichloro-3,5-dimethoxyphenyl)quinazolin-2-yl)amino)pyrrolidin-1-carboxylate (800 mg, 1.3064 mmol, 1 eq) was dissolved in acetonitrile (10 mL), added with TMSCN (259 mg, 2.6128 mmol, 2 eq) and an appropriate amount of tetraethylammonium fluoride at room temperature, warmed to 60° C. and reacted overnight. The completion of the reaction was detected by TLC. The reaction solution was cooled, added with 100 ml of water, extracted with DCM (200 ml×3) for solution separation. The organic phase was dried over anhydrous sodium sulfate, filtered, concentrated to dryness under reduced pressure, and separated by column chromatography (eluent, PE:EA=5:1-4:1) to give tert-butyl (2S,4S)-2-(cyanomethyl)-4-((6-(2,6-dichloro-3,5-dimethoxyphenyl)quinazolin-2-yl)amino)pyrrolidin-1-carboxylate (215 mg, yield of 29.5%).

Step 3: Synthesis of 2-((2S,4S)-4-((6-(2,6-dichloro-3,5-dimethoxyphenyl)quinazolin-2-yl)amino)pyrrolidin-2-yl)acetonitrile

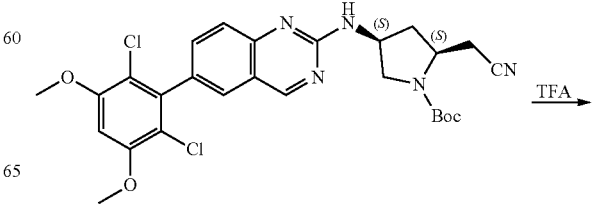

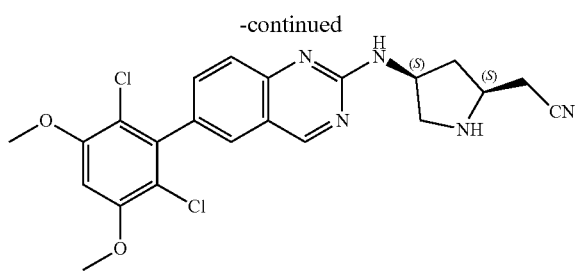

The intermediate tert-butyl (2S,4S)-2-(cyanomethyl)-4-((6-(2,6-dichloro-3,5-dimethoxyphenyl)quinazolin-2-yl)amino)pyrrolidin-1-carboxylate (215 mg) was dissolved in DCM (4 mL), cooled to 0° C., and added with TFA (3 ml). After that, the reaction system was slowly warmed to room temperature, and the completion of the reaction was detected by TLC. The mixture was concentrated to dryness under reduced pressure at room temperature, added with DCM and concentrated to dryness under reduced pressure. TFA in the system was removed as much as possible. 2-((2S,4S)-4-((6-(2,6-dichloro-3,5-dimethoxyphenyl)quinazolin-2-yl)amino)pyrrolidin-2-yl)acetonitrile (theoretical yield, 176 mg) was obtained and used directly in the next step.

Step 4: Synthesis of 2-((2S,4S)-1-acryloyl-4-((6-(2,6-dichloro-3,5-dimethoxyphenyl)quinazolin-2-yl)amino)pyrrolidin-2-yl)acetonitrile

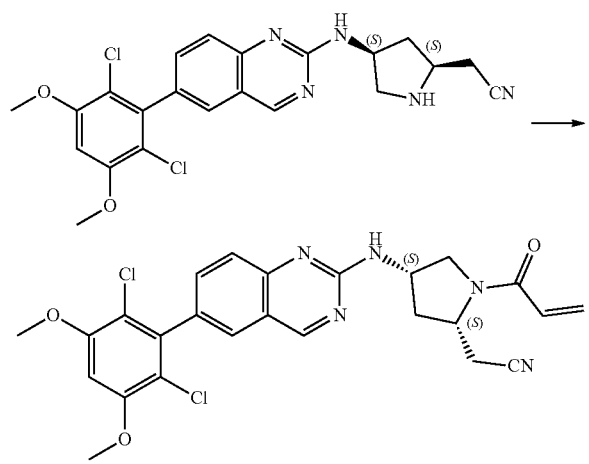

The intermediate 2-((2S,4S)-4-((6-(2,6-dichloro-3,5-dimethoxyphenyl)quinazolin-2-yl)amino)pyrrolidin-2-yl)acetonitrile (in a theoretical value of 176 mg, 0.3840 mmol) was dissolved in THF (4 mL), added with TEA, and cooled to −10° C. Acryloyl chloride (41 mg, 0.4608 mmol, 1.2 eq, dissolved in 1 ml DCM) solution was slowly added dropwise to the reaction system. The completion of the reaction was detected by TLC. A saturated sodium bicarbonate solution was added under cooling to obtain an alkaline reaction system, followed by extraction with DCM (100 mL×3) for solution separation. The organic phases were combined, dried over anhydrous sodium sulfate, and filtered. The filtrate was concentrated and subjected to column chromatography (DCM:MeOH=200:1 to 50:1) to obtain 2-((2S,4S)-1-acryloyl-4-((6-(2,6-dichloro-3,5-dimethoxyphenyl)quinazolin-2-yl)amino)pyrrolidin-2-yl)acetonitrile (138 mg, yield: 70.4%).

$^1$HNMR (400 MHz, DMSO) δ (ppm): 9.21 (s, 1H), 7.98-8.00 (d, 1H), 7.70-7.71 (d, 1H), 7.52-7.61 (m, 2H), 7.02 (s, 1H), 6.60-6.67 (q, 1H), 6.18-6.23 (q, 1H), 5.72-5.76 (t, 1H), 4.57-4.59 (t, 1H), 4.51-4.53 (d, 1H), 4.24-4.25 (d, 2H), 3.98 (s, 3H), 3.48-3.50 (d, 3H), 3.42-3.43 (d, 2H), 3.13-3.22 (m, 1H), 3.01-3.10 (m, 1H), 1.98-2.05 (q, 1H).

Molecular formula: $C_{25}H_{23}Cl_2N_5O_3$, Molecular weight: 512.39, LC-MS (Pos, Example 11: Synthesis of (2S,4S)-1-acryloyl-4-((6-(2,6-dichloro-3,5-dimethoxyphenyl)quinazolin-2-yl)amino)pyrrolidin-2-carbonitrile (Compound 28)

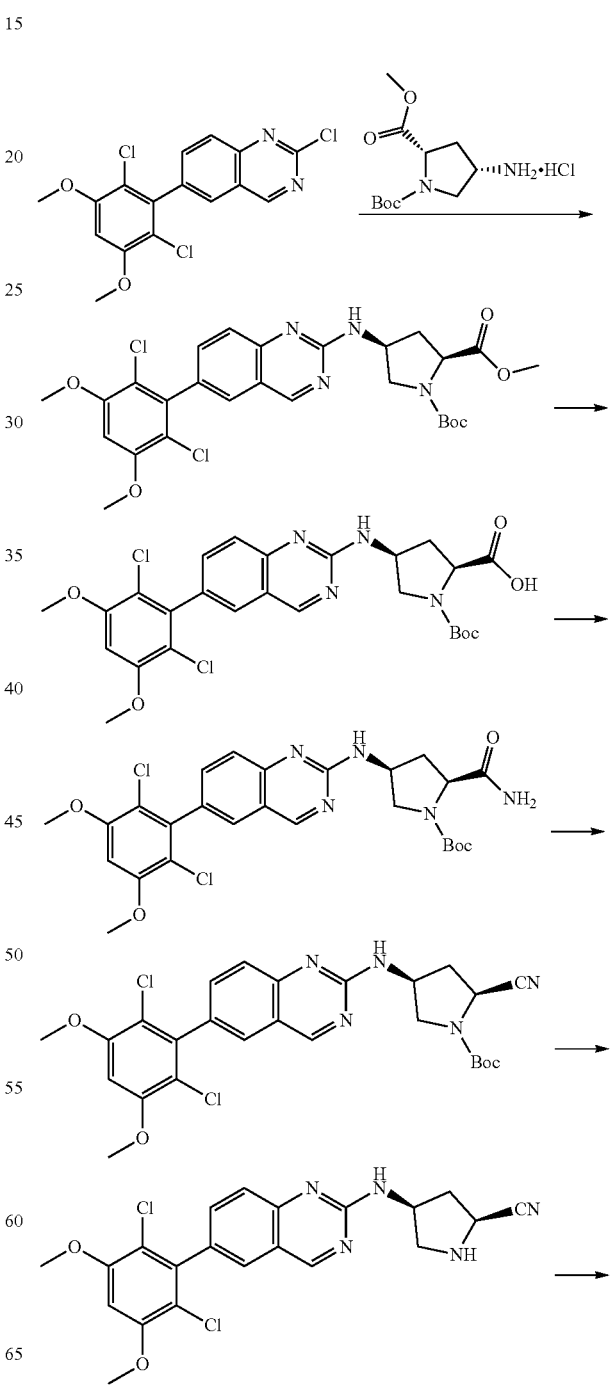

-continued

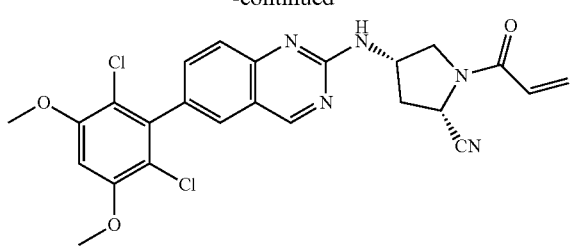

Step 1: Synthesis of 1-tert-butyl 2-methyl (2S,4S)-4-((6-(2,6-dichloro-3,5-dimethoxyphenyl)quinazolin-2-yl)amino)pyrrolidin-1,2-dicarboxylate

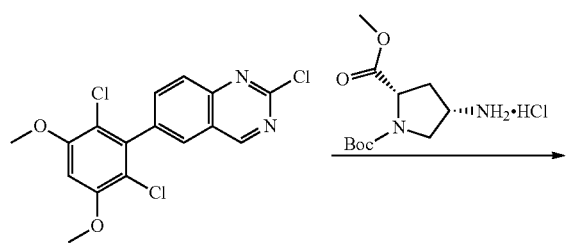

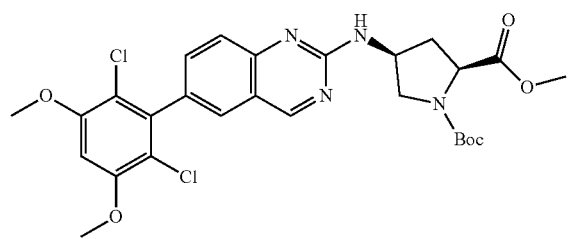

The materials 2-chloro-6-(2,6-dichloro-3,5-dimethoxyphenyl)quinazoline (500.0 mg, 1.353 mmol, 1.0 eq), 1-tert-butyl 2-methyl(2S,4S)-4-aminopyrrolidine-1,2-dicarboxylate hydrochloride (644 mg, 2.030 mmol, 1.5 eq) and N,N-diisopropylethylamine (874.4 mg, 6.765 mmol, 5.0 eq) were dissolved in N-methylpyrrolidone (5 mL), heated to 120° C. and reacted overnight. The completion of the reaction was detected by TLC on the next morning. The reaction solution was poured into ice water (20 mL), and brown solid was precipitated. The mixture was filtered by suction, and the filtrate was extracted with ethyl acetate (10 mL×3). The brown solid was dissolved in ethyl acetate, and the organic phases were combined, washed with water (20 mL×3) for solution separation. The organic phase was dried over anhydrous sodium sulfate, filtered, and the filter cake was rinsed with ethyl acetate. The mother liquor was concentrated under reduced pressure, and the crude product was subjected to silica gel column chromatography (PE:EA=5:1) to give a solid of 1-tert-butyl 2-methyl (2S,4S)-4-((6-(2,6-dichloro-3,5-dimethoxyphenyl)quinazolin-2-yl)amino)pyrrolidin-1,2-dicarboxylate (384 mg, yield: 49%).

Step 2: Synthesis of (2S,4S)-1-tert-butoxycarbonyl-4-((6-(2,6-dichloro-3,5-dimethoxyphenyl)quinazolin-2-yl)amino)pyrrolidin-2-carboxylic acid

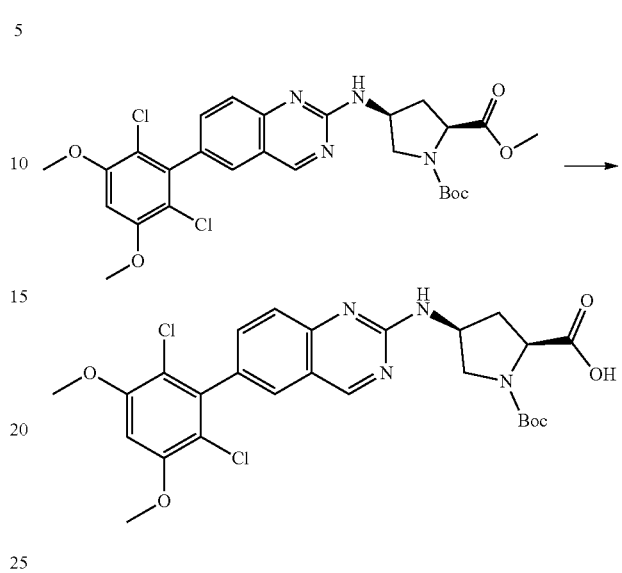

1-tert-butyl 2-methyl(2S,4S)-4-((6-(2,6-dichloro-3,5-dimethoxyphenyl)quinazolin-2-yl)amino) pyrrolidin-1,2-dicarboxylate (300 mg, 0.5195 mmol, 1.0 eq) was dissolved in methanol (5 mL), stirred and dissolved, cooled to 0° C., and dropwise added with a solution of lithium hydroxide monohydrate (65 mg, 1.558 mmol, 3.0 eq) in water (1 mL). After reaction for 3 h, TLC was used to detect the remaining of materials. The solution of lithium hydroxide monohydrate (65 mg, 1.558 mmol, 3.0 eq) in water (1 mL) was added. Methanol was added to obtain a clarified system and allowed to react overnight. The completion of the reaction was detected by TLC, and the reaction system was concentrated under reduced pressure, added with water (10 mL) and methyl tert-butyl ether (10 mL), stirred and separated. Ethyl acetate (20 mL) was added into the aqueous phase and cooled to 0° C. The pH was adjusted to 5-6 with citric acid and the organic phase was separated. The aqueous phase was extracted with ethyl acetate (10 mL). The organic phases were combined, dried over anhydrous sodium sulfate and filtered. The filter cake was rinsed with ethyl acetate. The mother liquor was concentrated under reduced pressure to give (2S,4S)-1-(tert-butoxycarbonyl)-4-((6-(2,6-dichloro-3,5-dimethoxyphenyl)quinazolin-2-yl)amino)pyrrolidin-2-carboxylic acid (260 mg, yield: 89%) as a pale yellow solid.

Step 3: Synthesis of Tert-Butyl (2S,4S)-2-carbamoyl-4-((6-(2,6-dichloro-3,5-dimethoxyphenyl)quinazolin-2-yl)amino)pyrrolidin-1-carboxylate

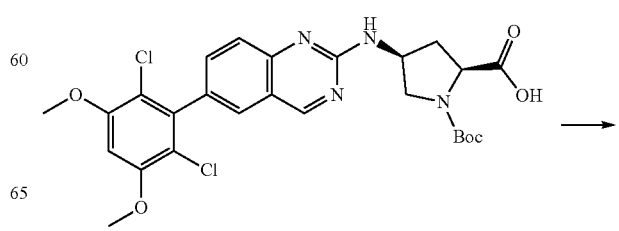

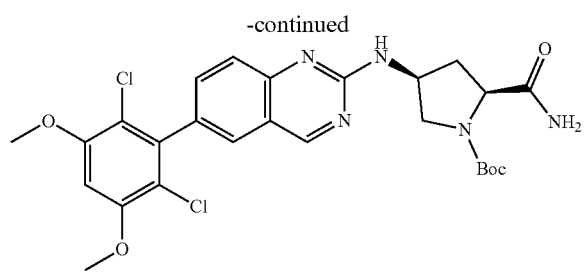

(2S,4S)-1-(tert-butoxycarbonyl)-4-((6-(2,6-dichloro-3,5-dimethoxyphenyl)quinazol in-2-yl)amino)pyrrolidin-2-carboxylic acid (260 mg, 0.462 mmol, 1.0 eq) was dissolved in THF (10 mL), added with triethylamine (140.1 mg, 1.384 mmol, 3.0 eq), cooled to about −15° C., and slowly added isobutyl chloroformate (75.64 mg, 0.554 mmol, 1.2 eq). After reaction for 2 h, the completion of the reaction was detected by TLC. The reaction solution was added dropwise to an aqueous ammonia solution cooled to 0° C. (5 mL). After reaction for 3 h, the completion of the reaction was detected by TLC. Saturated potassium carbonate solution (10 mL), saturated brine (10 mL), and MTBE (20 mL) were added, stirred and separated. The aqueous phase was extracted with MTBE (10 mL). The organic phases were combined, dried and concentrated to give tert-butyl (2S,4S)-2-carbamoyl-4-((6-(2,6-dichloro-3,5-dimethoxyphenyl)quinazolin-2-yl)amino)pyrrolidin-1-carboxylate (350 mg crude) as a pale yellow solid.

Step 4: Synthesis of Tert-Butyl (2S,4S)-2-cyano-4-((6-(2,6-dichloro-3,5-dimethoxyphenyl)quinazolin-2-yl)amino) pyrrolidin-1-carboxylate

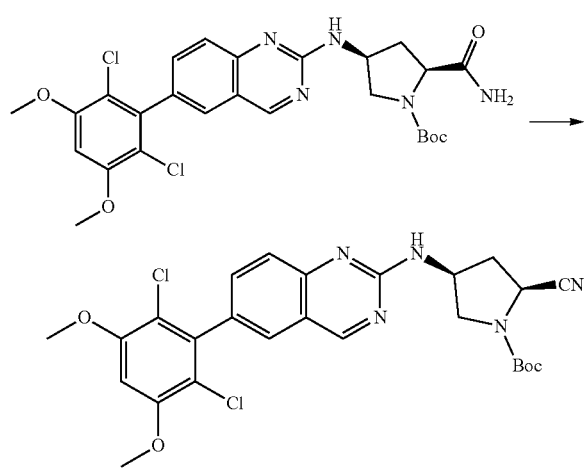

tert-butyl (2S,4S)-2-carbamoyl-4-((6-(2,6-dichloro-3,5-dimethoxyphenyl)quinazolin-2-yl)amino)pyrrolidin-1-carboxylate (250 mg, 0.445 mmol, 1.0 eq) was dissolved in THF (10 mL), added with triethylamine (112.6 mg, 1.113 mmol, 2.5 eq), cooled to about 0° C., and slowly added with TFAA (186.9 mg, 0.89 mmol, 2.0 eq). After 0.5 h, the temperature was raised to 40° C., and reacted overnight. The residue of material was detected by TLC. TFAA (93.46 mg, 0.445 mmol, 1.0 eq) was added and the reaction was continued for 1 h. The completion of the reaction was detected by TLC. The reaction solution was cooled, added with DCM (20 mL) and saturated sodium bicarbonate (10 mL), stirred and separated. The organic phase was separated, dried over anhydrous sodium sulfate and filtered. The filter cake was rinsed with DCM, and the mother liquor was concentrated under reduced pressure to give a solid of tert-butyl (2S,4S)-2-cyano-4-((6-(2,6-dichloro-3,5-dimethoxyphenyl)quinazolin-2-yl)amino) pyrrolidin-1-carboxylate (350 mg crude).

Step 5: Synthesis of (2S,4S)-4-((6-(2,6-dichloro-3,5-dimethoxyphenyl)quinazolin-2-yl)amino)pyrrolidin-2-carbonitrile

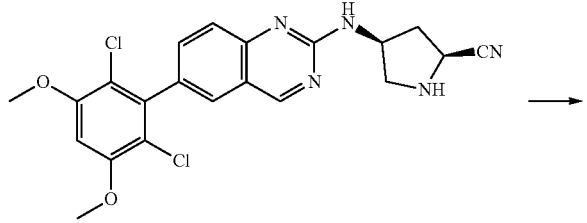

The intermediate tert-butyl (2S,4S)-2-cyano-4-((6-(2,6-dichloro-3,5-dimethoxyphenyl)quinazolin-2-yl)amino) pyrrolidin-1-carboxylate (350 mg, 0.445 mmol, 1.0 eq) was dissolved in DCM (5 mL), added with trifluoroacetic acid (5 mL), heated to 30° C. and reacted for 4 h. The completion of the reaction was detected by TLC and the reaction solution was concentrated. The crude product was added with EA and concentrated, repeated for three times. MTBE (20 mL) was added, and solid was precipitated, followed by suction filtration to give a solid of (2S,4S)-4-((6-(2,6-dichloro-3,5-dimethoxyphenyl)quinazolin-2-yl)amino)pyrrolidin-2-carbonitrile (143 mg, yield: 50%).

Step 6: Synthesis of (2S,4S)-1-acryloyl-4-((6-(2,6-dichloro-3,5-dimethoxyphenyl)quinazolin-2-yl)amino)pyrrolidin-2-carbonitrile (Compound 28)

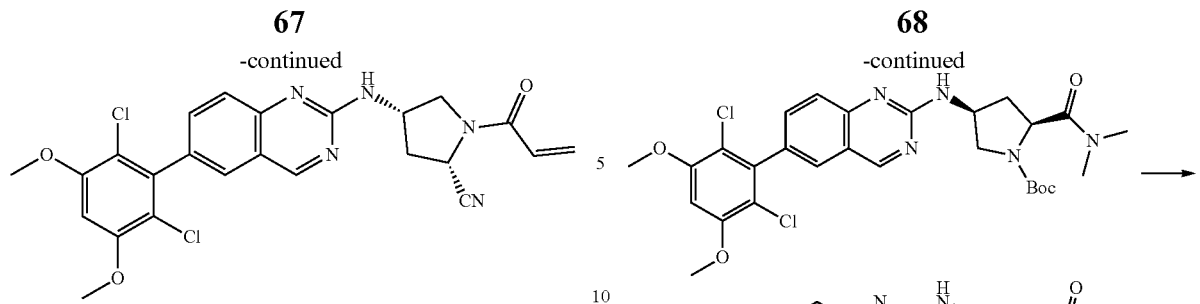

(2S,4S)-4-((6-(2,6-dichloro-3,5-dimethoxyphenyl)quinazolin-2-yl)amino)pyrrolidin-2-carbonitrile (143 mg, 0.322 mmol, 1.0 eq) was dissolved in THF (10 mL), added with triethylamine (162.81 mg, 1.61 mmol, 5.0 eq), cooled to 0° C., slowly added with acryloyl chloride (29.12 mg, 0.322 mmol, 1.0 eq). The completion of the reaction was detected by TLC after reaction for 4 h. A saturated sodium bicarbonate solution (10 mL) was added for solution separation. The aqueous phase was extracted with EA (10 mL×3), and the organic phases were combined and concentrated. The crude product was separated by a thick preparative silica gel plate (PE:EA=2:1) to obtain a solid of (2S,4S)-1-acryloyl-4-((6-(2,6-dichloro-3,5-dimethoxyphenyl)quinazolin-2-yl)amino)pyrrolidin-2-carbonitrile (10 mg, yield: 6%).

$^1$HNMR (400 MHz, DMSO) δ (ppm): 9.04 (s, 1H), 7.72 (m, 1H), 7.60-7.70 (m, 2H), 6.65 (s, 1H), 6.51-6.55 (m, 1H), 6.42-6.51 (m, 1H), 5.81-5.84 (m, 1H), 5.65 (s, 1H), 5.30-5.36 (m, 1H), 4.90 (s, 2H), 4.13-4.16 (m, 1H), 4.01 (s, 6H), 3.98 (m, 1H), 2.74 (m, 1H), 2.50 (m 1H), 2.20 (m, 1H), 2.00 (s, 2), 1.63 (in, 1H).

Molecular formula: $C_{24}H_{21}Cl_2N_5O_3$ Molecular weight: 498.36 LC-MS (m/z)=498.1 [M–H$^+$].

Example 12: Synthesis of (2S,4S)-1-acryloyl-4-((6-(2,6-dichloro-3,5-dimethoxyphenyl)quinazolin-2-yl)amino)-N,N-dimethylpyrrolidin-2-carboxamide (compound 30)

Step 1: Synthesis of 1-tert-butyl 2-methyl (2S,4S)-4-((6-(2,6-dichloro-3,5-dimethoxyphenyl)quinazolin-2-yl)amino)pyrrolidin-1,2-dicarboxylate

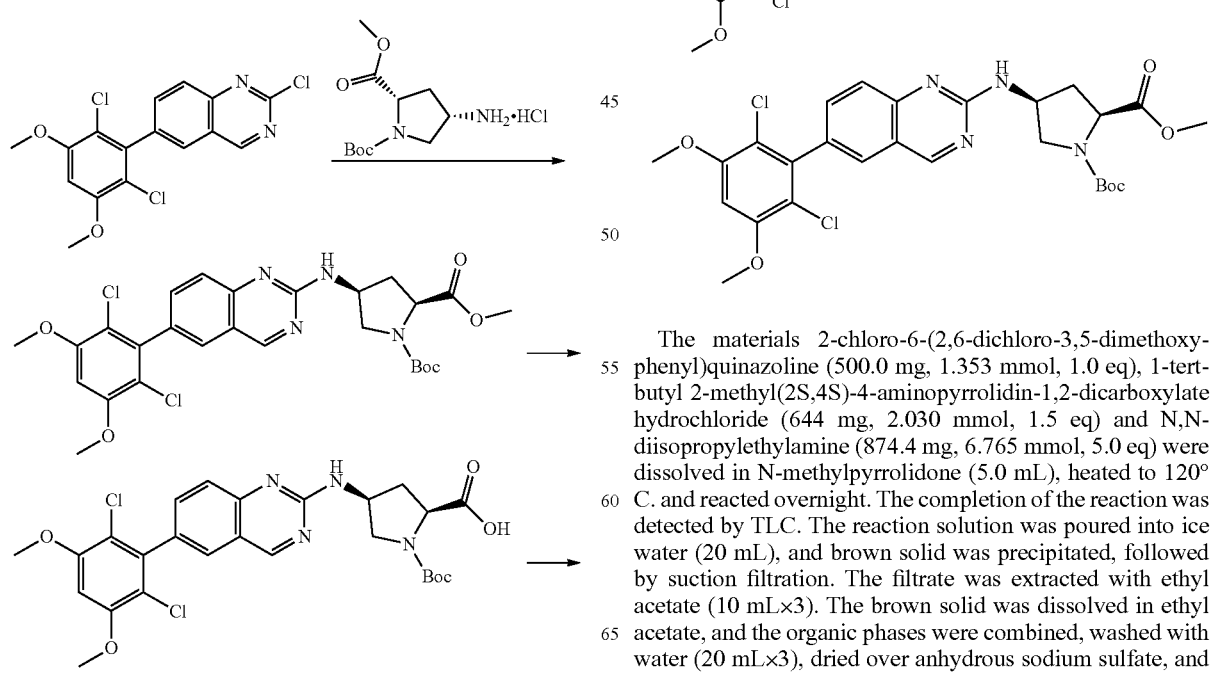

The materials 2-chloro-6-(2,6-dichloro-3,5-dimethoxyphenyl)quinazoline (500.0 mg, 1.353 mmol, 1.0 eq), 1-tert-butyl 2-methyl(2S,4S)-4-aminopyrrolidine-1,2-dicarboxylate hydrochloride (644 mg, 2.030 mmol, 1.5 eq) and N,N-diisopropylethylamine (874.4 mg, 6.765 mmol, 5.0 eq) were dissolved in N-methylpyrrolidone (5.0 mL), heated to 120° C. and reacted overnight. The completion of the reaction was detected by TLC. The reaction solution was poured into ice water (20 mL), and brown solid was precipitated, followed by suction filtration. The filtrate was extracted with ethyl acetate (10 mL×3). The brown solid was dissolved in ethyl acetate, and the organic phases were combined, washed with water (20 mL×3), dried over anhydrous sodium sulfate, and filtered. The filter cake was rinsed with ethyl acetate. The mother liquor was concentrated under reduced pressure and the crude product was subjected to silica gel column chromatography (PE:EA=5:1) to give a solid of 1-tert-butyl 2-methyl (2S,4S)-4-((6-(2,6-dichloro-3,5-dimethoxyphenyl)quinazolin-2-yl)amino)pyrrolidin-1,2-dicarboxylate (384 mg, yield: 49%).

Step 2: Synthesis of (2S,4S)-1-(tert-butoxycarbonyl)-4-((6-(2,6-dichloro-3,5-dimethoxyphenyl)quinazolin-2-yl)amino)pyrrolidin-2-carboxylic Acid

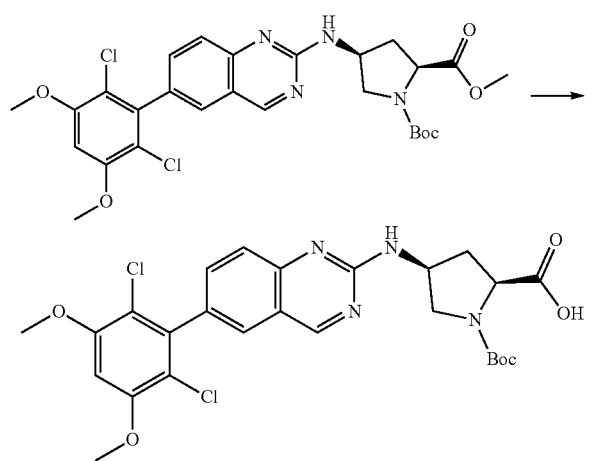

The intermediate 1-tert-butyl 2-methyl(2S,4S)-4-((6-(2,6-dichloro-3,5-dimethoxyphenyl)quinazolin-2-yl)amino) pyrrolidin-1,2-dicarboxylate (300 mg, 0.520 mmol, 1.0 eq) was dissolved in methanol (5 mL), stirred and dissolved, cooled to 0° C., and dropwise added with a solution of lithium hydroxide monohydrate (65 mg, 1.558 mmol, 3.0 eq) in water (1 mL). After reaction for 3 h, TLC was used to detect the residue of material, and the solution of lithium hydroxide monohydrate (65 mg, 1.558 mmol, 3.0 eq) in water (1 mL) was added. Methanol was added to obtain a clarified system and reacted overnight. The completion of the reaction was detected by TLC, and the reaction solution was concentrated under reduced pressure, added with water (10 mL) and methyl tert-butyl ether (10 mL), stirred and separated. Ethyl acetate (20 mL) was added into the aqueous phase and cooled to 0° C. The pH was adjusted to 5-6 with citric acid and the organic phase was separated. The aqueous phase was extracted with ethyl acetate (10 mL). The organic phases were combined and concentrated under reduced pressure to give (2S,4S)-1-(tert-butoxycarbonyl)-4-((6-(2,6-dichloro-3,5-dimethoxyphenyl)quinazolin-2-yl)amino)pyrrolidin-2-carboxylic acid (260 mg, yield: 89%) as a pale yellow solid.

Step 3: Synthesis of tert-butyl (2S,4S)-4-((6-(2,6-dichloro-3,5-dimethoxyphenyl)quinazolin-2-yl)amino)-2-(dimethylcarbamoyl)pyrrolidin-1-carboxylate

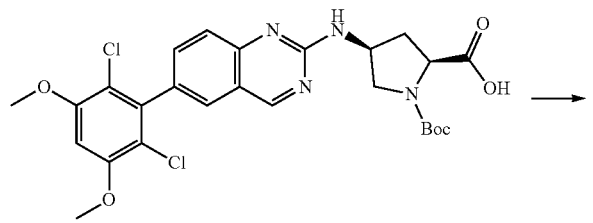

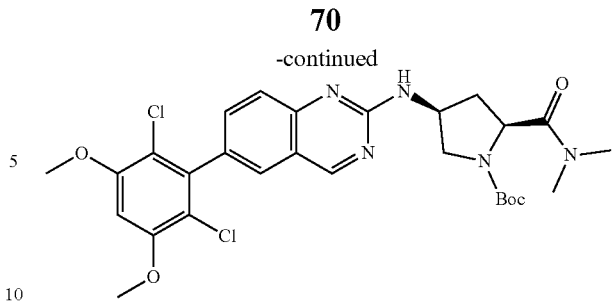

The intermediate (2S,4S)-1-(tert-butoxycarbonyl)-4-((6-(2,6-dichloro-3,5-dimethoxyphenyl)quinazolin-2-yl) amino)pyrrolidin-2-carboxylic acid (200 mg, 0.355 mmol, 1.0 eq) was dissolved in THF (15 mL), added with trimethylamine (107.8 mg, 1.065 mmol, 3.0 eq), cooled to about −15° C., and slowly added with isobutyl chloroformate (48.49 mg, 0.355 mmol, 1.0 eq) diluted with THF. After reaction for 1 h, the completion of the reaction was detected by TLC, and the reaction solution was dropwise added to a dimethylamine/tetrahydrofuran solution (5 mL) cooled to 0° C. After reaction for 4 h, the completion of the reaction was detected by TLC. Saturated potassium carbonate solution (10 mL), saturated brine (10 mL), and EA (20 mL) were added, stirred and separated. The aqueous phase was extracted with EA (10 mL×2). The organic phases were combined, dried and concentrated. The crude product was used in the next step without purification.

Step 4: Synthesis of (2S,4S)-4-((6-(2,6-dichloro-3,5-dimethoxyphenyl)quinazolin-2-yl)amino)-N,N-dimethylpyrrolidin-2-carboxamide

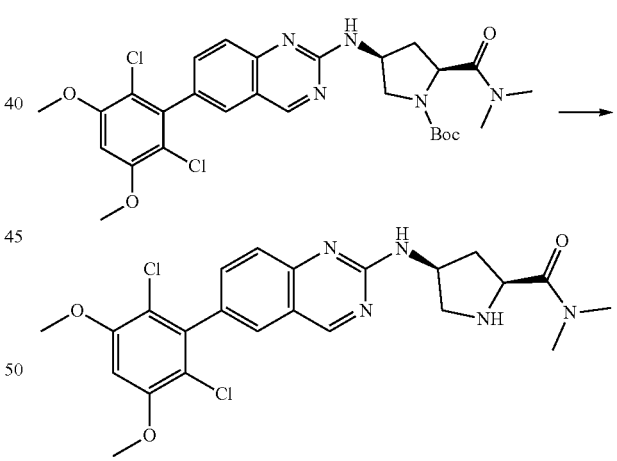

The intermediate tert-butyl (2S,4S)-4-((6-(2,6-dichloro-3,5-dimethoxyphenyl)quinazolin-2-yl)amino)-2-(dimethylcarbamoyl)pyrrolidin-1-carboxylate (the crude product obtained in the previous step) was dissolved in DCM (10 mL), added with trifluoroacetic acid (10 mL), heated to 30° C. and reacted overnight. The completion of the reaction was detected by TLC on the next morning and the reaction solution was concentrated under reduced pressure. The crude product was added to ethyl acetate and concentrated, repeated for three times. MTBE (10 mL) was added, and solid was precipitated, followed by suction filtration to give a solid of (2S,4S)-4-((6-(2,6-dichloro-3,5-dimethoxyphenyl)quinazolin-2-yl)amino)-N,N-dimethylpyrrolidine-2-carboxamide (60 mg, yield: 34%).

Step 5: Synthesis of (2S,4S)-1-acryloyl-4-((6-(2,6-dichloro-3,5-dimethoxyphenyl)quinazolin-2-yl)amino)-N,N-dimethylpyrrolidin-2-carboxamide (Compound 30)

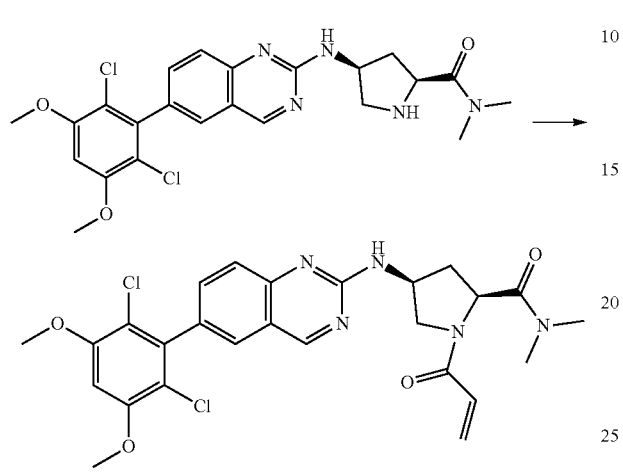

The intermediate (2S,4S)-4-((6-(2,6-dichloro-3,5-dimethoxyphenyl)quinazolin-2-yl)amino)-N,N-dim ethylpyrrolidin-2-carboxamide (60 mg, 0.122 mmol, 1.0 eq) was dissolved in THF (100 mL), added with TEA (61.73 mg, 0.61 mmol, 5.0 eq), cooled to 0° C., and slowly added with acryloyl chloride (11.04 mg, 0.122 mmol, 1.0 eq) diluted with THF. The completion of the reaction was detected by TLC after reaction for 2 h. A saturated sodium bicarbonate solution (10 mL) was added for solution separation. The aqueous phase was extracted with EA (10 mL×3), and the organic phases were combined, concentrated, and separated by a thick preparative silica gel plate (DCM:MeOH=15:1) to obtain a solid of (2S,4S)-1-acryloyl-4-((6-(2,6-dichloro-3,5-dimethoxyphenyl)quinazolin-2-yl)amino)-N,N-dimethyl-pyrrolidin-2-carboxamide (7 mg, yield: 10%).

¹HNMR (400 MHz, DMSO) δ (ppm): 9.17 (s, 1H), 7.81 (s, 1H), 7.69 (s, 1H), 7.50-7.58 (m, 2H), 7.00 (s, 1H), 6.62-6.67 (m, 1H), 6.10-6.14 (m, 1H), 5.66-5.69 (m, 1H), 5.32 (s, 1H), 4.91 (m, 1H), 4.75 (m, 1H), 4.14-4.16 (s, 1H), 3.97 (s, 6H), 3.11 (s, 1H), 3.11-3.32 (m, 2H), 2.85 (s, 3H), 2.00 (m, 2H), 1.23 (s, 6H), 1.10 (s, 2H).

Molecular formula: $C_{26}H_{27}Cl_2N_5O_4$ Molecular weight: 544.43 LC-MS (Neg, m/z)=544.2 [M−H⁺].

Example 13: Synthesis of 1-((2R,4R)-4-((6-(2,6-dichloro-3,5-dimethoxyphenyl)quinazolin-2-yl)amino)-2-(2-hydroxypropyl-2-yl)pyrrolidin-1-yl)prop-2-en-1-one (Compound 31)

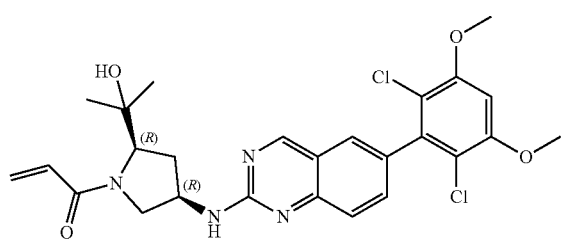

Step 1: Synthesis of 1-(tert-butyl)-2-methyl (2R,4R)-4-((6-(2,6-dichloro-3,5-dimethoxyphenyl)quinazolin-2-yl)amino)pyrrolidin-1,2-dicarboxylate

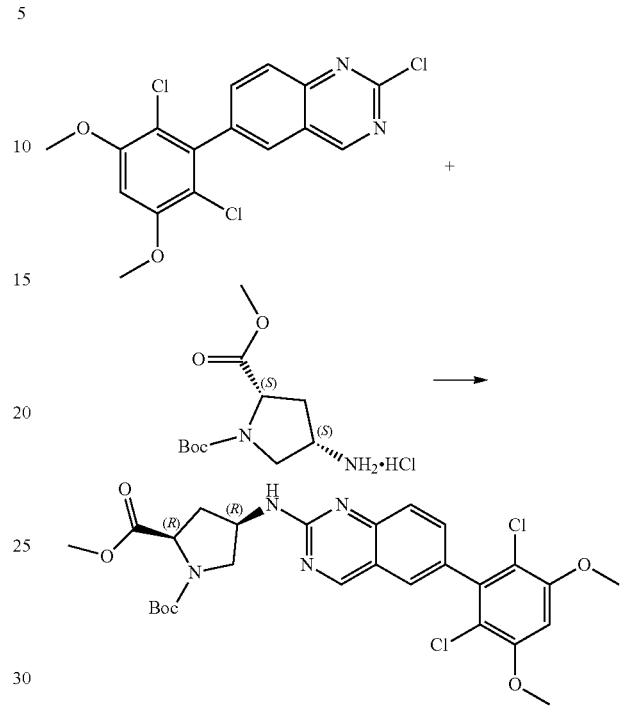

The materials 2-chloro-6-(2,6-dichloro-3,5-dimethoxyphenyl)quinazoline (500.0 mg, 1.353 mmol, 1.0 eq), 1-(tert-butyl)-2-methyl (2R,4R)-4-aminopyrrolidin-1,2-dicarboxylate hydrochloride (644 mg, 2.030 mmol, 1.5 eq) and N,N-diisopropylethylamine (874.4 mg, 6.765 mmol, 5.0 eq) were dissolved in N-methylpyrrolidone (5.0 mL), heated to 120° C. and reacted for 16 h. The completion of the reaction was detected by TLC. The reaction solution was poured into cold water (20 mL), and brown solid was precipitated, followed by suction filtration. The filtrate was extracted with ethyl acetate (10 mL×3). The brown solid was dissolved in ethyl acetate, and the organic phases were combined, washed with water (20 mL×3), dried over anhydrous sodium sulfate, then concentrated under reduced pressure, and subjected to column chromatography (PE:EA=5:1) to give 1-(tert-butyl)-2-methyl (2R,4R)-4-((6-(2,6-dichloro-3,5-dimethoxyphenyl)quinazolin-2-yl)amino)pyrrolidin-1,2-dicarboxylate (384 mg, yield: 49%).

Step 2: Synthesis of Tert-Butyl (2R,4R)-4-((6-(2,6-dichloro-3,5-dimethoxyphenyl)quinazolin-2-yl)amino)-2-(2-hydroxypropyl-2-yl)pyrrolidin-1-carboxylate

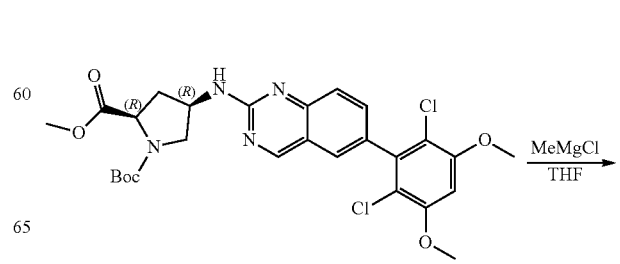

-continued

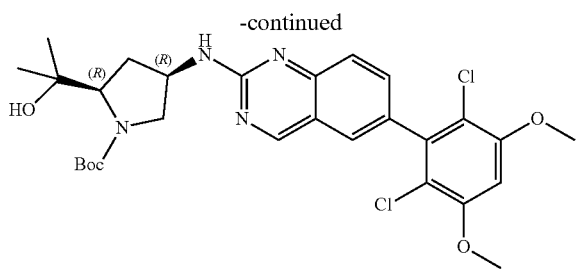

1-(tert-butyl)-2-methyl (2R,4R)-4-((6-(2,6-dichloro-3,5-dimethoxyphenyl)quinazolin-2-yl)amino)pyrrolidin-1,2-dicarboxylate (300 mg, 0.5195 mmol, 1.0 eq) was dissolved in THF (5 mL), stirred to obtain a clarified solution, cooled to 0° C., and dropwise added with a 3M solution of methylmagnesium chloride (0.8 mL, 2.5975 mmol, 5.0 eq) in THF. After reaction for 1 h at 0° C., there was no starting material detected by TLC. A saturated ammonium chloride solution (5 mL) was added followed by extraction with dichloromethane (20 mL×3). After separation, the aqueous phases were discarded. The organic phases were combined, dried over anhydrous sodium sulfate and filtered. The mother liquor was concentrated under reduced pressure to give a crude product. The crude product was subjected to column chromatography, and the eluent was methanol:dichloromethane=1:50. The desirable component was collected and concentrated under reduced pressure to give tert-butyl (2R,4R)-4-((6-(2,6-dichloro-3,5-dimethoxyphenyl)quinazolin-2-yl)amino)-2-(2-hydroxypropyl-2-yl)pyrrolidin-1-carboxylate (150 mg, yield: 50%).

Step 3: Synthesis of 2-((2R,4R)-4-((6-(2,6-dichloro-3,5-dimethoxyphenyl)quinazolin-2-yl)amino)pyrrolidin-2-yl)propan-2-ol

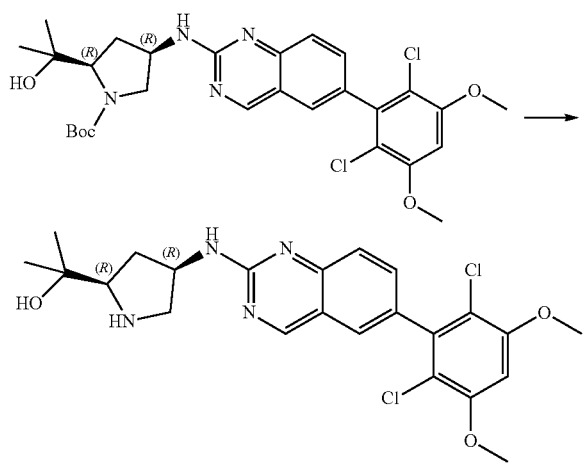

tert-butyl (2R,4R)-4-((6-(2,6-dichloro-3,5-dimethoxyphenyl)quinazolin-2-yl)amino)-2-(2-hydroxypropyl-2-yl) pyrrolidin-1-carboxylate (150 mg, 0.2597 mmol, 1.0 eq) was dissolved in methanol (5 mL), stirred to obtain a clarified solution, cooled to 0° C., dropwise added with 35% hydrochloric acid ethanol solution (5 mL), stirred at room temperature for 2 h. There was no starting material detected by TLC. The reaction solution was concentrated, dissolved by adding THF (50 mL) and concentrated, repeated for three times to give 2-((2R,4R)-4-((6-(2,6-dichloro-3,5-dimethoxyphenyl)quinazolin-2-yl)amino)pyrrolidin-2-yl)propan-2-ol. The next reaction was carried out directly according to the theoretical amount.

Step 4: Synthesis of 1-((2R,4R)-4-((6-(2,6-dichloro-3,5-dimethoxyphenyl)quinazolin-2-yl)amino)-2-(2-hydroxypropyl-2-yl)pyrrolidin-1-yl)prop-2-en-1-one

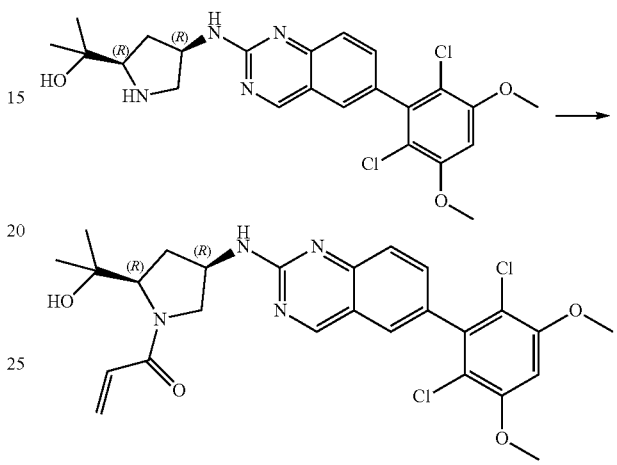

2-((2R,4R)-4-((6-(2,6-dichloro-3,5-dimethoxyphenyl) quinazolin-2-yl)amino)pyrrolidin-2-yl)propan-2-ol (123 mg, 0.2597 mmol, 1.0 eq) was dissolved in THF (10 mL), added with TEA (131 mg, 1.2985 mmol, 5.0 eq), cooled to 0° C., and slowly added with acryloyl chloride (15.7 mg, 0.2597 mmol, 1.0 eq). The completion of the reaction was detected by TLC after reaction for 4 h. A saturated sodium bicarbonate solution (10 mL) was added for solution separation, and the aqueous phase was extracted with EA (10 mL×3). The organic phases were combined, concentrated, and separated by a thick preparative silica gel plate (PE: EA=2:1) to obtain 1-((2R,4R)-4-((6-(2,6-dichloro-3,5-dimethoxyphenyl)quinazolin-2-yl)amino)-2-(2-hydroxypropyl-2-yl)pyrrolidin-1-yl)prop-2-en-1-one (8 mg, yield: 6%).

$^1$HNMR (400 MHz, DMSO) δ (ppm): 9.18 (s, 1H), 7.69 (s, 1H), 7.50-7.57 (d, 3H), 7.01 (s, 1H), 6.21 (m, 1H), 6.17 (m, 1H), 5.76 (m, 1H), 4.44 (s, 6H), 4.24 (m, 1H), 3.51 (m, 1H), 3.22-3.41 (m, 2H), 2.67-2.70 (m, 2H), 1.24 (s, 6H).

Molecular formula: $C_{26}H_{28}Cl_2N_4O_4$, Molecular weight: 531.43, LC-MS (Pos, m/z)=531.1 [M–H$^+$].

Example 14: Synthesis of N-(((2S,4S)-1-acryloyl-4-((6-(2,6-dichloro-3,5-dimethoxyphenyl)quinazolin-2-yl)amino)pyrrolidin-2-yl)methyl)acetamide (Compound 32)

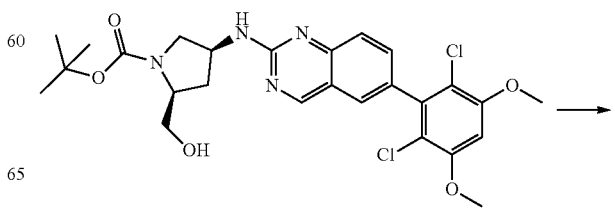

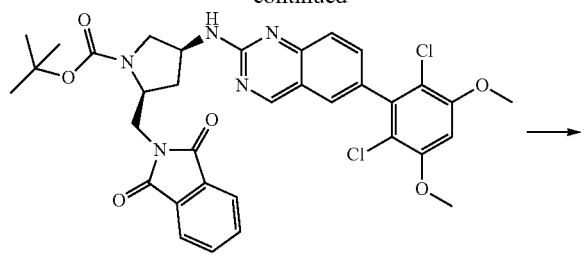
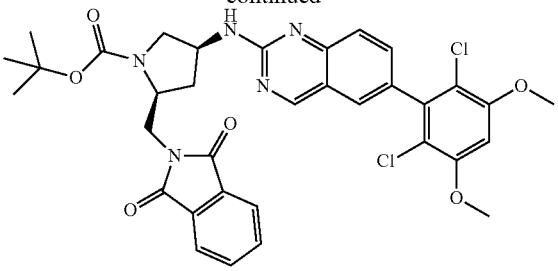

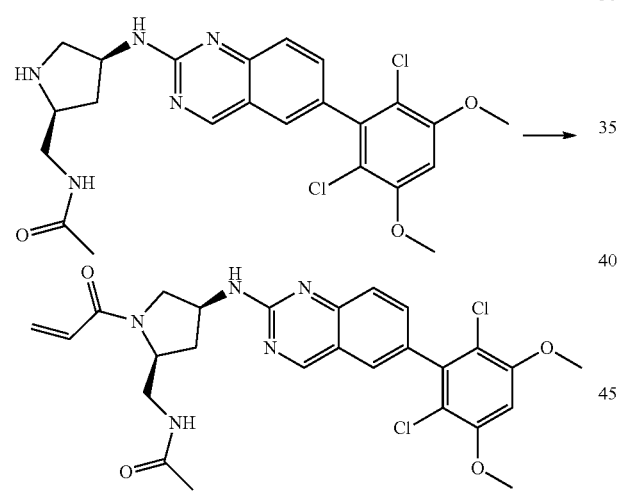

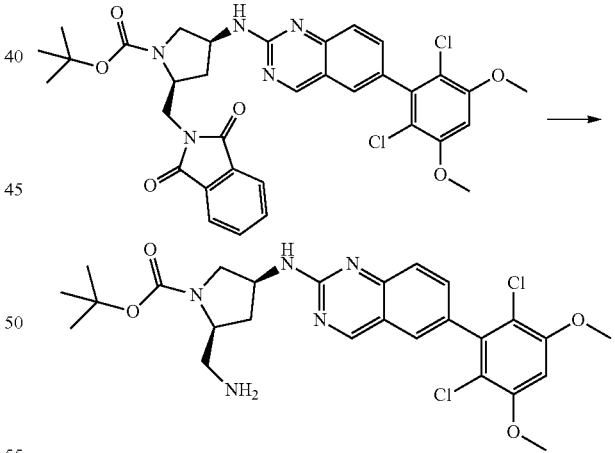

Step 1: Synthesis of Tert-Butyl (2S,4S)-4-((6-(2,6-dichloro-3,5-dimethoxyphenyl)quinazolin-2-yl)amino)-2-((1,3-dioxoisoindolin-2-yl)amino)methyl)pyrrolidin-1-carboxylate Tert-butyl (2S,4S)-4-((6-(2,6-dichloro-3,5-dimethoxyphenyl)quinazolin-2-yl)amino)-2-(hydroxymethyl)pyrrolidin-1-carboxylate (550.0 mg, 1.0 mol, 1.0 eq) was dissolved in tetrahydrofuran (15 mL), added with triphenylphosphine (918.0 mg, 3.5 mmol, 1.5 eq) and phthalimide (206.1 mg, 1.4 mmol, 1.4 eq), cooled to 0° C. in an ice bath, added with diethyl azodicarboxylate (523.0 mg, 3.0 mmol) at 0° C., and slowly warmed to room temperature overnight. The completion of the reaction was detected by TLC, and reaction was quenched with $H_2O$ (2 mL). The solvent was removed by evaporation. $H_2O$ (5 mL) and ethyl acetate (20 mL) were added. The organic phase was separated and concentrated. The crude product was purified by silica gel column chromatography (DCM:MeOH=100:1 to 40:1) to obtain tert-butyl (2S,4S)-4-((6-(2,6-dichloro-3,5-dimethoxyphenyl)quinazolin-2-yl)amino)-2-((1,3-dioxoisoindolin-2-yl)amino)methyl)pyrrolidin-1-carboxylate (600.0 mg, yield: 88.6%) as a yellow colloidal solid.

Step 2: Synthesis of Tert-Butyl (2S,4S)-2-(aminomethyl)-4-((6-(2,6-dichloro-3,5-dimethoxyphenyl)quinazolin-2-yl)amino)pyrrolidin-1-carboxylate Tert-butyl (2S,4S)-4-((6-(2,6-dichloro-3,5-dimethoxyphenyl)quinazolin-2-yl)amino)-2-((1,3-dioxoisoindolin-2-yl)amino)methyl)pyrrolidin-1-carboxylate (600 mg, 0.88 mmol, 1.0 eq) was dissolved in ethanol (12 mL), added with hydrazine hydrate (6 mL), and reacted at room temperature for 2 h. The completion of the reaction was detected by TLC. $H_2O$ (6 mL) was added, and the reaction solution was concentrated. The aqueous phase was extracted with ethyl acetate. The organic phases were combined and dried over anhydrous sodium sulfate. The crude product was purified by silica gel column chromatography (DCM:MeOH=100:1

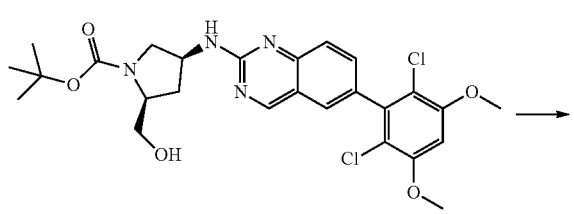

to 40:1) to obtain tert-butyl (2S,4S)-2-(aminomethyl)-4-((6-(2,6-dichloro-3,5-dimethoxyphenyl)quinazolin-2-yl)amino)pyrrolidin-1-carboxylate (500.0 mg, yield 100%) as a yellow colloidal solid.

Step 3: Synthesis of Tert-Butyl (2S,4S)-2-(acetylaminomethyl)-4-((6-(2,6-dichloro-3,5-dimethoxyphenyl)quinazolin-2-yl)amino)pyrrolidin-1-carboxylate

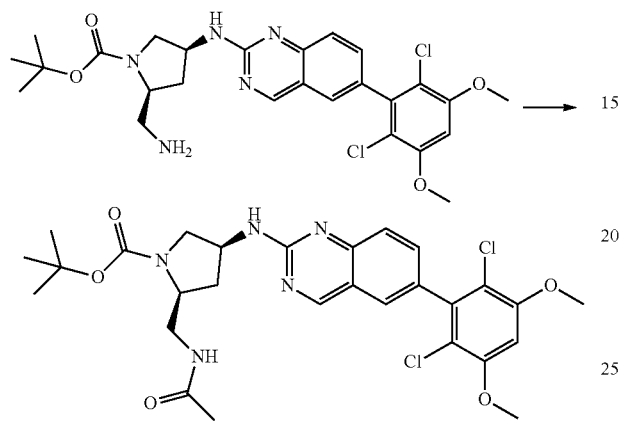

tert-butyl (2S,4S)-2-(aminomethyl)-4-((6-(2,6-dichloro-3,5-dimethoxyphenyl)quinazolin-2-yl)amino)pyrrolidin-1-carboxylate (150.0 mg, 0.274 mmol, 1.0 eq) was dissolved in DCM (3 mL), cooled to 0° C. in an ice bath, added with triethylamine (55.7 mg, 0.55 mmol) and acetic anhydride (30.61 mg, 0.3 mmol), and slowly warmed to room temperature and reacted overnight. The completion of the reaction was detected by TLC. Dichloromethane (5 mL) was added to the reaction solution, and the organic phase was washed with saturated ammonium chloride followed by water and saturated brine, dried over anhydrous magnesium sulfate, filtered and concentrated to give tert-butyl (2S,4S)-2-(acetylaminomethyl)-4-((6-(2,6-dichloro-3,5-dimethoxyphenyl)quinazolin-2-yl)amino)pyrrolidin-1-carboxylate (100.0 mg, yield: 62.1%) as a white colloidal solid.

Step 4: Synthesis of N-(((2S,4S)-4-((6-(2,6-dichloro-3,5-dimethoxyphenyl)quinazolin-2-yl)amino)pyrrolidin-2-yl)methyl)acetamide

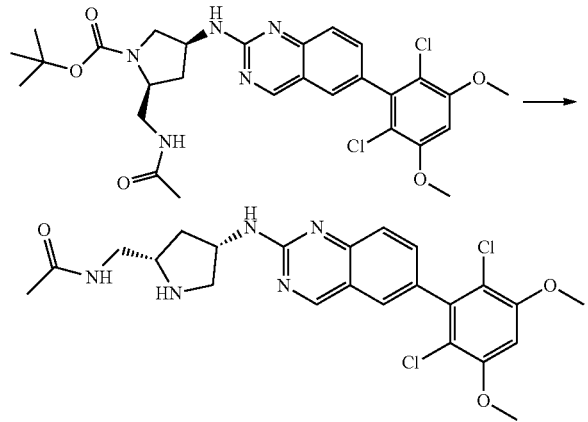

Tert-butyl (2S,4S)-2-(acetylaminomethyl)-4-((6-(2,6-dichloro-3,5-dimethoxyphenyl)quinazolin-2-yl)amino)pyrrolidin-1-carboxylate (100.0 mg, 0.17 mmol, 1.0 eq) was dissolved in DCM (4 mL), cooled to 0° C. in an ice bath, added with trifluoroacetic acid (2 mL) at 0° C., slowly warmed to room temperature overnight and stirred for 2 h. The completion of the reaction was detected by TLC, and the reaction solution was concentrated to dryness to give N-(((2S,4S)-4-((6-(2,6-dichloro-3,5-dimethoxyphenyl)quinazolin-2-yl)amino)pyrrolidin-2-yl)methyl)acetamide (136.0 mg crude) as a yellow colloidal solid.

Step 5: Synthesis of N-(((2S,4S)-1-acryloyl-4-((6-(2,6-dichloro-3,5-dimethoxyphenyl)quinazolin-2-yl)amino)pyrrolidin-2-yl)methyl)acetamide (Compound 32)

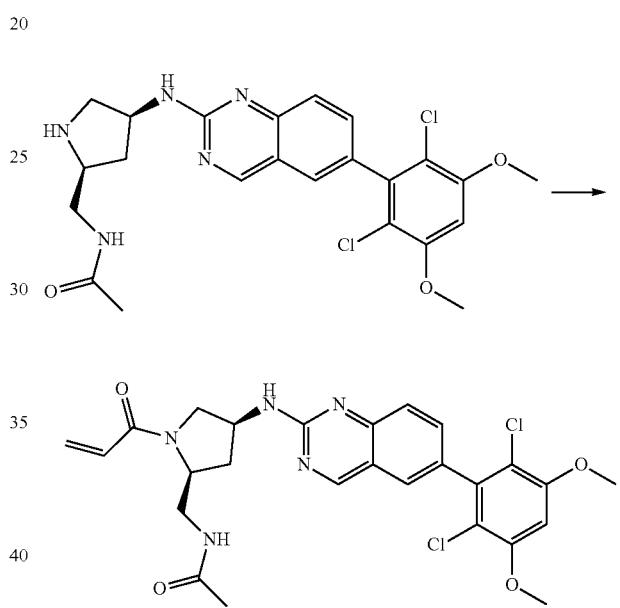

N-(((2S,4S)-4-((6-(2,6-dichloro-3,5-dimethoxyphenyl)quinazolin-2-yl)amino)pyrrolidin-2-yl)methyl)acetamide (134.0 mg crude, 0.17 mmol, 1.0 eq) was dissolved in DCM (2 mL), cooled to 0° C. in an ice bath, added with triethylamine (83.2 mg, 0.822 mmol) and acryloyl chloride (37.2 mg, 0.41 mmol) at 0° C., slowly warmed to room temperature and stirred for 2 h. The completion of the reaction was detected by TLC, and the reaction solution was concentrated. The crude product was subjected to silica gel column chromatography (DCM:MeOH=200:1 to 100:1) to obtain N-(((2S,4S)-1-acryloyl-4-((6-(2,6-dichloro-3,5-dimethoxyphenyl)quinazolin-2-yl)amino)pyrrolidin-2-yl)methyl)acetamide (20.0 mg, yield 13.3%) as a white solid.

$^1$HNMR (400 MHz, CDCl$_3$) δ (ppm): 9.19 (s, 1H), 8.14-7.91 (m, 2H), 7.89 (s, 1H), 7.70-7.51 (m, 2H), 7.01 (s, 1H), 6.80-6.55 (m, 2H), 6.23-6.17 (t, 1H), 5.72-5.66 (t, 1H), 4.48-4.45 (t, 1H), 4.18-4.10 (m, 2H), 4.08 (s, 6H), 3.53-3.49 (m, 1H), 3.21-3.11 (m, 1H), 2.33-3.32 (d, 1H), 2.01-1.99 (d, 1H), 1.85-1.81 (d, 3H).

Molecular formula: $C_{26}H_{27}Cl_2N_5O_4$ Molecular weight: 544.43 LC-MS (Pos, m/z)=544.2 [M+H$^+$].

Example 15: Synthesis of N-(((2S,4S)-1-acryloyl-4-((6-(2,6-dichloro-3,5-dimethoxyphenyl)quinazolin-2-yl)amino)pyrrolidin-2-yl)methyl)methanesulfonamide (Compound 33)

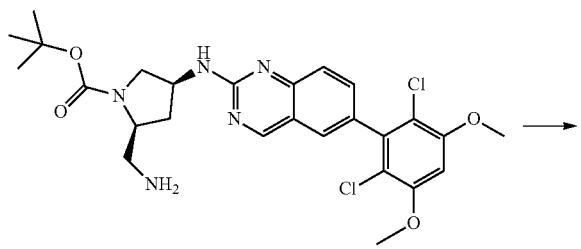

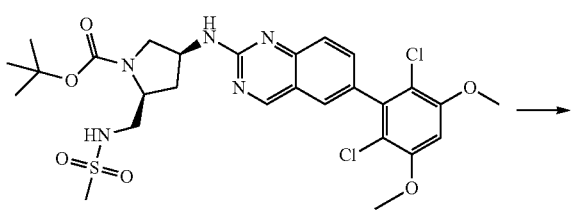

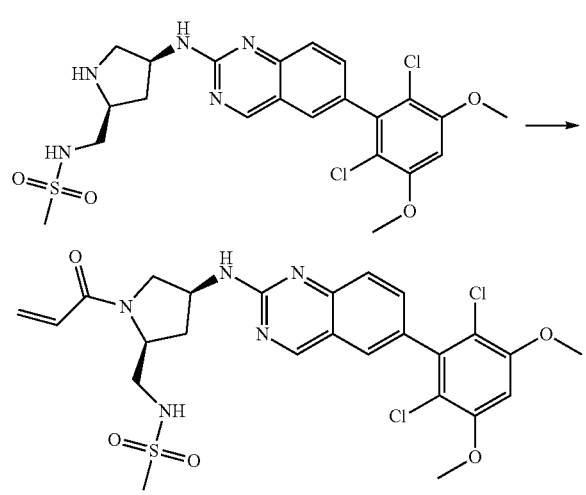

Step 1: Synthesis of Tert-Butyl (2S,4S)-4-((6-(2,6-dichloro-3,5-dimethoxyphenyl)quinazolin-2-yl)amino)-2-(methylsulfonylaminomethyl)pyrrolidin-1-carboxylate

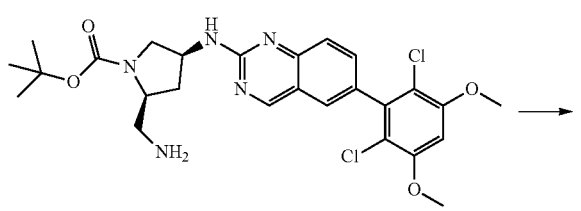

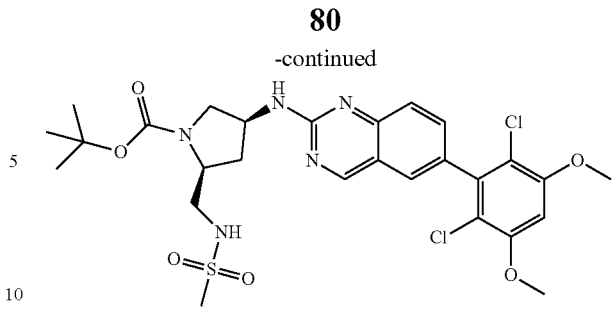

The intermediate tert-butyl (2S,4S)-2-(aminomethyl)-4-((6-(2,6-dichloro-3,5-dimethoxyphenyl)quinazolin-2-yl)amino)pyrrolidin-1-carboxylate (150.0 mg, 0.274 mmol, 1.0 eq) was dissolved in DCM (3 mL), cooled to 0° C. in an ice bath, added with trimethylamine (55.7 mg, 0.55 mmol), then added with methanesulfonyl chloride (36.9 mg, 0.324 mmol) at 0° C., slowly warmed to room temperature and reacted overnight. The completion of the reaction was detected by TLC. Dichloromethane (5 mL) was added to the reaction solution, and the organic phase was washed with saturated ammonium chloride, water and saturated brine successively, dried over anhydrous magnesium sulfate, filtered and concentrated to give tert-butyl (2S,4S)-4-((6-(2,6-dichloro-3,5-dimethoxyphenyl)quinazolin-2-yl)amino)-2-(methylsulfonylaminomethyl)pyrrolidin-1-carboxylate (90.0 mg, yield: 53.3%) as a yellow colloidal solid.

Step 2: Synthesis of N-(((2S,4S)-4-((6-(2,6-dichloro-3,5-dimethoxyphenyl)quinazolin-2-yl)amino)pyrrolidin-2-yl)methyl)methanesulfonamide

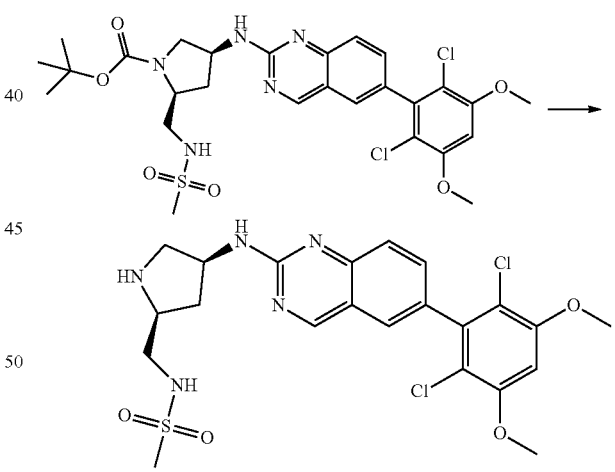

Tert-butyl (2S,4S)-4-((6-(2,6-dichloro-3,5-dimethoxyphenyl)quinazolin-2-yl)amino)-2-(methylsulfonylaminomethyl)pyrrolidin-1-carboxylate (90.0 mg, 0.27 mmol, 1.0 eq) was dissolved in DCM (4 mL), cooled to 0° C. in an ice bath, added with trifluoroacetic acid (2 mL), and slowly warmed to room temperature overnight and stirred for 2 h. The completion of the reaction was detected by TLC, and the reaction solution was concentrated in vacuum to give N-(((2S,4S)-4-((6-(2,6-dichloro-3,5-dimethoxyphenyl)quinazolin-2-yl)amino)pyrrolidin-2-yl)methyl)methanesulfonamide (142.0 mg, yield: 100%).

Step 3: Synthesis of N-(((2S,4S)-1-acryloyl-4-((6-(2,6-dichloro-3,5-dimethoxyphenyl)quinazolin-2-yl)amino)pyrrolidin-2-yl)methyl)methanesulfonamide (Compound 33)

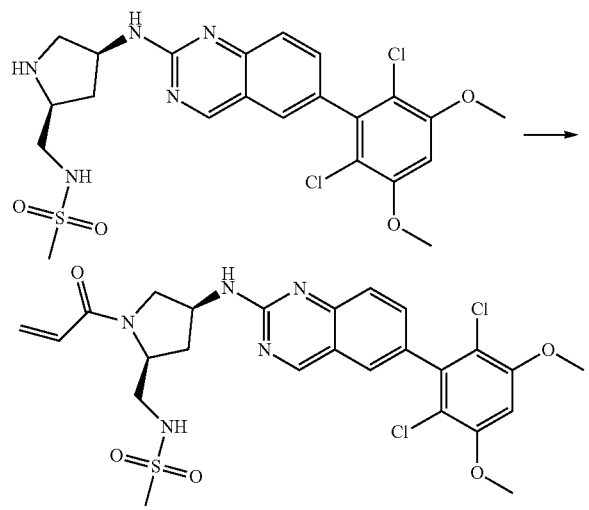

N-(((2S,4S)-4-((6-(2,6-dichloro-3,5-dimethoxyphenyl)quinazolin-2-yl)amino)pyrrolidin-2-yl)methyl)methanesulfonamide (141.8 mg, 0.27 mmol, 1.0 eq) was dissolved in THF (2 mL), cooled to 0° C. in an ice bath, added with triethylamine (83.2 mg, 0.822 mmol) and acryloyl chloride (37.2 mg, 0.41 mmol) successively, slowly warmed to room temperature and stirred for 2 h. The completion of the reaction was detected by TLC, and the reaction solution was concentrated. The crude product was subjected to silica gel column chromatography (DCM:MeOH=200:1 to 100:1) to obtain N-(((2S,4S)-1-acryloyl-4-((6-(2,6-dichloro-3,5-dimethoxyphenyl)quinazolin-2-yl)amino)pyrrolidin-2-yl)methyl)methanesulfonamide (compound 33) (21.0 mg, yield 13.3%) as a white solid.

$^1$HNMR (400 MHz, CDCl$_3$) δ (ppm): 9.19 (s, 1H), 7.81-7.80 (d, 1H), 7.70 (s, 1H), 7.59-7.51 (m, 2H), 7.30-7.17 (m, 1H), 7.01 (s, 1H), 6.80-6.55 (m, 2H), 6.23-6.17 (t, 1H), 5.72-5.66 (t, 1H), 4.48-4.45 (t, 1H), 4.18-4.10 (m, 2H), 4.08 (s, 6H), 3.53-3.49 (m, 1H), 3.21-3.11 (m, 1H), 2.73 (s, 3H), 2.33-3.32 (d, 1H), 2.01-1.99 (d, 1H).

Molecular formula: C$_{25}$H$_{27}$Cl$_2$N$_5$O$_5$S Molecular weight: 580.48 LC-MS (Pos, m/z)=580.1 [M+H$^+$].

Example 16: Synthesis of 1-((2S,4S)-2-(azetidine-1-carbonyl)-4-((6-(2,6-dichloro-3,5-dimethoxyphenyl)quinazolin-2-yl)amino)pyrrolidin-1-yl)prop-2-en-1-one (Compound 35)

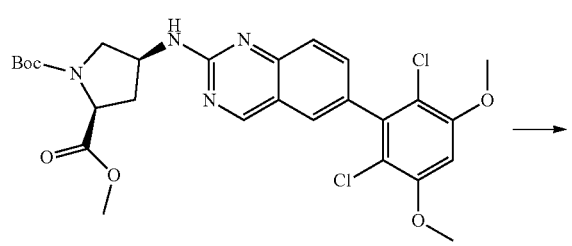

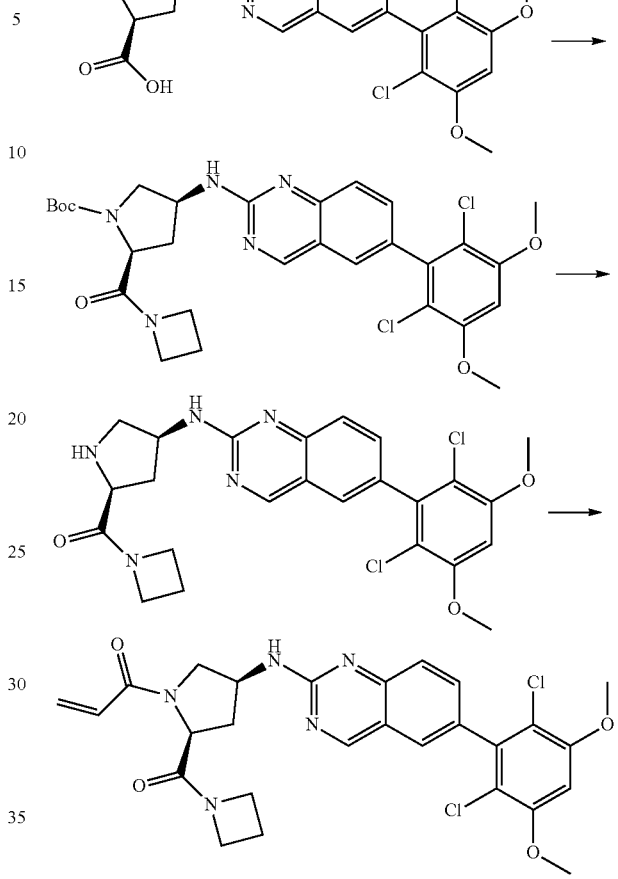

Step 1: Synthesis of (2S,4S)-1-(tert-butoxycarbonyl)-4-((6-(2,6-dichloro-3,5-dimethoxyphenyl)quinazolin-2-yl)amino)pyrrolidin-2-carboxylic Acid

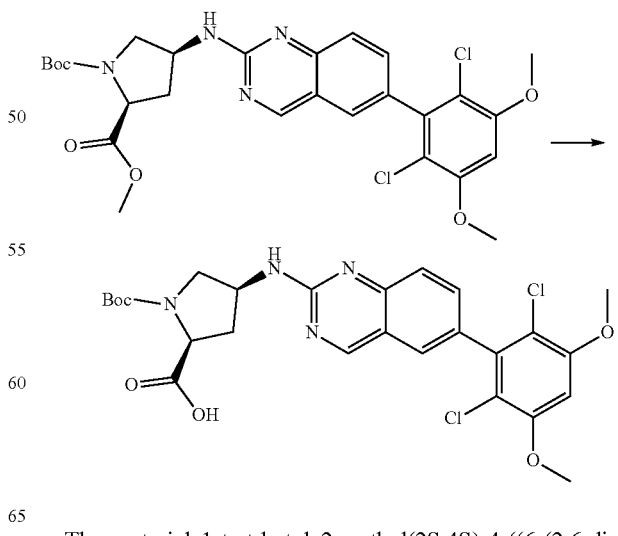

The material 1-tert-butyl 2-methyl(2S,4S)-4-((6-(2,6-dichloro-3,5-dimethoxyphenyl)quinazolin-2-yl)amino) pyrrolidin-1,2-dicarboxylate (400.7 mg, 0.69 mmol, 1.0 eq) was dissolved in methanol (6 mL), cooled to 0° C., added with an aqueous solution (3 ml) of lithium hydroxide monohydrate (87.34 mg, 2.08 mmol, 3.0 eq), then slowly warmed to room temperature and stirred overnight. The completion of the reaction was detected by TLC. The reaction solution was concentrated, pulped with methyl tert-butyl ether (5 mL) for 30 min, and then filtered by suction. The filter cake was dissolved in water (10 mL). The pH was adjusted to 5-6 with aqueous saturated sodium bicarbonate solution, followed by extraction with DCM (20 mL×1). The organic phase was dried over anhydrous sodium sulfate, filtered by suction and concentrated to give (2S,4S)-1-(tert-butoxycarbonyl)-4-((6-(2,6-dichloro-3,5-dimethoxyphenyl)quinazol in-2-yl) amino)pyrrolidin-2-carboxylic acid (288.7 mg, yield: 73.8%).

Step 2: Synthesis of Tert-Butyl (2S,4S)-2-(azetidine-1-carbonyl)-4-((6-(2,6-dichloro-3,5-dimethoxyphenyl)quinazolin-2-yl)amino)pyrrolidin-1-carboxylate

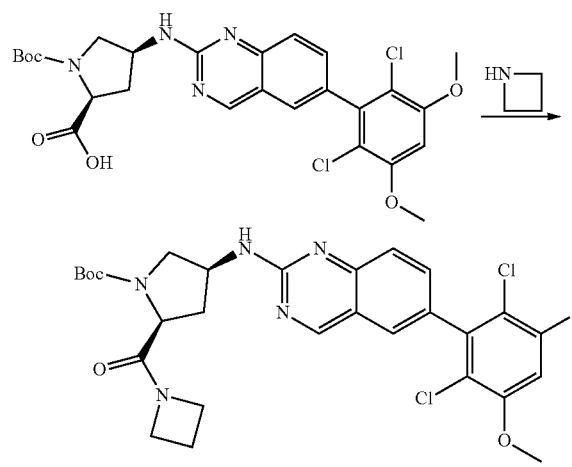

(2S,4S)-1-(tert-butoxycarbonyl)-4-((6-(2,6-dichloro-3,5-dimethoxyphenyl)quinazol in-2-yl)amino)pyrrolidin-2-carboxylic acid (421.3 mg, 0.74 mmol, 1.0 eq) was dissolved in a mixed solvent of tetrahydrofuran (6 mL) and acetonitrile (1 mL), cooled to 0° C. under stirring, slowly added with 2-(7-O-benzotriazole)-N,N,N',N'-tetramethyluronium hexafluorophosphate (312.7 mg, 0.82 mmol, 1.1 eq) in batches, and then dropwise added with N,N-diisopropylethylamine (193.1 mg, 1.49 mmol, 2.0 eq). After the dropwise addition, the reaction was carried out at 0° C. for 1 h. A solution of azetidine (42.68 mg, 0.74 mmol, 1.0 eq) in tetrahydrofuran (0.5 mL) was added dropwise. After that, the mixture was warmed to room temperature and stirred overnight under nitrogen atmosphere. The completion of the reaction was detected by TLC. The system was concentrated, added with saturated aqueous sodium chloride (30 mL), and extracted with ethyl acetate (3×10 mL). The organic phase was dried over anhydrous sodium sulfate, filtered by suction, and concentrated. The crude product was purified by column chromatography (200-300 mesh silica gel, dichloromethane:methanol=200:1 to 100:1) to give tert-butyl (2S,4S)-2-(azetidine-1-carbonyl)-4-((6-(2,6-dichloro-3,5-dimethoxyphenyl)quinazolin-2-yl)amino)pyrrolidin-1-carboxylate (194.3 mg, yield: 43.1%).

Step 3: Synthesis of azetidine-1-yl ((2S,4S)-4-((6-(2,6-dichloro-3,5-dimethoxyphenyl)quinazolin-2-amino)pyrrolidin-2-yl)methanone

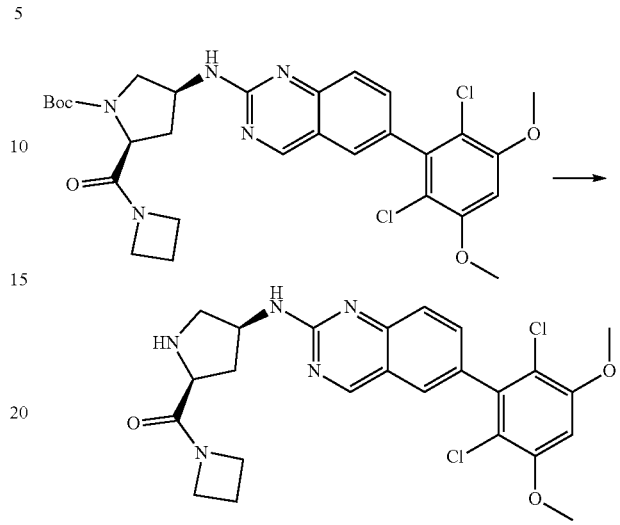

Tert-butyl (2S,4S)-2-(azetidine-1-carbonyl)-4-((6-(2,6-dichloro-3,5-dimethoxyphenyl)quinazolin-2-yl)amino)pyrrolidin-1-carboxylate (194.3 mg, 0.32 mmol, 1.0 eq) was dissolved in DCM (5 mL), cooled to 0° C., and dropwise added with trifluoroacetic acid (5 mL). After the addition, the mixture was warmed to room temperature and reacted for 2.5 h. The completion of the reaction was detected by TLC, and the temperature of the system was cooled to 0° C. The pH of the system was adjusted to 7-8 with a saturated sodium carbonate aqueous solution, followed by extraction by adding dichloromethane (3×10 mL). The organic phase was dried over anhydrous sodium sulfate, filtered by suction, and concentrated to give azetidine-1-yl ((2S,4S)-4-((6-(2,6-dichloro-3,5-dimethoxyphenyl)quinazolin-2-amino)pyrrolidin-2-yl)methanone (151.1 mg, yield: 93.2%).

Step 4: Synthesis of 1-((2S,4S)-2-(azetidine-1-carbonyl)-4-((6-(2,6-dichloro-3,5-dimethoxyphenyl)quinazolin-2-yl)amino)pyrrolidin-1-yl)prop-2-en-1-one (Compound 35)

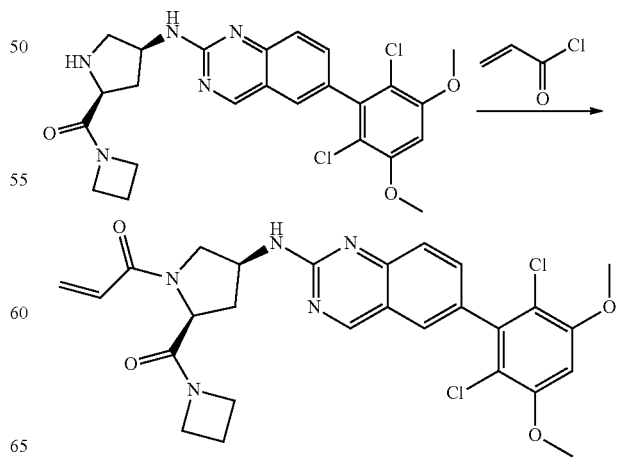

Azetidine-1-yl((2S,4S)-4-(6-(2,6-dichloro-3,5-dimethoxyphenyl)quinazolin-2-amino)pyrrolidin-2-yl)methanone (150 mg, 0.32 mmol, 1.0 eq) was dissolved in THF (3 mL), cooled to 0° C., dropwise added with triethylamine (65.2 mg, 0.64 mmol, 2.0 eq) and acryloyl chloride (35.0 mg, 0.39 mmol, 1.2 eq) successively. After the addition, the mixture was gradually warmed to room temperature and stirred for 4 h. The completion of the reaction was detected by TLC. A saturated aqueous ammonium chloride solution was added, followed by extraction with ethyl acetate (3×10 mL). The organic phases were combined and dried over anhydrous sodium sulfate, filtered by suction, and concentrated. The crude product was purified by column chromatography (200-300 mesh silica gel, dichloromethane:methanol=100:1) to give a product of 1-((2S,4S)-2-(azetidine-1-carbonyl)-4-((6-(2,6-dichloro-3,5-dimethoxyphenyl)quinazolin-2-yl)amino)pyrrolidin-1-yl)prop-2-en-1-one (41.0 mg, yield: 22.3%).

¹HNMR (400 MHz, DMSO) δ (ppm): 9.18 (s, 1H), 7.95 (s, 1H), 7.51-7.70 (m, 3H), 7.01 (s, 1H), 6.61-6.65 (m, 1H), 6.14-6.19 (m, 1H), 5.69-5.76 (m, 1H), 4.74 (m, 1H), 4.41-4.48 (m, 4H), 1.11-1.12 (s, 6H), 3.84-3.92 (m, 1H), 3.50-3.54 (t, 1H), 1.90-1.91 (m, 1H), 2.55-2.89 (m, 1H).

Molecular formula: $C_{27}H_{27}Cl_{12}N_5O_4$ Molecular weight: 555.14 LC-MS(Neg, m/z)=556.2 [M+H⁺].

Example 17: Synthesis of ethyl (2S,4S)-1-acryloyl-4-((6-(2,6-dichloro-3,5-dimethoxyphenyl)quinazolin-2-yl)amino)pyrrolidin-2-carboxylate (Compound 36)

Step 1: Synthesis of Ethyl (2S,4S)-4-((6-(2,6-dichloro-3,5-dimethoxyphenyl)quinazolin-2-yl)amino)pyrrolidin-2-carboxylate

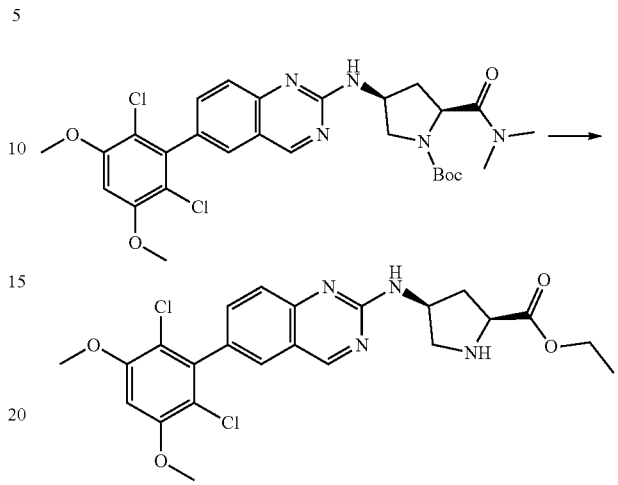

The intermediate tert-butyl (2S,4S)-4-((6-(2,6-dichloro-3,5-dimethoxyphenyl)quinazolin-2-yl)amino)-2-(dimethylcarbamoyl)pyrrolidin-1-carboxylate (183 mg, 0.310 mmol, 1.0 eq) was dissolved into HCl-ethanol (15 mL), and reacted for 3 h at 45° C. The completion of the reaction was detected by TLC. The reaction solution was concentrated. The crude product was dissolved in THF and concentrated, repeated for three times. The crude product was used in the next step without purification (theoretical amount: 170 mg).

Step 2: Synthesis of Ethyl (2S,4S)-1-acryloyl-4-((6-(2,6-dichloro-3,5-dimethoxyphenyl)quinazolin-2-yl)amino)pyrrolidin-2-carboxylate (Compound 36)

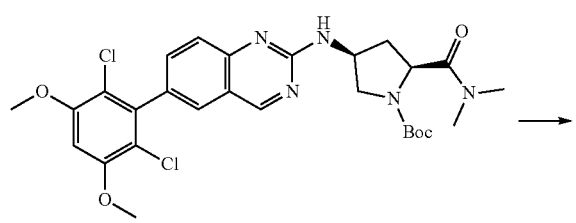

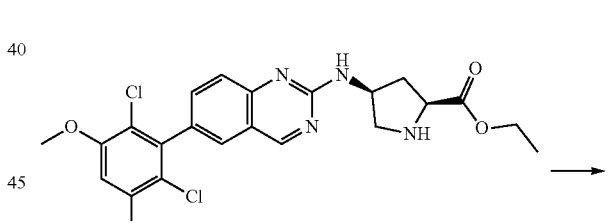

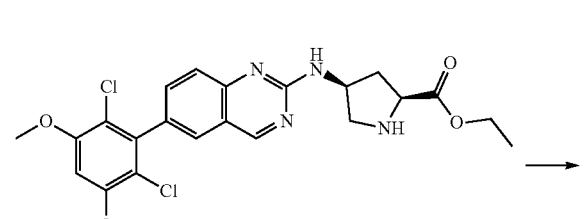

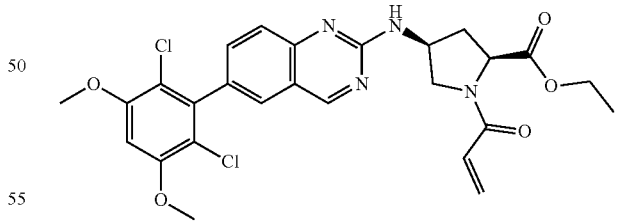

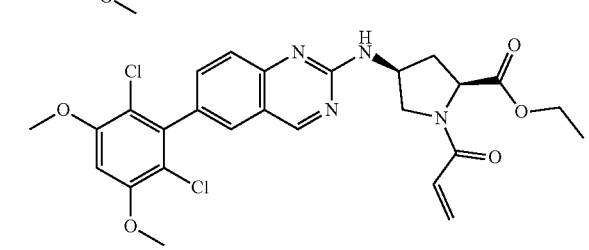

The intermediate ethyl (2S,4S)-4-((6-(2,6-dichloro-3,5-dimethoxyphenyl) quinazolin-2-yl)amino)pyrrolidin-2-carboxylate (170 mg, 0.347 mmol, 1.0 eq) was dissolved in THF (15 mL), added with trimethylamine (175.6 mg, 1.735 mmol, 5.0 eq), cooled to 0° C., and slowly added with acryloyl chloride (31.4 mg, 0.347 mmol, 1.0 eq) diluted with THF. After reaction for 2 h, the completion of the reaction was detected by TLC, and saturated sodium bicarbonate solution (10 mL) was added. After separation, the aqueous phase was extracted with EA (10 mL×3), and the organic phases were combined, concentrated, and separated by thin layer chromatography (DCM:MeOH=15:1) to give a solid of ethyl (2S,4S)-1-acryloyl-4-((6-(2,6-dichloro-3,5-dimethoxyphenyl)quinazolin-2-yl)amino)pyrrolidin-2-carboxylate (21 mg, yield: 11%).

¹HNMR (400 MHz, DMSO) δ (ppm): 9.02 (s, 1H), 7.70 (m, 1H), 7.68 (s, 2H), 6.66 (s, 1H), 6.45-6.47 (m, 2H), 6.11-6.13 (m, 1H), 5.73-5.76 (m, 1H), 5.00 (s, 1H), 4.66 (m, 1H), 4.28 (m, 2H), 4.12-4.14 (m, 1H), 3.99 (s, 6H), 3.77-3.80 (m, 1H), 2.69 (m, 1H), 2.15 (m, 1H), 1.23-1.25 (m, 2H), 1.25-1.27 (m, 3H).

Molecular formula: $C_{26}H_{26}Cl_2N_4O_5$ Molecular weight: 545.42 LC-MS (Pos, m/z)=545.1 [M−H⁺].

Example 18: Synthesis of 1-((2S,4S)-4-((6-(2,6-dichloro-3,5-dimethoxyphenyl)quinazolin-2-yl)amino)-2-(methoxymethyl)pyrrolidin-1-yl)prop-2-en-1-one (Compound 53)

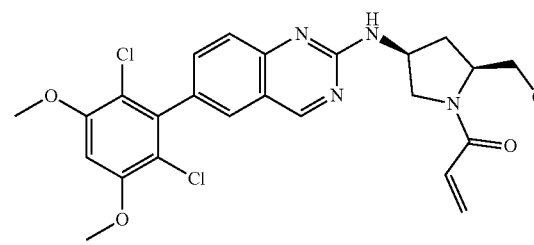

Step 1: Synthesis of Tert-Butyl (2S,4S)-4-((6-(2,6-dichloro-3,5-dimethoxyphenyl)quinazolin-2-yl)amino)-2-(methoxymethyl)pyrrolidin-1-carboxylate

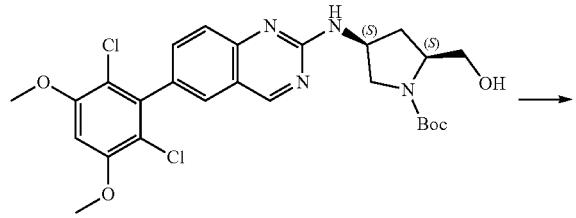

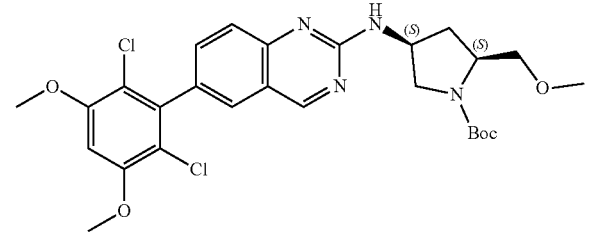

The materials tert-butyl (2S,4S)-4-((6-(2,6-dichloro-3,5-dimethoxyphenyl)quinazolin-2-yl)amino)-2-(hydroxymethyl)pyrrolidin-1-carboxylate (210 mg, 0.382 mmol, 1.0 eq) and sodium tert-butoxide (91.78 mg, 0.955 mmol, 2.5 eq) were dissolved in THF (10 mL), cooled to 0° C., and stirred for 1 h. Then iodomethane (108.44 mg, 0.764 mmol, 2.0 eq) diluted with THF (1 mL) was injected to react overnight. It is detected by TLC that a small amount of starting material was remained on next morning. Saturated ammonium chloride solution (10 mL) and DCM (20 mL) were added for solution separation. There is no product detected by TLC in the aqueous phase. The organic phase was dried, concentrated, and subjected to the column chromatography (PE:EA=5:1) to give tert-butyl (2S,4S)-4-((6-(2,6-dichloro-3,5-dimethoxyphenyl)quinazolin-2-yl)amino)-2-(methoxymethyl)pyrrolidin-1-carboxylate (200 mg, yield: 93%).

Step 2: Synthesis of 6-(2,6-dichloro-3,5-dimethoxyphenyl)-N-((3S,5S)-5-(methoxymethyl)pyrrolidin-3-yl)quinazolin-2-amine

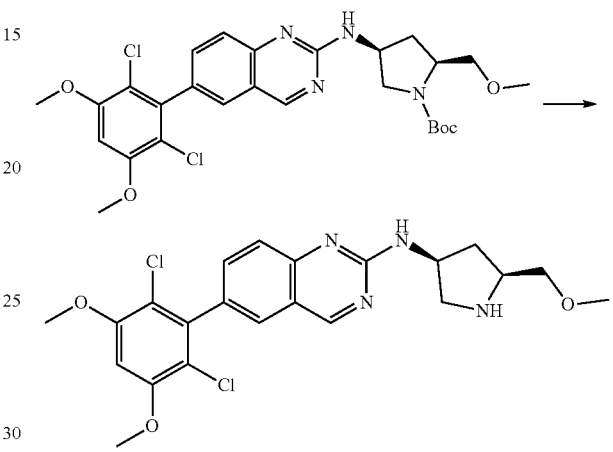

The intermediate tert-butyl (2S,4S)-4-((6-(2,6-dichloro-3,5-dimethoxyphenyl)quinazolin-2-yl)amino)-2-(methoxymethyl)pyrrolidin-1-carboxylate (200 mg, 0.355 mmol, 1.0 eq) was dissolved in DCM (5 mL), stirred to obtain a clarified solution, cooled to 0° C., and added with trifluoroacetic acid (5 mL). After reaction for 1.5 h, the completion of the reaction was detected by TLC. The reaction solution was concentrated, dissolved by adding THF (50 mL) and concentrated, repeated for three times. The crude product was used in the next step.

Step 3: Synthesis of 1-((2S,4S)-4-((6-(2,6-dichloro-3,5-dimethoxyphenyl)quinazolin-2-yl)amino)-2-(methoxymethyl)pyrrolidin-1-yl)prop-2-en-1-one

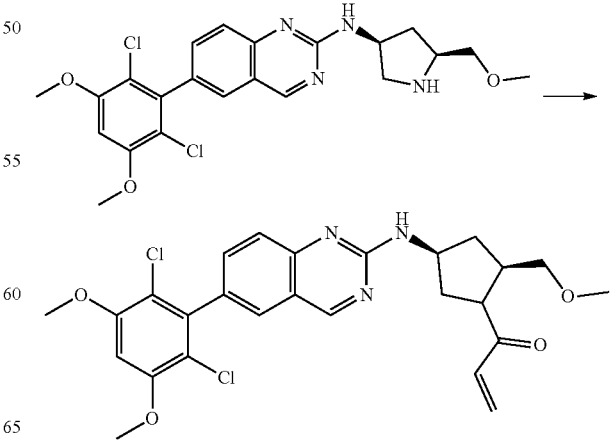

The intermediate 6-(2,6-dichloro-3,5-dimethoxyphenyl)-N-((3S,5S)-5-(methoxymethyl)pyrrolidin-3-yl)quinazolin-2-amine (160 mg, 0.345 mmol, 1.0 eq) and triethylamine (174.55 mg, 1.725 mmol, 5.0 eq) were dissolved in THF (10 mL), cooled to 0° C. Acryloyl chloride (31.22 mg, 0.345 mmol, 1.0 eq) diluted with THF (1 mL) was injected to react overnight. The completion of the reaction was detected by TLC on the next morning. Saturated sodium bicarbonate solution (10 mL) and EA (20 mL) were added for solution separation. The aqueous phase was extracted with EA. There is no product detected by TLC in the aqueous phase. The organic phases were combined, dried, concentrated, and subjected to the column chromatography (PE:EA=5:1 to 3:1) to obtain 1-((2S,4S)-4-((6-(2,6-dichloro-3,5-dimethoxyphenyl)quinazolin-2-yl)amino)-2-(methoxymethyl)pyrrolidin-1-yl)prop-2-en-1-one (34 mg, yield: 19%).

$^1$HNMR (400 MHz, DMSO) δ (ppm): 9.19 (s, 1H), 7.80 (s, 1H), 7.69 (s, 1H), 7.51-7.59 (m, 2H), 7.02 (s, 1H), 6.70-6.75 (m, 1H), 6.57-6.70 (m, 1H), 6.18 (m, 1H), 5.67-5.76 (m, 1H), 4.44-4.52 (m, 2H), 4.22-4.36 (m, 2H), 3.98 (s, 6H), 3.61 (s, 1H), 3.28-3.32 (m, 1H), 3.22 (s, 3H), 2.02 (s, 1H), 1.23 (s, 1H). Molecular formula: $C_{25}H_{26}Cl_2N_4O_4$, Molecular weight: 517.41, LC-MS (Neg, m/z)=517.2 [M–H$^+$].

Example 19: Synthesis of 1-((2S,4S)-4-((6-(2,6-dichloro-3,5-dimethoxyphenyl)quinazolin-2-yl)amino)-2-(pyrrolidin-1-carbonyl)pyrrolidin-1-yl)prop-2-en-1-one (Compound 55)

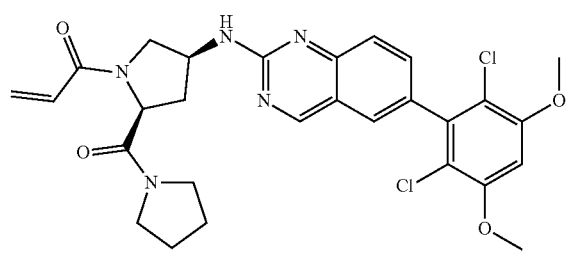 [SMILES: C=CC(=O)N1C[C@@H](Nc2ncc3cc(-c4c(Cl)c(OC)cc(OC)c4Cl)ccc3n2)C[C@H]1C(=O)N1CCCC1]

Step 1: Synthesis of 1-(tert-butyl)-2-methyl (2S,4S)-4-((6-(2,6-dichloro-3,5-dimethoxyphenyl)quinazolin-2-yl)amino)pyrrolidin-1,2-dicarboxylate

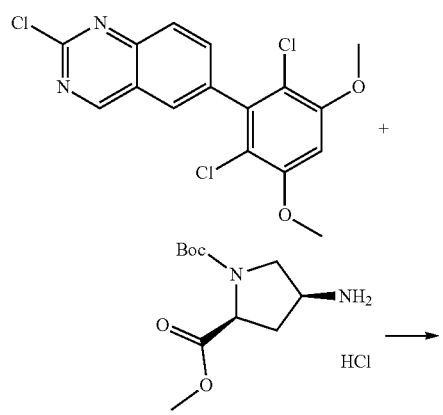

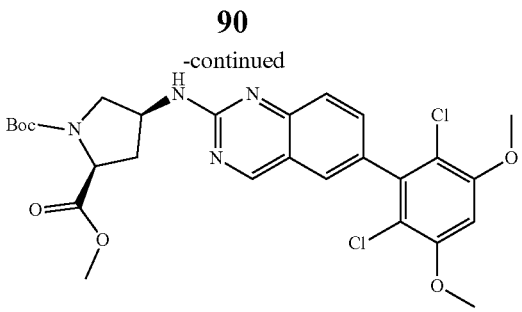

The material 2-chloro-6-(2,6-dichloro-3,5-dimethoxyphenyl)quinazoline (3.28 g, 8.87 mmol, 1.0 eq) was dissolved in N-methylpyrrolidone (8 mL). N,N-diisopropylethylamine (3.44 g, 26.6 mmol, 3.0 eq) and 1-(tert-butyl)-2-methyl (2S,4S)-4-aminopyrrolidin-1,2-dicarboxylate hydrochloride (3.73 g, 13.3 mmol, 1.5 eq) were added into the system at room temperature. After the addition, the system was heated to 120° C. to reflux and stirred overnight. The completion of the reaction was detected by TLC on the next day. After the reaction solution was cooled, water (32 mL) was added, and a solid was precipitated. After stirring for 2 h, a solid was obtained by suction filtration and extracted with dichloromethane (150×3 mL). The organic phase was dried over anhydrous sodium sulfate and then purified by column chromatography (PE:EA=5:1) to obtain 1-(tert-butyl)-2-methyl (2S,4S)-4-((6-(2,6-dichloro-3,5-dimethoxyphenyl)quinazolin-2-yl)amino)pyrrolidin-1,2-dicarboxylate (1.91 g, 38.1%).

Step 2: Synthesis of (2S,4S)-1-(tert-butoxycarbonyl)-4-((6-(2,6-dichloro-3,5-dimethoxyphenyl)quinazolin-2-yl)amino)pyrrolidin-2-carboxylic Acid

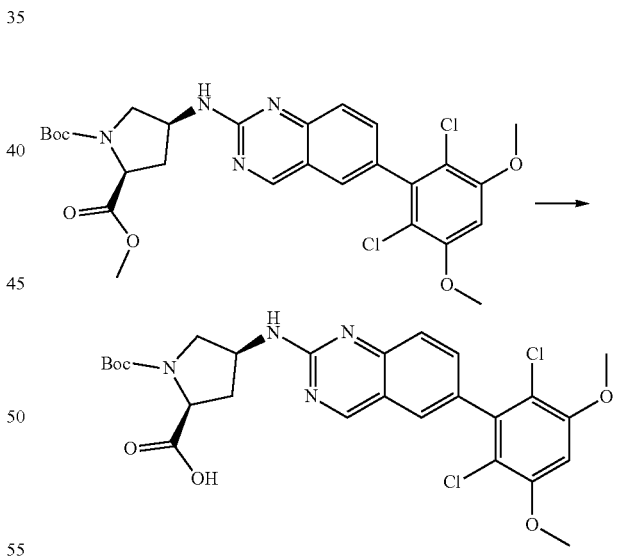

The intermediate 1-(tert-butyl)-2-methyl (2S,4S)-4-((6-(2,6-dichloro-3,5-dimethoxyphenyl)quinazolin-2-yl)amino)pyrrolidin-1,2-dicarboxylate (1.05 g, 1.81 mmol, 1.0 eq) was dissolved in methanol (14 mL), cooled to about 0° C. under stirring at room temperature, and dropwise added with an aqueous solution (5.5 ml) of lithium hydroxide monohydrate (229.5 mg, 5.46 mmol, 3.0 eq). After the addition, the mixture was slowly warmed to room temperature and stirred overnight. The completion of the reaction was detected by TLC on the next day. The system was concentrated to dryness, added with methyl tert-butyl ether (30 ml) and stirred for 0.5 h, and then filtered by suction. The filter cake was dissolved with water (20 ml), and the pH was adjusted to 6-7, and then dichloromethane (40 ml) was added for extraction. The organic phase was dried over anhydrous sodium sulfate and then concentrated to give a product of (2S,4S)-(tert-butoxycarbonyl)-4-((6-(2,6-dichloro-3,5-dimethoxyphenyl)quinazol in-2-yl)amino)pyrrolidin-2-carboxylic acid (900.8 mg, yield: 89.8%).

Step 3: Synthesis of Tert-Butyl (2S,4S)-4-((6-(2,6-dichloro-3,5-dimethoxyphenyl)quinazolin-2-yl)amino)-2-(pyrrolidin-1-carbonyl)pyrrolidin-1-carboxylate

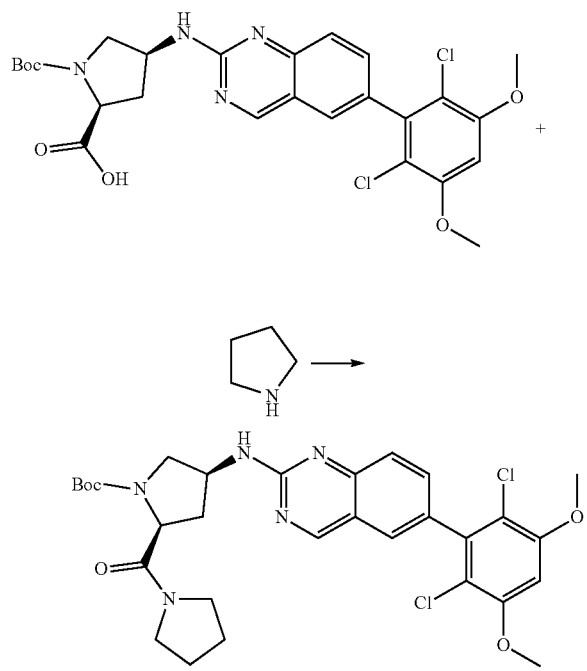

(2S,4S)-1-(tert-butoxycarbonyl)-4-((6-(2,6-dichloro-3,5-dimethoxyphenyl)quinazol in-2-yl)amino)pyrrolidin-2-carboxylic acid (287.3 mg, 0.50 mmol, 1.0 eq) was dissolved in a mixed solution of tetrahydrofuran (11 mL) and acetonitrile (1.5 ml), cooled to about 0° C. under stirring, and dropwise added with 7-azobenzotriazole (213.27 mg, 0.56 mmol, 1.1 eq) and N,N-diisopropylethylamine (131.7 mg, 1.01 mmol, 2.0 eq). After the addition, the system was reacted at 0° C. for 1 h. After that, pyrrolidine was added dropwise at the same temperature to react for 3 h. Then, the completion of the reaction was detected by TLC. The system was concentrated to dryness and then washed with ethyl acetate (30 ml) and saturated aqueous sodium chloride (15 ml) for three times. The organic phases were combined and dried over anhydrous sodium sulfate and then concentrated to give (2S,4S)-4-((6-(2,6-dichloro-3,5-dimethoxyphenyl)quinazolin-2-yl)amino)-2-(pyrrolidin-1-carbonyl)pyrrolidin-1-carboxylate (471.8 mg, yield: 100%).

Step 4: Synthesis of ((2S,4S)-4-((6-(2,6-dichloro-3,5-dimethoxyphenyl)quinazolin-2-yl)amino)pyrrolidin-2-yl)(pyrrolidin-1-yl)methanone

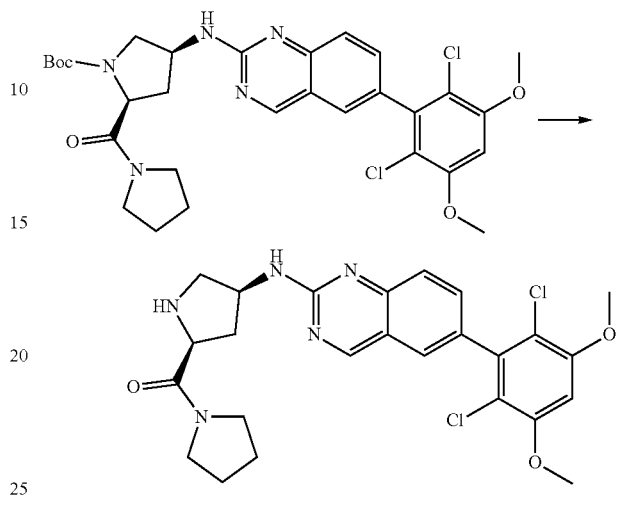

tert-butyl (2S,4S)-4-((6-(2,6-dichloro-3,5-dimethoxyphenyl)quinazolin-2-yl)amino)-2-(pyrrolidin-1-carbonyl)pyrrolidin-1-carboxylate (374.1 mg, 0.60 mmol, 1.0 eq) was dissolved in DCM (6 mL), cooled to about 0° C. under stirring, and dropwise added with trifluoroacetic acid (4 ml). After the addition, the system was slowly warmed to room temperature and stirred for 3 h. After that, the completion of the reaction was detected by TLC. The temperature of the system was cooled to about 0° C. The pH of the system was adjusted to 6-7 by dropwise adding a saturated aqueous sodium bicarbonate solution, followed by adding dichloromethane (15 mL) for extraction. The organic phase was dried over anhydrous sodium sulfate and then concentrated to give ((2S,4S)-4-((6-(2,6-dichloro-3,5-dimethoxyphenyl)quinazolin-2-yl)amino)pyrrolidin-2-yl)(pyrrolidin-1-yl)methanone (226.0 mg, yield: 72.2%).

Step 5: Synthesis of 1-((2S,4S)-4-((6-(2,6-dichloro-3,5-dimethoxyphenyl)quinazolin-2-yl)amino)-2-(pyrrolidin-1-carbonyl)pyrrolidin-1-yl)prop-2-en-1-one

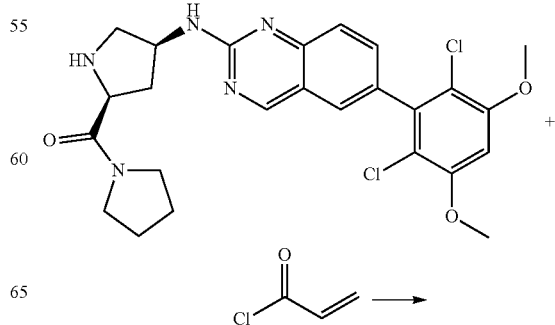

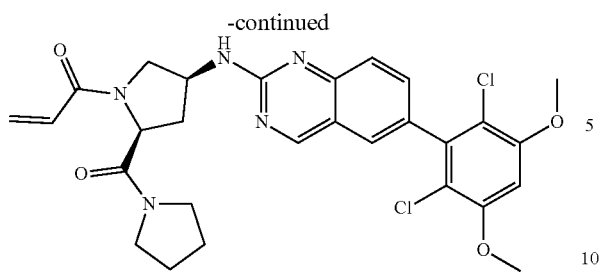

((2S,4S)-4-((6-(2,6-dichloro-3,5-dimethoxyphenyl)quinazolin-2-yl)amino)pyrrolidin-2-yl)(pyrrolidin-1-yl)methanone was dissolved in THF (5 mL), cooled to 0° C. under stirring, and dropwise added with triethylamine (132.8 mg, 1.31 mmol, 3.0 eq) and acryloyl chloride (55.4 mg, 0.61 mmol, 1.4 eq) successively. After the addition, the system was warmed to room temperature and stirred overnight. The completion of the reaction was detected by TLC on the next day. A saturated aqueous ammonium chloride solution (10 ml) and DCM (20 ml) were added to the system for separation. The organic phase was dried over anhydrous sodium sulphate, concentrated to dryness, then added with methyl tert-butyl ether (10 ml), stirred for 2 h, and then filtered by suction to obtain a product of 1-((2S,4S)-4-((6-(2,6-dichloro-3,5-dimethoxyphenyl)quinazolin-2-yl)amino)-2-(pyrrolidin-1-carbonyl)pyrrolidin-1-yl)prop-2-en-1-one (162.8 mg, yield: 66.1%).

$^1$HNMR (400 MHz, DMSO) δ (ppm): 9.18 (s, 1H), 7.95 (s, 1H), 7.70 (s, 1H), 7.51-7.59 (m, 2H), 7.01 (s, 1H), 6.63-6.67 (m, 1H), 6.12-6.16 (m, 1H), 5.67-5.70 (m, 1H), 4.70-4.71 (m, 1H), 4.68 (s, 1H), 4.13 (s, 5H), 4.21 (m, 1H), 3.74-3.76 (m, 1H), 3.49-3.54 (m, 1H), 1.89-1.94 (m, 3H), 1.78-1.83 (m, 2H).

Molecular formula: $C_{28}H_{29}Cl_2N_5O_4$ Molecular weight: 569.16 LC-MS(Neg, m/z)=570.2 [M+H$^+$].

Example 20: Synthesis of 1-((3S,4R)-3-((6-(2,6-dichloro-3,5-dimethoxyphenyl)quinazolin-2-yl)amino)-4-methylpyrrolidin-1-yl)prop-2-yn-1-one (Compound 56)

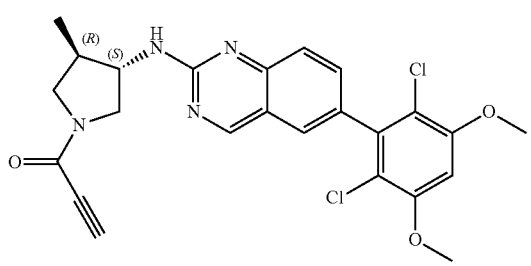

Step 1: Synthesis of Tert-Butyl (3S,4R)-3-((6-(2,6-dichloro-3,5-dimethoxyphenyl)quinazolin-2-yl)amino)-4-methylpyrrolidin-1-carboxylate

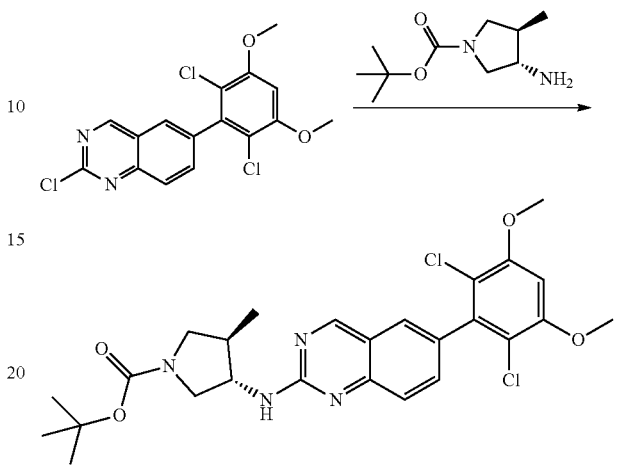

The materials 2-chloro-6-(2,6-dichloro-3,5-dimethoxyphenyl)quinazoline (400.0 mg, 1.1 mmol, 1.0 eq) and tert-butyl (3S,4R)-3-amino-4-methylpyrrolidin-1-carboxylate (440.6 mg, 2.2 mmol, 2.0 eq) were dissolved in N-methylpyrrolidone (3.0 mL), added with N,N-diisopropylethylamine (568.7 mg, 4.4 mmol, 4.0 eq), and gradually heated to 110° C. and reacted overnight. The completion of the reaction was detected by TLC. The reaction solution was cooled to room temperature, added with ice water (15 mL) and filtered. The filter cake was washed with a small amount of ice water, dissolved in ethyl acetate (20 mL). The ethyl acetate phase was washed with saturated brine (10 mL), and dried over anhydrous sodium sulfate, filtered and concentrated. The crude product was subjected to silicon gel column chromatography (DCM:MeOH=200:1 to 100:1) to give tert-butyl (3S,4R)-3-((6-(2,6-dichloro-3,5-dimethoxyphenyl)quinazolin-2-yl)amino)-4-methylpyrrolidin-1-carboxylate (320.6 mg, yield: 54.7%) as a yellow solid.

Step 2: Synthesis of (6-(2,6-dichloro-3,5-dimethoxyphenyl)-N-((3S,4R)-4-methylpyrrolidin-3-yl)quinazolin-2-amine Hydrochloride

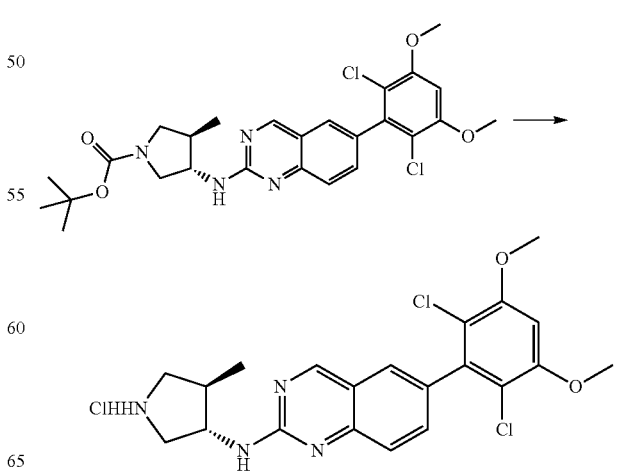

The material tert-butyl (3S,4R)-3-((6-(2,6-dichloro-3,5-dimethoxyphenyl)quinazolin-2-yl)amino)-4-methylpyrrolidin-1-carboxylate (320.6 mg, 1.0 eq) was dissolved in ethanol (8.0 mL), cooled to 0° C. in an ice bath, added with hydrogen chloride ethanol solution (8.0 mL), stirred and reacted for 2 h. The completion of the reaction was detected by TLC. The reaction solution was directly concentrated to give (6-(2,6-dichloro-3,5-dimethoxyphenyl)-N-((3S,4R)-4-methylpyrrolidin-3-yl)quinazolin-2-amine hydrochloride (339.2 mg crude, yield: 100%) as a pale yellow solid.

Step 3: Synthesis of 1-((3S,4R)-3-((6-(2,6-dichloro-3,5-dimethoxyphenyl)quinazolin-2-yl)amino)-4-methylpyrrolidin-1-yl)prop-2-yn-1-one

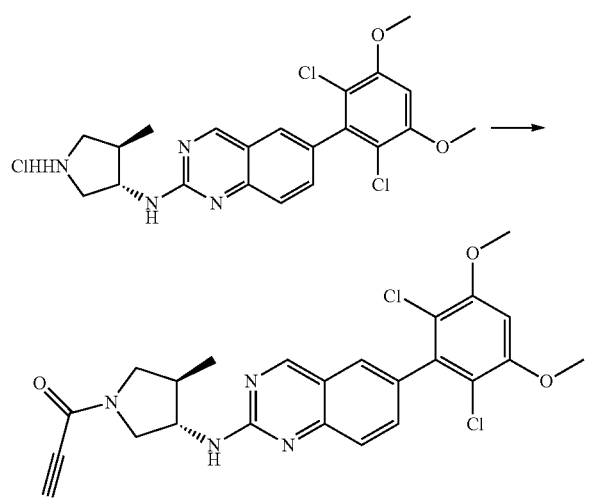

6-(2,6-dichloro-3,5-dimethoxyphenyl)-N-((3S,4R)-4-methylpyrrolidin-3-yl)quinazolin-2-amine hydrochloride (339.2 mg) was dissolved in THF (10.0 mL), added with triethylamine (203.0 mg, 2.0 mmol, 3.0 eq), sonicated for 5 min, added with water (15 mL) and ethyl acetate (10 mL), and separated. The aqueous phase was extracted with ethyl acetate (8.0 mL×2). The organic phases were combined, washed with saturated brine, dried over anhydrous sodium sulfate, filtered and concentrated to give a pale yellow solid (216.0 mg). The treated solid (108.0 mg, 0.25 mmol) was dissolved in dichloromethane (2 mL), added with propiolic acid (37.8 mg, 0.54 mmol), 4-dimethylaminopyridine (3.1 mg, 0.025 mmol) and N,N'-dicyclohexylcarbimide (56.5 mg, 0.27 mmol), and reacted in a microwave at 40° C. for 30 min. The completion of the reaction was detected by TLC. The reaction solution was washed with water (5 mL×3), concentrated to dryness, and separated with a preparative thin layer chromatography plate to give 1-((3S,4R)-3-((6-(2,6-dichloro-3,5-dimethoxyphenyl)quinazolin-2-yl)amino)-4-methylpyrrolidin-1-yl)prop-2-yn-1-one (24.2 mg, yield: 20%) as a yellow solid.

$^1$HNMR (400 MHz, DMSO-$d_6$) δ (ppm): 9.20-9.19 (d, 1H), 7.96 (s, 1H), 7.86-7.81 (t, 1H), 7.69 (s, 1H), 7.56-7.52 (m, 2H), 7.01 (s, 1H), 4.49-4.42 (d, 1H), 4.25-4.15 (t, 3H), 3.97 (s, 6H), 4.03 (s, 6H), 3.77-3.72 (m, 1H), 3.45-3.41 (m, 1H), 3.20-3.15 (m, 1H), 3.06-3.01 (m, 1H), 2.89 (s, 2H), 2.73 (s, 2H), 2.40-2.33 (d, 2H), 1.24 (s, 2H), 1.10 (s, 3H).

Molecular formula: $C_{24}H_{22}Cl_2N_4O_3$ Molecular weight: 485.37 LC-MS (Pos, m/z)=485.43 [M+H$^+$].

Example 21: Synthesis of 1-(6-((6-(2,6-dichloro-3,5-dimethoxyphenyl)quinazolin-2-yl)amino)-2-azaspiro[3.3]heptan-2-yl)prop-2-en-1-one (Compound 65)

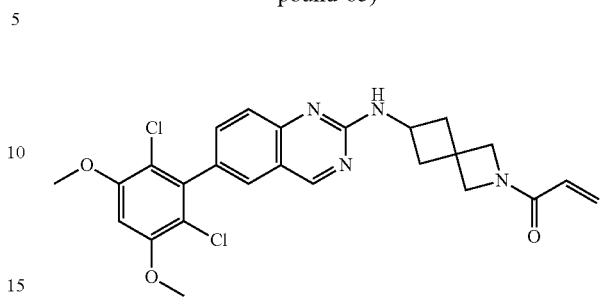

Step 1: Synthesis of Tert-Butyl 6-((6-(2,6-dichloro-3,5-dimethoxyphenyl)quinazolin-2-yl)amino)-2-azaspiro[3.3]heptan-2-carboxylate

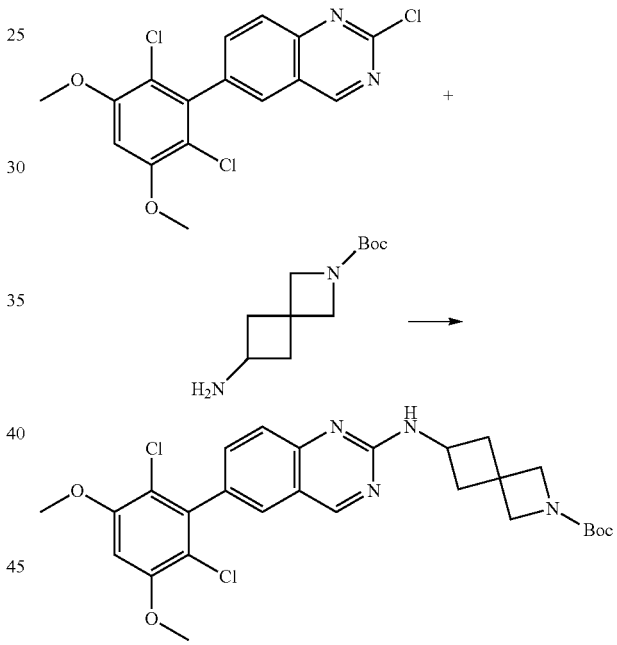

The materials 2-chloro-6-(2,6-dichloro-3,5-dimethoxyphenyl)quinazoline (400 mg, 1.082 mmol, 1.0 eq) and tert-butyl 6-amino-2-azaspiro[3.3]heptane-2-carboxylate (248.53 mg, 1.082 mmol, 1.0 eq) were dissolved in NMP (1.5 mL), added with DIPEA (699.24 mg, 5.41 mmol, 5.0 eq), and heated to 110° C. and reacted overnight. The completion of the reaction was detected by TLC on the next morning. After cooling, the reaction solution was slowly poured into water (50 mL) and filtered by suction. The filter cake was dissolved in DCM. The aqueous phase was extracted with EA (100 mL×2) and separated. There is no product detected by TLC in the aqueous phase. The organic phases were combined, dried and concentrated, and then subjected to column chromatography (PE:EA=5:1) to give tert-butyl 6-((6-(2,6-dichloro-3,5-dimethoxyphenyl)quinazolin-2-yl)amino)-2-azaspiro[3.3]heptan-2-carboxylate (812 mg) as a thick liquid, which was used directly for the next reaction.

97

Step 2: Synthesis of 6-(2,6-dichloro-3,5-dimethoxy-phenyl)-N-(2-azaspiro[3.3]heptane-6-yl)quinazolin-2-amine

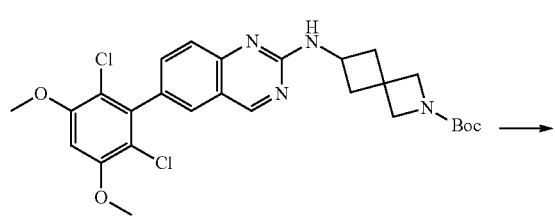

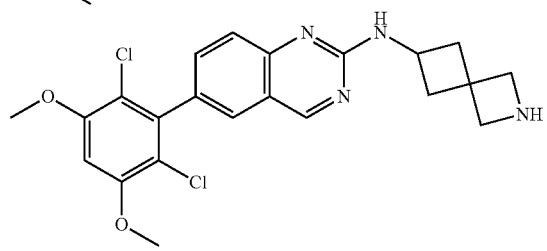

The intermediate tert-butyl 6-((6-(2,6-dichloro-3,5-dimethoxyphenyl)quinazolin-2-yl)amino)-2-azaspiro[3.3]heptan-2-carboxylate (590.3 mg, 0.355 mmol, 1.0 eq) was dissolved in DCM (5 mL), stirred to obtain a clarified solution, cooled to 0° C., added with trifluoroacetic acid (5 mL) and reacted for 1 h. Then, the completion of the reaction was detected by TLC. The reaction solution was concentrated, and dissolved by adding THF (50 mL) and concentrated, repeated for three times. The crude product was used in the next step.

Step 3: Synthesis of 1-(6-((6-(2,6-dichloro-3,5-dimethoxyphenyl)quinazolin-2-yl)amino)-2-azaspiro[3.3]heptan-2-yl)prop-2-en-1-one

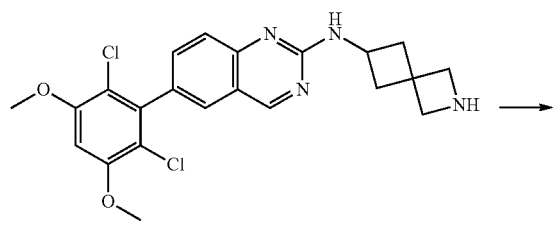

98

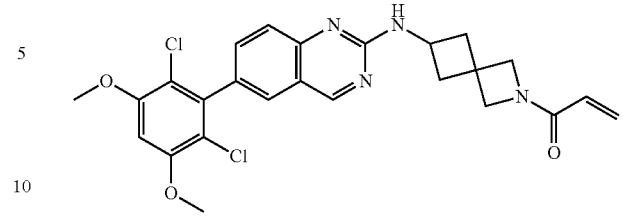

The intermediate 6-(2,6-dichloro-3,5-dimethoxyphenyl)-N-(2-azaspiro[3.3]heptan-6-yl)quinazolin-2-amine (480 mg, 1.08 mmol, 1.0 eq), and triethylamine (546.4 mg, 5.4 mmol, 5.0 eq) were dissolved in THF (10 mL). The pH of the system was adjusted to about 8 and then cooled to 0° C. Acryloyl chloride (97.74 mg, 1.08 mmol, 1.0 eq) diluted with THF (1 mL) was injected. After 1 h, it is detected by TLC that a small amount of starting material was remained. A drop of acryloyl chloride was added. After 0.5 h, it is detected by TLC that a small amount of starting material was remained. Saturated sodium bicarbonate solution (10 mL) and EA (20 mL) were added, stirred and separated. The aqueous phase was extracted with EA (10 mL×2). There is no product detected by TLC in the aqueous phase. The organic phases were combined, dried, concentrated, and subjected to the column chromatography (PE:EA=2:1 to 1:1) to obtain 1-(6-((6-(2,6-dichloro-3,5-dimethoxyphenyl)quinazolin-2-yl)amino)-2-azaspiro[3.3]heptan-2-yl)prop-2-en-1-one (337 mg, yield: 62%).

$^1$HNMR (400 MHz, DMSO) δ (ppm): 9.14 (s, 1H), 7.81 (s, 1H), 7.66 (s, 1H), 7.48-7.52 (m, 2H), 7.01 (s, 1H), 6.31-6.34 (m, 1H), 6.07-6.11 (m, 1H), 5.64-5.68 (m, 1H), 4.54 (s, 1H), 4.40 (s, 1H), 4.26 (m, 1H), 4.20 (s, 1H), 3.98 (s, 6H), 3.80 (s, 1H), 2.62 (s, 2H), 2.26 (s, 2H).

Molecular formula: $C_{25}H_{24}Cl_2N_4O_3$, Molecular weight: 499.39, LC-MS (Neg, m/z)=499.1 [M−H$^+$].

Referring to the above preparation method, the following compounds can be prepared:

| No. | Structure | HNMR | LC-MS |
|---|---|---|---|
| 7 | 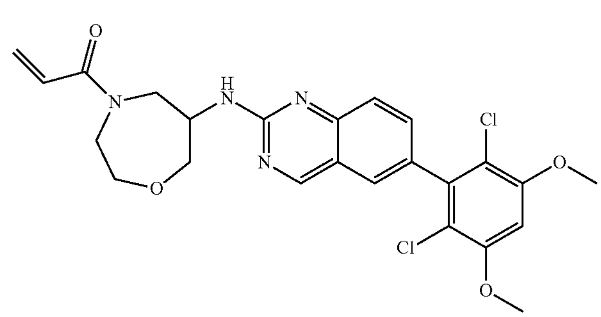 [SMILES: C=CC(=O)N1CCOCC(Nc2ncc3cc(-c4c(Cl)c(OC)cc(OC)c4Cl)ccc3n2)C1] | $^1$HNMR (400 MHz, DMSO-d$_6$) δ (ppm): 9.21 (m, 1H), 7.61-7.69 (m, 1H), 7.57-7.58 (m, 2H), 7.50-7.55 (m, 1H), 7.02 (m, 1H), 6.19-6.23 (m, 1H), 5.72-5.75 (m, 1H), 3.35-4.13 (m, 13H), 1.16-1.27 (m, 2H). | N/A |

| No. | Structure | HNMR | LC-MS |
|---|---|---|---|
| 9 | 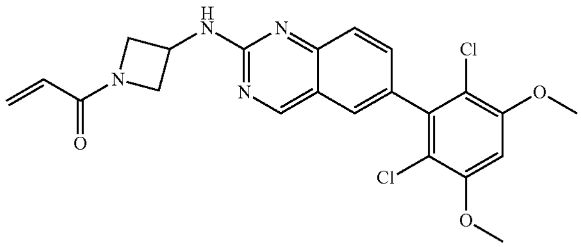 [SMILES: C=CC(=O)N1CC(Nc2ncc3cc(-c4c(Cl)c(OC)cc(OC)c4Cl)ccc3n2)C1] | ¹HNMR (400 MHz, DMSO-d₆) δ (ppm): 9.12 (m, 1H), 8.21-8.23 (m, 1H), 7.71 (m, 1H), 7.52-7.58 (m, 2H), 7.01 (m, 1H), 6.32-6.39 (m, 1H), 6.10-6.15 (m, 1H), 5.66-5.69 (m, 1H), 4.76-4.77 (m, 1H), 4.58-4.62 (m, 1H), 4.26-4.30 (m, 1H), 4.14-4.17 (m, 1H), 3.98 (s, 6H). | LC-MS (Pos, m/z) = 459.26 [M + H⁺] |
| 20 | 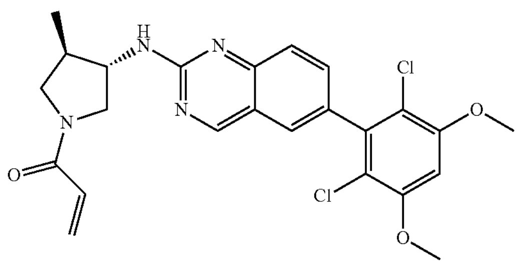 [SMILES: C=CC(=O)N1C[C@@H](C)[C@H](Nc2ncc3cc(-c4c(Cl)c(OC)cc(OC)c4Cl)ccc3n2)C1] | ¹HNMR (400 MHz, DMSO-c16) δ (ppm): 9.18 (s, 1H), 7.82 (s, 1H), 7.79 (s, 1H), 7.49-7.54 (m, 2H), 7.02 (s, 1H), 6.60-6.71 (m, 1H), 6.16 (d, 1H), 5.67 (m, 1H), 4.12-4.20 (m, 2H), 4.03 (s, 6H), 3.97 (m, 1H), 3.24 (m, 1H), 3.05 (m, 1H), 2.48 (m, 1H), 1.23 (s, 3H). | LC-MS (Pos, m/z) = 489.0 [M + H⁺] |
| 23 | 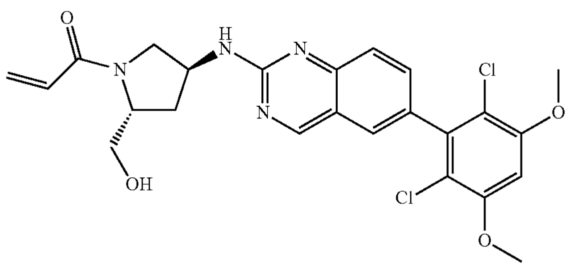 [SMILES: C=CC(=O)N1C[C@@H](Nc2ncc3cc(-c4c(Cl)c(OC)cc(OC)c4Cl)ccc3n2)C[C@@H]1CO] | ¹HNMR (400 MHz, DMSO-d₆) δ (ppm): 9.18 (s, 1H), 7.81 (m, 1H), 7.69 (s, 1H), 7.50-7.56 (m, 2H), 7.01 (s, 1H), 6.52-6.70 (m, 1H), 6.10-6.18 (m, 1H), 5.61-5.68 (m, 1H), 4.88-5.04 (m, 1H), 4.88 (s, 1H), 4.23-4.25 (m, 1H), 3.98 (s, 6H), 3.51-3.57 (m, 3H), 2.24 (m, 1H), 2.09 (m, 1H). | LC-MS (Pos, rn/z) = 503.4 [M + H⁺] |
| 25 | 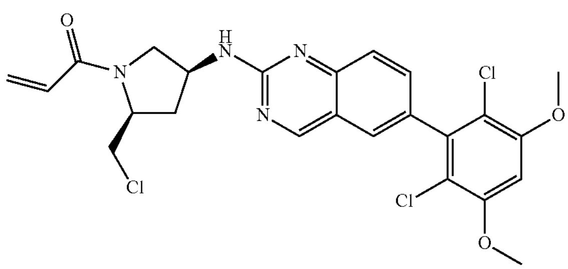 | ¹HNMR (400 MHz, DMSO) δ (ppm): 9.20 (s, 1H), 7.70 (d, 1H), 7.57 (d, 1H), 7.54 (d, 2H), 7.01 (s, 1H), 6.59-6.66 (m, 1H), 6.17-6.21 (d, 1H), 5.71-5.73 (m, 1H), 4.51-4.52 (m, 2H), 4.33-4.35 (m, 2H), 4.22 (m, 1H), 4.21 (m, 1H), 4.04 (s, 3H), 4.01 (s, 3H), 2.07-2.09 (m, 2H). | LC-MS (Pos, m/z) = 521.1 [M + H⁺] |
| 26 | 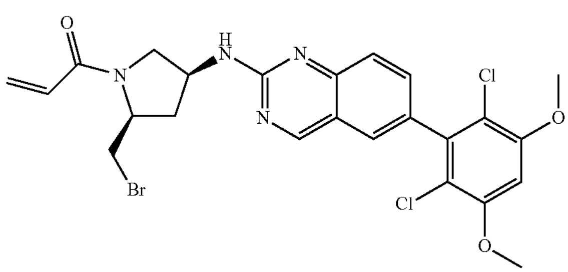 | ¹HNMR (400 MHz, DMSO) δ (ppm): 9.21 (s, 2H), 7.99 (s, 2H), 7.60-7.74 (m, 6H), 7.02 (s, 2H), 6.59-6.65 (q, 1H), 6.17-6.21 (d, 1H), 5.71-5.74 (d, 1H), 4.52-4.53 (d, 2H), 4.32-4.33 (d, 1H), 4.22-4.24 (d, 1H) 3.82-3.90 (t, 12H), 1.89-2.20 (m, 6H). | LC-MS (Pos, m/z) = 567.1 [M + H⁺] |
| 29 | 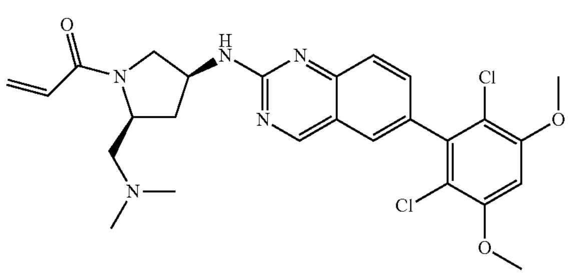 [SMILES: C=CC(=O)N1C[C@@H](Nc2ncc3cc(-c4c(Cl)c(OC)cc(OC)c4Cl)ccc3n2)C[C@H]1CN(C)C] | ¹HNMR (400 MHz, DMSO) δ (ppm): 9.22 (s, 1H), 7.91-7.92 (m, 1H), 7.79 (s, 1H), 7.60 (s, 1H), 7.58-7.56 (m, 2H), 6.71-6.69 (m, 1H), 6.67-6.65 (m, 1H), 5.85-5.82 (m, 1H), 4.57-4.55 (m, 2H), 4.21 (m, 1H), 4.19-4.17 (m, 6H), 3.45 (m, 3H), 3.28-3.27 (m, 2H), 3.23-3.20 (m, 6H). | LC-MS (Pos, m/z) = 530.2 [M + H⁺] |

| No. | Structure | HNMR | LC-MS |
|---|---|---|---|
| 38 | 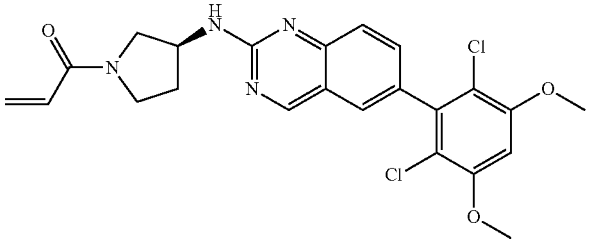 [SMILES: C=CC(=O)N1CC[C@H](Nc2ncc3cc(-c4c(Cl)c(OC)cc(OC)c4Cl)ccc3n2)C1] | ¹HNMR (400 MHz, DMSO-d₆) δ (ppm): 9.19 (m, 1H), 7.82 (m, 2H), 7.51-7.69 (m, 2H), 7.02 (s, 1H), 6.53-6.63 (m, 1H), 6.11-6.17 (m, 1H), 5.62-5.69 (m, 1H), 4.53-5.61 (d, 1H), 3.97 (s, 6H), 3.52-3.78 (m, 3H), 2.07-2.29 (m, 3H). | N/A |
| 39 | 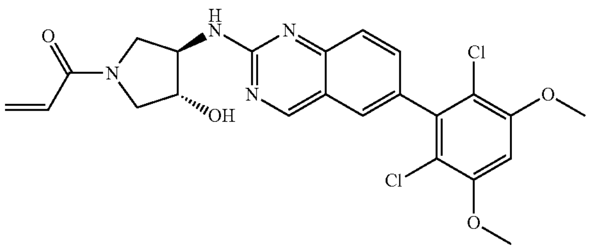 [SMILES: C=CC(=O)N1C[C@@H](O)[C@H](Nc2ncc3cc(-c4c(Cl)c(OC)cc(OC)c4Cl)ccc3n2)C1] | ¹HNMR (400 MHz, DMSO-d₆) δ (ppm): 9.19 (s, 1H), 8.80-8.82 (dd, 1H), 7.75-7.76 (d, 1H), 7.51-7.69 (m, 2H), 7.16-7.18 (m, 1H), 7.01 (s, 11-1), 6.10-6.16 (m, 1H), 5.62-5.75 (m, 1H), 5.40 (s, 0.5H) 5.49 (s, 0.5H), 4.21-4.39 (m, 2H), 3.97 (s, 6H), 3.31-3.90 (m, 3H), 1.90 (m, 1H). | LC-MS (Pos, m/z) = 489.1 [M + H⁺] |
| 41 | 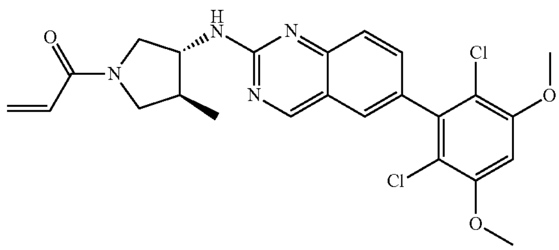 [SMILES: C=CC(=O)N1C[C@H](Nc2ncc3cc(-c4c(Cl)c(OC)cc(OC)c4Cl)ccc3n2)[C@@H](C)C1] | ¹HNMR (400 MHz, DMSO-d₆) δ (ppm): 9.18 (m, 1H), 7.50-7.81 (m, 4H), 7.01 (m, 1H), 6.56 (m, 1H), 6.12-6.15 (m, 1H), 5.66-5.69 (m, 1H), 4.03-4.22 (m, 2H), 3.97 (s, 6H), 3.71-3.78 (m, 1H), 3.17-3.22 (m, 2H), 2.21-2.29 (m, 2H), 1.10 (m, 3H) | LC-MS (Pos, m/z) = 487.18 [M + H⁺] |
| 43 | 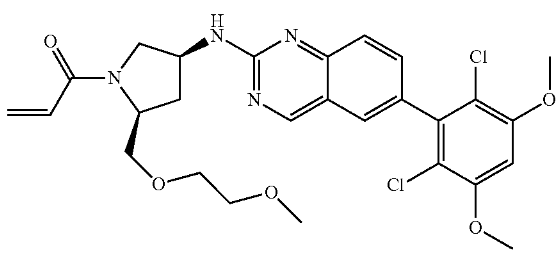 [SMILES: C=CC(=O)N1C[C@@H](Nc2ncc3cc(-c4c(Cl)c(OC)cc(OC)c4Cl)ccc3n2)C[C@H]1COCCOC] | ¹HNMR (400 MHz, DMSO-d₆) δ (ppm): 9.18 (s, 1H), 7.49-7.78 (m, 4H), 7.01 (s, 1H), 6.55-6.73 (m, 1H), 6.12-6.16 (d, 1H), 5.65-5.67 (d, 1H), 4.13-4.54 (m, 5H), 3.96 (s, 6H), 3.20-3.68 (m, 8H), 2.00-2.02 (m, 2H). | LC-MS (Pos, m/z) = 561.3 [M + H⁺] |
| 44 | 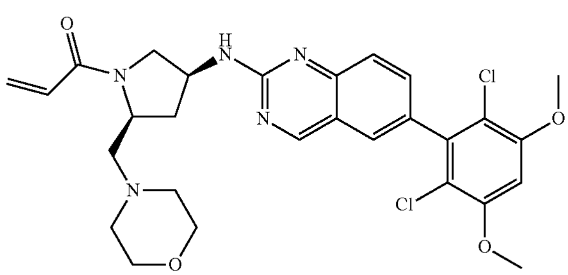 [SMILES: C=CC(=O)N1C[C@@H](Nc2ncc3cc(-c4c(Cl)c(OC)cc(OC)c4Cl)ccc3n2)C[C@H]1CN1CCOCC1] | ¹HNMR (400 MHz, DMSO-d₆) δ (ppm): 9.17 (s, 1H), 7.67 (s, 1H), 7.51-7.58 (m, 2H), 6.96 (m, 1H), 6.50-6.68 (m, 1H), 6.09-6.17 (m, 1H), 3.52-4.50 (m, 18H), 2.37-2.62 (m, 3H), 1.96 (m, 1H). | LC-MS (Pos, m/z) = 572.4 [M + H⁺] |
| 45 | 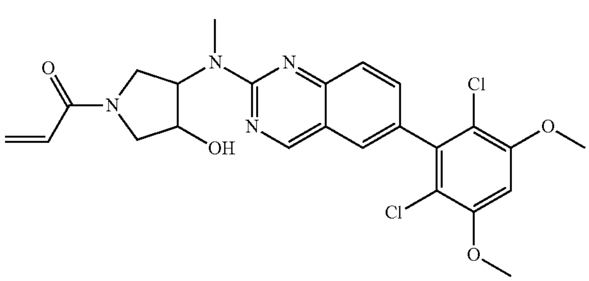 [SMILES: C=CC(=O)N1CC(O)C(N(C)c2ncc3cc(-c4c(Cl)c(OC)cc(OC)c4Cl)ccc3n2)C1] | ¹HNMR (400 MHz, DMSO-d₆) δ (ppm): 9.2689-9.2620 (d, 2H), 7.72 (s, 2H), 7.70 (s, 1H), 7.62-7.60 (d, 1H), 7.59-7.54 (d, 1H), 7.01 (s, 1H), 6.65-6.57 (m, 2H), 6.19-6.14 (t, 1H), 5.72-5.66 (t, 2H), 5.52-5.38 (m, 2H), 5.32-5.15 (m, 3H), 4.49-46.73 (d, 2H), 3.97 (s, 6H), 3.82-3.80 (m, 3H), 3.63-3.59 (t, 2H), 3.47 (s, 2H), 3.19-3.17 (d, 4H), 2.20 (s, 2H). | LC-MS (Pos, m/z) = 503.1 [M + H⁺] |

-continued

| No. | Structure | HNMR | LC-MS |
|---|---|---|---|
| 46 | 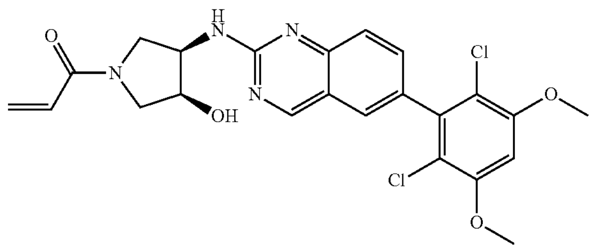 [SMILES: C=CC(=O)N1C[C@H](O)[C@H](Nc2ncc3cc(-c4c(Cl)c(OC)cc(OC)c4Cl)ccc3n2)C1] | ¹HNMR (400 MHz, DMSO-d₆) δ (ppm): 9.20 (s, 1H), 7.70 (s, 1H), 7.51-7.59 (m, 2H), 7.13-7.20 (dd, 1H), 7.01 (s, 1H), 6.58 (m, 1H), 6.17 (m, 1H), 5.65-5.69 (m, 1H), 5.33-5.37 (m, 1H), 4.47 (m, 2H), 3.82-4.03 (m, 8H), 3.51-3.62 (m, 2H), 3.37 (m, 1H). | LC-MS (Pos, m/z) = 489.3 [M + H⁺] |
| 48 | 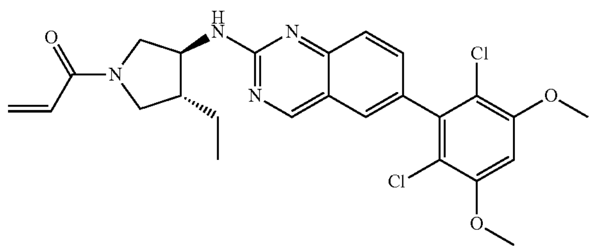 [SMILES: C=CC(=O)N1C[C@@H](CC)[C@H](Nc2ncc3cc(-c4c(Cl)c(OC)cc(OC)c4Cl)ccc3n2)C1] | ¹HNMR (400 MHz, DMSO-d₆) δ (ppm): 9.19 (s, 1H), 7.86-7.95 (m, 2H), 7.70 (s, 1H), 7.52-7.60 (m, 2H), 7.01 (s, 1H), 6.53-6.64 (m, 1H), 6.11-6.17 (m, 1H), 5.64-5.69 (m, 1H), 4.52-4.57 (m, 1H), 3.86-3.97 (m, 9H), 3.44-3.48 (m, 3H) | LC-MS (Pos, m/z) = 503.52 [M + H⁺] |
| 50 | 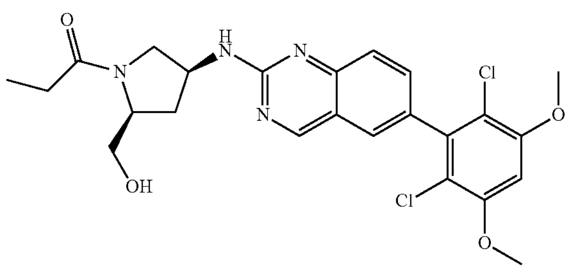 [SMILES: CCC(=O)N1C[C@@H](Nc2ncc3cc(-c4c(Cl)c(OC)cc(OC)c4Cl)ccc3n2)C[C@H]1CO] | ¹HNMR (400 MHz, DMSO-d₆) δ (ppm): 9.16 (s, 1H), 7.85-7.86 (m, 1H), 7.76-7.78 (d, 1H), 7.01 (s, 1H), 5.08 (m, 1H), 4.51-4.53 (m, 1H), 4.39 (m, 0.5H), 4.18 (m, 0.5H), 4.03-4.04 (m, 1H), 3.96 (s, 6H), 3.52-3.66 (m, 2H), 2.23-2.37 (m, 3H), 1.93-1.97 (m, 3H), 0.96-1.00 (t, 3H). | LC-MS (Pos, m/z) = 507.2 [M + H⁺] |
| 51 | 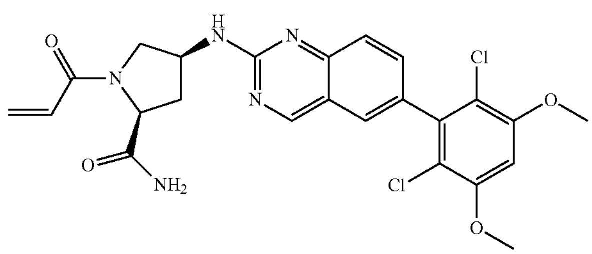 [SMILES: C=CC(=O)N1C[C@@H](Nc2ncc3cc(-c4c(Cl)c(OC)cc(OC)c4Cl)ccc3n2)C[C@H]1C(N)=O] | ¹HNMR (400 MHz, DMSO) δ (ppm): 9.18 (s, 1H), 7.71 (d, 1H), 7.70 (d, 1H), 7.69-7.67 (m, 2H), 6.20 (d, 1H), 5.70 (m, 1H), 5.32 (d, 1H), 4.50 (m, 1H), 4.30 (m, 2H), 4.00 (s, 6H), 3.50 (m, 2H). | LC-MS (Pos, m/z) = 516.1 [M + H⁺]. |
| 52 | 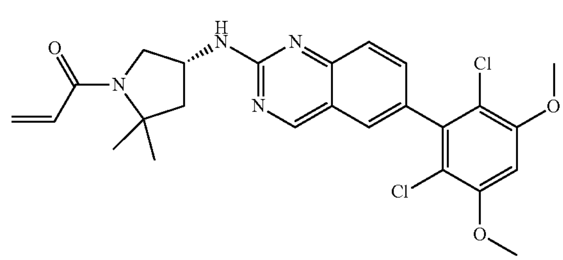 [SMILES: C=CC(=O)N1C[C@H](Nc2ncc3cc(-c4c(Cl)c(OC)cc(OC)c4Cl)ccc3n2)CC1(C)C] | ¹HNMR (400 MHz, DMSO-d₆) δ (ppm): 9.18 (s, 1H), 7.65-7.68 (s, 2H), 7.51-7.53 (m, 2H), 7.00 (s, 1H), 6.54-6.57 (m, 1H), 6.12-6.16 (d, 1H), 5.64-5.69 (m, 1H), 4.5-4.70 (d, 1H), 3.97 (s, 6H), 3.25-3.61 (m, 4H), 1.03-1.23 (s, 6H). | LC-MS (Pos, m/z) = 501.2 [M⁺H⁺] |
| 54 | 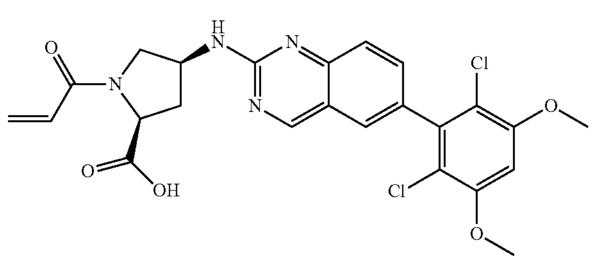 [SMILES: C=CC(=O)N1C[C@@H](Nc2ncc3cc(-c4c(Cl)c(OC)cc(OC)c4Cl)ccc3n2)C[C@H]1C(=O)O] | ¹HNMR (400 MHz, DMSO-d₆) δ (ppm): 9.19 (s, 1H), 7.70 (s, 1H), 7.51-7.59 (m, 2H), 7.19 (s, 1H), 7.01 (s, 1H), 6.60-6.67 (m, 1H), 6.14-6.18 (m, 1H), 5.30-5.33 (m, 1H), 4.22-4.83 (m, 3H), 3.97 (m, 6H), 1.45-1.46 (s, 2H) | LC-MS (Pos, m/z) = 518.62 [M + H⁺] |

| No. | Structure | HNMR | LC-MS |
|---|---|---|---|
| 57 | 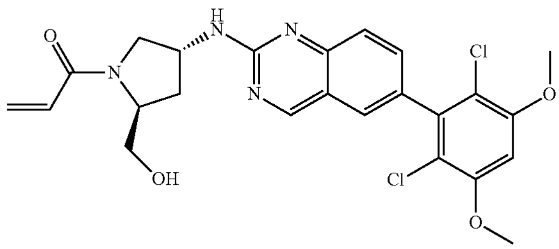 [SMILES: C=CC(=O)N1C[C@H](Nc2ncc3cc(-c4c(Cl)c(OC)cc(OC)c4Cl)ccc3n2)C[C@H]1CO] | ¹HNMR (400 MHz, DMSO-d₆) δ (ppm): 9.18 (s, 1H), 7.69-7.80 (m, 1H), 7.57 (s, 1H), 6.52-6.56 (m, 1H), 6.10-6.18 (m, 1H), 5.62-5.69 (m, 1H), 4.89-5.04 (m, 2H), 4.24-4.27 (m, 1H), 3.98 (s, 6H), 3.46-3.57 (m, 2H), 3.33 (s, 1H), 2.08-2.26 (m, 3H). | LC-MS (Pos, m/z) = 503.1 [M + H⁺] |
| 58 | 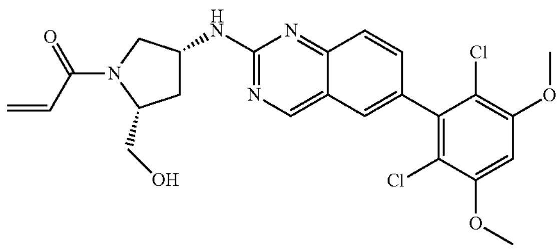 [SMILES: C=CC(=O)N1C[C@H](Nc2ncc3cc(-c4c(Cl)c(OC)cc(OC)c4Cl)ccc3n2)C[C@@H]1CO] | ¹HNMR (400 MHz, DMSO-d₆) δ (ppm): 9.18 (s, 1H), 7.87-7.89 (dd, 1H), 7.80 (s, 1H), 7.50-7.58 (m, 2H), 7.05 (s, 1H), 6.56-6.63 (m, 1H), 6.12-6.17 (m, 1H), 5.65-5.68 (dd, 1H), 5.08-5.10 (t, 1H), 4.54-4.56 (m, 1H), 4.11-4.21 (m, 2H), 3.97 (s, 6H), 3.41-3.62 (m, 3H), 2.39 (m, 1H), 2.00-2.03 (m, 1H). | LC-MS (Pos, m/z) = 504.7 [M + H⁺] |
| 59 | 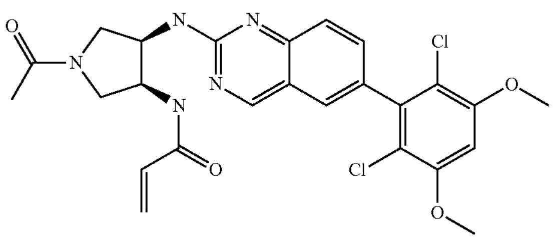 [SMILES: C=CC(=O)N[C@H]1CN(C(C)=O)C[C@H]1Nc1ncc2cc(-c3c(Cl)c(OC)cc(OC)c3Cl)ccc2n1] | ¹HNMR (400 MHz, DMSO-d₆) δ (ppm): 9.18 (s, 1H), 8.18-8.14 (t, 1H), 7.69 (s, 1H), 7.54-7.43 (m, 3H), 7.00 (s, 1H), 6.25-6.19 (m, 2H), 6.06-6.02 (d, 2H), 5.5835-5.5535 (d, 1H), 4.71-4.64 (d, 4H), 3.96 (s, 6H), 3.83-3.81 (d, 1H), 3.74-3.71 (t, 1H), 1.9484-1.9404 (d, 3H), 1.46-1.45 (d, 2H), 1.35-1.33 (d, 2H). | LC-MS (Pos, m/z) = 530.4 [M + H⁺] |
| 60 | 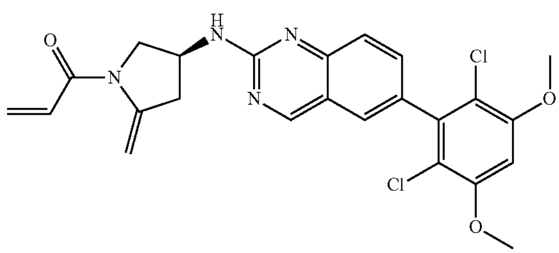 [SMILES: C=CC(=O)N1C[C@@H](Nc2ncc3cc(-c4c(Cl)c(OC)cc(OC)c4Cl)ccc3n2)CC1=C] | ¹HNMR (400 MHz, DMSO-d₆) δ (ppm): 9.24 (s, 1H), 7.72 (s, 1H), 7.52-7.60 (m, 2H), 7.01 (s, 1H), 6.77-6.84 (m, 0.6H), 6.38-6.44 (m, 0.4H), 6.11-6.17 (m, 1H), 5.62-5.71 (m, 1H), 5.12 (m, 1H), 4.90-5.00 (d, 1H), 3.97 (s, 6H), 3.52-3.74 (m, 3H), 1.95-2.13 (m, 2H). | LC-MS (Pos, m/z) = 487.2 [M + H⁺] |
| 61 | 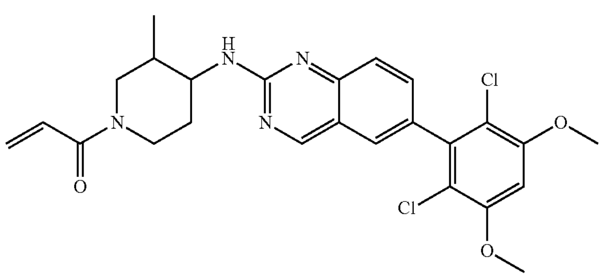 [SMILES: C=CC(=O)N1CCC(Nc2ncc3cc(-c4c(Cl)c(OC)cc(OC)c4Cl)ccc3n2)C(C)C1] | ¹HNMR (400 MHz, DMSO-d₆) δ (ppm): 9.12-9.16 (d, 1H), 7.54-7.61 (m, 4H), 6.93 (s, 1H), 6.80-6.90 (m, 1H), 6.09 (m, 1H), 5.65-5.69 (m, 1H), 4.35-4.43 (m, 1H), 3.68-4.14 (m, 8H), 3.48-3.51 (m, 1H), 2.80-2.92 (m, 1H), 1.65-2.32 (m, 3H), 0.98 (m, 3H). | LC-MS (Pos, m/z) = 501.13 [M + H⁺] |
| 62 | 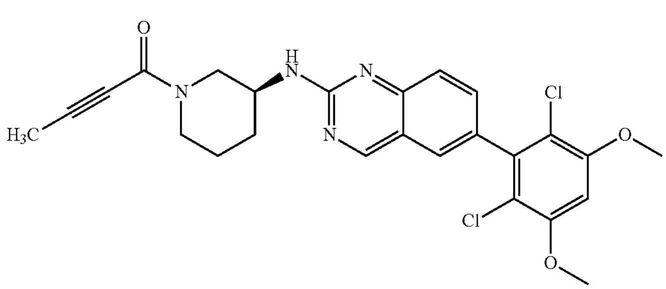 [SMILES: CC#CC(=O)N1CCC[C@H](Nc2ncc3cc(-c4c(Cl)c(OC)cc(OC)c4Cl)ccc3n2)C1] | ¹HNMR (400 MHz, DMSO-d₆) δ (ppm): 9.19 (m, 1H), 7.67-7.69 (m, 1H), 7.50-7.61 (m, 3H), 7.01 (m, 1H), 3.97 (s, 6H), 3.71-3.78 (m, 1H), 3.51-3.59 (m, 2H), 2.92-2.98 (m, 1H), 2.04 (m, 3H), 1.71-1.88 (m, 3H), 1.50 (m, 4H). | LC-MS (Pos, m/z) = 499.26 [M + H⁺] |

| No. | Structure | HNMR | LC-MS |
|---|---|---|---|
| 63 | 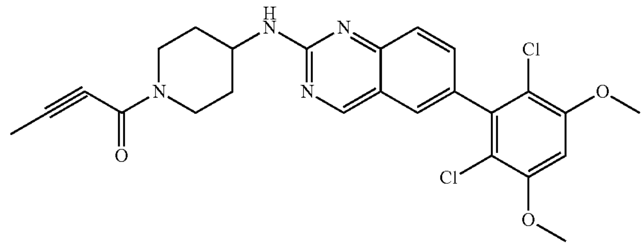 [SMILES: CC#CC(=O)N1CCC(Nc2ncc3cc(-c4c(Cl)c(OC)cc(OC)c4Cl)ccc3n2)CC1] | ¹HNMR (400 MHz, DMSO-d₆) δ (ppm): 9.16 (m, 1H), 7.66 (m, 1H), 7.48-7.57 (m, 3H), 7.01 (m, 1H), 4.21-4.24 (m, 4H), 3.97 (s, 6H), 2.96-3.08 (m, 1H), 2.03 (m, 5H), 1.37-1.50 (m, 3H) | LC-MS (Pos, m/z) = 499.22 [M + H⁺] |
| 64 | 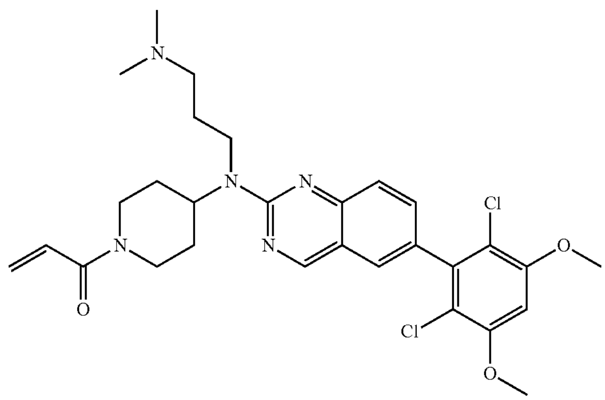 [SMILES: C=CC(=O)N1CCC(N(CCCN(C)C)c2ncc3cc(-c4c(Cl)c(OC)cc(OC)c4Cl)ccc3n2)CC1] | ¹HNMR (400 MHz, DMSO-d₆) δ (ppm): 9.28 (m, 2H), 7.73-7.74 (m, 1H), 7.56-7.59 (m, 2H), 7..02 (s, 1H), 6.85-6.92 (m, 1H), 6.12-6.16 (m, 1H), 5.72 (d, 1H), 5.00 (m, 1H), 4.61-4.64 (m, 1H), 4.20-4.23 (m, 1H), 4.00 (s, 6H), 3.58-3.59 (m, 2H), 3.16 (m, 2H), 2.82 (m, 6H), 1.97 (m, 2H), 1.78 (m, 4H). | LC-MS (Pos, m/z) = 572.31 [M + H⁺] |
| 66 | 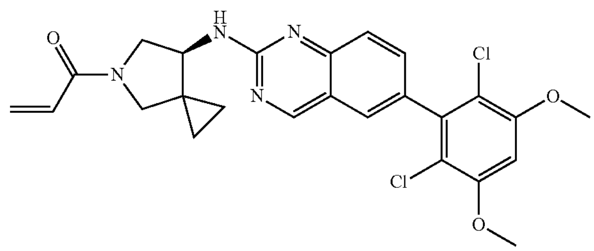 [SMILES: C=CC(=O)N1C[C@@H](Nc2ncc3cc(-c4c(Cl)c(OC)cc(OC)c4Cl)ccc3n2)C2(CC2)C1] | ¹HNMR (400 MHz, DMSO-d₆) δ (ppm): 9.16 (s, 1H), 7.83 (m, 1H), 7.67 (s, 1H), 7.51-7.54 (m, 1H), 7.01 (s, 1H), 6.48-6.55 (m, 1H), 6.11-6.16 (m, 1H), 5.64-5.68 (m, 1H), 4.25-4.39 (m, 1H), 3.92-4.03 (m, 7H), 3.75-3.77 (m, 2H), 0.60-0.89 (m, 4H). | LC-MS (Pos, m/z) = 499.0 [M + H⁺] |
| 67 | 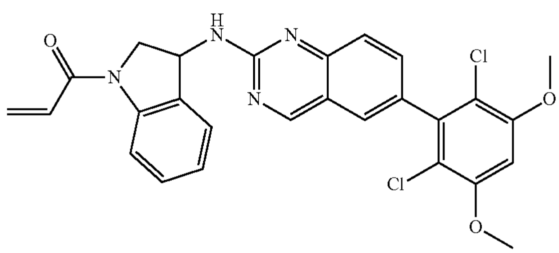 [SMILES: C=CC(=O)N1CC(Nc2ncc3cc(-c4c(Cl)c(OC)cc(OC)c4Cl)ccc3n2)c2ccccc21] | ¹HNMR (400 MHz, DMSO-d₆) δ (ppm): 9.21 (s, 2H), 8.24-8.17 (t, 3H), 7.71 (s, 1H), 7.60-7.52 (m, 3H), 7.45-7.44 (d, 1H), 7.31-7.28 (t, 2H), 7.07-7.01 (m, 2H), 6.82-6.75 (m, 1H), 6.35-6.31 (d, 2H), 5.89 (s, 1H), 5.86-5.81 (t, 1H), 4.65-4.60 (t, 2H), 4.15-4.13 (d, 2H), 3.97 (s, 6H). | LC-MS (Neg, m/z) = 520.2 [M + H⁺] |

The present invention can be better understood from the following experimental examples. However, those skilled in the art will easily understand that the description of the experimental examples is only intended to illustrate the invention, and should not and will not limit the invention described in detail in claims.

Experimental Example 1: Enzymatic Activity Test of the Compounds of the Present Invention Test substance: The compounds of the present invention, the structures of which are shown above.

Test Instrument: The LabChip EZ Reader II drug screening platform.

Test Method:
1. Preparation for Compound Plate
    a) 96-well plates, 10 dose groups, 3-fold serial dilutions, added DMSO to each well, maximal concentration of 500 μM.
    b) 384-well plates, diluted with IX kinase buffer (50 mM HEPES, pH 7.5; 0.0015% Brij-35; 2 mM DTT), each well containing 5× compound dissolved in 5 L of 10% DMSO. The negative control well was 5 μL of 1× kinase buffer containing 10% DMSO.
2. Experimental Procedure
    FGFR1-4(h) in 1× kinase buffer were reacted with 2.5× enzyme solution at room temperature for 10 min, and then the FAM-labelled polypeptide substrate and ATP were added to initiate reaction. After incubation for 30 min, 25 μL of terminal solution (100 mM HEPES, pH 7.5; 0.015% Brij-35;

0.2% Coating Reagent #3; 50 mM EDTA) was added to terminate the reaction, and the final data were read by Caliper.

The test results are shown in Table 1.

TABLE 1

Inhibitory activity of the compounds of the present invention against FGFR (IC50)

| Compound | FGFR1 (nM) | FGFR2 (nM) | FGFR3 (nM) | FGFR4 (nM) |
|---|---|---|---|---|
| 1 | — | — | — | 153 |
| 6 | <3 | — | 18 | 780 |
| 5 | 5.4 | 5.5 | 18 | 175 |
| 9 | <3 | — | 8 | 301 |
| 10 | <3 | — | 7 | 177 |
| 11 | 21 | — | — | 198 |
| 20 | 15 | 15 | 34 | 68 |
| 21 | 8.0 | — | — | 330 |
| 22 | 4.6 | 4.4 | 19 | 101 |
| 27 | 18 | — | — | 261 |
| 30 | 9.0 | — | — | 657 |
| 31 | 3.7 | — | — | 103 |
| 37 | 8.9 | — | — | 317 |
| 39 | <3 | — | — | 318 |
| 41 | 7 | — | — | — |
| 46 | 5.8 | 8.2 | 22 | — |
| 48 | 17 | 25 | 75 | — |
| 61 | 6 | — | — | 268 |
| 62 | 7 | — | — | — |
| 63 | <3 | — | — | 196 |
| 66 | 15 | — | — | 318 |
| 67 | 8 | 56 | — | 129 |

"—" means untested.

As can be seen from the experimental results in Table 1, the compounds of the present invention have good inhibitory activity against FGFR, indicating that the compounds of the present invention have a good clinical application potential in the treatment of diseases mediated by FGFR abnormality.

Experimental Example 2: Cellular Activity Test of the Compounds of the Present Invention Hep3B is a cell with abnormal FGFR in hepatocellular carcinoma RT112/84 is a cell with abnormal FGFR in bladder cancer DMS114 is a cell with abnormal FGFR in small cell lung cancer AN3CA is a cell with abnormal FGFR in endometrial cancer SNU-16 is a cell with abnormal FGFR in gastric cancer Test substance: The compounds of the present invention, the structures of which are shown above.

Test instrument: The Espire multi-function microplate reader.

Test Method:

Each cell line was seeded into a 96-well plate, and adherent cultured overnight. Then, the compounds at different concentrations (12 dose groups, 3×DMSO serial dilutions) were added to a final concentration of 0.17-30000 nM, with the final content of DMSO of 5‰. The negative control well was medium containing 5‰ DMSO. After incubation at 37° C., 5% $CO_2$, 95% humidity for 72 h, the cultures would be test. 30 μL of Cell titer-Glo reagent was added to each well and incubated for 30 min at room temperature. The final data were read by Espire microplate reader.

The test results are shown in Table 2.

TABLE 2

Inhibitory activity of the compounds of the present invention against cells (IC50)

| compound | Hep3B (nM) | RT112/84 (nM) | DMS114 (nM) | AN3CA (nM) | SNU-16 (nM) |
|---|---|---|---|---|---|
| 5 | 153 | 56 | 58 | — | — |
| 20 | 50.2 | 77 | 113 | — | — |
| 21 | — | 54 | — | 176 | — |
| 22 | 32.2 | 40 | 25 | 59 | 11 |
| 23 | 26 | 50 | 31 | 86 | 22 |
| 24 | 46 | 153 | — | — | 48 |
| 27 | 82 | 127 | 72 | — | — |
| 30 | 77.5 | 117 | — | — | — |
| 31 | 46 | 70 | 25 | 117 | — |
| 32 | 147 | 78 | 48 | 167 | — |
| 33 | 75.4 | 65 | 34 | 149 | — |
| 35 | 95.0 | 60 | 52 | 112 | — |
| 36 | 70.7 | — | — | — | — |
| 53 | — | 97 | 82 | — | — |
| 55 | — | 54 | 21 | 66 | — |
| 65 | 66 | 161 | — | — | 92 |

"—" means untested.

It can be seen from the experimental results in Table 2 that the compounds of the present invention have good inhibitory activity against cells with abnormal FGFR, such as Hep3B, RT112/84, DMS114, AN3CA, SNU-16, etc., indicating that the compounds of the present invention can be used for treating cancers mediated by FGF/FGFR abnormality, such as liver cancer, gastric cancer, small cell cancer, bladder cancer, endometrial cancer, and have very good clinical use value.

The invention claimed is:

1. A compound represented by general formula (I), or a pharmaceutically acceptable salt or a stereoisomer thereof:

(I)

[Chemical structure showing a pyrimidine ring with substituents $R_3$, $R_4$, connected to ring A with $(R_1)m_1$ and Ar with $(R_2)m_2$ substituents, ring B, and Warhead group]

wherein,
$R_1$ and $R_2$ are each independently selected from the group consisting of hydrogen, hydroxyl, amino, cyano, nitro, halogen atom, carboxyl, $C_{1-6}$ alkyl, $C_{1-6}$ alkoxy, $C_{1-6}$ alkylamino, $(C_{1-6}$ alkyl$)_2$ amino, halo $C_{1-6}$ alkyl, halo $C_{1-6}$ alkoxy, $C_{2-8}$ alkenyl, $C_{2-8}$ alkynyl, $C_{1-6}$ alkylsulfonyl, $C_{1-6}$ alkylcarbonylamino, $C_{1-6}$ alkyl-substituted 3-8 membered cycloalkyl, and $C_{1-6}$ alkyl-substituted 3-8 membered heterocyclyl, alternatively, $R_1$ and $R_2$ together with two atoms on an aromatic ring or heteroaromatic ring to which they are connected respectively may form a 3-8 membered cycloalkyl, a 3-8 membered heterocyclyl, a 6-14 membered aryl or a 5-10 membered heteroaryl, and a S atom in any ring may be optionally oxidized to S(O) or S(O)$_2$, and a carbon atom in any ring may be optionally oxidized to C(O);

$R_3$ and $R_4$ are each independently selected from the group consisting of hydrogen, hydroxyl, amino, cyano, nitro, halogen atom, carboxyl, $C_{1-6}$ alkyl, $C_{1-6}$ alkoxy, $C_{1-6}$ alkylamino, $(C_{1-6}$ alkyl$)_2$ amino, $(C_{1-6}$ alkyl$)_2$ amino $C_{1-6}$ alkyl, halo $C_{1-6}$ alkyl, halo $C_{1-6}$ alkoxy, $C_{2-8}$ alkenyl, $C_{2-8}$ alkynyl, $C_{1-6}$ alkylsulfonyl, $C_{1-6}$ alkylcarbonylamino, $C_{1-6}$ alkylaminocarbonyl, 3-8 membered cycloalkyl, 3-8 membered heterocyclyl, 6-14 membered aryl or 5-10 membered heteroaryl, $C_{1-6}$ alkyl-substituted 3-8 membered cycloalkyl, $C_{1-6}$ alkyl-substituted 3-8 membered heterocyclyl, $C_{1-6}$ alkyl-substituted 6-14 membered aryl or $C_{1-6}$ alkyl-substituted 5-10 membered heteroaryl;

Ar is 6-14 membered aromatic ring group or 5-10 membered heteroaryl optionally containing 0-3 O, S and/or N atom;

Ring A is selected from the group consisting of 3-8 membered cycloalkyl, 3-8 membered heterocyclyl, 6-14 membered aryl, and 5-10 membered heteroaryl containing 0-3 O, S and/or N atom, optionally substituted with 1-3 $R_5$, wherein a S atom in any ring may be optionally oxidized to $S(O)$ or $S(O)_2$, and a carbon atom in any ring may be optionally oxidized to $C(O)$;

Ring B is 3-10 membered saturated or unsaturated heterocyclyl containing at least one N hetero atom or 5-6 membered N-containing heteroaryl, optionally substituted with 1-3 $R_6$, and the N atom on ring B is directly bonded to Warhead, wherein any S atom in ring B can be optionally oxidized to $S(O)$ or $S(O)_2$, and any carbon atom in ring B can be optionally oxidized to $C(O)$;

X is N;

$R_5$, $R_6$, and $R_7$ are each independently selected from the group consisting of
(i) hydrogen,
(ii) hydroxyl, amino, carboxyl, cyano, nitro, halogen atom, or $=CH_2$,
(iii) $C_{1-6}$ alkyl, $C_{1-6}$ alkoxy, $C_{1-6}$ alkylamino, $(C_{1-6}$ alkyl$)_2$ amino, halo $C_{1-6}$ alkyl, halo $C_{1-6}$ alkoxy, $C_{2-8}$ alkenyl, $C_{2-8}$ alkynyl, $C_{1-6}$ alkylsulfonyl, or $C_{1-6}$ alkylthio optionally substituted with hydroxyl, amino, carboxyl, cyano, nitro, halogen, $C_{1-6}$ alkyl, $C_{1-6}$ alkoxy, $C_{1-6}$ alkoxy $C_{1-6}$ alkoxy, $C_{1-6}$ alkylamino, $(C_{1-6}$ alkyl$)_2$ amino, $C_{1-6}$ alkylcarbonylamino, $C_{1-6}$alkylsulfonylamino, or 3-8 membered heterocyclyl, wherein the 3-8 membered heterocyclyl may be optionally substituted with hydroxyl, amino, carboxyl, cyano, nitro, halogen, $C_{1-6}$ alkyl, $C_{1-6}$ alkoxy, $C_{1-6}$ alkylamino, or $(C_{1-6}$ alkyl$)_2$ amino,
(iv) 3-8 membered cycloalkyl or 3-8 membered heterocyclyl optionally substituted with hydroxyl, amino, carboxyl, cyano, nitro, halogen, $C_{1-6}$ alkyl, $C_{1-6}$ alkoxy, $C_{1-6}$ alkylamino, or $(C_{1-6}$ alkyl$)_2$ amino, and
(v) aminocarbonyl, cyanocarbonyl, $C_{1-6}$ alkylcarbonyl, $C_{1-6}$ alkylamino carbonyl, $(C_{1-6}$ alkyl$)_2$ aminocarbonyl, $C_{1-6}$ alkoxycarbonyl, 3-8 membered cycloalkylcarbonyl, or 3-8 membered heterocyclyl carbonyl;

$m_1$ and $m_2$ represent 1, 2 or 3, and the sum of $m_1$ and $m_2$ is less than or equal to 5;

Warhead is selected from the group consisting of

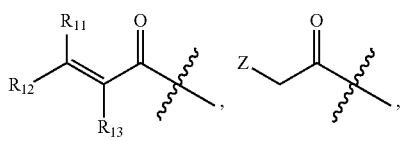

-continued

Z refers to a leaving group or an activated hydroxyl moiety, $R_{11}$, $R_{12}$, and $R_{13}$ are each independently selected from the group consisting of hydrogen, halogen, cyano, $C_{1-4}$ alkyl, halo $C_{1-4}$ alkyl, 3-8 membered cycloalkyl, 3-8 membered heterocyclyl, 5-8 membered aryl and 5-10 membered heteroaryl, the $C_{1-4}$ alkyl, halo $C_{1-4}$ alkyl, 3-8 membered cycloalkyl, 3-8 membered heterocyclyl, 5-8 membered aryl or 5-10 membered heteroaryl is optionally substituted with a substituent, wherein the substituent is selected from the group consisting of hydroxyl, amino, carboxyl, cyano, nitro, halogen, $C_{1-4}$ alkyl, $C_{1-4}$ alkoxy, $C_{1-4}$ alkoxy C$_{1-4}$ alkoxy, C$_{1-4}$ alkylamino, (C$_{1-4}$ alkyl)$_2$ amino, C$_{1-4}$ alkylcarbonylamino, C$_{1-4}$ alkylsulfonylamino, and 3-8 membered heterocyclyl.

2. The compound or the pharmaceutically acceptable salt or the stereoisomer thereof according to claim 1, wherein,
R$_1$ is selected from the group consisting of hydrogen, halogen, and hydroxyl;
R$_2$ is selected from the group consisting of hydrogen, halogen, hydroxyl, C$_{1-4}$ alkyl, C$_{1-4}$ alkoxy, cyano, halo C$_{1-4}$ alkyl, and halo C$_{1-4}$ alkoxy;
Ar is 6-14 membered aromatic ring group or 5-6 membered heteroaryl optionally containing 0-3 O, S and/or N atom;
m$_1$ and m$_2$ represent 1, 2 or 3, and the sum of m$_1$ and m$_2$ is less than or equal to 5.

3. The compound or the pharmaceutically acceptable salt or the stereoisomer thereof according to claim 2, wherein,
R$_1$ is selected from the group consisting of hydrogen, halogen, and hydroxyl;
R$_2$ is selected from the group consisting of hydrogen, halogen, hydroxyl, C$_{1-4}$ alkyl, C$_{1-4}$ alkoxy, cyano, halo C$_{1-4}$ alkyl, and halo C$_{1-4}$ alkoxy;
R$_3$ and R$_4$ are each independently selected from the group consisting of hydrogen, hydroxyl, amino, cyano, nitro, halogen atom, carboxyl, C$_{1-4}$ alkyl, C$_{1-4}$ alkoxy, C$_{1-4}$ alkylamino, (C$_{1-4}$ alkyl)$_2$ amino, (C$_{1-4}$ alkyl)$_2$ amino C$_{1-4}$ alkyl, halo C$_{1-4}$ alkyl, halo C$_{1-4}$ alkoxy, C$_{2-4}$ alkenyl, C$_{2-4}$ alkynyl, C$_{1-4}$ alkylsulfonyl, and C$_{1-4}$ alkylcarbonylamino;
Ar is phenyl;
Ring A is phenyl optionally substituted with 1-3 R$_5$,
Ring B is 4-10 membered saturated or unsaturated heterocyclyl containing at least one N hetero atom, optionally substituted with 1-3 R$_6$, and the N atom on ring B is directly bonded to Warhead;
X is N;
R$_5$ and R$_7$ are each independently selected from the group consisting of hydrogen, hydroxyl, amino, carboxyl, cyano, nitro, halogen atom, C$_{1-4}$ alkyl, and C$_{1-4}$ alkoxy;
R$_6$ is selected from the group consisting of
  (i) hydrogen,
  (ii) hydroxyl, amino, carboxyl, cyano, nitro, halogen atom, or =CH$_2$,
  (iii) C$_{1-4}$ alkyl, C$_{1-4}$ alkoxy, C$_{1-4}$ alkylamino, (C$_{1-4}$ alkyl)$_2$ amino, halo C$_{1-4}$ alkyl, halo C$_{1-4}$ alkoxy, C$_{2-4}$ alkenyl, C$_{2-4}$ alkynyl, C$_{1-4}$ alkylsulfonyl, or C$_{1-4}$ alkylthio optionally substituted with hydroxyl, amino, carboxyl, cyano, nitro, halogen, C$_{1-4}$ alkyl, C$_{1-4}$ alkoxy, C$_{1-4}$ alkoxy C$_{1-4}$ alkoxy, C$_{1-4}$ alkylamino, (C$_{1-4}$ alkyl)$_2$ amino, C$_{1-4}$ alkylcarbonylamino, C$_{1-4}$alkylsulfonylamino, or 3-8 membered heterocyclyl, wherein the 3-8 membered heterocyclyl may be optionally substituted with hydroxyl, amino, carboxyl, cyano, nitro, halogen, C$_{1-4}$ alkyl, C$_{1-4}$ alkoxy, C$_{1-4}$ alkylamino, or (C$_{1-4}$ alkyl)$_2$ amino,
  (iv) 3-8 membered cycloalkyl or 3-8 membered heterocyclyl optionally substituted with hydroxyl, amino, carboxyl, cyano, nitro, halogen, C$_{1-4}$ alkyl, C$_{1-4}$ alkoxy, C$_{1-4}$ alkylamino, or (C$_{1-4}$ alkyl)$_2$ amino, and
  (v) aminocarbonyl, cyanocarbonyl, C$_{1-4}$ alkylcarbonyl, C$_{1-4}$ alkylamino carbonyl, (C$_{1-4}$ alkyl)$_2$ aminocarbonyl, C$_{1-4}$ alkoxycarbonyl, 3-8 membered cycloalkylcarbonyl, or 3-8 membered heterocyclyl carbonyl;
m$_1$ and m$_2$ represent 1, 2 or 3, and the sum of m$_1$ and m$_2$ is less than or equal to 5;

Warhead is selected from the group consisting of

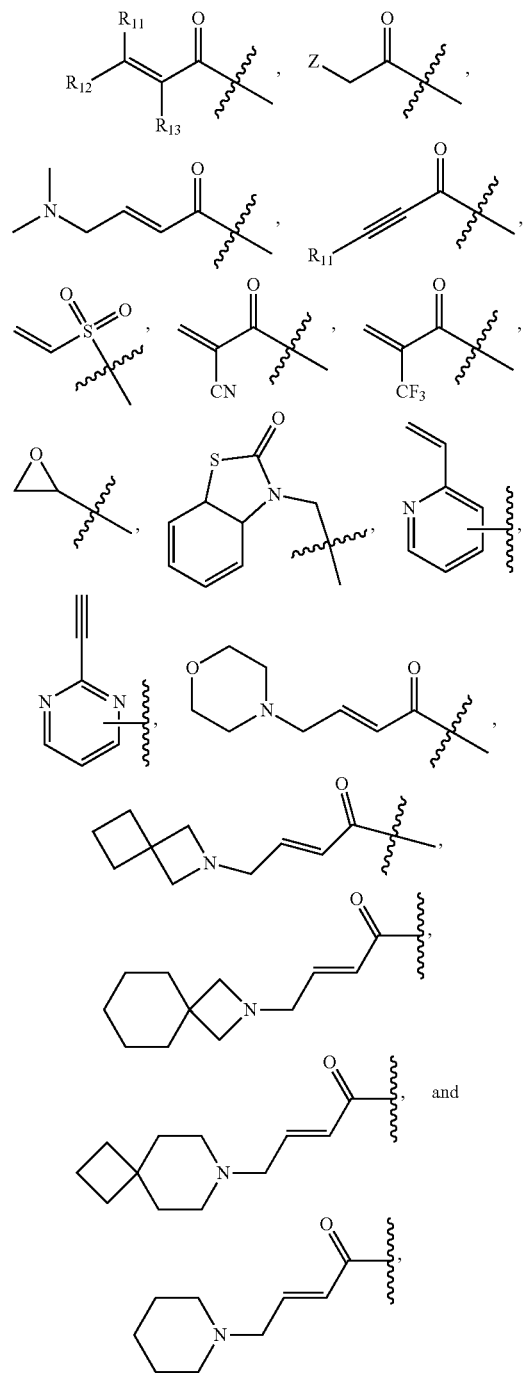

Z refers to a leaving group or an activated hydroxyl moiety,
R$_{11}$, R$_{12}$, and R$_{13}$ are each independently selected from the group consisting of hydrogen, halogen, cyano, C$_{1-4}$ alkyl, halo C$_{1-4}$ alkyl, 3-8 membered cycloalkyl, 3-8 membered heterocyclyl, 5-8 membered aryl and 5-10 membered heteroaryl, the C$_{1-4}$ alkyl, halo C$_{1-4}$ alkyl, 3-8 membered cycloalkyl, 3-8 membered heterocyclyl, 5-8 membered aryl or 5-10 membered heteroaryl is optionally substituted with a substituent, wherein the substituent is selected from the group consisting of hydroxyl, amino, carboxyl, cyano, nitro, halogen, $C_{1-4}$ alkyl, $C_{1-4}$ alkoxy, $C_{1-4}$ alkoxy $C_{1-4}$ alkoxy, $C_{1-4}$ alkylamino, $(C_{1-4}$ alkyl$)_2$ amino, $C_{1-4}$ alkylcarbonylamino, $C_{1-4}$ alkylsulfonylamino, and 3-8 membered heterocyclyl.

4. The compound of formula (I) or the pharmaceutically acceptable salt or the stereoisomer thereof according to claim 1, having a structure as shown in general formula (II):

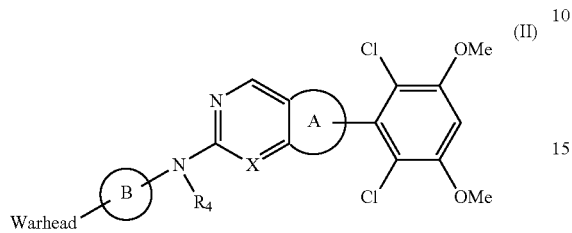

$R_4$ is selected from the group consisting of hydrogen, $C_{1-4}$ alkyl, and $(C_{1-6}$ alkyl$)_2$ amino $C_{1-6}$ alkyl;

Ring A is phenyl;

Ring B is selected from the group consisting of 4-6 membered saturated or unsaturated monoheterocyclyl and 6-10 membered saturated or unsaturated fused heterocyclyl containing at least one N hetero atom optionally substituted with 1-3 $R_6$, and the N atom on ring B is directly bonded to Warhead;

X is N;

$R_6$ is selected from the group consisting of (i) hydrogen, (ii) hydroxyl, amino, carboxyl, cyano, nitro, halogen atom, or $=CH_2$, (iii) $C_{1-4}$ alkyl, $C_{1-4}$ alkoxy, $C_{1-4}$ alkylamino, $(C_{1-4}$ alkyl$)_2$ amino, halo $C_{1-4}$ alkyl, halo $C_{1-4}$ alkoxy, $C_{2-4}$ alkenyl, $C_{2-4}$ alkynyl, $C_{1-4}$ alkylsulfonyl, or $C_{1-4}$ alkylthio optionally substituted with hydroxyl, amino, carboxyl, cyano, nitro, halogen, $C_{1-4}$ alkyl, $C_{1-4}$ alkoxy, $C_{1-4}$ alkoxy $C_{1-4}$ alkoxy, $C_{1-4}$ alkylamino, $(C_{1-4}$ alkyl$)_2$ amino, $C_{1-4}$ alkylcarbonylamino, $C_{1-4}$ alkylsulfonylamino, or 3-8 membered heterocyclyl, wherein the 3-8 membered heterocyclyl may be optionally substituted with hydroxyl, amino, carboxyl, cyano, nitro, halogen, $C_{1-4}$ alkyl, $C_{1-4}$ alkoxy, $C_{1-4}$ alkylamino, or $(C_{1-4}$ alkyl$)_2$ amino, and (iv) aminocarbonyl, cyanocarbonyl, $C_{1-4}$ alkylcarbonyl, $C_{1-4}$ alkylamino carbonyl, $(C_{1-4}$ alkyl$)_2$ aminocarbonyl, $C_{1-4}$ alkoxycarbonyl, 3-8 membered cycloalkylcarbonyl, or 3-8 membered heterocyclyl carbonyl;

Warhead is selected from the group consisting of

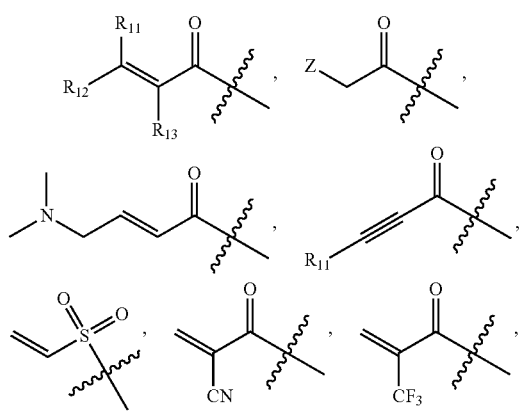

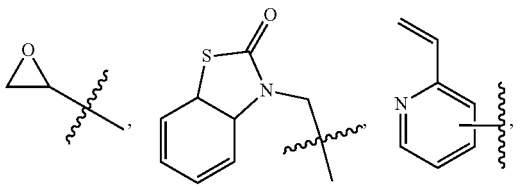

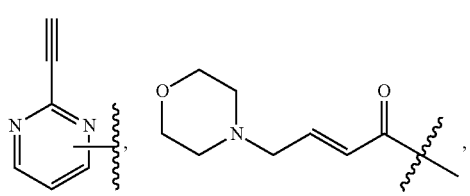

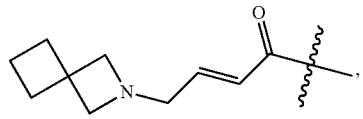

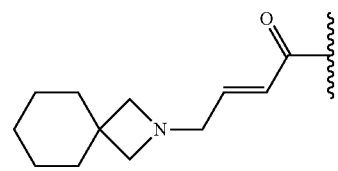

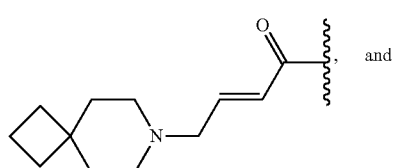, and

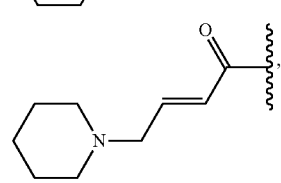

Z refers to a leaving group or an activated hydroxyl moiety, $R_{11}$, $R_{12}$, and $R_{13}$ are each independently selected from the group consisting of hydrogen, halogen, cyano, $C_{1-4}$ alkyl, halo $C_{1-4}$ alkyl, 3-8 membered cycloalkyl, 3-8 membered heterocyclyl, 5-8 membered aryl and 5-10 membered heteroaryl, the $C_{1-4}$ alkyl, halo $C_{1-4}$ alkyl, 3-8 membered cycloalkyl, 3-8 membered heterocyclyl, 5-8 membered aryl or 5-10 membered heteroaryl is optionally substituted with a substituent, wherein the substituent is selected from the group consisting of hydroxyl, amino, carboxyl, cyano, nitro, halogen, $C_{1-4}$ alkyl, $C_{1-4}$ alkoxy, $C_{1-4}$ alkoxy $C_{1-4}$ alkoxy, $C_{1-4}$ alkylamino, $(C_{1-4}$ alkyl$)_2$ amino, $C_{1-4}$ alkylcarbonylamino, $C_{1-4}$ alkylsulfonylamino, and 3-8 membered heterocyclyl.

5. The compound or the pharmaceutically acceptable salt or the stereoisomer thereof according to claim 1, having a structure as shown in general formula (II):

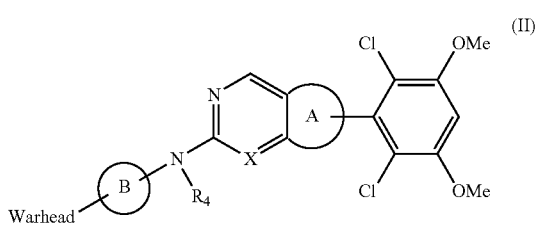

Warhead is directly connected to an N atom on ring B as follows:

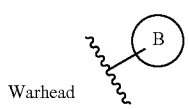

Ring B is selected from the group consisting of:

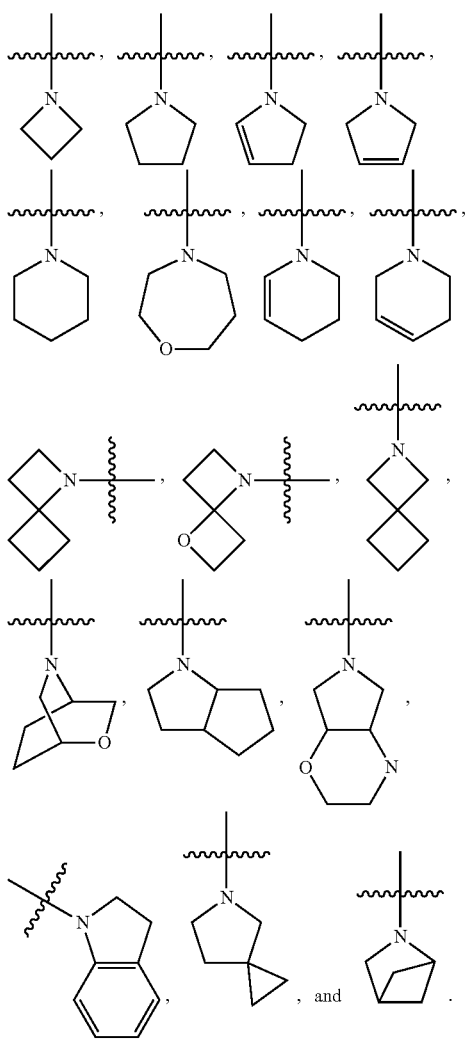

6. The compound or the pharmaceutically acceptable salt or the stereoisomer thereof according to claim 1, wherein Warhead is selected from the group consisting of:

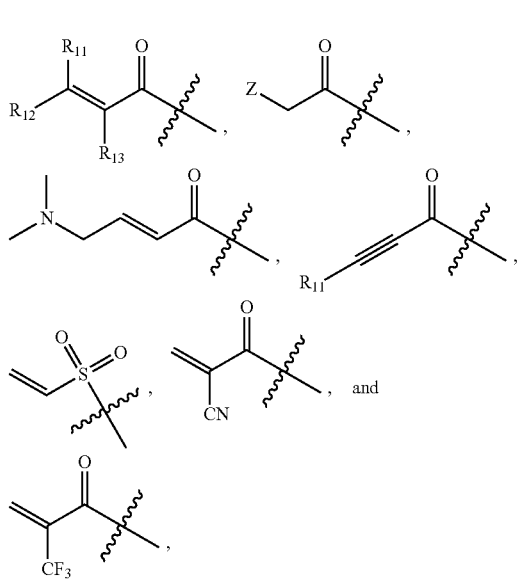

Z refers to a leaving group or an activated hydroxyl moiety, and $R_{11}$, $R_{12}$, and $R_{13}$ are each independently H or $C_{1-4}$ alkyl.

7. The compound or the pharmaceutically acceptable salt or the stereoisomer thereof according to claim 1, wherein the compound has a structure selected from the group consisting of:

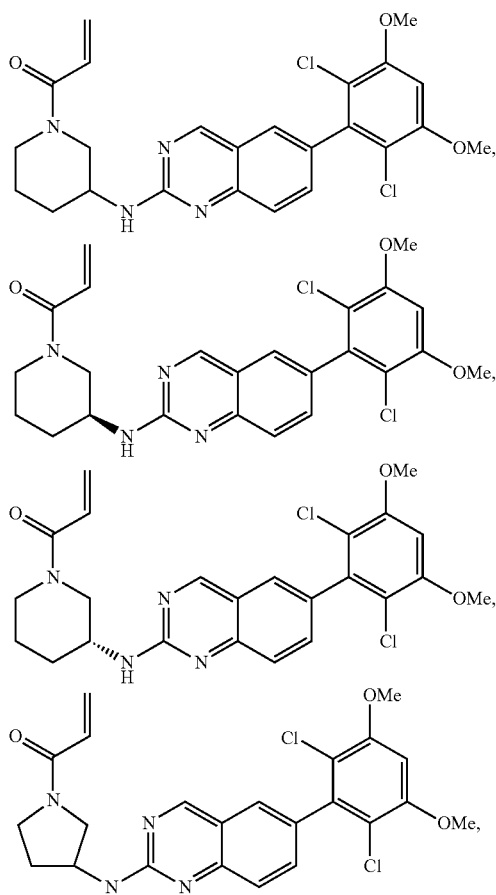

119
-continued
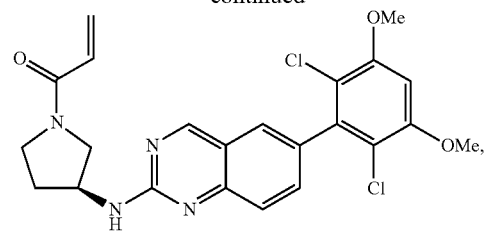
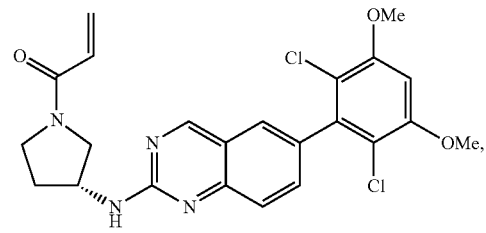
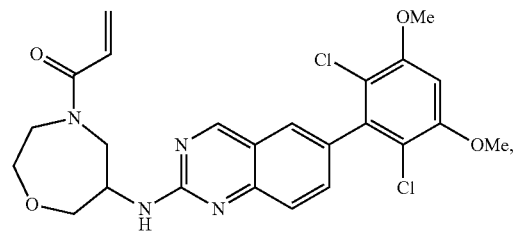
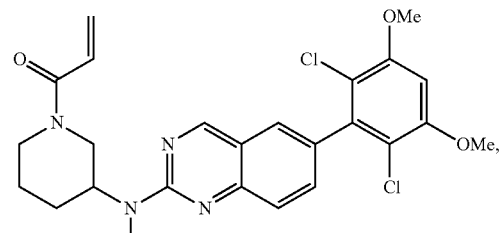
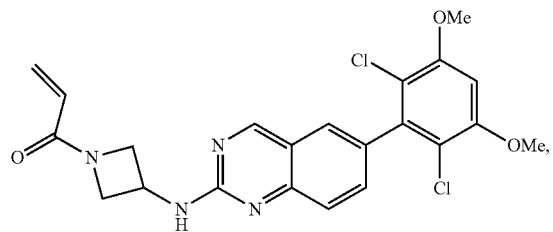
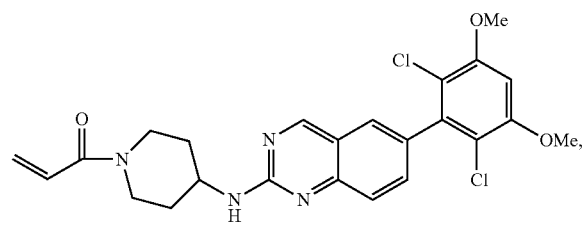
120
-continued
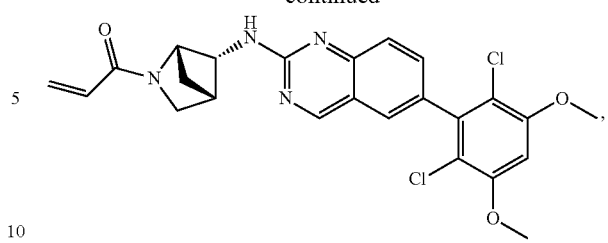
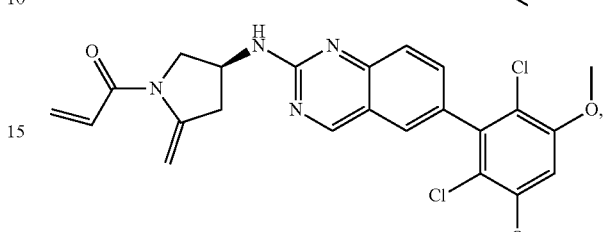
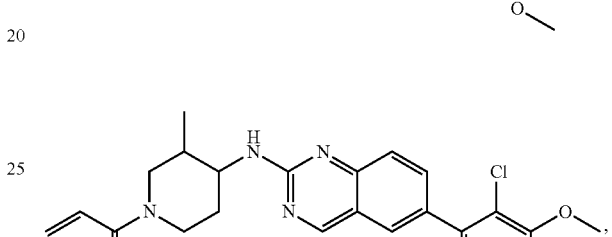
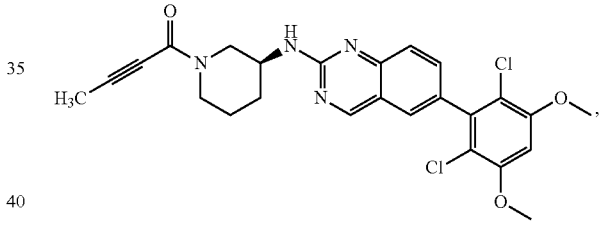
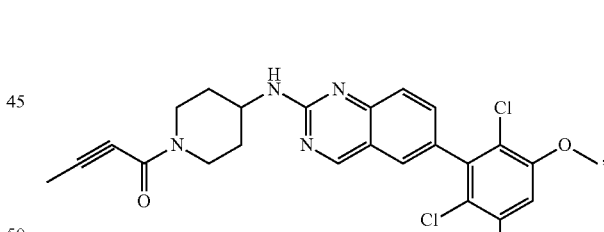
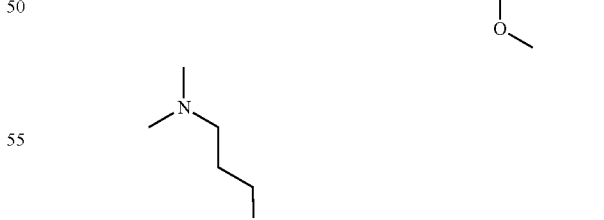
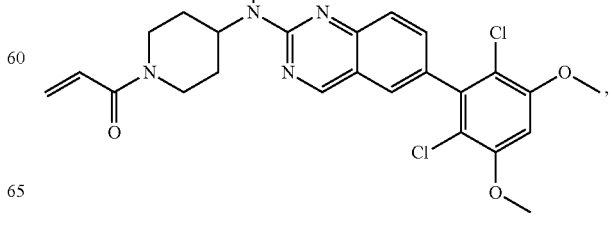

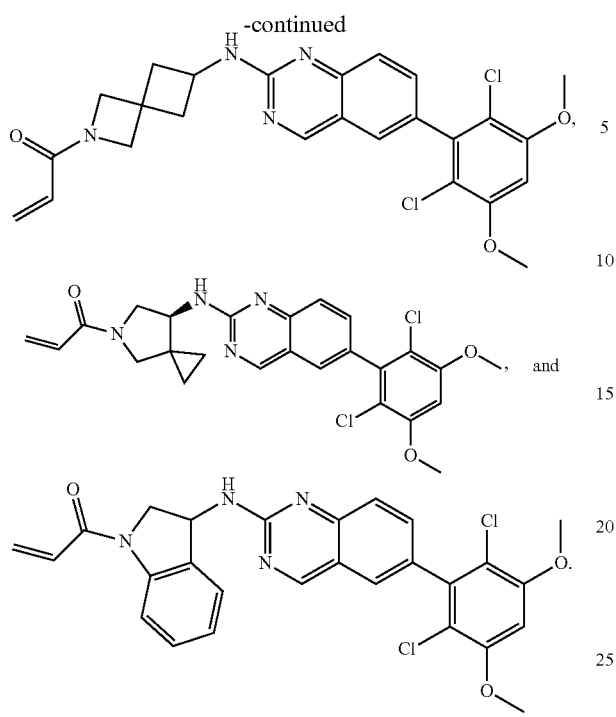

8. The compound or the pharmaceutically acceptable salt or the stereoisomer thereof according to claim 4, wherein Ring B is selected from 5-6 membered saturated monoheterocyclyl containing at least one N hetero atom optionally substituted with 1-3 $R_6$, and the N atom on ring B is directly bonded to Warhead.

9. The compound or the pharmaceutically acceptable salt or the stereoisomer thereof according to claim 8, having a structure as shown in general formula (III):

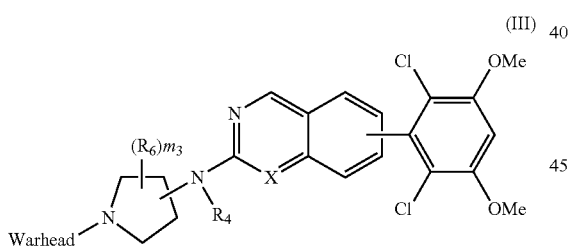

$R_4$ is H or $C_{1-4}$ alkyl;
X is N;
$R_6$ is selected from the group consisting of
(i) hydrogen,
(ii) hydroxyl, amino, carboxyl, cyano, nitro, or halogen atom,
(iii) $C_{1-4}$ alkyl, $C_{1-4}$ alkoxy, $C_{1-4}$ alkylamino, $(C_{1-4}$ alkyl$)_2$ amino, halo $C_{1-4}$ alkyl, halo $C_{1-4}$ alkoxy, $C_{2-4}$ alkenyl, $C_{2-4}$ alkynyl, $C_{1-4}$ alkylsulfonyl, or $C_{1-4}$ alkylthio optionally substituted with hydroxyl, amino, carboxyl, cyano, nitro, halogen, $C_{1-4}$ alkyl, $C_{1-4}$ alkoxy, $C_{1-4}$ alkoxy $C_{1-4}$ alkoxy, $C_{1-4}$ alkylamino, $(C_{1-4}$ alkyl$)_2$ amino, $C_{1-4}$ alkylcarbonylamino, $C_{1-4}$ alkylsulfonylamino, or 3-8 membered heterocyclyl, wherein the 3-8 membered heterocyclyl may be optionally substituted with hydroxyl, amino, carboxyl, cyano, nitro, halogen, $C_{1-4}$ alkyl, $C_{1-4}$ alkoxy, $C_{1-4}$ alkylamino, or $(C_{1-4}$ alkyl$)_2$ amino, and (iv) aminocarbonyl, cyanocarbonyl, $C_{1-4}$ alkylcarbonyl, $C_{1-4}$ alkylamino carbonyl, $(C_{1-4}$ alkyl$)_2$ aminocarbonyl, $C_{1-4}$ alkoxycarbonyl, 3-8 membered cycloalkylcarbonyl, or 3-8 membered heterocyclyl carbonyl;

m is an integer from 1 to 3;

Warhead is selected from the group consisting of

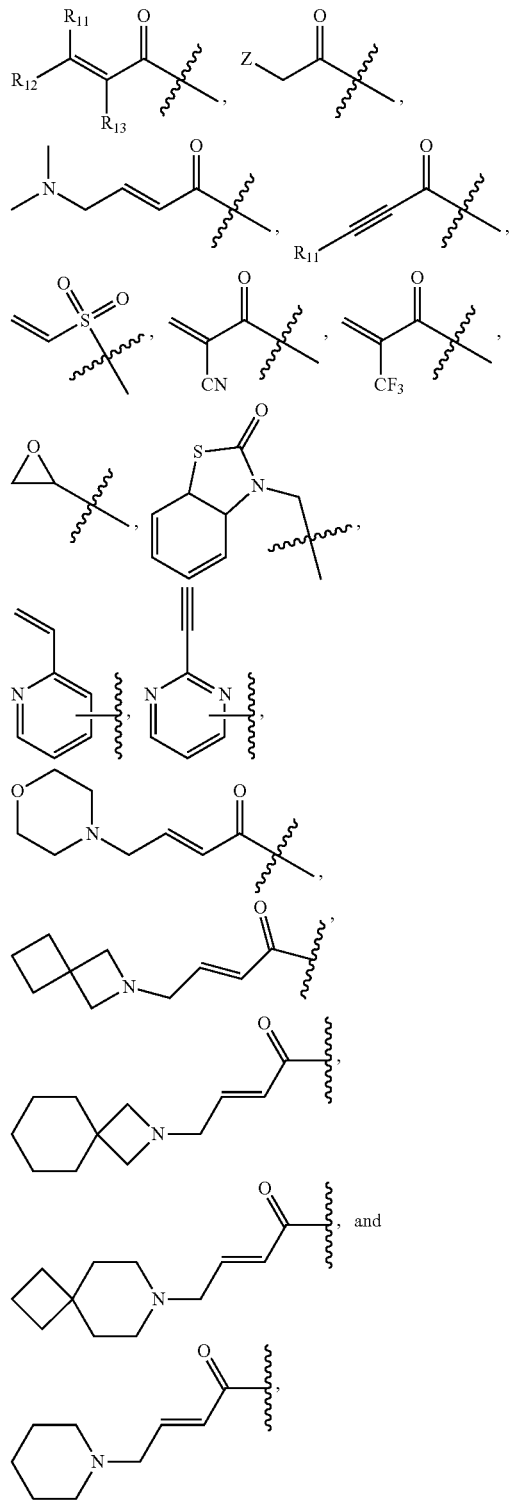

Z refers to a leaving group or an activated hydroxyl moiety;

$R_{11}$, $R_{12}$, and $R_{13}$ are each independently selected from the group consisting of hydrogen, halogen, cyano, $C_{1-4}$ alkyl, halo $C_{1-4}$ alkyl, 3-8 membered cycloalkyl, 3-8 membered heterocyclyl, 5-8 membered aryl and 5-10 membered heteroaryl, the $C_{1-4}$ alkyl, halo $C_{1-4}$ alkyl, 3-8 membered cycloalkyl, 3-8 membered heterocyclyl, 5-8 membered aryl or 5-10 membered heteroaryl is optionally substituted with a substituent, wherein the substituent is selected from the group consisting of hydroxyl, amino, carboxyl, cyano, nitro, halogen, $C_{1-4}$ alkyl, $C_{1-4}$ alkoxy, $C_{1-4}$ alkoxy $C_{1-4}$ alkoxy, $C_{1-4}$ alkylamino, $(C_{1-4}$ alkyl$)_2$ amino, $C_{1-4}$ alkylcarbonylamino, $C_{1-4}$ alkylsulfonylamino, and 3-8 membered heterocyclyl.

10. The compound or the pharmaceutically acceptable salt or the stereoisomer thereof according to claim 9, wherein $R_6$ is selected from the group consisting of (i) hydrogen, (ii) hydroxyl, amino, carboxyl, cyano, nitro, or halogen atom, (iii) $C_{1-4}$ alkyl, or $C_{1-4}$ alkoxy optionally substituted with hydroxyl, amino, carboxyl, cyano, nitro, halogen, $C_{1-4}$ alkyl, $C_{1-4}$ alkoxy, $C_{1-4}$ alkoxy $C_{1-4}$ alkoxy, $C_{1-4}$ alkylamino, $(C_{1-4}$ alkyl$)2$ amino, $C_{1-4}$ alkylcarbonylamino, $C_{1-4}$ alkylsulfonylamino, or 3-8 membered heterocyclyl, wherein the 3-8 membered heterocyclyl may be optionally substituted with hydroxyl, amino, carboxyl, cyano, nitro, halogen, $C_{1-4}$ alkyl, $C_{1-4}$ alkoxy, $C_{1-4}$ alkylamino, or $(C_{1-4}$ alkyl$)_2$ amino; and (iv) aminocarbonyl, cyanocarbonyl, $C_{1-4}$ alkylcarbonyl, $C_{1-4}$ alkylamino carbonyl, $(C_{1-4}$ alkyl$)_2$ aminocarbonyl, $C_{1-4}$ alkoxycarbonyl, 3-8 membered cycloalkylcarbonyl, or 3-8 membered heterocyclyl carbonyl;

m is an integer from 1 to 3;

Warhead is selected from the group consisting of

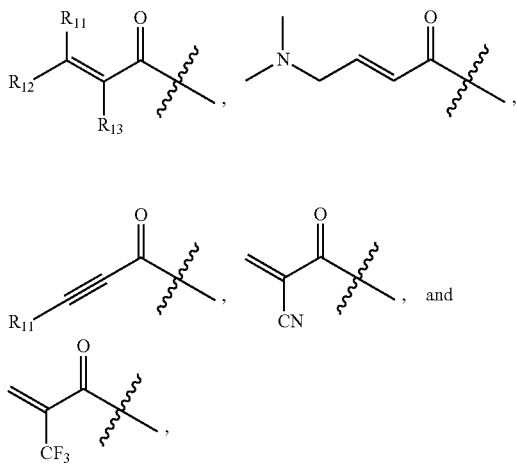

$R_{11}$, $R_{12}$, and $R_{13}$ are each independently H or $C_{1-4}$ alkyl.

11. The compound or the pharmaceutically acceptable salt or the stereoisomer thereof according to claim 10, having a structure selected from the group consisting of:

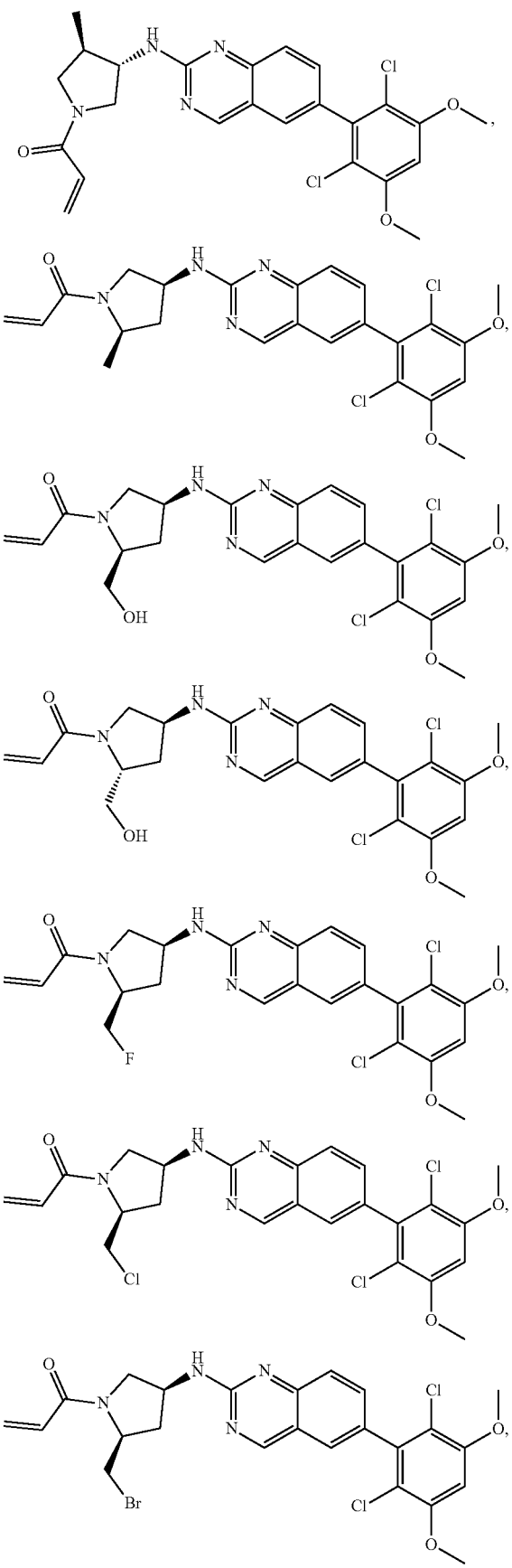

125
-continued
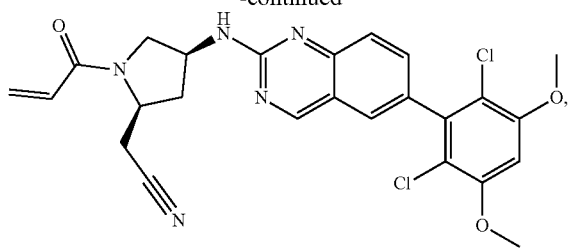
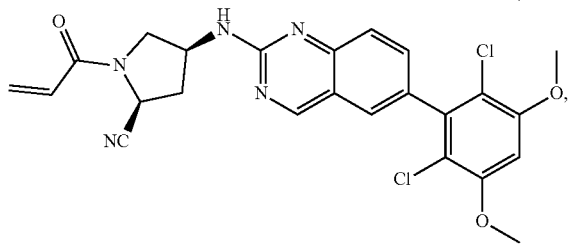
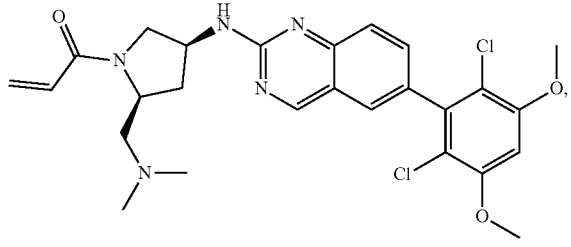
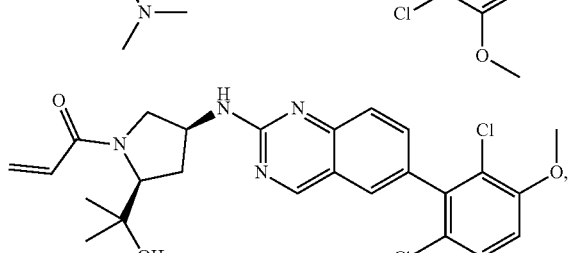
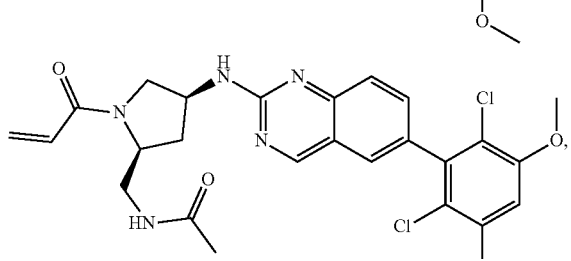
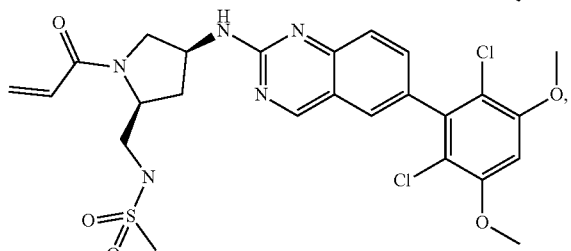
126
-continued
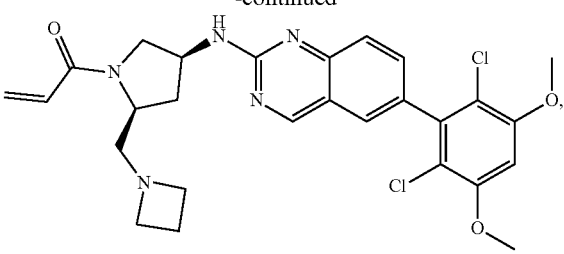
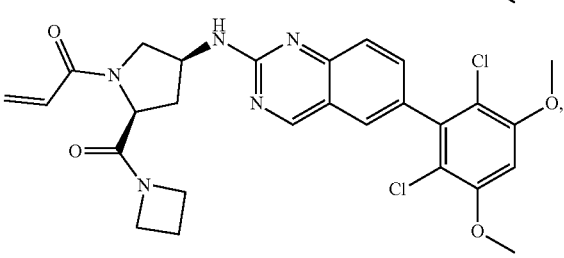
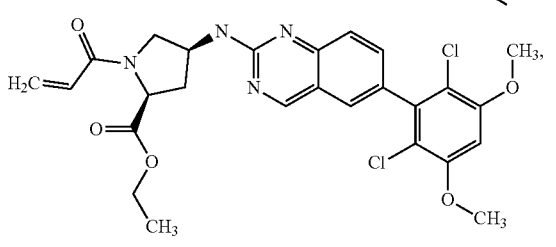
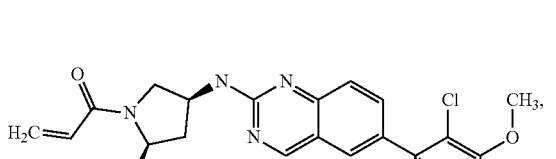
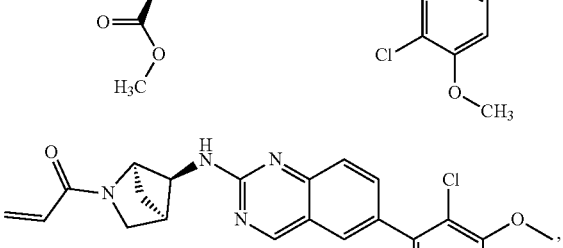
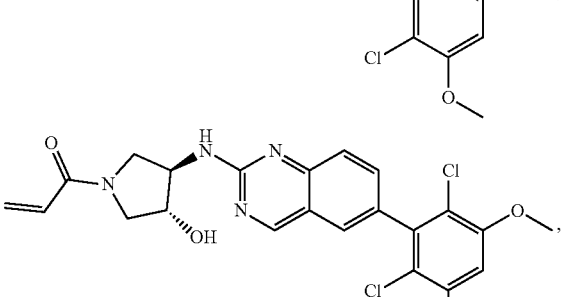
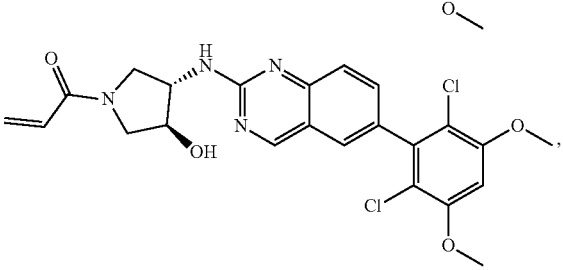

127
-continued
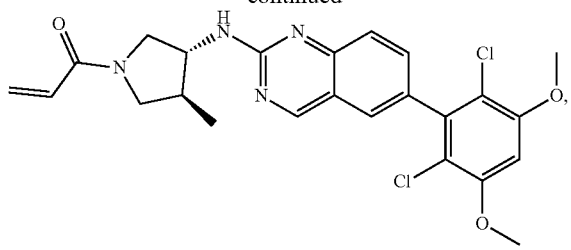
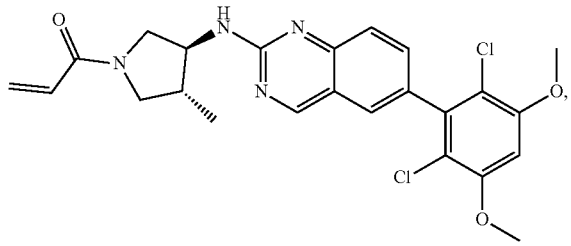
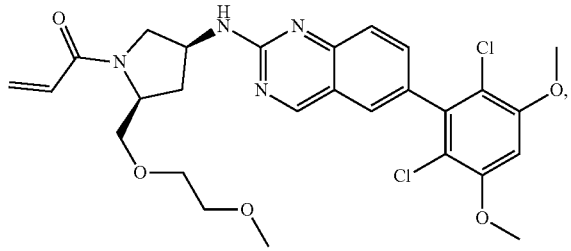
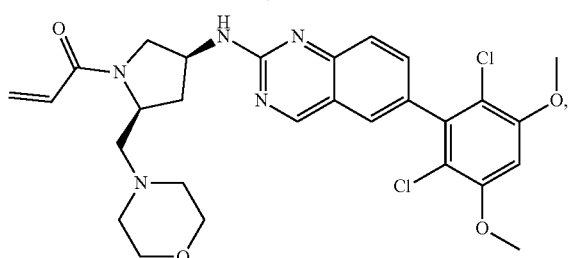
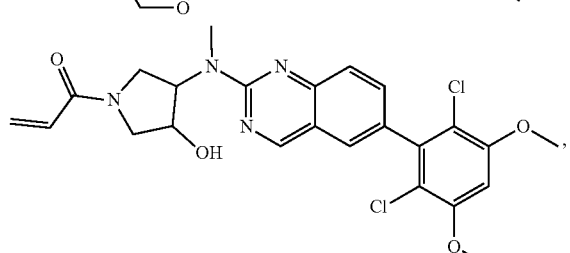
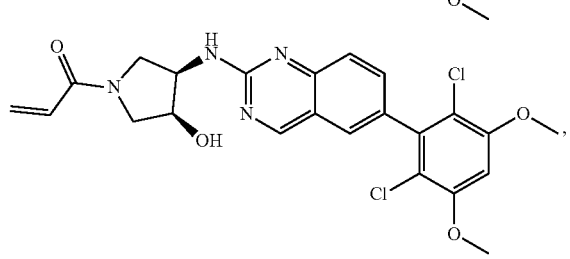
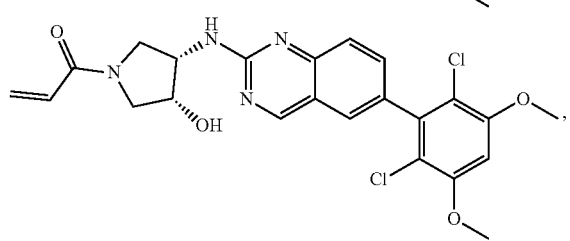
128
-continued
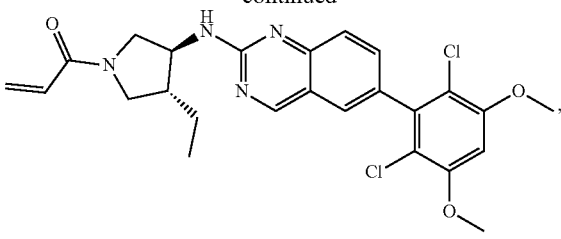
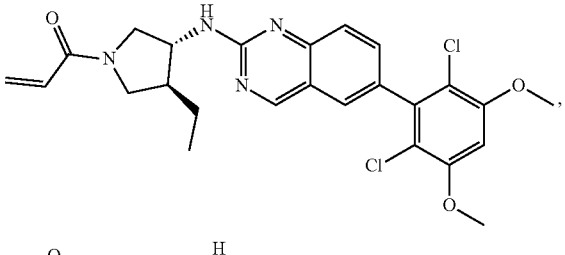
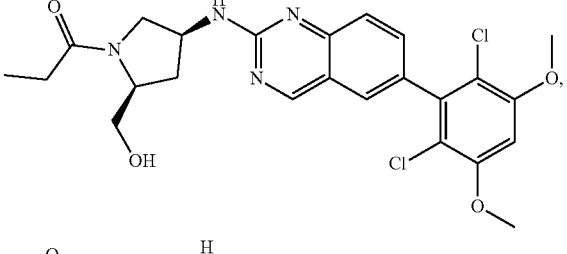
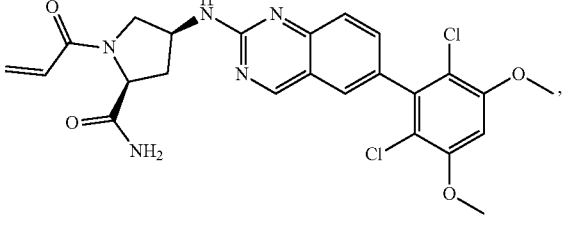
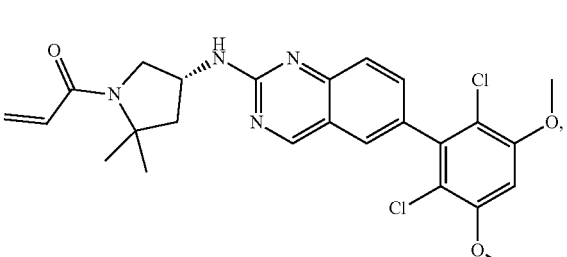
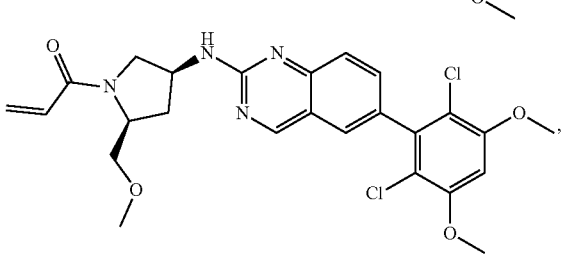
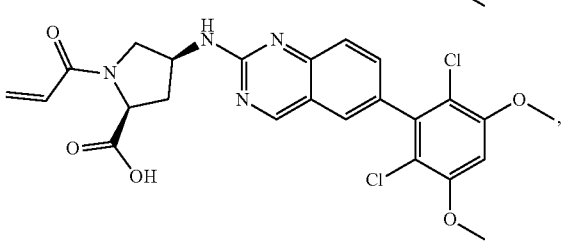

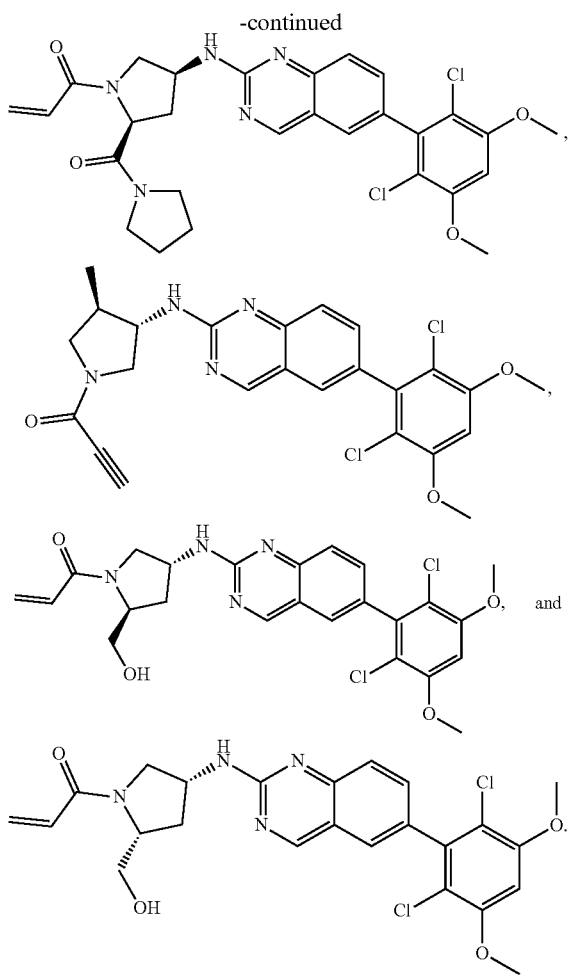

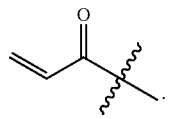 [SMILES: *C(=O)C=C]

12. The compound or the pharmaceutically acceptable salt or the stereoisomer thereof according to claim 4, wherein $R_{11}$, $R_{12}$ and $R_{13}$ are hydrogen.

13. The compound or the pharmaceutically acceptable salt or the stereoisomer thereof according to claim 9, wherein $R_{11}$, $R_{12}$ and $R_{13}$ are hydrogen.

14. The compound or the pharmaceutically acceptable salt or the stereoisomer thereof according to claim 10, wherein the warhead is 15. A pharmaceutical formulation containing the compound or the pharmaceutically acceptable salt or the stereoisomer thereof according to claim 1, and one or more pharmaceutical acceptable carriers.

16. The pharmaceutical formulation according to claim 15, further comprising one or more second therapeutically active agents, wherein the second therapeutically active agents are antimetabolites, growth factor inhibitors, mitotic inhibitors, antitumor hormones, alkylating agents, metals, topoisomerase inhibitors, hormone drugs, immunomodulators, tumor suppressor genes, cancer vaccines, or antibodies and small molecule drugs related to immune checkpoint or tumor immunotherapy.

17. A method for inhibiting FGF/FGFR, wherein the inhibition is for treating a disease mediated by FGF/FGFR abnormality, comprising administering to a subject in need thereof the compound or the pharmaceutically acceptable salt or the stereoisomer thereof according to claim 1, or the pharmaceutical formulation containing the compound or the pharmaceutically acceptable salt or the stereoisomer thereof according to claim 1, and one or more pharmaceutical acceptable carriers.

18. The method according to claim 17, wherein the disease is a cancer.

19. The method according to claim 18, wherein the cancer is lung cancer, squamous epithelial cell carcinoma, bladder cancer, gastric cancer, ovarian cancer, peritoneal cancer, breast cancer, breast ductal carcinoma, head and neck cancer, endometrial cancer, uterine corpus carcinoma, rectal cancer, liver cancer, kidney cancer, renal pelvic cancer, esophageal cancer, esophageal adenocarcinoma, glioma, prostate cancer, thyroid cancer, female reproductive system cancer, carcinoma in situ, lymphoma, neurofibromatosis, bone cancer, skin cancer, brain cancer, colon cancer, testicular cancer, gastrointestinal stromal tumor, oral cancer, pharyngeal cancer, multiple myeloma, leukemia, non-Hodgkin's lymphoma, chorioadenoma of large intestine, melanoma, cytoma and sarcoma, or myelodysplastic syndrome.

* * * * *

UNITED STATES PATENT AND TRADEMARK OFFICE
CERTIFICATE OF CORRECTION

PATENT NO. : 10,744,139 B2  
APPLICATION NO. : 16/328817  
DATED : August 18, 2020  
INVENTOR(S) : Frank Wu Page 1 of 3

It is certified that error appears in the above-identified patent and that said Letters Patent is hereby corrected as shown below:

In the Specification

At Column 5, Line numbers 43-50, replace " " with -- -- ;

At Column 10, Line numbers 60-67, replace " " with -- -- ;

At Column 29, Line numbers 1-7, replace " " with -- -- ;

At Column 62, Line number 9, replace "LC-MS (Pos," with -- LC-MS (Pos, m/z)=512.1 [M+H+]. --;

Signed and Sealed this  
Thirteenth Day of October, 2020

Andrei Iancu  
*Director of the United States Patent and Trademark Office*

At Column 88, Line numbers 58-66, replace
" 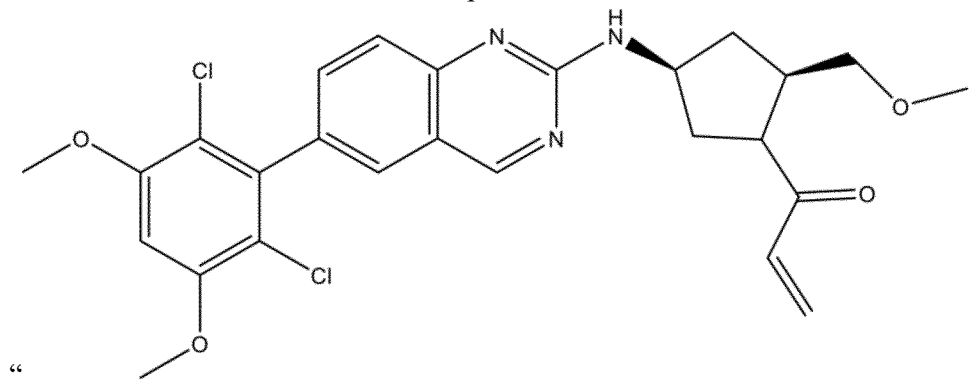 " with
-- 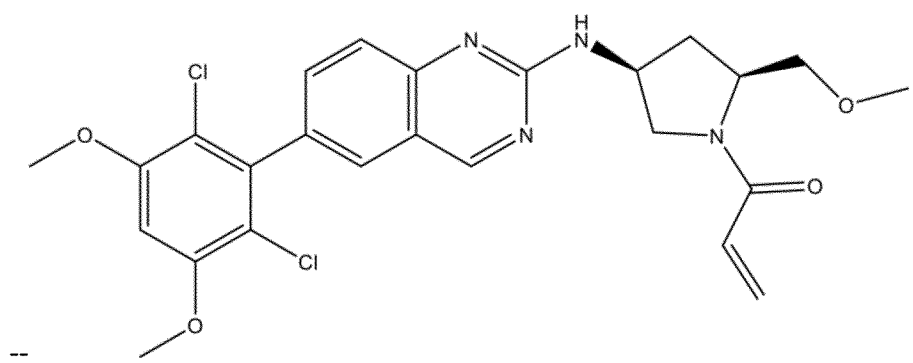 --;
In the Claims
At Column 110, Claim number 1, Line numbers 37-45, replace
" 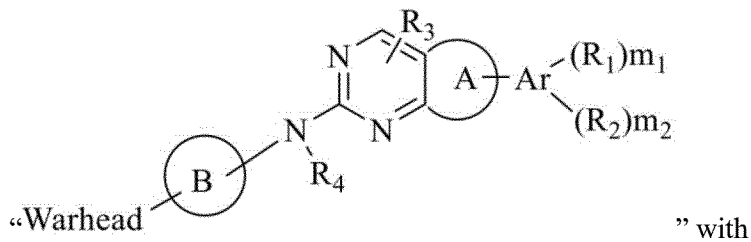 " with
-- 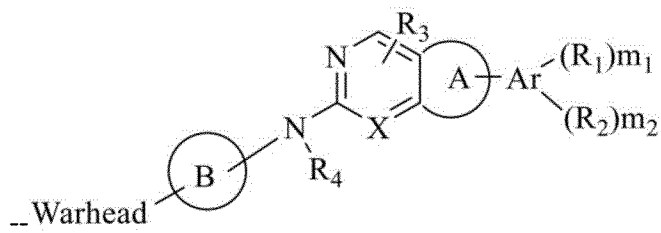 --;
At Column 123, Claim number 10, Line number 29, replace "($C_{1-4}$ alkyl)2 amino," with -- ($C_{1-4}$ alkyl)$_2$ amino, --;

CERTIFICATE OF CORRECTION (continued)
U.S. Pat. No. 10,744,139 B2

At Column 126, Claim number 11, Line numbers 30-40, replace

" 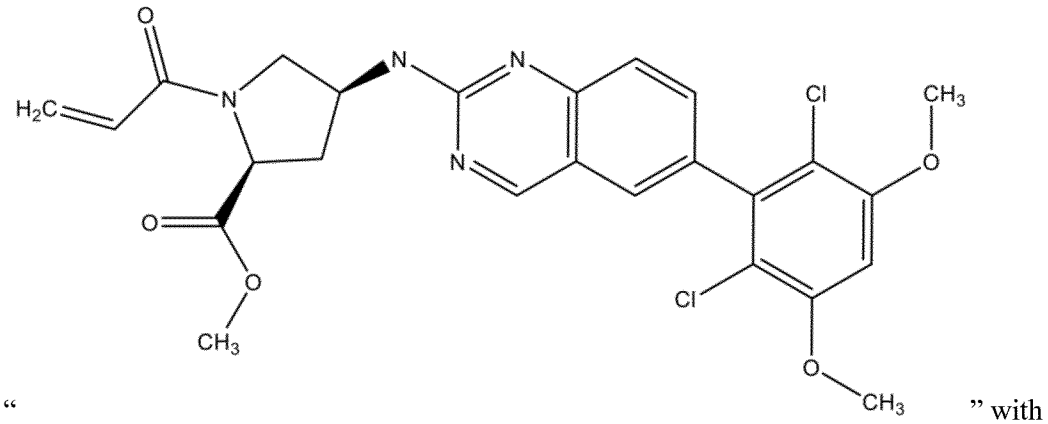 " with

-- 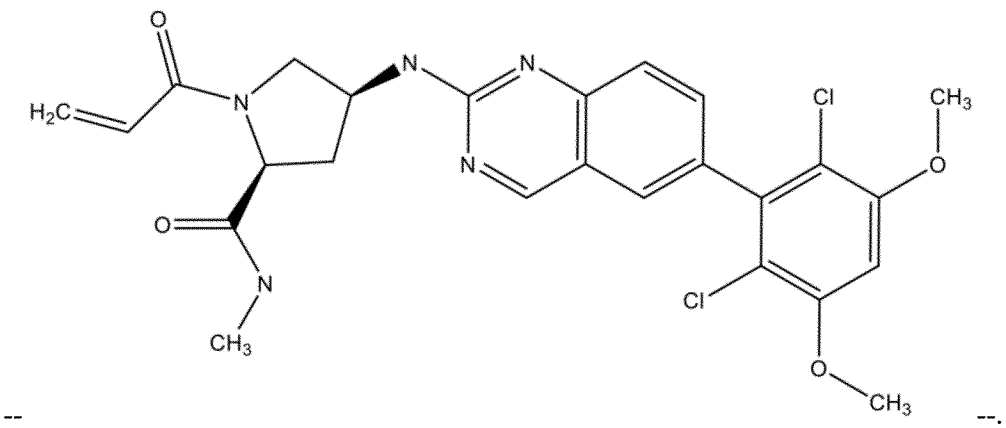 --.